United States Patent
Mertz et al.

(10) Patent No.: US 10,081,617 B2
(45) Date of Patent: Sep. 25, 2018

(54) FACTOR XIA INHIBITORS

(71) Applicant: MERCK SHARP & DOHME CORP., Rahway, NJ (US)

(72) Inventors: Eric Mertz, Christianburg, VA (US); Scott D. Edmondson, Concord, MA (US); Sung-Sau So, Verona, NJ (US); Wanying Sun, Edison, NJ (US); Weiguo Liu, Princeton, NJ (US); Santhosh F. Neelamkavil, Edison, NJ (US); Ying-Duo Gao, Holmdel, NJ (US); Alan Hruza, Hackettstown, NJ (US); Yi Zang, Princeton Junction, NJ (US); Amjad Ali, Freehold, NJ (US); Rudrajit Mal, Piscataway, NJ (US); Jiafang He, South Brunswick, NJ (US); Rongze Kuang, Green Brook, NJ (US); Heping Wu, Edison, NJ (US); Anthony K. Ogawa, New Providence, NJ (US); Andrew F. Nolting, Trenton, NJ (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 0 days.

(21) Appl. No.: 15/565,748

(22) PCT Filed: Apr. 11, 2016

(86) PCT No.: PCT/US2016/026858
§ 371 (c)(1),
(2) Date: Oct. 11, 2017

(87) PCT Pub. No.: WO2016/168098
PCT Pub. Date: Oct. 20, 2016

(65) Prior Publication Data
US 2018/0079743 A1    Mar. 22, 2018

Related U.S. Application Data

(60) Provisional application No. 62/148,391, filed on Apr. 16, 2015.

(51) Int. Cl.
*C07D 401/14* (2006.01)
*C07D 413/14* (2006.01)
*C07D 409/14* (2006.01)

(52) U.S. Cl.
CPC ......... *C07D 401/14* (2013.01); *C07D 409/14* (2013.01); *C07D 413/14* (2013.01)

(58) Field of Classification Search
CPC ................. C07D 401/14; C07D 413/14
See application file for complete search history.

(56) References Cited

U.S. PATENT DOCUMENTS

| | | | |
|---|---|---|---|
| 9,663,527 B2* | 5/2017 | Neelamkavil | C07D 487/08 |
| 9,676,723 B2* | 6/2017 | Neelamkavil | C07D 401/14 |
| 9,868,727 B2* | 1/2018 | Liu | C07D 409/14 |
| 2003/0065176 A1 | 4/2003 | Kang et al. | |

FOREIGN PATENT DOCUMENTS

| | | |
|---|---|---|
| WO | WO2015047973 A1 | 4/2015 |
| WO | 2016015593 A1 | 2/2016 |
| WO | 2016018701 A1 | 2/2016 |
| WO | WO2016018702 A1 | 2/2016 |
| WO | 2016118403 A1 | 7/2016 |

OTHER PUBLICATIONS

International Search Report and Written Opinion for PCT/US2016/026858 dated Sep. 8, 2016, 10 pages.
PubChem SID 80542016, Jun. 12, 2009, pp. 1-5 (CID 11858114).
Schumacher, W.A., et al., Inhibition of Factor XIa as a New Approach to Anticoagulation, Arteriosclerosis Thrombosis and Vascular Biology, 2010, pp. 388-392, 30.

* cited by examiner

*Primary Examiner* — Golam M Shameem
(74) *Attorney, Agent, or Firm* — Nicole M. Beeler; John C. Todaro

(57) ABSTRACT

The present invention provides a compound of Formula (I); and pharmaceutical compositions comprising one or more said compounds, and methods for using said compounds for treating or preventing thromboses, embolisms, hypercoagulability or fibrotic changes. The compounds are selective Factor XIa inhibitors or dual inhibitors of Factor XIa and plasma kallikrein.

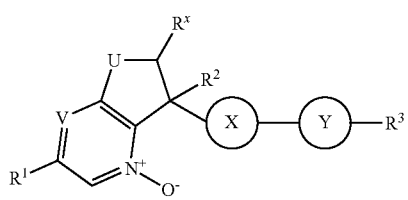

11 Claims, No Drawings

FACTOR XIA INHIBITORS

CROSS REFERENCE TO RELATED APPLICATIONS

This application is a U.S. National Phase application under 35 U.S.C. § 371 of PCT Application No. PCT/US2016/026858 filed Apr. 11, 2016, which claims priority from U.S. Provisional Application Ser. No. 62/148,391 filed Apr. 16, 2015.

BACKGROUND OF THE INVENTION

Factor XIa is a plasma serine protease involved in the regulation of blood coagulation. While blood coagulation is a necessary and important part of the regulation of an organism's homeostasis, abnormal blood coagulation can also have deleterious effects. For instance, thrombosis is the formation or presence of a blood clot inside a blood vessel or cavity of the heart. Such a blood clot can lodge in a blood vessel; blocking circulation and inducing a heart attack or stroke. Thromboembolic disorders are the largest cause of mortality and disability in the industrialized world.

Blood clotting is a process of control of the blood stream essential for the survival of mammals. The process of clotting, and the subsequent dissolution of the clot after wound healing has taken place, commence after vascular damage, and can be divided into four phases. The first phase, vasoconstriction or vasocontraction, can cause a decrease in blood loss in the damaged area. In the next phase, platelet activation by thrombin, platelets attach to the site of the vessel wall damage and form a platelet aggregate. In the third phase, formation of clotting complexes leads to massive formation of thrombin, which converts soluble fibrinogen to fibrin by cleavage of two small peptides. In the fourth phase, after wound healing, the thrombus is dissolved by the action of the key enzyme of the endogenous fibrinolysis system, plasmin.

Two alternative pathways can lead to the formation of a fibrin clot, the intrinsic and the extrinsic pathway. These pathways are initiated by different mechanisms, but in the later phase they converge to give a common final path of the clotting cascade. In this final path of clotting, clotting factor X is activated. The activated factor X is responsible for the formation of thrombin from the inactive precursor prothrombin circulating in the blood. The formation of a thrombus on the bottom of a vessel wall abnormality without a wound is the result of the intrinsic pathway. Fibrin clot formation as a response to tissue damage or an injury is the result of the extrinsic pathway. Both pathways comprise a relatively large number of proteins, which are known as clotting factors. The intrinsic pathway requires the clotting factors V, VIII, IX, X, XI and XII and also prekallikrein, high molecular weight kininogen, calcium ions and phospholipids from platelets. The activation of factor XIa is a central point of intersection between the two pathways of activation of clotting. Factor XIa has an important role in blood clotting.

Coagulation is initiated when blood is exposed to artificial surfaces (e.g., during hemodialysis, "on-pump" cardiovascular surgery, vessel grafts, bacterial sepsis), on cell surfaces, cellular receptors, cell debris, DNA, RNA, and extracellular matrices. This process is also termed contact activation. Surface absorption of factor XII leads to a conformational change in the factor XII molecule, thereby facilitating activation to proteolytic active factor XII molecules (factor 25 XIIa and factor XIIf). Factor XIIa (or XIIf) has a number of target proteins, including plasma prekallikrein and factor XI. Active plasma kallikrein further activates factor XII, leading to an amplification of contact activation. Alternatively, the serine protease prolylcarboxylpeptidase can activate plasma kallikrein complexed with high molecular weight kininogen in a multiprotein complex formed on the surface of cells and matrices (Shariat-Madar et al., Blood, 108:192-199 (2006)). Contact activation is a surface mediated process responsible in part for the regulation of thrombosis and inflammation, and is mediated, at least in part, by fibrinolytic-, complement-, kininogen/kinin-, and other humoral and cellular pathways (for review, Coleman, R., "Contact Activation Pathway", Hemostasis and Thrombosis, pp. 103-122, Lippincott Williams & Wilkins (2001); Schmaier, A. H., "Contact Activation", Thrombosis and Hemorrhage, pp. 105-128 (1998)). The biological relevance of the contact activation system for thromboembolic diseases is supported by the phenotype of factor XII deficient mice. More specifically, factor XII deficient mice were protected from thrombotic vascular occlusion in several thrombosis models as well as stroke models and the phenotype of the XII deficient mice was identical to XI deficient mice (Renne et al., J Exp. Med., 202:271-281 (2005); Kleinschmitz et al., J Exp. Med., 203:513-518 (2006)). The fact that factor XI is downstream from factor XIIa, combined with the identical phenotype of the XII and XI deficient mice suggest that the contact activation system could play a major role in factor XI activation in vivo. Plasma kallikrein is a zymogen of a trypsin-like serine protease and is present in plasma. The gene structure is similar to that of factor XI. Overall, the amino acid sequence of plasma kallikrein has 58% homology to factor XI. Proteolytic activation by factor XIIa at an internal I389-R390 bond yields a heavy chain (371 amino acids) and a light chain (248 amino acids). The active site of plasma kallikrein is contained in the light chain. The light chain of plasma kallikrein reacts with protease 15 inhibitors, including alpha 2 macroglobulin and C1-inhibitor. Interestingly, heparin significantly accelerates the inhibition of plasma kallikrein by antithrombin III in the presence of high molecular weight kininogen (HMWK). In blood, the majority of plasma kallikrein circulates in complex with HMWK. Plasma kallikrein cleaves HMWK to liberate bradykinin. Bradykinin release results in increase of vascular permeability and vasodilation (for review, Coleman, R., "Contact Activation Pathway", Hemostasis and Thrombosis, pp. 103-122, Lippincott Williams & Wilkins (2001); Schmaier A. H., "Contact Activation", Thrombosis and Hemorrhage, pp. 105-128 (1998)). Factor XIa inhibitor compounds are described in WO2016036893, WO2016015593, WO2016018702, WO2016018701, WO2016011940, JP2015013821, WO2015183709, WO2015164308, WO2015123093, WO2015123091, WO2015123090, WO2015120777, WO2015120062, WO2015116885, WO2015116882, WO2015107724, WO2015063093, WO2015054087, WO2015047973, WO2015044174, WO2015044173, WO2015044172, WO2015044170, WO2015044169, WO2015044167, WO2015044165, WO2015044163, WO2015002611, WO2015011087, WO2014160668, WO2014160592, WO2014059214, WO2014059203, WO2014059202, WO2014022767, WO2014022766, WO2014014050, WO2013174937, WO2013022814, WO 2013022818, WO 2013055984, WO2013056034, WO2013056060, WO2013118805, WO2013093484, WO2002042273, WO2002037937, WO2002060894, WO2003015715, WO2004002405, US20040180855, WO2004080971, WO2004094372, US20050228000, US20050282805, WO2005123680, US20090036438, US20120088758, US20060074103, WO2006062972, WO2006076246, US20060154915, US20090062287, US20060183771, WO2007070818, WO2007070816, WO2007070826, WO2008076805, WO2008157162, WO2009114677, WO2011100402, and WO2011100401.

SUMMARY OF THE INVENTION

The present invention relates to compounds of Formula I:

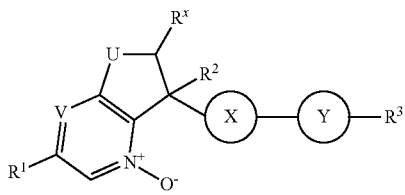

or pharmaceutically acceptable salts thereof. The compounds of Formula I are selective Factor XIa inhibitors or dual inhibitors of Factor XIa and plasma kallikrein, and as such may be useful in the treatment, inhibition or amelioration of one or more disease states that could benefit from inhibition of Factor XIa or plasma kallikrein, including thromboses, embolisms, hypercoagulability or fibrotic changes. The compounds of this invention could further be used in combination with other therapeutically effective agents, including but not limited to, other drugs useful for the treatment of thromboses, embolisms, hypercoagulability or fibrotic changes. The invention furthermore relates to processes for preparing compounds of Formula I, and pharmaceutical compositions which comprise compounds of Formula I.

DETAILED DESCRIPTION OF THE INVENTION

The present invention relates to compounds of Formula I:

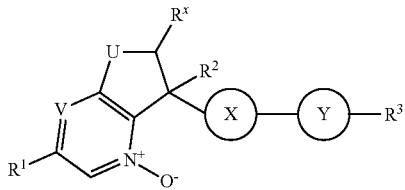

wherein (X) is heteroaryl, aryl, heterocyclyl or $C_{3-6}$ cycloalkyl, wherein said heteroaryl, aryl, heterocyclyl and cycloalkyl groups are optionally substituted with one or two groups independently selected from the group consisting of halo, cyano, oxo, $C_{1-6}$ alkyl, $C_{2-6}$ alkenyl, $C_{2-6}$ alkynyl, $OR^4$, $NR^4R^5$, $NH(C=O)R^4$ and $NH(C=O)OR^4$;

(Y) is absent, aryl or heteroaryl, wherein said aryl and heteroaryl groups are optionally substituted with halo or $C_{1-6}$ alkyl;
U is S, O, $CHR^x$ or $CHR^xCH_2$;
V is N or $CR^y$;

$R^1$ is aryl, heteroaryl, heterocyclyl or $C_{3-6}$ cycloalkyl, wherein said aryl, heteroaryl, heterocyclyl and cycloalkyl groups are optionally substituted with one to three substituents independently selected from the group consisting of halo, nitro, cyano, oxo, $R^4$, $OR^4$, $(C=O)R^4$, $(C=O)OR^4$, $NR^4R^5$, $NH(C=O)R^4$, $NH(C=O)OR^4$, $C_{3-6}$ cycloalkyl and heteroaryl (which is optionally substituted with cyano, halo, or $R^4$);
$R^2$ is hydrogen, hydroxy, $C_{1-6}$ alkyl, $C_{1-3}$ alkyl-$OR^4$, $C_{3-6}$ cycloalkyl, $OR^4$, $OC_{1-3}$ alkyl-$C_{3-6}$ cycloalkyl, $O(C_{3-6}$ cycloalkyl) or halo;
$R^3$ is halo, hydroxy, nitro, cyano, oxo, $R^4$, $OR^4$, $C_{1-6}$ alkyl, $C_{2-6}$ alkenyl, $C_{2-6}$ alkynyl, $SO_mR^4$, $NHSO_mR^4$, $(C=O)NHSO_mR^4$, $(C=O)R^4$, $(C=O)OR^4$, $O(C=O)R^4$, $O(C=O)OR^4$, $NR^4R^5$, $NH(C=O)R^4$, $NH(C=O)OR^4$, $(C=O)OCHR^4$—$O(C=O)OC_{3-6}$ cycloalkyl, heteroaryl, aryl, heterocyclyl or $C_{3-6}$ cycloalkyl, wherein said heteroaryl, aryl, heterocyclyl and cycloalkyl groups are optionally substituted with one or two groups independently selected from the group consisting of halo, cyano, oxo, $R^4$ and $OR^4$;
$R^4$ is hydrogen or $C_{1-6}$ alkyl, which is optionally substituted with one to three groups independently selected from the group consisting of halo, hydroxy and methoxy;
$R^5$ is hydrogen or $C_{1-6}$ alkyl, which is optionally substituted with one to three groups independently selected from the group consisting of halo and hydroxy;
$R^x$ is hydrogen, hydroxy, halo, $R^4$, $OR^4$, phenyl or benzyl;
$R^y$ is hydrogen, halo, $OR^4$, $(C=O)R^4$, $(C=O)OR^4$, $(C=O)NR^4R^5$, $C_{3-6}$ cycloalkyl or $O(C_{3-6}$ cycloalkyl);
m is an integer between 0 and 2;
or a pharmaceutically acceptable salt thereof.

An embodiment of the present invention relates to compounds of Formula Ia:

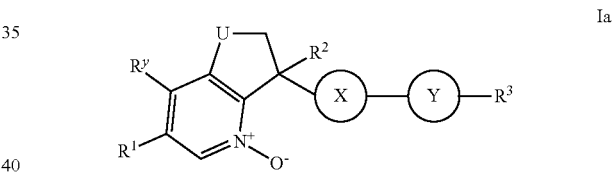

wherein (X) is heteroaryl, which is optionally substituted with halo or $C_{1-6}$ alkyl;

(Y) is aryl or heteroaryl, wherein said aryl and heteroaryl groups are optionally substituted with halo or methyl;
U is $CHR^x$,
$R^1$ is aryl, which is optionally substituted with one to three substituents independently selected from the group consisting of halo, nitro, cyano, $R^4$, $OR^4$ (c=O)$R^4$, $(C=O)OR^4$, $NR^4R^5$, $NH(C=O)R^4$, $NH(C=O)OR^4$, $C_{3-6}$ cycloalkyl and heteroaryl (which is optionally substituted with cyano, halo, or $R^4$);
$R^2$ is hydrogen, hydroxy, methyl, methoxy, cyclopropyl or halo;
$R^3$ is halo, hydroxy, nitro, cyano, oxo, $R^4$, $OR^4$, $(C=O)R^4$, $(C=O)OR^4$, $NR^4R^5$, $NH(C=O)R^4$ and $NH(C=O)OR^4$;
$R^4$ is hydrogen or $C_{1-6}$ alkyl, which is optionally substituted with one to three groups independently selected from the group consisting of halo, hydroxy and methoxy;
$R^5$ is hydrogen or $C_{1-6}$ alkyl, which is optionally substituted with one to three groups independently selected from the group consisting of halo and hydroxy;
$R^x$ is hydrogen, hydroxy or halo;
$R^y$ is hydrogen, hydroxy, methoxy or halo;
or a pharmaceutically acceptable salt thereof.

The present invention also relates to compounds of Formula II:

wherein Ⓨ is aryl or heteroaryl, wherein said aryl and heteroaryl groups are optionally substituted with halo;
R$^1$ is phenyl, which is optionally substituted with one to three substituents independently selected from the group consisting of halo or heteroaryl (which is optionally substituted with cyano, halo, or R$^4$);
R$^3$ is halo, hydroxy, R$^4$, OR$^4$, (C=O)R$^4$, (C=O)OR$^4$, NR$^4$R$^5$, NH(C=O)R$^4$ and NH(C=O)OR$^4$;
R$^4$ is hydrogen or C$_{1-6}$ alkyl, which is optionally substituted with one to three groups independently selected from the group consisting of halo and hydroxy;
R$^5$ is hydrogen or C$_{1-6}$ alkyl, which is optionally substituted with one to three groups independently selected from the group consisting of halo and hydroxy;
R$^y$ is hydrogen, hydroxy, methoxy or halo;
or a pharmaceutically acceptable salt thereof.

The present invention also relates to compounds of Formula I:

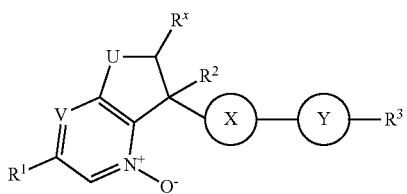

wherein Ⓧ is heteroaryl, aryl, heterocyclyl or C$_{3-6}$ cycloalkyl, wherein said heteroaryl, aryl, heterocyclyl and cycloalkyl groups are optionally substituted with one or two groups independently selected from the group consisting of halo, cyano, oxo, C$_{1-6}$ alkyl, C$_{2-6}$ alkenyl, C$_{2-6}$ alkynyl, OR$^4$, NR$^4$R$^5$, NH(C=O)R$^4$ and NH(C=O)OR$^4$;

Ⓨ is absent, aryl or heteroaryl, wherein said aryl and heteroaryl groups are optionally substituted with halo or C$_{1-6}$ alkyl;
U is S, O, CHR$^x$ or CHR$^x$ CH$_2$;
V is N or CR$^y$;
R$^1$ is aryl, heteroaryl, heterocyclyl or C$_{3-6}$ cycloalkyl, wherein said aryl, heteroaryl, heterocyclyl and cycloalkyl groups are optionally substituted with one to three substituents independently selected from the group consisting of halo, nitro, cyano, oxo, R$^4$, OR$^4$, (C=O)R$^4$, (C=O)OR$^4$, NR$^4$R$^5$, NH(C=O)R$^4$, NH(C=O)OR$^4$, C$_{3-6}$ cycloalkyl and heteroaryl (which is optionally substituted with cyano or R$^4$);
R$^2$ is hydrogen, hydroxy, C$_{1-6}$ alkyl, C$_{3-6}$ cycloalkyl, OR$^4$, O(C$_{1-3}$ alkyl)(C$_{3-6}$ cycloalkyl), O(C$_{3-6}$ cycloalkyl) or halo;
R$^3$ is halo, hydroxy, nitro, cyano, oxo, R$^4$, OR$^4$, C$_{1-6}$ alkyl, C$_{2-6}$ alkenyl, C$_{2-6}$ alkynyl, SO$_m$R$^4$, NHSO$_m$R$^4$, (C=O)R$^4$, (C=O)OR$^4$, O(C=O)R$^4$, O(C=O)OR$^4$, NR$^4$R$^5$, NH(C=O)R$^4$, NH(C=O)OR$^4$, heteroaryl, aryl, heterocyclyl or C$_{3-6}$ cycloalkyl, wherein said heteroaryl, aryl, heterocyclyl and cycloalkyl groups are optionally substituted with one or two groups independently selected from the group consisting of halo, cyano, oxo, R$^4$ and OR$^4$;
R$^4$ is hydrogen or C$_{1-6}$ alkyl, which is optionally substituted with one to three groups independently selected from the group consisting of halo, hydroxy and methoxy;
R$^5$ is hydrogen or C$_{1-6}$ alkyl, which is optionally substituted with one to three groups independently selected from the group consisting of halo and hydroxy;
R$^x$ is hydrogen, hydroxy, halo, R$^4$, OR$^4$, phenyl or benzyl;
R$^y$ is hydrogen, halo, OR$^4$, (C=O)R$^4$, (C=O)OR$^4$, (C=O)NR$^4$R$^5$, C$_{3-6}$ cycloalkyl or O(C$_{3-6}$ cycloalkyl);
m is an integer between 0 and 2;
or a pharmaceutically acceptable salt thereof.

In an embodiment of the invention, Ⓧ is heteroaryl, which is optionally substituted with halo or C$_{1-6}$ alkyl. In a class of the embodiment, Ⓧ is imidazolyl, oxazolyl, oxadiazolyl, benzimidazolyl or pyrazolyl, wherein said imidazolyl is substituted with methyl or halo. In a subclass of the embodiment, Ⓧ is imidazolyl.

In an embodiment of the invention, Ⓨ is aryl or heteroaryl, wherein said aryl and heteroaryl groups are optionally substituted with halo or C$_{1-6}$ alkyl. In a class of the embodiment, Ⓨ is thiophenyl, pyridinyl, 1,2,3,4-tetrahydroquinolinyl or phenyl, wherein said thiophenyl, pyridinyl, 1,2,3,4-tetrahydroquinolinyl or phenyl groups are optionally substituted with halo. In a subclass of the embodiment, Ⓨ is phenyl, which is optionally substituted with halo. In another subclass of the embodiment, Ⓨ is phenyl.

In an embodiment of the invention, U is CH$_2$. In another embodiment of the invention, U is CH$_2$CH$_2$.

In an embodiment of the invention, V is CR$^y$. In a class of the embodiment, V is CH.

In an embodiment of the invention, R$^1$ is aryl wherein said aryl groups is optionally substituted with one to three substituents independently selected from the group consisting of halo, nitro, cyano, R$^4$, OR$^4$, (C=O)R$^4$, (C=O)OR$^4$, NR$^4$R$^5$, NH(C=O)R$^4$, NH(C=O)OR$^4$, C$_{3-6}$ cycloalkyl and heteroaryl (which is optionally substituted with cyano, halo, or R$^4$). In a class of the embodiment, R$^1$ is phenyl, which is optionally substituted with one to three substituents independently selected from the group consisting of halo or heteroaryl (which is optionally substituted with cyano, halo, or R$^4$). In a subclass of the embodiment, R$^1$ is phenyl, which is substituted with two or three substituents independently selected from the group consisting of halo and heteroaryl. In a subclass of the embodiment, R$^1$ is phenyl, which is substituted with halo and heteroaryl, selected from tetrazolyl, oxazolyl or triazolyl. In another subclass of the embodiment, R$^1$ is phenyl, which is substituted with halo and tetrazolyl. In another subclass of the embodiment, R$^1$ is phenyl, which is substituted with three halo.

In an embodiment of the invention, $R^2$ is hydrogen. In another embodiment of the invention, $R^2$ is hydroxy. In another embodiment of the invention, $R^2$ is methyl. In another embodiment of the invention, $R^2$ is methoxy. In another embodiment of the invention, $R^2$ is cyclopropyl. In another embodiment of the invention, $R^2$ is halo. In another embodiment of the invention, $R^2$ is $C_{1-3}$ alkyl-$OR^4$.

In an embodiment of the invention, $R^3$ is halo, hydroxy, nitro, cyano, oxo, $R^4$, $OR^4$, $(C=O)R^4$, $(C=O)OR^4$, $NR^4R^5$, $NH(C=O)R^4$ or $NH(C=O)OR^4$. In a class of the embodiment, $R^3$ is halo, hydroxy, $R^4$, $OR^4$, $(C=O)R^4$, $(C=O)OR^4$, $NR^4R^5$, $NH(C=O)R^4$ or $NH(C=O)OR^4$. In a subclass of the embodiment, $R^3$ is halo. In another subclass of the embodiment, $R^3$ is hydroxy. In another subclass of the embodiment, $R^3$ is oxo. In another subclass of embodiment, $R^3$ is $R^4$. In another subclass of the embodiment, $R^3$ is $(C=O)OR^4$. In another subclass of the embodiment, $R^3$ is $NR^4R^5$. In another subclass of the embodiment, $R^3$ is $NH(C=O)R^4$. In another subclass of the embodiment, $R^3$ is $NH(C=O)OR^4$. In another subclass of the embodiment, $R^3$ is $(C=O)NHSO_mR^4$. In another subclass of the embodiment, $R^3$ is $(C=O)OCHR^4$—$O(C=O)OC_{3-6}$ cycloalkyl, In an embodiment of the invention, $R^x$ is hydrogen. In another embodiment of the invention, $R^x$ is hydroxy. In another embodiment of the invention, $R^x$ is halo. In another embodiment of the invention, $R^x$ is $R^4$. In another embodiment of the invention, $R^x$ is $OR^4$. In another embodiment of the invention, $R^x$ is phenyl. In another embodiment of the invention, $R^x$ is benzyl.

In an embodiment of the invention, $R^y$ is hydrogen. In another embodiment of the invention, $R^y$ is hydroxy. In another embodiment of the invention, $R^y$ is methoxy.

Reference to the preferred classes and subclasses set forth above is meant to include all combinations of particular and preferred groups unless stated otherwise.

Specific embodiments of the present invention include, but are not limited to the compounds identified herein as Examples 1 to 134, or pharmaceutically acceptable salts thereof.

Also included within the scope of the present invention is a pharmaceutical composition which is comprised of a compound of Formula I, Formula Ia or Formula II as described above and a pharmaceutically acceptable carrier. The invention is also contemplated to encompass a pharmaceutical composition which is comprised of a pharmaceutically acceptable carrier and any of the compounds specifically disclosed in the present application. These and other aspects of the invention will be apparent from the teachings contained herein.

The invention also includes compositions for inhibiting loss of blood platelets, inhibiting formation of blood platelet aggregates, inhibiting formation of fibrin, inhibiting thrombus formation, inhibiting embolus formation, treating inflammatory disorders, treating diabetic retinopathy and treating hereditary angioedema in a mammal, comprising a compound of the invention in a pharmaceutically acceptable carrier. These compositions may optionally include anticoagulants, antiplatelet agents, and thrombolytic agents. The compositions can be added to blood, blood products, or mammalian organs in order to effect the desired inhibitions.

The invention also includes compositions for preventing or treating unstable angina, refractory angina, myocardial infarction, transient ischemic attacks, atrial fibrillation, thrombotic stroke, embolic stroke, deep vein thrombosis, disseminated intravascular coagulation, ocular buildup of fibrin, and reocclusion or restenosis of recanalized vessels, in a mammal, comprising a compound of the invention in a pharmaceutically acceptable carrier. These compositions may optionally include anticoagulants, antiplatelet agents, and thrombolytic agents.

The invention also includes a method for reducing the thrombogenicity of a surface in a mammal by attaching to the surface, either covalently or noncovalently, a compound of the invention.

Compounds of the invention are Factor XIa inhibitors and may have therapeutic value in, for example, preventing coronary artery disease. The compounds are selective Factor XIa inhibitors or dual inhibitors of Factor XIa and plasma kallikrein.

It will be understood that, as used herein, compounds of the instant invention can include the pharmaceutically acceptable salts, and also salts that are not pharmaceutically acceptable when they are used as precursors to the free compounds or their pharmaceutically acceptable salts or in other synthetic manipulations.

The compounds of the present invention may be administered in the form of a pharmaceutically acceptable salt. The term "pharmaceutically acceptable salt" refers to salts prepared from pharmaceutically acceptable non-toxic bases or acids including inorganic or organic bases and inorganic or organic acids. Salts of basic compounds encompassed within the term "pharmaceutically acceptable salt" refer to non-toxic salts of the compounds of this invention which are generally prepared by reacting the free base with a suitable organic or inorganic acid. Representative salts of basic compounds of the present invention include, but are not limited to, the following: acetate, ascorbate, adipate, alginate, aspirate, benzenesulfonate, benzoate, bicarbonate, bisulfate, bitartrate, borate, bromide, butyrate, camphorate, camphorsulfonate, camsylate, carbonate, chloride, clavulanate, citrate, cyclopentane propionate, diethylacetic, digluconate, dihydrochloride, dodecylsulfanate, edetate, edisylate, estolate, esylate, ethanesulfonate, formic, fumarate, gluceptate, glucoheptanoate, gluconate, glutamate, glycerophosphate, glycollylarsanilate, hemi sulfate, heptanoate, hexanoate, hexylresorcinate, hydrabamine, hydrobromide, hydrochloride, 2-hydroxyethanesulfonate, hydroxynaphthoate, iodide, isonicotinic, isothionate, lactate, lactobionate, laurate, malate, maleate, mandelate, mesylate, methylbromide, methylnitrate, methylsulfate, methanesulfonate, mucate, 2-naphthalenesulfonate, napsylate, nicotinate, nitrate, N-methylglucamine ammonium salt, oleate, oxalate, pamoate (embonate), palmitate, pantothenate, pectinate, persulfate, phosphate/diphosphate, pimelic, phenylpropionic, polygalacturonate, propionate, salicylate, stearate, sulfate, subacetate, succinate, tannate, tartrate, teoclate, thiocyanate, tosylate, triethiodide, trifluoroacetate, undeconate, valerate and the like. Furthermore, where the compounds of the invention carry an acidic moiety, suitable pharmaceutically acceptable salts thereof include, but are not limited to, salts derived from inorganic bases including aluminum, ammonium, calcium, copper, ferric, ferrous, lithium, magnesium, manganic, mangamous, potassium, sodium, zinc, and the like. Particularly preferred are the ammonium, calcium, magnesium, potassium, and sodium salts. Salts derived from pharmaceutically acceptable organic non-toxic bases include salts of primary, secondary, and tertiary amines, cyclic amines, dicyclohexyl amines and basic ion-exchange resins, such as arginine, betaine, caffeine, choline, N,N-dibenzylethylenediamine, diethylamine, 2-diethylaminoethanol, 2-dimethylaminoethanol, ethanolamine, ethylamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like. Also, included are the basic nitrogen-containing groups may be quaternized with such agents as lower alkyl halides, such as methyl, ethyl, propyl, and butyl chloride, bromides and iodides; dialkyl sulfates like dimethyl, diethyl, dibutyl; and diamyl sulfates, long chain halides such as decyl, lauryl, myristyl and stearyl chlorides, bromides and iodides, aralkyl halides like benzyl and phenethyl bromides and others.

These salts can be obtained by known methods, for example, by mixing a compound of the present invention with an equivalent amount and a solution containing a desired acid, base, or the like, and then collecting the desired salt by filtering the salt or distilling off the solvent. The compounds of the present invention and salts thereof may form solvates with a solvent such as water, ethanol, or glycerol. The compounds of the present invention may form an acid addition salt and a salt with a base at the same time according to the type of substituent of the side chain.

The present invention encompasses all stereoisomeric forms of the compounds of Formula I, Formula Ia and Formula II. Unless a specific stereochemistry is indicated, the present invention is meant to comprehend all such isomeric forms of these compounds. Centers of asymmetry that are present in the compounds of Formula I, Formula Ia and Formula II can all independently of one another have (R) configuration or (S) configuration. When bonds to the chiral carbon are depicted as straight lines in the structural Formulas of the invention, it is understood that both the (R) and (S) configurations of the chiral carbon, and hence both enantiomers and mixtures thereof, are embraced within the Formula. Similarly, when a compound name is recited without a chiral designation for a chiral carbon, it is understood that both the (R) and (S) configurations of the chiral carbon, and hence individual enantiomers and mixtures thereof, are embraced by the name. The production of specific stereoisomers or mixtures thereof may be identified in the Examples where such stereoisomers or mixtures were obtained, but this in no way limits the inclusion of all stereoisomers and mixtures thereof from being within the scope of this invention.

The invention includes all possible enantiomers and diastereomers and mixtures of two or more stereoisomers, for example mixtures of enantiomers and/or diastereomers, in all ratios. Thus, enantiomers are a subject of the invention in enantiomerically pure form, both as levorotatory and as dextrorotatory antipodes, in the form of racemates and in the form of mixtures of the two enantiomers in all ratios. In the case of a cis/trans isomerism the invention includes both the cis form and the trans form as well as mixtures of these forms in all ratios. The preparation of individual stereoisomers can be carried out, if desired, by separation of a mixture by customary methods, for example by chromatography or crystallization, by the use of stereochemically uniform starting materials for the synthesis or by stereoselective synthesis. Optionally a derivatization can be carried out before a separation of stereoisomers. The separation of a mixture of stereoisomers can be carried out at an intermediate step during the synthesis of a compound of Formula I, Formula Ia or Formula II or it can be done on a final racemic product. Absolute stereochemistry may be determined by X-ray crystallography of crystalline products or crystalline intermediates which are derivatized, if necessary, with a reagent containing a stereogenic center of known configuration. Where compounds of this invention are capable of tautomerization, all individual tautomers as well as mixtures thereof are included in the scope of this invention. Unless a particular isomer, salt, solvate (including hydrates) or solvated salt of such racemate, enantiomer, diastereomer or tautomer is indicated, the present invention includes all such isomers, as well as salts, solvates (including hydrates) and solvated salts of such racemates, enantiomers, diastereomers and tautomers and mixtures thereof.

In the compounds of the invention, the atoms may exhibit their natural isotopic abundances, or one or more of the atoms may be artificially enriched in a particular isotope having the same atomic number, but an atomic mass or mass number different from the atomic mass or mass number predominantly found in nature. The present invention is meant to include all suitable isotopic variations of the specifically and generically described compounds. For example, different isotopic forms of hydrogen (H) include protium ($^{1}H$) and deuterium ($^{2}H$). Protium is the predominant hydrogen isotope found in nature. Enriching for deuterium may afford certain therapeutic advantages, such as increasing in vivo half-life or reducing dosage requirements, or may provide a compound useful as a standard for characterization of biological samples. Isotopically-enriched compounds can be prepared without undue experimentation by conventional techniques well known to those skilled in the art or by processes analogous to those described in the general process schemes and examples herein using appropriate isotopically-enriched reagents and/or intermediates.

When any variable (e.g. $R^4$, etc.) occurs more than one time in any constituent, its definition on each occurrence is independent at every other occurrence. Also, combinations of substituents and variables are permissible only if such combinations result in stable compounds. Lines drawn into the ring systems from substituents represent that the indicated bond may be attached to any of the substitutable ring atoms. If the ring system is bicyclic, it is intended that the bond be attached to any of the suitable atoms on either ring of the bicyclic moiety.

It is understood that one or more silicon (Si) atoms can be incorporated into the compounds of the instant invention in place of one or more carbon atoms by one of ordinary skill in the art to provide compounds that are chemically stable and that can be readily synthesized by techniques known in the art from readily available starting materials. Carbon and silicon differ in their covalent radius leading to differences in bond distance and the steric arrangement when comparing analogous C-element and Si-element bonds. These differences lead to subtle changes in the size and shape of silicon-containing compounds when compared to carbon. One of ordinary skill in the art would understand that size and shape differences can lead to subtle or dramatic changes in potency, solubility, lack of off-target activity, packaging properties, and so on. (Diass, J. O. et al. Organometallics (2006) 5:1188-1198; Showell, G. A. et al. Bioorganic & Medicinal Chemistry Letters (2006) 16:2555-2558).

It is understood that substituents and substitution patterns on the compounds of the instant invention can be selected by one of ordinary skill in the art to provide compounds that are chemically stable and that can be readily synthesized by techniques known in the art, as well as those methods set forth below, from readily available starting materials. If a substituent is itself substituted with more than one group, it is understood that these multiple groups may be on the same carbon or on different carbons, so long as a stable structure results. The phrase "optionally substituted" (with one or more substituents) should be understood as meaning that the group in question is either unsubstituted or may be substituted with one or more substituents.

Furthermore, compounds of the present invention may exist in amorphous form and/or one or more crystalline forms, and as such all amorphous and crystalline forms and mixtures thereof of the compounds of Formula I, Formula Ia and Formula II are intended to be included within the scope of the present invention. In addition, some of the compounds of the instant invention may form solvates with water (i.e., a hydrate) or common organic solvents. Such solvates and hydrates, particularly the pharmaceutically acceptable solvates and hydrates, of the instant compounds are likewise encompassed within the scope of this invention, along with un-solvated and anhydrous forms.

Also, in the case of a carboxylic acid (—COOH) or alcohol group being present in the compounds of the present invention, pharmaceutically acceptable esters of carboxylic acid derivatives, such as methyl, ethyl, or pivaloyloxymethyl, or acyl derivatives of alcohols, such as O-acetyl, O-pivaloyl, O-benzoyl, and O-aminoacyl, can be employed. Included are those esters and acyl groups known in the art for modifying the solubility or hydrolysis characteristics for use as sustained-release or prodrug formulations.

If the compounds of Formula I, Formula Ia or Formula II simultaneously contain acidic and basic groups in the molecule the invention also includes, in addition to the salt forms mentioned, inner salts or betaines (zwitterions). Salts can be obtained from the compounds of Formula I, Formula Ia and Formula II by customary methods which are known to the person skilled in the art, for example by combination with an organic or inorganic acid or base in a solvent or dispersant, or by anion exchange or cation exchange from other salts. The present invention also includes all salts of the compounds of Formula I, Formula Ia and Formula II which, owing to low physiological compatibility, are not directly suitable for use in pharmaceuticals but which can be used, for example, as intermediates for chemical reactions or for the preparation of pharmaceutically acceptable salts.

Any pharmaceutically acceptable pro-drug modification of a compound of this invention which results in conversion in vivo to a compound within the scope of this invention is also within the scope of this invention. For example, esters can optionally be made by esterification of an available carboxylic acid group or by formation of an ester on an available hydroxy group in a compound. Similarly, labile amides can be made. Pharmaceutically acceptable esters or amides of the compounds of this invention may be prepared to act as pro-drugs which can be hydrolyzed back to an acid (or —COO— depending on the pH of the fluid or tissue where conversion takes place) or hydroxy form particularly in vivo and as such are encompassed within the scope of this invention. Examples of pharmaceutically acceptable pro-drug modifications include, but are not limited to, —C$_{1-6}$alkyl esters and —C$_{1-6}$alkyl substituted with phenyl esters.

Accordingly, the compounds within the generic structural formulas, embodiments and specific compounds described and claimed herein encompass salts, all possible stereoisomers and tautomers, physical forms (e.g., amorphous and crystalline forms), solvate and hydrate forms thereof and any combination of these forms, as well as the salts thereof, pro-drug forms thereof, and salts of pro-drug forms thereof, where such forms are possible unless specified otherwise.

Except where noted herein, the term "alkyl" is intended to include both branched- and straight-chain saturated aliphatic hydrocarbon groups having the specified number of carbon atoms. Commonly used abbreviations for alkyl groups are used throughout the specification, e.g. methyl, may be represented by conventional abbreviations including "Me" or CH$_3$ or a symbol that is an extended bond as the terminal group, e.g.

ethyl may be represented by "Et" or CH$_2$CH$_3$, propyl may be represented by "Pr" or CH$_2$CH$_2$CH$_3$, butyl may be represented by "Bu" or CH$_2$CH$_2$CH$_2$CH$_3$, etc. "C$_{1-4}$ alkyl" (or "C$_1$-C$_4$ alkyl") for example, means linear or branched chain alkyl groups, including all isomers, having the specified number of carbon atoms. For example, the structures

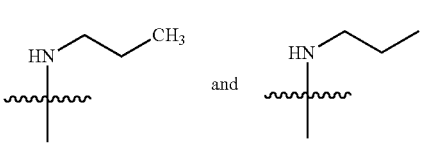

have equivalent meanings. C$_{1-4}$ alkyl includes n-, iso-, sec- and t-butyl, n- and iso-propyl, ethyl and methyl. If no number is specified, 1-4 carbon atoms are intended for linear or branched alkyl groups.

Except where noted herein, "alkanol" is intended to include aliphatic alcohols having the specified number of carbon atoms, such as methanol, ethanol, propanol, etc., where the —OH group is attached at any aliphatic carbon, e.g., propan-1-ol, propan-2-ol, etc.

Except where noted, the term "cycloalkyl" means a monocyclic or bicyclic saturated aliphatic hydrocarbon group having the specified number of carbon atoms. For example, "cycloalkyl" includes cyclopropyl, cyclobutyl, cyclopentyl, cyclohexyl, bicyclo[2.2.2]octanyl, and so on.

Except where noted, the term "halogen" or "halo" means fluorine, chlorine, bromine or iodine.

Except where noted, the term "heteroaryl", as used herein, represents a stable monocyclic or bicyclic ring of up to 10 atoms in each ring, wherein at least one ring is aromatic, and at least one ring contains from 1 to 4 heteroatoms selected from the group consisting of O, N and S. Heteroaryl can include bicyclic fused ring systems, containing from 1 to 4 heteroatoms selected from the group consisting of O, N and S, wherein one ring is aromatic and one is saturated. Heteroaryl groups within the scope of this definition include but are not limited to: benzoimidazolyl, benzofuranyl, benzofurazanyl, benzopyrazolyl, benzotriazolyl, benzothiophenyl, benzoxazolyl, carbazolyl, carbolinyl, cinnolinyl, furanyl, indolinyl, indolyl, indolazinyl, indazolyl, isobenzofuranyl, isoindolyl, isoquinolyl, isothiazolyl, isoxazolyl, naphthpyridinyl, oxadiazolyl, oxazolyl, oxazoline, isoxazoline, pyranyl, pyrazinyl, pyrazolyl, pyridazinyl, pyridopyridinyl, pyridyl, pyrimidinyl, pyrrolyl, quinazolinyl, quinolyl, quinoxalinyl, tetrazolyl, tetrazolopyridyl, thiadiazolyl, thiazolyl, thienyl, triazolyl, dihydrobenzoimidazolyl, dihydrobenzofuranyl, dihydrobenzothiophenyl, dihydrobenzoxazolyl, dihydroindolyl, dihydroquinolinyl, methylenedioxybenzene, benzothiazolyl, benzothienyl, quinolinyl, isoquinolinyl, oxazolyl, tetra-hydroquinoline and 1,2,3,4-tetrahydroquinolinyl. If the heteroaryl contains nitrogen atoms, it is understood that the corresponding N-oxides thereof are also encompassed by this definition.

Except where noted, the term "heterocycle" or "heterocyclyl" as used herein is intended to mean a stable monocyclic or bicyclic 5- to 10-membered nonaromatic ring, unless otherwise specified, containing from 1 to 4 heteroatoms selected from the group consisting of O, N, S, SO, or SO₂. "Heterocyclyl" therefore includes, but is not limited to the following: azetidinyl, piperazinyl, piperidinyl, pyrrolidinyl, morpholinyl, thiomorpholinyl, tetrahydropyranyl, dihydropiperidinyl, tetrahydrothiophenyl and the like. If the heterocycle contains a nitrogen, it is understood that the corresponding N-oxides thereof are also encompassed by this definition.

Except where noted, the term "aryl" is intended to mean any stable monocyclic or bicyclic carbon ring of up to 12 atoms in each ring, wherein at least one ring is aromatic. Examples of such aryl elements include phenyl, naphthyl, tetrahydronaphthyl and indanyl.

"Celite®" (Fluka) diatomite is diatomaceous earth, and can be referred to as "celite".

Except where noted herein, structures containing substituent variables such as variable "R" below:

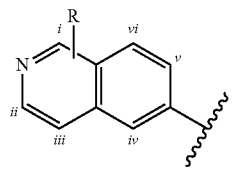

which are depicted as not being attached to any one particular bicyclic ring carbon atom, represent structures in which the variable can be optionally attached to any bicyclic ring carbon atom. For example, variable R shown in the above structure can be attached to any one of 6 bicyclic ring carbon atoms i, ii, iii, iv, v or vi.

Except where noted herein, bicyclic ring systems include fused ring systems, where two rings share two atoms, and spiro ring systems, where two rings share one atom.

The invention also includes derivatives of the compounds of Formula I, Formula Ia and Formula II, acting as prodrugs and solvates. Prodrugs, following administration to the patient, are converted in the body by normal metabolic or chemical processes, such as through hydrolysis in the blood, to the compound of Formula 1, Formula Ia or Formula II. Such prodrugs include those that demonstrate enhanced bioavailability, tissue specificity, and/or cellular delivery, to improve drug absorption of the compound of Formula I, Formula Ia or Formula II. The effect of such prodrugs may result from modification of physicochemical properties such as lipophilicity, molecular weight, charge, and other physicochemical properties that determine the permeation properties of the drug.

The preparation of pharmaceutically acceptable salts from compounds of the Formula I, Formula Ia and Formula II capable of salt formation, including their stereoisomeric forms is carried out in a manner known per se. With basic reagents such as hydroxides, carbonates, hydrogencarbonates, alkoxides and ammonia or organic bases, for example, trimethyl- or triethylamine, ethanolamine, diethanolamine or triethanolamine, trometamol or alternatively basic amino acids, for example lysine, ornithine or arginine, the compounds of the Formula I, Formula Ia and Formula II form stable alkali metal, alkaline earth metal or optionally substituted ammonium salts. If the compounds of the Formula I, Formula Ia and Formula II have basic groups, stable acid addition salts can also be prepared using strong acids. For this, inorganic and organic acids such as hydrochloric, hydrobromic, sulfuric, hemisulfuric, phosphoric, methanesulfonic, benzenesulfonic, p-toluenesulfonic, 4-bromobenzenesulfonic, cyclohexylamidosulfonic, trifluoromethylsulfonic, 2-hydroxyethanesulfonic, acetic, oxalic, tartaric, succinic, glycerolphosphoric, lactic, malic, adipic, citric, fumaric, maleic, gluconic, glucuronic, palmitic or trifluoroacetic acid are suitable.

The invention also relates to medicaments containing at least one compound of the Formula I, Formula Ia or Formula II and/or of a pharmaceutically acceptable salt of the compound of the Formula I, Formula Ia or Formula II and/or an optionally stereoisomeric form of the compound of the Formula I, Formula Ia or Formula II or a pharmaceutically acceptable salt of the stereoisomeric form of the compound of Formula I, Formula Ia or Formula II, together with a pharmaceutically suitable and pharmaceutically acceptable vehicle, additive and/or other active substances and auxiliaries.

Anticoagulant therapy is indicated for the treatment and prevention of a variety of thrombotic conditions, particularly coronary artery and cerebrovascular disease. Those experienced in this field are readily aware of the circumstances requiring anticoagulant therapy. The term "patient" used herein is taken to mean mammals such as primates, humans, sheep, horses, cattle, pigs, dogs, cats, rats, and mice.

Factor XIa or dual Factor XIa/plasma kallikrein inhibition are useful not only in the anticoagulant therapy of individuals having thrombotic conditions, but are useful whenever inhibition of blood coagulation is required such as to prevent coagulation of stored whole blood and to prevent coagulation in other biological samples for testing or storage. Thus, the Factor XIa or dual Factor XIa/plasma kallikrein inhibitors can be added to or contacted with any medium containing or suspected of containing thrombin and in which it is desired that blood coagulation be inhibited, e.g., when contacting the mammal's blood with material selected from the group consisting of vascular grafts, stents, orthopedic prosthesis, cardiac prosthesis, and extracorporeal circulation systems.

Compounds of the invention may be useful for treating or preventing venous thromboembolism (e.g., obstruction or occlusion of a vein by a detached thrombus; obstruction or occlusion of a lung artery by a detached thrombus), cardiogenic thromboembolism (e.g., obstruction or occlusion of the heart by a detached thrombus), arterial thrombosis (e.g., formation of a thrombus within an artery that may cause infarction of tissue supplied by the artery), atherosclerosis (e.g., arteriosclerosis characterized by irregularly distributed lipid deposits) in mammals, and for lowering the propensity of devices that come into contact with blood to clot blood.

Examples of venous thromboembolism which may be treated or prevented with compounds of the invention include obstruction of a vein, obstruction of a lung artery (pulmonary embolism), deep vein thrombosis, thrombosis associated with cancer and cancer chemotherapy, thrombosis inherited with thrombophilic diseases such as Protein C deficiency, Protein S deficiency, antithrombin III deficiency, and Factor V Leiden, and thrombosis resulting from acquired thrombophilic disorders such as systemic lupus erythematosus (inflammatory connective tissue disease). Also with regard to venous thromboembolism, compounds of the invention may be useful for maintaining patency of indwelling catheters.

Examples of cardiogenic thromboembolism which may be treated or prevented with compounds of the invention include thromboembolic stroke (detached thrombus causing neurological affliction related to impaired cerebral blood supply), cardiogenic thromboembolism associated with atrial fibrillation (rapid, irregular twitching of upper heart chamber muscular fibrils), cardiogenic thromboembolism associated with prosthetic heart valves such as mechanical heart valves, and cardiogenic thromboembolism associated with heart disease.

Examples of arterial thrombosis include unstable angina (severe constrictive pain in chest of coronary origin), myocardial infarction (heart muscle cell death resulting from insufficient blood supply), ischemic heart disease (local anemia due to obstruction (such as by arterial narrowing) of blood supply), reocclusion during or after percutaneous transluminal coronary angioplasty, restenosis after percutaneous transluminal coronary angioplasty, occlusion of coronary artery bypass grafts, and occlusive cerebrovascular disease. Also with regard to arterial thrombosis, compounds of the invention may be useful for maintaining patency in arteriovenous cannulas.

Examples of atherosclerosis include arteriosclerosis.

The compounds of the invention may also be kallikrein inhibitors and especially useful for treatment of hereditary angioedema.

Examples of devices that come into contact with blood include vascular grafts, stents, orthopedic prosthesis, cardiac prosthesis, and extracorporeal circulation systems.

The medicaments according to the invention can be administered by oral, inhalative, rectal or transdermal administration or by subcutaneous, intraarticular, intraperitoneal or intravenous injection. Oral administration is preferred. Coating of stents with compounds of Formula I, Formula Ia or Formula II and other surfaces which come into contact with blood in the body is possible.

The invention also relates to a process for the production of a medicament, which comprises bringing at least one compound of Formula I, Formula Ia or Formula II into a suitable administration form using a pharmaceutically suitable and pharmaceutically acceptable carrier and optionally further suitable active substances, additives or auxiliaries.

Suitable solid or galenical preparation forms are, for example, granules, powders, coated tablets, tablets, (micro) capsules, suppositories, syrups, juices, suspensions, emulsions, drops or injectable solutions and preparations having prolonged release of active substance, in whose preparation customary excipients such as vehicles, disintegrants, binders, coating agents, swelling agents, glidants or lubricants, flavorings, sweeteners and solubilizers are used. Frequently used auxiliaries which may be mentioned are magnesium carbonate, titanium dioxide, lactose, mannitol and other sugars, talc, lactose, gelatin, starch, cellulose and its derivatives, animal and plant oils such as cod liver oil, sunflower, peanut or sesame oil, polyethylene glycol and solvents such as, for example, sterile water and mono- or polyhydric alcohols such as glycerol.

The dosage regimen utilizing the Factor XIa inhibitors or dual Factor XIa/plasma kallikrein inhibitors is selected in accordance with a variety of factors including type, species, age, weight, sex and medical condition of the patient; the severity of the condition to be treated; the route of administration; the renal and hepatic function of the patient; and the particular compound or salt thereof employed. An ordinarily skilled physician or veterinarian can readily determine and prescribe the effective amount of the drug required to prevent, counter, or arrest the progress of the condition.

Oral dosages of the Factor XIa inhibitors or dual Factor XIa/plasma kallikrein inhibitors, when used for the indicated effects, will range between about 0.01 mg per kg of body weight per day (mg/kg/day) to about 30 mg/kg/day, preferably 0.025-7.5 mg/kg/day, more preferably 0.1-2.5 mg/kg/day, and most preferably 0.1-0.5 mg/kg/day (unless specified otherwise, amounts of active ingredients are on free base basis). For example, an 80 kg patient would receive between about 0.8 mg/day and 2.4 g/day, preferably 2-600 mg/day, more preferably 8-200 mg/day, and most preferably 8-40 mg/kg/day. A suitably prepared medicament for once a day administration would thus contain between 0.8 mg and 2.4 g, preferably between 2 mg and 600 mg, more preferably between 8 mg and 200 mg, and most preferably 8 mg and 40 mg, e.g., 8 mg, 10 mg, 20 mg and 40 mg. Advantageously, the Factor XIa inhibitors may be administered in divided doses of two, three, or four times daily. For administration twice a day, a suitably prepared medicament would contain between 0.4 mg and 4 g, preferably between 1 mg and 300 mg, more preferably between 4 mg and 100 mg, and most preferably 4 mg and 20 mg, e.g., 4 mg, 5 mg, 10 mg and 20 mg.

Intravenously, the patient would receive the active ingredient in quantities sufficient to deliver between 0.025-7.5 mg/kg/day, preferably 0.1-2.5 mg/kg/day, and more preferably 0.1-0.5 mg/kg/day. Such quantities may be administered in a number of suitable ways, e.g. large volumes of low concentrations of active ingredient during one extended period of time or several times a day, low volumes of high concentrations of active ingredient during a short period of time, e.g. once a day. Typically, a conventional intravenous formulation may be prepared which contains a concentration of active ingredient of between about 0.01-1.0 mg/mL, e.g. 0.1 mg/mL, 0.3 mg/mL, and 0.6 mg/mL, and administered in amounts per day of between 0.01 mL/kg patient weight and 10.0 mL/kg patient weight, e.g. 0.1 mL/kg, 0.2 mL/kg, 0.5 mL/kg. In one example, an 80 kg patient, receiving 8 mL twice a day of an intravenous formulation having a concentration of active ingredient of 0.5 mg/mL, receives 8 mg of active ingredient per day. Glucuronic acid, L-lactic acid, acetic acid, citric acid or any pharmaceutically acceptable acid/conjugate base with reasonable buffering capacity in the pH range acceptable for intravenous administration may be used as buffers. The choice of appropriate buffer and pH of a formulation, depending on solubility of the drug to be administered, is readily made by a person having ordinary skill in the art.

Compounds of the Formula I, Formula Ia and Formula II can be administered both as a monotherapy and in combination with other therapeutic agents, including antithrombotics (anticoagulants and platelet aggregation inhibitors), thrombolytics (plasminogen activators), other profibrinolytically active substances, hypotensives, blood sugar regulators, lipid-lowering agents and antiarrhythmics.

The Factor XIa inhibitors or dual Factor XIa/plasma kallikrein inhibitors can also be co-administered with suitable anticoagulants, including, but not limited to, other Factor XIa inhibitors, thrombin inhibitors, thrombin receptor antagonists, factor VIIa inhibitors, factor Xa inhibitors, factor IXa inhibitors, factor XIIa inhibitors, adenosine diphosphate antiplatelet agents (e.g., P2Y12 antagonists), fibrinogen receptor antagonists (e.g. to treat or prevent unstable angina or to prevent reocclusion after angioplasty and restenosis), other anticoagulants such as aspirin, and thrombolytic agents such as plasminogen activators or streptokinase to achieve synergistic effects in the treatment of various vascular pathologies. Such anticoagulants include, for example, apixaban, dabigatran, cangrelor, ticagrelor, vorapaxar, clopidogrel, edoxaban, mipomersen, prasugrel, rivaroxaban, and semuloparin. For example, patients suffering from coronary artery disease, and patients subjected to angioplasty procedures, would benefit from coadministration of fibrinogen receptor antagonists and thrombin inhibitors. Factor XIa inhibitors may be administered first following thrombus formation, and tissue plasminogen activator or other plasminogen activator is administered thereafter.

Alternatively or additionally, one or more additional pharmacologically active agents may be administered in combination with a compound of the invention. The additional active agent (or agents) is intended to mean a pharmaceutically active agent (or agents) that is active in the body, including pro-drugs that convert to pharmaceutically active form after administration, which is different from the compound of the invention, and also includes free-acid, free-base and pharmaceutically acceptable salts of said additional active agents when such forms are sold commercially or are otherwise chemically possible. Generally, any suitable additional active agent or agents, including but not limited to anti-hypertensive agents, additional diuretics, anti-atherosclerotic agents such as a lipid modifying compound, anti-diabetic agents and/or anti-obesity agents may be used in any combination with the compound of the invention in a single dosage formulation (a fixed dose drug combination), or may be administered to the patient in one or more separate dosage formulations which allows for concurrent or sequential administration of the active agents (co-administration of the separate active agents). Examples of additional active agents which may be employed include but are not limited to angiotensin converting enzyme inhibitors (e.g., alacepril, benazepril, captopril, ceronapril, cilazapril, delapril, enalapril, enalaprilat, fosinopril, imidapril, lisinopril, moveltipril, perindopril, quinapril, ramipril, spirapril, temocapril, or trandolapril); angiotensin II receptor antagonists also known as angiotensin receptor blockers or ARBs, which may be in free-base, free-acid, salt or pro-drug form, such as azilsartan, e.g., azilsartan medoxomil potassium (EDARBI®), candesartan, e.g., candesartan cilexetil (ATACAND®), eprosartan, e.g., eprosartan mesylate (TEVETAN®), irbesartan (AVAPRO®), losartan, e.g., losartan potassium (COZAAR®), olmesartan, e.g, olmesartan medoximil (BENICAR®), telmisartan (MICARDIS®), valsartan (DIOVAN®), and any of these drugs used in combination with a thiazide-like diuretic such as hydrochlorothiazide (e.g., HYZAAR®, DIOVAN HCT®, ATACAND HCT®), etc.); potassium sparing diuretics such as amiloride HCl, spironolactone, eplerenone, triamterene, each with or without HCTZ; neutral endopeptidase inhibitors (e.g., thiorphan and phosphoramidon); aldosterone antagonists; aldosterone synthase inhibitors; renin inhibitors; enalkrein; RO 42-5892; A 65317; CP 80794; ES 1005; ES 8891; SQ 34017; aliskiren (2(S),4(S),5(S),7(S)—N-(2-carbamoyl-2-methyl-propyl)-5-amino-4-hydroxy-2,7-diisopropyl-8-[4-methoxy-3-(3-methoxypropoxy)-phenyl]-octanamid hemifumarate) SPP600, SPP630 and SPP635); endothelin receptor antagonists; vasodilators (e.g. nitroprusside); calcium channel blockers (e.g., amlodipine, nifedipine, verapamil, diltiazem, felodipine, gallopamil, niludipine, nimodipine, nicardipine); potassium channel activators (e.g., nicorandil, pinacidil, cromakalim, minoxidil, aprilkalim, loprazolam); sympatholitics; beta-adrenergic blocking drugs (e.g., acebutolol, atenolol, betaxolol, bisoprolol, carvedilol, metoprolol, metoprolol tartate, nadolol, propranolol, sotalol, timolol); alpha adrenergic blocking drugs (e.g., doxazocin, prazocin or alpha methyldopa); central alpha adrenergic agonists; peripheral vasodilators (e.g. hydralazine); lipid lowering agents, e.g., HMG-CoA reductase inhibitors such as simvastatin and lovastatin which are marketed as ZOCOR® and MEVACOR® in lactone pro-drug form and function as inhibitors after administration, and pharmaceutically acceptable salts of dihydroxy open ring acid HMG-CoA reductase inhibitors such as atorvastatin (particularly the calcium salt sold in LIPITOR®), rosuvastatin (particularly the calcium salt sold in CRESTOR®), pravastatin (particularly the sodium salt sold in PRAVACHOL®), and fluvastatin (particularly the sodium salt sold in LESCOL®); a cholesterol absorption inhibitor such as ezetimibe (ZETIA®), and ezetimibe in combination with any other lipid lowering agents such as the HMG-CoA reductase inhibitors noted above and particularly with simvastatin (VYTORIN®) or with atorvastatin calcium; niacin in immediate-release or controlled release forms, and particularly niacin in combination with a DP antagonist such as laropiprant and/or with an HMG-CoA reductase inhibitor; niacin receptor agonists such as acipimox and acifran, as well as niacin receptor partial agonists; metabolic altering agents including insulin sensitizing agents and related compounds for the treatment of diabetes such as biguanides (e.g., metformin), meglitinides (e.g., repaglinide, nateglinide), sulfonylureas (e.g., chlorpropamide, glimepiride, glipizide, glyburide, tolazamide, tolbutamide), thiazolidinediones also referred to as glitazones (e.g., pioglitazone, rosiglitazone), alpha glucosidase inhibitors (e.g., acarbose, miglitol), dipeptidyl peptidase inhibitors, (e.g., sitagliptin (JANUVIA®), alogliptin, vildagliptin, saxagliptin, linagliptin, dutogliptin, gemigliptin), ergot alkaloids (e.g., bromocriptine), combination medications such as JANUMET® (sitagliptin with metformin), and injectable diabetes medications such as exenatide and pramlintide acetate; inhibitors of glucose uptake, such as sodium-glucose transporter (SGLT) inhibitors and its various isoforms, such as SGLT-1, SGLT-2 (e.g., ASP-1941, TS-071, BI-10773, tofogliflozin, LX-4211, canagliflozin, dapagliflozin, ertugliflozin, ipragliflozin and remogliflozin), and SGLT-3; a stimulator of soluble guanylate cyclase (sGC), such as riociguat, vericiguat; or with other drugs beneficial for the prevention or the treatment of the above-mentioned diseases including but not limited to diazoxide; and including the free-acid, free-base, and pharmaceutically acceptable salt forms, pro-drug forms, e.g., esters, and salts of pro-drugs of the above medicinal agents, where chemically possible. Trademark names of pharmaceutical drugs noted above are provided for exemplification of the marketed form of the active agent(s); such pharmaceutical drugs could be used in a separate dosage form for concurrent or sequential administration with a compound of the invention, or the active agent(s) therein could be used in a fixed dose drug combination including a compound of the invention.

Typical doses of Factor XIa inhibitors or Factor XIa/plasma kallikrein inhibitors of the invention in combination with other suitable anti-platelet agents, anticoagulation agents, or thrombolytic agents may be the same as those doses of Factor XIa inhibitors administered without coadministration of additional anti-platelet agents, anticoagulation agents, or thrombolytic agents, or may be substantially less that those doses of thrombin inhibitors administered without coadministration of additional anti-platelet agents, anticoagulation agents, or thrombolytic agents, depending on a patient's therapeutic needs.

The compounds are administered to a mammal in a therapeutically effective amount. By "therapeutically effective amount" it is meant an amount of a compound of the present invention that, when administered alone or in combination with an additional therapeutic agent to a mammal, is effective to treat (i.e. prevent, inhibit or ameliorate) the thromboembolic and/or inflammatory disease condition or treat the progression of the disease in a host.

The compounds of the invention are preferably administered alone to a mammal in a therapeutically effective amount. However, the compounds of the invention can also be administered in combination with an additional therapeutic agent, as defined below, to a mammal in a therapeutically effective amount. When administered in a combination, the combination of compounds is preferably, but not necessarily, a synergistic combination. Synergy, as described for example by Chou and Talalay, *Adv. Enzyme Regul.* 1984, 22, 27-55, occurs when the effect (in this case, inhibition of the desired target) of the compounds when administered in combination is greater than the additive effect of each of the compounds when administered individually as a single agent. In general, a synergistic effect is most clearly demonstrated at suboptimal concentrations of the compounds. Synergy can be in terms of lower cytotoxicity, increased anticoagulant effect, or some other beneficial effect of the combination compared with the individual components.

By "administered in combination" or "combination therapy" it is meant that the compound of the present invention and one or more additional therapeutic agents are administered concurrently to the mammal being treated. When administered in combination each component may be administered at the same time or sequentially in any order at different points in time. Thus, each component may be administered separately but sufficiently closely in time so as to provide the desired therapeutic effect.

The present invention is not limited in scope by the specific embodiments disclosed in the examples which are intended as illustrations of a few aspects of the invention and any embodiments that are functionally equivalent are within the scope of this invention. Indeed, various modifications of the invention in addition to those shown and described herein will become apparent to those skilled in the relevant art and are intended to fall within the scope of the appended claims.

For purposes of this specification, the following abbreviations have the indicated meanings:

LIST OF ABBREVIATIONS

ACN=acetonitrile
AcOH or HOAc=acetic acid
aq=aqueous
$BH_3DMS$=Borane dimethylsulfide
BOC=tert-butoxycarbonyl
DAST=Diethylaminosulfur trifluoride
DMF=dimethylformamide
DCM=dichloromethane
DCE=1,2-Dichloroethene
DEA=Diethylamine
DIBAL-H=Diisobutylaluminum hydride
DIEA=N,N-Diisopropylethylamine
DIPEA=N,N-Diisopropylethylamine
DMAP=N,N-dimethylaminopyridine
DMP=Dess-Martin periodinane
dppf=1,1'-Bis(diphenylphosphino)ferrocene
DMSO=Dimethyl sulfoxide
EA=ethyl acetate
EtOAc=ethyl acetate
EtOH=ethanol
h or hr=hour
Hex=Hexanes
HPLC=High Pressure Liquid Chromatography
IC=Ion Chromatography
RP HPLC=Reverse Phase High Pressure Liquid Chromatography
LCMS=Liquid chromatography-mass spectrometry
LDA=Lithium diisopropylamide
LHMDS=lithium hexamethyldisilazide
LiOH=lithium hydroxide
Me=methyl
MeOH=methanol
min=minute
MS=mass spectrometry
m-CPBA=meta-chloroperoxybenzoic acid
NBS=N-bromosuccinimide
NCS=N-chlorosuccinimide
PCC=Pyridinium chlorochromate
$PdCl_2$(dtbpf)=[1,1'-Bis(di-tert-butylphosphino)ferrocene]dichloropalladium(II)
PE=petroleum ether
p-TLC=preparative thin layer chromatography
iPrOH=isopropyl alcohol
rt or RT=room temperature
TEA=Triethylamine
THF=tetrahydrofuran
SEM=2-(trimethylsilyl)ethoxymethyl
SFC=supercritical fluid chromatography
SM=Starting material
Tetrakis=Tetrakis(triphenylphosphine)palladium(O)
THP=tetrahydropyranyl
TLC=thin layer chromatography
TFA=Trifluoroacetic acid
Vac=Vacuum
HATU=2-(1H-7-Azabenzotriazol-1-yl)-1,1,3,3-tetramethyluronium hexafluorophosphate Methanaminium Also, TLC is thin layer chromatography; Ts is tosyl; UV is ultraviolet; W is watts; wt. % is percentage by weight; ° C. is degrees Celsius; % w/v is percentage in weight of the former agent relative to the volume of the latter agent.

LCMS conditions: column: SUPELCO Ascentis Express C18 3×100 mm, 2.7 μm. Solvent system: A—0.05% TFA in water and B—0.05% TFA in Acetonitrile.

Gradient condition: 10% B to 99% B in 3.5 min.

SCHEME 1

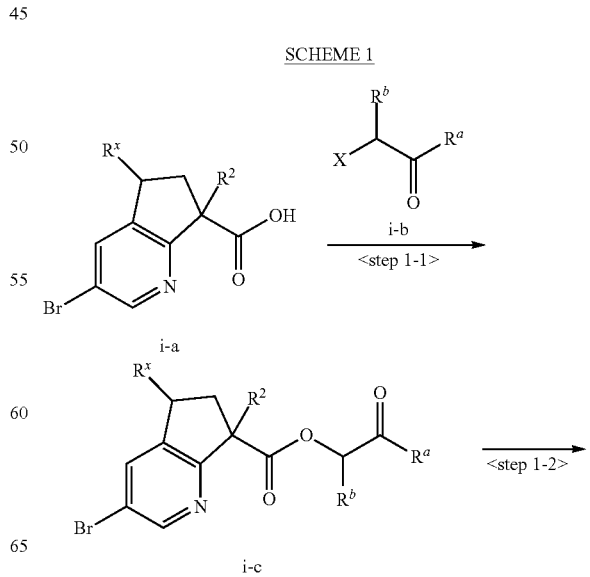

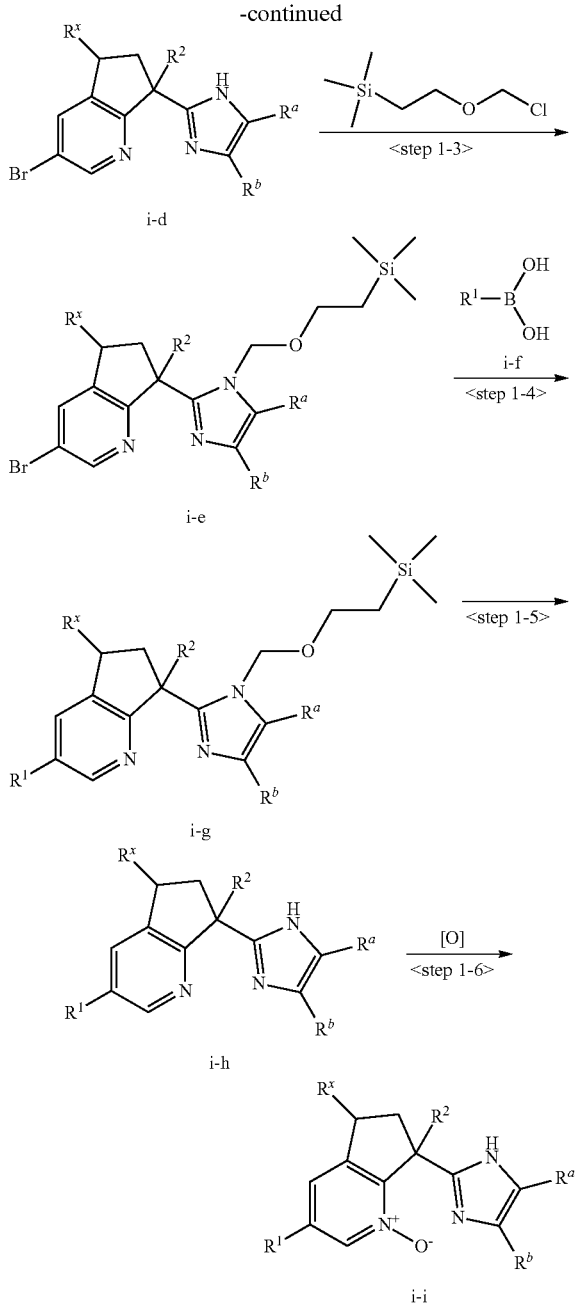

<Step 1-1>

A compound represented by formula (i-c) may be produced by allowing the intermediate 3-bromo-6,7-dihydro-5H-cyclopenta[b]pyridine-7-carboxylic acid (i-a) to react with a properly substituted α-haloketone (i-b), where X is Cl, Br, or I, following a well-known process or a process similar to that described in published documents, for example, Contour-Galcera, M.-O., Poitout, L.; Moinet, C.; Morgan, B.; Gordon, T.; Roubert, P.; Thurieau, C. Bioorganic and Medicinal Chemistry Letters, 2001, Volume 11, Issue 5, pages 741-745, in the presence of a base such as potassium carbonate, sodium carbonate, cesium carbonate, triethylamine, or DIEA in a solvent such as N,N-dimethylformamide, ethanol, methanol, water, or mixtures thereof, at a temperature between rt and 60° C.

<Step 1-2>

A compound represented by formula (i-d) may be produced by allowing a compound of formula (i-c) to react with ammonium acetate using a process similar to that described in published documents, for example, Contour-Galcera, M.-O., Poitout, L.; Moinet, C.; Morgan, B.; Gordon, T.; Roubert, P.; Thurieau, C. Bioorganic and Medicinal Chemistry Letters, 2001, Volume 11, Issue 5, pages 741-745. This process may occur in an inert solvent such as toluene, xylenes, or acetic acid, or mixtures thereof, at temperatures ranging from 110° C. and 150° C. The reaction can proceed using conventional heating or microwave irradiation.

<Step 1-3>

A compound represented by formula (i-e) may be produced by allowing a compound of formula (i-d) to react with 2-(trimethylsilyl)ethoxymethyl chloride following a well-known process which is described in published documents, for example, Whitten, J. P.; Matthews, D. P.; McCarthy, J. R. Journal of Organic Chemistry, 1986, Volume 51, pages 1891-1894. The reaction may occur in the presence of a base such as sodium hydride, DIEA, or potassium carbonate, and in an inert solvent such as DMF or dichloromethane. The reaction may occur at temperatures between 0° C. and 80° over several hours.

<Step 1-4>

A compound represented by formula (i-g) can be produced by a method commonly referred to as the Suzuki coupling reaction. Compounds of type (i-e) can be treated with an aryl boronic acid represented by formula (i-f), or alternatively, an aryl boronate ester, in the presence of a suitable palladium catalyst, such as $PdCl_2(dppf)$, or tetrakis, or the like, and a mild base, such as sodium carbonate, sodium phosphate tribasic, cesium fluoride, or the like (Miyaura, Norio; Suzuki, Akira Chemical Reviews, 1996, Volume 96, pages 2457-2483). The reaction is usually performed in a suitable degassed inert organic solvent, such as toluene or dioxane, at elevated temperatures, generally between 70° C. and the reflux temperature of the solvent mixture, for a period of 3-24 hours. Water may be added as a co-solvent to the reaction. Alternatively, those skilled in the art can perform the Suzuki reaction described above in a suitable vessel that enables heating in a microwave reactor to superheated reaction temperatures that can reduce reaction times to between 1 minute and 1 hour. Recently, conditions suitable for performing Suzuki coupling reactions at rt have been published (for example, see: Kinzel, Tom; Zhang, Yong; Buchwald, Stephen L. Journal of the American Chemical Society, 2010, Volume 132, pages 14073-14075, and references therein).

<Step 1-5>

A compound represented by formula (i-h) can be obtained following a procedures which are described in published documents, for example, Whitten, J. P.; Matthews, D. P.; McCarthy, J. R. Journal of Organic Chemistry, 1986, Volume 51, pages 1891-1894. The reaction can occur by treating a solution of compound (i-g) with an excess of an acid such as trifluoroacetic acid or hydrochloric acid. The reaction can be performed in a suitable solvent such as THF, dichloromethane, or ethanol at rt for one hour to several hours.

<Step 1-6>

A compound represented by formula (i-i) can be obtained by allowing the suitably substituted pyridine of formula (i-h) to react with an oxidizing reagent such as hydrogen peroxide, meta-chloroperbenzoic acid, oxone, dimethyldioxirane, or peracetic acid in a proper solvent including water, methylene chloride and acetic acid. The reaction is usually performed at a temperature between 0° C. to 70° C. in a time period ranging from a few minutes to a few days. In some cases, the use of a suitable catalyst, such as methylrhenium trioxide, may facilitate the oxidation reaction. Such a process or processes are similar to that are described in published documents (For example, see, Deng, Lisheng; Sundriyal, Sandeep; Rubio, Valentina; Shi, Zheng-zheng; Song, Yongcheng, Journal of Medicinal Chemistry, 2009, Volume 52(21), pages 6539-6542). For some example compounds in which $R^2$ is hydrogen, over-oxidation may occur during this step, giving a mixture of products of type i-I in which $R^2$ is either hydrogen or —OH.

SCHEME 2

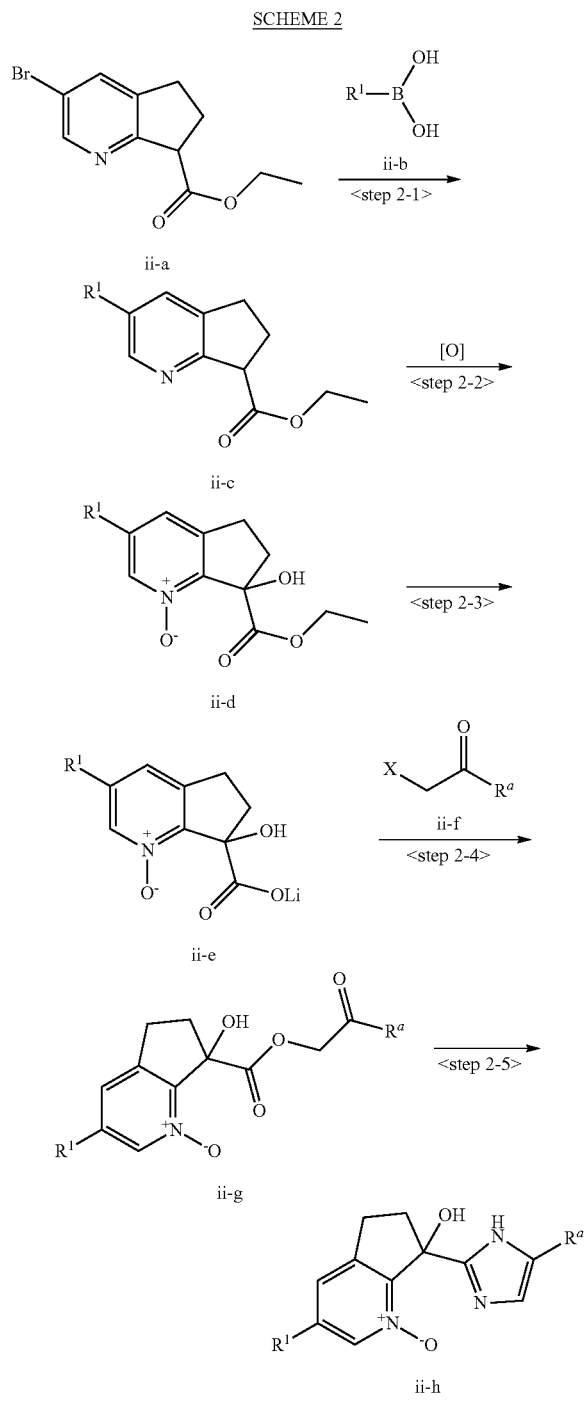

<Step 2-1>

A compound of formula (ii-c) can be obtained from intermediate (ii-a) by a method commonly referred to as the Suzuki coupling reaction. Compounds of type (ii-a) can be treated with an aryl boronic acid represented by formula (ii-b), or alternatively, an aryl boronate ester of formula $R^1$—$B(OR)_2$, in the presence of a suitable palladium catalyst, such as $PdCl_2(dppf)$ or Tetrakis, or the like, and a mild base, such as sodium carbonate, potassium carbonate, sodium phosphate tribasic, cesium fluoride, or the like (Miyaura, Norio; Suzuki, Akira Chemical Reviews, 1996, Volume 96, pages 2457-2483). The reaction is usually performed in a suitable degassed inert organic solvent, such as toluene or dioxane, at elevated temperatures, generally between 70° C. and the reflux temperature of the solvent mixture, for a period of 3-24 hours. Water may be added as a co-solvent to the reaction. Alternatively, the Suzuki reaction described above may be performed in a suitable vessel that enables heating in a microwave reactor to superheated reaction temperatures that can reduce reaction times to between 1 minute and 1 hour. Conditions suitable for performing Suzuki coupling reactions at rt have been published (for example, see: Kinzel, Tom; Zhang, Yong; Buchwald, Stephen L. Journal of the American Chemical Society, 2010, Volume 132, pages 14073-14075, and references therein).

<Step 2-2>

A compound represented by formula (ii-d) can be obtained by allowing the suitably substituted pyridine of formula (ii-c) to react with an oxidizing reagent such as hydrogen peroxide, meta-chloroperbenzoic acid, oxone, dimethyldioxirane, or peracetic acid in a proper solvent including water, methylene chloride and acetic acid. The reaction is usually performed at a temperature between 0° C. to 70° C. in a time period ranging from a few minutes to a few days. In some cases, the use of a suitable catalyst, such as methylrhenium trioxide, may facilitate the oxidation reaction. Such a process or processes are similar to that are described in published documents (For example, see, Deng, Lisheng; Sundriyal, Sandeep; Rubio, Valentina; Shi, Zhengzheng; Song, Yongcheng, Journal of Medicinal Chemistry, 2009, Volume 52(21), pages 6539-6542).

<Step 2-3>

A compound of type (ii-e) can be obtained from intermediate (ii-d) using a process which is well known to one skilled in the art. For example, this transformation may occur in the presence of lithium hydroxide in a suitable solvent such as THF or ethanol in the presence or absence of water. The reaction may occur at temperatures ranging from 0° C. to the solvent reflux temperature over reaction times ranging from several minutes to several hours.

<Step 2-4>

A compound of type (ii-g) may be produced by allowing the intermediate (ii-e) to react with a properly substituted α-haloketone (ii-f), where X is Cl, Br, or I, following a well-known process or a process similar to that described in published documents, for example, Contour-Galcera, M.-O., Poitout, L.; Moinet, C.; Morgan, B.; Gordon, T.; Roubert, P.; Thurieau, C. Bioorganic and Medicinal Chemistry Letters, 2001, Volume 11, Issue 5, pages 741-745, in the presence of a base such as potassium carbonate, sodium carbonate, cesium carbonate, triethylamine, or DIEA in a solvent such as DMF at a temperature between rt and 60° C.

<Step 2-5>

A compound represented by formula (ii-h) may be produced by allowing a compound of formula (ii-g) to react with ammonium acetate using a process similar to that described in published documents, for example, Contour-Galcera, M.-O., Poitout, L.; Moinet, C.; Morgan, B.; Gordon, T.; Roubert, P.; Thurieau, C. Bioorganic and Medicinal Chemistry Letters, 2001, Volume 11, Issue 5, pages 741-745. This process may occur in an inert solvent such as toluene, xylenes, or acetic acid, or mixtures thereof, at temperatures ranging from 110° C. and 150° C. The reaction can proceed using conventional heating or microwave irradiation.

SCHEME 3

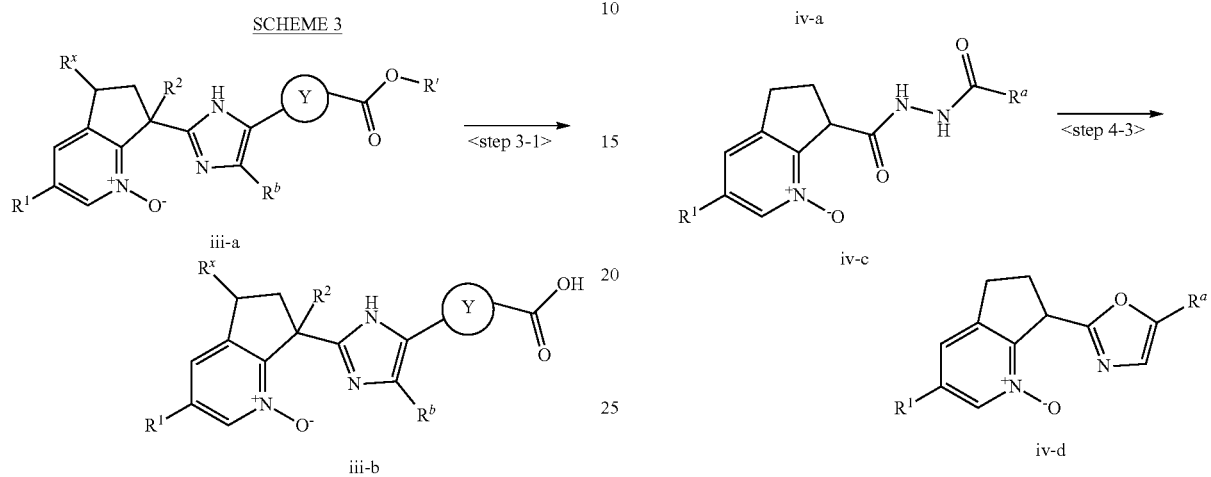

iii-a iii-b

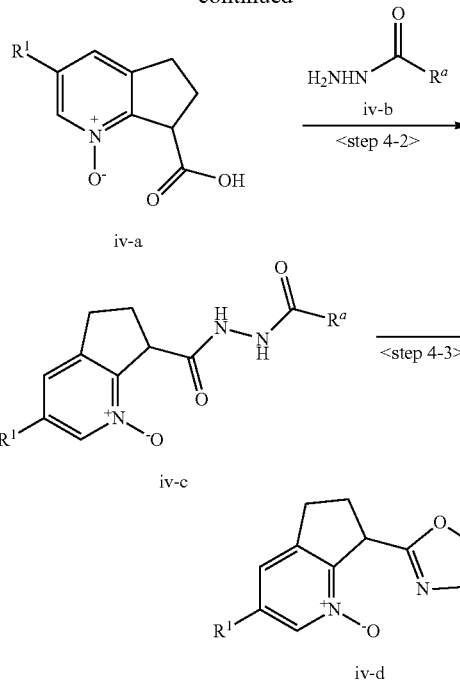

iv-a iv-c iv-d

<Step 3-1>

In the specific case where a compound of the invention of type (iii-b) contains a carboxylic acid appended to Y, an additional step may be required as illustrated in Scheme 3. The penultimate alkyl ester intermediate (iii-a) can be converted to the corresponding carboxylic acid following a well-known process or a process similar to that described in published documents, for example, Greene, T. W., et. al., *Protective Groups in Organic Synthesis* (2007), 4th Ed. In some cases, this transformation may occur in the presence of an acid such as trifluoroacetic acid, formic acid, hydrochloric acid, or acetic acid in a solvent which is inactive to the reaction, such as a halogenated solvent, e.g., dichloromethane or chloroform, or an ethereal solvent, e.g., dioxane or tetrahydrofuran, at a temperature in the range of 0° C. to the solvent reflux temperature. In other cases, this process may occur in the presence of a base such as sodium hydroxide, potassium hydroxide, or lithium hydroxide in a solvent such as tetrahydrofuran, ethanol, or methanol, at a temperature in the range of 0° C. to the solvent reflux temperature.

The general reaction schemes as described above can generate compounds of formula (i-i), (ii-i) and (iii-b) as a racemic mixtures or mixtures of several stereoisomers. A compound of formula (i-i), (ii-i) or (iii-b) can be obtained as a single stereoisomer using a chiral resolution process such as chiral preparatory HPLC or chiral SFC.

SCHEME 4

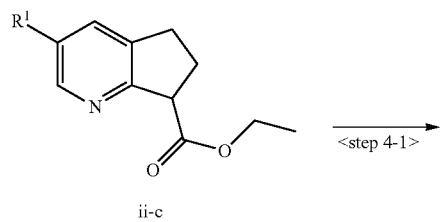

ii-c

<Step 4-1>

A compound of type (iv-a) can be obtained from intermediate (ii-c) using a process as described in step 2-3.

<Step 4-2>

A compound represented by formula (iv-c) may be produced by allowing the intermediate (iv-a) to react with a properly substituted acyl hydrazide (iv-b) by a well-known process or a process similar to that described in published documents, for example, Organic synthesis IV, Acids, amino acids, and peptides, pp. 191-309, 1992, Maruzen Co., Ltd., in the presence of a condensing agent such as 1,3-dicyclohexylcarbodiimide (DCC), 1-ethyl-3-(3'-dimethylaminopropyl)carbodiimide hydrochloride (WSC.HCl or EDC HCl), O-(7-azabenzotriazol-1-yl)-N,N,N',N'-tetramethyluronium hexafluorophosphate (HATU), benzotriazol-1-yloxy tris(dimethylamino)-phosphonium hexafluorophosphate (BOP reagent), or bis(2-oxo-3-oxazolidinyl)phosphinic chloride (BOP-Cl), in a solvent which is inactive to the reaction, such as a halogenated solvent, e.g., dichloromethane or chloroform, an ethereal solvent, e.g., diethyl ether or tetrahydrofuran, an aromatic hydrocarbon solvent, e.g., toluene or benzene, a polar solvent, e.g., N,N-dimethylformamide, or an alcoholic solvent, e.g., methanol, ethanol, or 2-propanol, in the presence or absence of a base such as triethylamine or DIEA at a temperature in the range of 0° C. to the solvent reflux temperature.

<Step 4-3>

A compound represented by formula (iv-d) may be produced by allowing a compound of formula (iv-c) to react with a dehydrating reagent, such as phosphorous oxychloride or the Burgess Reagent or the like, using a process similar to that described in published documents, for example, Brain, Christopher, et al. *Tetrahedron Lett.* 1999, 40, 3275. This process may occur in an inert solvent such as THF, 1,4-dioxane, toluene, or mixtures thereof, at elevated temperatures, specifically the boiling temperature of the solvent. The reaction can proceed using conventional heating or microwave irradiation.

INTERMEDIATES

Ethyl 3-bromo-6,7-dihydro-5H-cyclopenta[b]pyridine-7-carboxylate

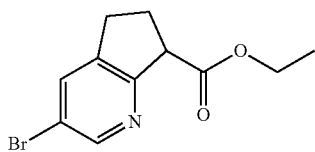

To as −78° C. solution of 3-bromo-6,7-dihydro-5H-cyclopenta[b]pyridine (4.95 g, 25.0 mmol) in THF (250 mL) was added a 1 M THF solution of LHMDS (62.5 mL, 62.5 mmol) dropwise via a syringe over 15 min. The resulting mixture was stirred at −78° C. for 65 min, then diethyl carbonate was added dropwise via a syringe at −78° C. The low temperature bath was removed and the reaction mixture stirred with warming to rt overnight. The reaction was quenched by addition of a saturated aq. solution of NH$_4$Cl (60 mL). The mixture was partitioned between brine (300 mL) and EtOAc (300 mL). The organic layer was dried over MgSO$_4$, filtered and concentrated in vacuo. The product was purified by silica gel chromatography (0-30% EtOAc in hexanes) to yield the product ethyl 3-bromo-6,7-dihydro-5H-cyclopenta[b]pyridine-7-carboxylate. MS (ESI) m/z 270.56 (M+H).

Ethyl 3-bromo-7-methyl-6,7-dihydro-5H-cyclopenta[b]pyridine-7-carboxylate

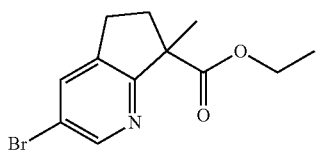 [SMILES: CCOC(=O)C1(C)CCc2cc(Br)cnc21]

To a stirred, cooled (−78° C.) solution of ethyl 3-bromo-6,7-dihydro-5H-cyclopenta[b]pyridine-7-carboxylate (described above, 500 mg, 1.85 mmol) in THF (10 mL) under an atmosphere of nitrogen was added a solution of LDA in THF (2.22 mL, 2.22 mmol) in 0.5 mL of anhydrous THF. The reaction mixture was allowed to stir for 10 min then warmed to 0° C. over 30 min. The mixture was then cooled to −78° C. and a solution of methyl iodide (0.116 mL, 1.85 mmol) in 0.1 mL THF was added. The resulting mixture was allowed to warm to ambient temperature and was stirred for 2 h. LCMS showed desired product. The reaction was quenched with 1 mL of a saturated ammonium chloride solution and extracted with EtOAc. The organic layer was then separated and concentrated. The residue was purified by column chromatography on silica gel, eluting with EtOAc/hexane (0-20%) to give the desired product. MS (ESI) m/z 285.14 (M+H).

ethyl 3-bromo-7-hydroxy-6,7-dihydro-5H-cyclopenta[b]pyridine-7-carboxylate ethyl (R)-3-bromo-7-hydroxy-6,7-dihydro-5H-cyclopenta[b]pyridine-7-carboxylate ethyl (S)-3-bromo-7-hydroxy-6,7-dihydro-5H-cyclopenta[b]pyridine-7-carboxylate

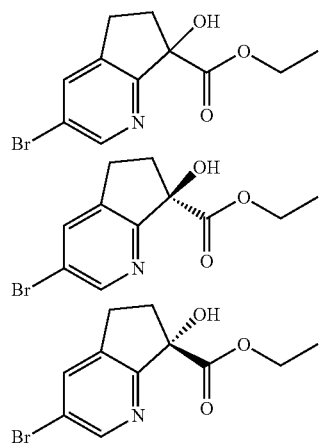

Ethyl 3-bromo-6,7-dihydro-5H-cyclopenta[b]pyridine-7-carboxylate (10 g, 35 mmol) in DMSO (100 mL) was mixed with cesium carbonate (2.3 g, 7 mmol). Dry air was bubbling through the reaction mixture while stirring. The temperature was maintained below 30° C. with cooling. After 4 hours, the mixture was diluted with cool water (300 mL) and brine (100 mL). Product was extracted with ethyl acetate (200 mL). The organic layer was separated, dried over MgSO$_4$, and then concentrated. The crude was crystallized from heptane to give ethyl 3-bromo-7-hydroxy-6,7-dihydro-5H-cyclopenta[b]pyridine-7-carboxylate as a solid. MS (ESI) m/z 288.07 (M+H). The racemic product was separated by SFC on an IA column, eluting with 20% EtOH (0.2% NH$_4$OH)/CO$_2$, to give ethyl (R)-3-bromo-7-hydroxy-6,7-dihydro-5H-cyclopenta[b]pyridine-7-carboxylate (fast eluting enantiomer), MS (ESI) m/z 288.07 (M+H), and ethyl (S)-3-bromo-7-hydroxy-6,7-dihydro-5H-cyclopenta[b]pyridine-7-carboxylate, (slow eluting enantiomer), MS (ESI) m/z 288.07 (M+H). The absolute configurations of both enantiomers were assigned using Vibrational Circular Dichroism (VCD) spectroscopy.

3-bromo-7-(ethoxycarbonyl)-7-hydroxy-6,7-dihydro-5H-cyclopenta[b]pyridine-1-oxide

(R)-3-bromo-7-(ethoxycarbonyl)-7-hydroxy-6,7-dihydro-5H-cyclopenta[b]pyridine-1-oxide

(S)-3-bromo-7-(ethoxycarbonyl)-7-hydroxy-6,7-dihydro-5H-cyclopenta[b]pyridine-1-oxide

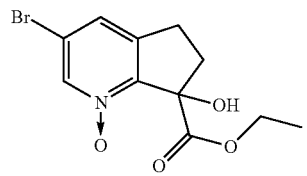

-continued

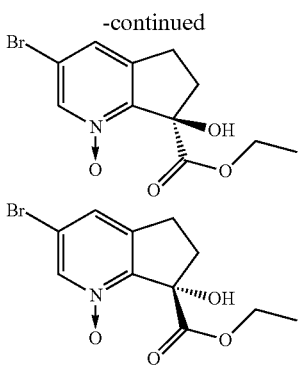

A mixture of ethyl 3-bromo-6,7-dihydro-5H-cyclopenta[b]pyridine-7-carboxylate (3 g, 11.11 mmol), methyl trioxorhenium(VII) (500 mg, 2.01 mmol) and hydrogen peroxide (50 mL, 571 mmol) in DCM (50 mL) was stirred at 25° C. for 4 days, then at 50° C. for 24 hours. LCMS showed the reaction was complete. The mixture was poured into aq. sat. sodium sulfite (500 mL) dropwise at 25° C. and extracted with DCM (200 mL). The organic layer was dried over $Na_2SO_4$, filtered and concentrated in vacuo. The residue was purified by chromatography on silica gel (100~200 mesh) (24 g) (pet. Ether:EtOAc=50:50) to give the title compound. MS (ESI) m/z 301.9 (M+H). The racemic product was separated by SFC on an AD column, to give (R)-enantiomer (fast eluting) and (S)-enantiomer (slow eluting) based on FXIa activity of the final products in comparison with compounds of known stereochemistry, both MS (ESI) m/z 301.9 (M+H).

Lithium 3-bromo-6,7-dihydro-5H-cyclopenta[b]pyridine-7-carboxylate

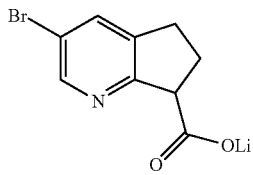

To a solution of ethyl 3-bromo-6,7-dihydro-5H-cyclopenta[b]pyridine-7-carboxylate (5 g, 18.51 mmol) in MeOH (30 mL) and water (6 mL) was added lithium hydroxide hydrate (0.49 g, 20.36 mmol) and the mixture was stirred at 50° C. for 30 min. LCMS showed the reaction was complete. The mixture was then concentrated to give the title compound which was used directly for next step without further purification. MS (ESI) m/z 241.9 (M+H).

3-(2-((tert-butoxycarbonyl)amino)-5-chlorophenyl)-7-carboxy-7-hydroxy-6,7-dihydro-5H-cyclopenta[b]pyridine-1-oxide

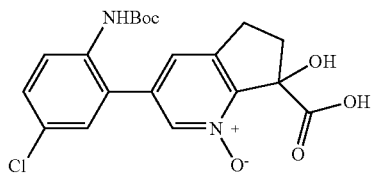

Step 1: 4-chloro-2-(4,4,5,5-tetramethyl-1,3,2-dioxaborolan-2-yl)aniline

To a solution of 2-bromo-4-chloroaniline (2.06 g, 9.98 mmol), $Pd(PPh_3)_2Cl_2$ (0.20 g, 0.285 mmol) and TEA (5.60 mL, 40.2 mmol) in dioxane (100 mL) was added 4,4,5,5-tetramethyl-1,3,2-dioxaborolane (4.33 mL, 29.90 mmol) and stirred at 120° C. for 16 hours under $N_2$. LCMS showed the reaction was complete. The mixture was poured into aq. sat. $NH_4Cl$ (100 mL) and extracted with DCM (200 mL). The organic layer was dried over $Na_2SO_4$, concentrated in vacuo and purified by chromatography on silica gel (100~200 mesh) (24 g) (pet. Ether:EtOAc=95:5) to give the title compound. MS (ESI) m/z 254.1 (M+H).

Step 2: ethyl 3-(2-amino-5-chlorophenyl)-6,7-dihydro-5H-cyclopenta[b]pyridine-7-carboxylate A mixture of 4-chloro-2-(4,4,5,5-tetramethyl-1,3,2-dioxaborolan-2-yl)aniline (12.20 g, 48.1 mmol), ethyl 3-bromo-6,7-dihydro-5H-cyclopenta[b]pyridine-7-carboxylate (10 g, 37.00 mmol), potassium carbonate (15.35 g, 111 mmol) and $PdCl_2(dppf)$ (500 mg, 0.683 mmol) in dioxane (150 mL) and water (30 mL) was stirred at 100° C. for 16 hours. LCMS showed the reaction was complete and the reaction was extracted with DCM (1 L) and washed with water (300 mL). The organic layer was dried over $Na_2SO_4$, filtrated and the filtrate was concentrated in vacuo. The residue was purified by chromatography on silica gel (120 g) (100~200 mesh) (petroleum ether:EtOAc=70:30 to 20:80) to give the title compound. MS (ESI) m/z 316.9 (M+H).

Step 3: ethyl 3-(2-((di-tert-butoxycarbonyl)amino)-5-chlorophenyl)-6,7-dihydro-5H-cyclopenta[b]pyridine-7-carboxylate A solution of di-tert-butyl dicarbonate (31.90 mL, 137 mmol), ethyl 3-(2-amino-5-chlorophenyl)-6,7-dihydro-5H-cyclopenta[b]pyridine-7-carboxylate (12 g, 37.90 mmol), DMAP (100 mg, 0.82 mmol) and DIEA (30 mL, 172 mmol) in THF (150 mL) was stirred at 50° C. for 16 hours. LCMS and TLC showed the reaction was complete. The mixture was concentrated in vacuo and purified by chromatography on silica gel (100~200 mesh) (120 g) (petroleum ether:EtOAc=80:20 to 50:50) to give the title compound. MS (ESI) m/z 517.3 (M+H).

Step 4: 3-(2-((di-tert-butoxycarbonyl)amino)-5-chlorophenyl)-7-(ethoxycarbonyl)-7-hydroxy-6,7-dihydro-5H-cyclopenta[b]pyridine-1-oxide To a solution of ethyl 3-(2-((di-tert-butoxycarbonyl)amino)-5-chlorophenyl)-6,7-dihydro-5H-cyclopenta[b]pyridine-7-carboxylate (15 g, 29.00 mmol) and methyl trioxorhenium(VII) (1 g, 4.01 mmol) in DCM (150 mL) was added $H_2O_2$ (50 mL, 489 mmol) and stirred at 25° C. for 4 days. LCMS showed the reaction was complete. To the mixture was added sodium sulfite (solid) to quench excess $H_2O_2$. The organic layer was dried over $Na_2SO_4$, filtered and concentrated in vacuo. The residue was purified by chromatography on silica gel (100~200 mesh) (120 g) (petroleum ether:EtOAc=70:30) to give the title compound. MS (ESI) m/z 549.2 (M+H).

Step 5: 3-(2-((tert-butoxycarbonyl)amino)-5-chlorophenyl)-7-carboxy-7-hydroxy-6,7-dihydro-5H-cyclopenta[b]pyridine-1-oxide To a mixture of 3-(2-((di-tert-butoxycarbonyl)amino)-5-chlorophenyl)-7-(ethoxycarbonyl)-7-hydroxy-6,7-dihydro- 5H-cyclopenta[b]pyridine-1-oxide (10.20 g, 18.58 mmol) in MeOH (30 mL) and water (90 mL) was added lithium hydroxide hydrate (4 g, 167 mmol) and stirred at 50° C. for 16 hours. LCMS showed the reaction was complete. The mixture was adjusted to pH 2 with the addition of 1N HCl, extracted with EtOAc (1 L), dried over Na$_2$SO$_4$, filtered and concentrated in vacuo. To the residue was added EtOAc (50 mL), then it was stirred and filtered. The solid was collected and washed with EtOAc (20 mL) to give the title compound. MS (ESI) m/z 421.0 (M+H).

$^1$HNMR (DMSO-d$_6$ 400 MHz): δ 13.10 (br s, 1H), 8.90 (br s, 1H), 8.07 (s, 1H), 7.42-7.51 (m, 2H), 7.32-7.39 (m, 1H), 7.29 (s, 1H), 5.71 (br s, 1H), 3.03-3.17 (m, 1H), 2.89-3.02 (m, 1H), 2.50-2.60 (m, 1H), 2.16-2.30 (m, 1H), 1.20-1.40 (m, 9H).

3-(2-((tert-Butoxycarbonyl)amino)-5-chlorophenyl)-7-carboxy-7-methoxy-6,7-dihydro-5H-cyclopenta[b]pyridine-1-oxide

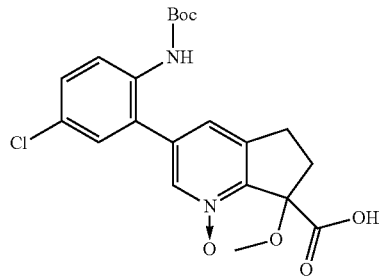 [SMILES: COC1(C(=O)O)CCc2cc(-c3cc(Cl)ccc3NC(=O)OC(C)(C)C)c[n+]([O-])c21]

Step 1: 3-(2-((di-tert-butoxycarbonyl)amino)-5-chlorophenyl)-7-(ethoxycarbonyl)-7-methoxy-6,7-dihydro-5H-cyclopenta[b]pyridine-1-oxide To a solution of 3-(2-((di-tert-butoxycarbonyl)amino)-5-chlorophenyl)-7-(ethoxycarbonyl)-7-hydroxy-6,7-dihydro-5H-cyclopenta[b]pyridine-1-oxide (1.10 g, 2.00 mmol) and cesium carbonate (1.30 g, 3.99 mmol) in DMF (12 mL) was added iodomethane (4.27 g, 30.10 mmol). After addition, the mixture was stirred at 25° C. for 16 h. TLC showed SM was consumed. The mixture was diluted with water (50 mL) and extracted with EtOAc (50 mL×3). The combined organic phases were washed with water (100 mL×3) and brine (100 mL), dried over Na$_2$SO$_4$, filtered and concentrated. The residue was purified by chromatography on silica gel (EtOAc:PE=25:75) to give the title compound. MS (ESI) m/z 563.2 (M+H).

Step 2: 3-(2-((tert-butoxycarbonyl)amino)-5-chlorophenyl)-7-carboxy-7-methoxy-6,7-dihydro-5H-cyclopenta[b]pyridine-1-oxide To a solution of 3-(2-((di-tert-butoxycarbonyl)amino)-5-chlorophenyl)-7-(ethoxycarbonyl)-7-methoxy-6,7-dihydro-5H-cyclopenta[b]pyridine-1-oxide (710 mg, 1.26 mmol) in MeOH (10 mL) and water (3 mL) was added lithium hydroxide hydrate (302 mg, 12.61 mmol). After addition, the mixture was stirred at 50° C. for 16 h. LCMS showed the reaction was complete. The mixture was concentrated, diluted with EtOAc (15 mL) and adjusted with aqueous HCl (1 M) to pH~5-6. The organic phase was separated, dried over Na$_2$SO$_4$, filtered and concentrated to give the title compound which was used for the next step without further purification. MS (ESI) m/z 435.0 (M+H).

$^1$HNMR (MeOH-d$_4$, 400 MHz): δ 8.16 (s, 1H), 7.52 (s, 1H), 7.46-7.42 (m, 3H), 3.38 (s, 3H), 3.27-3.25 (m, 1H), 3.13-3.11 (m, 1H), 2.68-2.64 (m, 1H), 2.49-2.47 (m, 1H), 1.35 (s, 9H).

Lithium 3-(5-chloro-2-(oxazol-5-yl)phenyl)-7-hydroxy-1-oxido-6,7-dihydro-5H-cyclopenta[b]pyridine-7-carboxylate

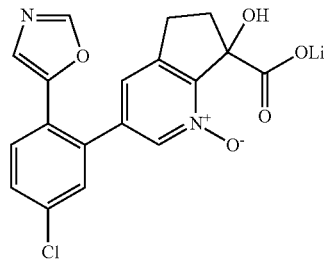

Step 1: 2-bromo-4-chloro-N-methoxy-N-methylbenzamide

To a round bottom flask was added 2-bromo-4-chlorobenzoic acid (10 g, 42.50 mmol), DCM (150 mL), HATU (19.38 g, 51.00 mmol), N,O-dimethylhydroxylamine hydrogen chloride (12.43 g, 127 mmol) and triethylamine (29.60 mL, 212 mmol). The reaction mixture was stirred for 18 h at 15° C. LCMS showed the reaction was complete. The mixture was quenched with water (200 mL) and extracted with DCM (100 mL×3). The combined organic layers were dried over Na$_2$SO$_4$, filtered and concentrated in vacuo. The residue was purified by chromatography on silica gel (PE:EtOAc=10:1) to give the title compound. MS (ESI) m/z 280.1 (M+H).

Step 2: 2-bromo-4-chlorobenzaldehyde

To a round bottom flask was added 2-bromo-4-chloro-N-methoxy-N-methylbenzamide (11 g, 39.50 mmol), THF (150 mL) and DIBAL-H (71.1 mL, 71.1 mmol) dropwise at −78° C. The reaction mixture was stirred for 1 h at −78° C. TLC (SiO$_2$, PE:EtOAc=5:1) showed starting material disappeared and a new spot formed. The mixture was quenched with sat. potassium sodium tartrate solution (300 mL), then EtOAc (200 mL) was added. The mixture was stirred for 20 min and filtered and extracted with EtOAc (200 mL×3). The combined organic layers were dried over Na$_2$SO$_4$, filtered and concentrated in vacuo to give the title compound which was directly used for next step without further purification.

Step 3: 5-(2-bromo-4-chlorophenyl)oxazole

To a round bottom flask was added 2-bromo-4-chlorobenzaldehyde (8 g, 36.5 mmol), MeOH (200 mL), 1-((isocyanomethyl)sulfonyl)-4-methylbenzene (10.68 g, 54.70 mmol) and potassium carbonate (15.11 g, 109 mmol). The mixture was stirred for 3 h at 70° C. LCMS showed the reaction was complete. The mixture was concentrated in vacuo then added water (200 mL) and extracted with EtOAc (150 mL×3). The combined organic extracts were dried over Na$_2$SO$_4$, filtered and concentrated in vacuo. The residue was purified by normal phase chromatography (SiO$_2$, 0-10% EtOAc/PE, 50 min, dry loaded) to give the title compound. MS (ESI) m/z 260.1 (M+H).

Step 4: 5-(4-chloro-2-(4,4,5,5-tetramethyl-1,3,2-dioxaborolan-2-yl)phenyl)-oxazole To a round bottom flask was added 5-(2-bromo-4-chlorophenyl)oxazole (5.5 g, 21.28 mmol), potassium acetate (5.22 g, 53.20 mmol), 4,4,4',4',5,5,5',5'-octamethyl-2,2'-bi (1,3,2-dioxaborolane) (5.40 g, 21.28 mmol), dioxane (75 mL) and PdCl$_2$(dppf) (1.56 g, 2.13 mmol) at 100° C. The reaction mixture was stirred for 18 h at 100° C. LCMS showed reaction was complete. The mixture was filtered and the filtrate was concentrated in vacuo. The residue was purified by normal phase chromatography (SiO$_2$, 0-15% EtOAc/PE, 40 min, dry loaded) to give the title compound. MS (ESI) m/z 306.2 (M+H).

Step 5: 3-(5-chloro-2-(oxazol-5-yl)phenyl)-7-(ethoxycarbonyl)-7-hydroxy-6,7-dihydro-5H-cyclopenta[b]pyridine-1-oxide To a round bottom flask were added 5-(4-chloro-2-(4,4,5,5-tetramethyl-1,3,2-dioxaborolan-2-yl)phenyl)oxazole (900 mg, 2.95 mmol), 3-bromo-7-(ethoxycarbonyl)-7-hydroxy-6,7-dihydro-5H-cyclopenta[b]pyridine-1-oxide (890 mg, 2.95 mmol), potassium phosphate tribasic (1876 mg, 8.84 mmol), THF (20 mL), water (3 mL) and PdCl$_2$(dtbpf) (192 mg, 0.30 mmol). The reaction mixture was stirred for 18 h at 100° C. LCMS showed the reaction was complete. The mixture was filtered and the filtrate was concentrated in vacuo and the residue was purified by normal phase chromatography (SiO$_2$, 0-5% MeOH/EtOAc, dry loaded) to give the title compound. MS (ESI) m/z 401. (M+H).

Step 6: lithium 3-(5-chloro-2-(oxazol-5-yl)phenyl)-7-hydroxy-1-oxido-6,7-dihydro-5H-cyclopenta[b]pyridine-7-carboxylate To a round bottom flask was added 3-(5-chloro-2-(oxazol-5-yl)phenyl)-7-(ethoxycarbonyl)-7-hydroxy-6,7-dihydro-5H-cyclopenta[b]pyridine-1-oxide (910 mg, 2.27 mmol), MeOH (20 mL), water (4 mL) and lithium hydroxide hydrate (95 mg, 2.270 mmol). The reaction mixture was stirred for 3 h at 50° C. LCMS showed the reaction was complete. The mixture was concentrated in vacuo to give the title compound which was directly used for next step without further purification. MS (ESI) m/z 373.1 (M+H). $^1$HNMR (MeOH-d$_4$, 400 MHz): δ 8.16 (s, 1H), 7.97 (s, 1H), 7.79 (d, J=8.4 Hz, 1H), 7.59 (dd, J=8.4, 1.9 Hz, 1H), 7.50 (d, J=1.8 Hz, 1H), 7.34 (s, 1H), 6.96 (s, 1H), 3.09-3.17 (m, 2H), 2.66-2.73 (m, 1H), 2.22-2.29 (m, 1H).

Lithium 3-(5-chloro-2-cyanophenyl)-7-hydroxy-1-oxido-6,7-dihydro-5H-cyclopenta[b]pyridine-7-carboxylate

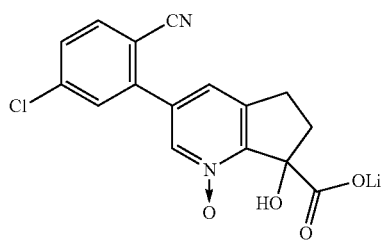

Step 1: 3-(5-chloro-2-cyanophenyl)-7-(ethoxycarbonyl)-7-hydroxy-6,7-dihydro-5H-cyclopenta[b]pyridine-1-oxide To a solution of 3-bromo-7-(ethoxycarbonyl)-7-hydroxy-6,7-dihydro-5H-cyclopenta[b]pyridine-1-oxide (160 mg, 0.53 mmol), 4-chloro-2-(4,4,5,5-tetramethyl-1,3,2-dioxaborolan-2-yl)benzonitrile (233 mg, 0.53 mmol) in dioxane (3 mL) was added potassium phosphate tribasic (225 mg, 1.06 mmol) and PdCl$_2$(dppf) (38.8 mg, 0.05 mmol) at 15° C. under N$_2$ in a 30 mL schlenk flask. The mixture was stirred at 60° C. for 22 h under N$_2$. LCMS showed the reaction was complete. The reaction mixture was quenched with water (15 mL), extracted with EtOAc (10 mL×4), washed with brine (10 mL×2), dried with Na$_2$SO$_4$ and filtered. The filtrate was concentrated and purified by p-TLC (SiO$_2$, PE/EtOAc=2/3) to give the title compound. MS (ESI) m/z 359.2 (M+H).

Step 2: lithium 3-(5-chloro-2-cyanophenyl)-7-hydroxy-1-oxido-6,7-dihydro-5H-cyclopenta[b]pyridine-7-carboxylate To a solution of 3-(5-chloro-2-cyanophenyl)-7-(ethoxycarbonyl)-7-hydroxy-6,7-dihydro-5H-cyclopenta[b]pyridine-1-oxide (220 mg, 0.61 mmol) in MeOH (4 mL) and water (1 mL) was added lithium hydroxide hydrate (25.7 mg, 0.613 mmol) at 15° C. under N$_2$ in a round bottom flask. The mixture was stirred at 60° C. for 2 h under N$_2$. LCMS showed the reaction was complete. The mixture was concentrated in vacuo to give the title compound which was used for the next step without further purification. MS (ESI) m/z 330.8 (M+H).

Lithium 3-(5-chloro-2-cyanophenyl)-7-hydroxy-4-methoxy-1-oxido-6,7-dihydro-5H-cyclopenta[b]pyridine-7-carboxylate

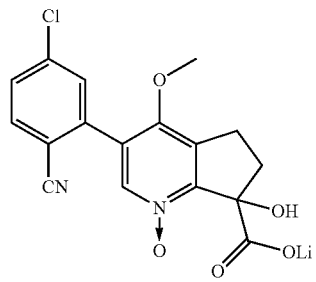

Step 1: 6,7-dihydro-5H-cyclopenta[b]pyridine-1-oxide

To a solution of 6,7-dihydro-5H-cyclopenta[b]pyridine (50 g, 420 mmol) and methyl trioxorhenium(VII) (0.3 g, 1.204 mmol) in DCM (400 mL) was added hydrogen peroxide (86 mL, 839 mmol, 30% wt). After addition, the mixture was stirred at 20° C. for 16 h. TLC showed SM was consumed. The mixture was quenched with sodium sulfite (about 75 g solid) portion-wise at ice bath and extracted with CHCl$_3$ (500 mL×3). The combined organic phases were dried over Na$_2$SO$_4$, filtered and concentrated to give the title compound which was used for the next step without further purification.

Step 2: 4-chloro-6,7-dihydro-5H-cyclopenta[b]pyridine

To a solution of 6,7-dihydro-5H-cyclopenta[b]pyridine-1-oxide (56 g, 414 mmol) in DCE (500 mL) was added POCl$_3$ (80 mL, 858 mmol) slowly at 0° C. After addition, the mixture was stirred at 20° C. for 1 h, heated to 85° C. slowly and further stirred at this temperature for 7 h. TLC showed SM was consumed. The excess POCl$_3$ was removed under reduced pressure and the black residue was diluted with EtOAc (500 mL) and sat. sodium carbonate (500 mL). The organic phase was separated, dried over Na$_2$SO$_4$, filtered and concentrated. The residue was purified by chromatography on silica gel (EtOAc:PE=10:90) to give the title compound.

Step 3: 4-chloro-6,7-dihydro-5H-cyclopenta[b]pyridine-1-oxide

To a solution of 4-chloro-6,7-dihydro-5H-cyclopenta[b]pyridine (38 g, 247 mmol) and methyl trioxorhenium(VII) (400 mg, 1.61 mmol) in DCM (250 mL) was added hydrogen peroxide (76 mL, 742 mmol, 30% wt). After addition, the mixture was stirred at 20° C. for 48 h. TLC showed SM was consumed. The mixture was diluted with DCM (300 mL) and water (150 mL), quenched with solid powder sodium sulfite portionwise until potassium iodide-starch test paper (the paper wetted by 1 mol/L aqueous HCl) did not turn blue. The organic phase was separated and the aqueous phase was extracted with CHCl$_3$ (500 mL×3). The combined organic phases were dried over Na$_2$SO$_4$, filtered and concentrated to give the title compound, which was used for the next step without further purification.

Step 4: 4-methoxy-6,7-dihydro-5H-cyclopenta[1)]pyridine-1-oxide

4-Chloro-6,7-dihydro-5H-cyclopenta[b]pyridine-1-oxide (15 g, 88 mmol) was added to a solution of sodium methoxide in MeOH (3.26 M, 400 mL) portion-wise at 20° C. After addition, the mixture was stirred at 80° C. for 24 h. TLC showed SM was consumed. The mixture was quenched by 4M MeOH—HCl solution to pH~6.5 and concentrated. The mixture was diluted with DCM (400 mL) and filtered. The filtrate was concentrated to give the title compound which was used for the next step without further purification. MS (ESI) m/z 166.0 (M+H).

Step 5: 4-methoxy-6,7-dihydro-5H-cyclopenta[b]pyridine-1-oxide

To a solution of 4-methoxy-6,7-dihydro-5H-cyclopenta[b]pyridine-1-oxide (7 g, 42.40 mmol) in MeOH (150 mL) was added Pd/C (2 g, 1.88 mmol, 10% wt). After addition, the mixture was degassed and refilled with H$_2$ for 3 times, and then stirred at 20° C. for 3 h with a H$_2$ balloon. TLC showed little starting material and a major new spot. The mixture was filtered and the filtrate was concentrated. The residue was purified by column chromatography on silica gel (eluting with EtOAc) to give the title compound.

Step 6: 3-bromo-4-methoxy-6,7-dihydro-5H-cyclopenta[b]pyridine

To a solution of 4-methoxy-6,7-dihydro-5H-cyclopenta[b]pyridine (3.8 g, 25.5 mmol) in H$_2$SO$_4$ (20 mL) at 0° C. was added 1-bromopyrrolidine-2,5-dione (5.89 g, 33.1 mmol) and the reaction mixture was stirred at 60° C. for 3 h. LCMS and TLC showed the reaction completed. The mixture was poured into water (60 mL), adjusted the pH to 10 with 10% NaOH aq. solution and extracted with EtOAc (100 mL×3). The combined organic layers were washed with brine (200 mL), dried over Na$_2$SO$_4$, filtered and concentrated. The residue was purified by column chromatography on silica gel (PE:EtOAc=5:1) to give the title compound. MS (ESI) m/z 228.2 (M+H).

Step 7: ethyl 3-bromo-4-methoxy-6,7-dihydro-5H-cyclopenta[b]pyridine-7-carboxylate To a round bottom flask was added 3-bromo-4-methoxy-6,7-dihydro-5H-cyclopenta[b]pyridine (2.5 g, 10.96 mmol), THF (50 mL) and diethyl carbonate (5.18 g, 43.80 mmol). To the stirred mixture at −78° C., LDA (12.06 mL, 24.11 mmol) was added. The reaction mixture was further stirred for 1 h at −78° C. LCMS showed starting material was consumed completely. The mixture was quenched with NH$_4$Cl (sat., aq, 30 mL) and extracted with EtOAc (50 mL×4). The combined organic layers were dried over Na$_2$SO$_4$, filtered and concentrated in vacuo. The residue was further purified by column chromatography on silica gel (PE:EtOAc=5:1) to give the title compound. MS (ESI) m/z 300.0 (M+H).

Step 8: ethyl 3-(5-chloro-2-cyanophenyl)-4-methoxy-6,7-dihydro-5H-cyclopenta[b]pyridine-7-carboxylate To a round bottom flask was added ethyl 3-bromo-4-methoxy-6,7-dihydro-5H-cyclopenta[b]pyridine-7-carboxylate (1.50 g, 5.00 mmol), DMF (20 mL), and 4-chloro-2-(4,4,5,5-tetramethyl-1,3,2-dioxaborolan-2-yl)benzonitrile (1.98 g, 7.50 mmol), PdCl$_2$(dtbpf) (300 mg, 0.46 mmol), and potassium phosphate tribasic (3.18 g, 14.99 mmol), then the mixture was warmed up to 80° C. and stirred for 3 h under N$_2$ protection. LCMS showed the ~70% of starting material consumed. The mixture was filtered and concentrated under reduced pressure. The residue was purified by column chromatography on silica gel (PE:EtOAc=1:1) to give the title compound. MS (ESI) m/z 357.1 (M+H).

Step 9: ethyl 3-(5-chloro-2-cyanophenyl)-7-hydroxy-4-methoxy-6,7-dihydro-5H-cyclopenta[b]pyridine-7-carboxylate To a round bottom flask was added ethyl 3-(5-chloro-2-cyanophenyl)-4-methoxy-6,7-dihydro-5H-cyclopenta[b]pyridine-7-carboxylate (50 mg, 0.14 mmol), DMSO (1 mL) and cesium carbonate (9.13 mg, 0.03 mmol). The mixture was purged with O$_2$ for three times and stirred for 1 h. LCMS showed the reaction was complete. The mixture was quenched with water (2 mL) and extracted with EtOAc (3 mL×4). The combined organic layers were washed with brine (10 mL×2), dried over Na$_2$SO$_4$, filtered and concentrated in vacuo to give the title compound which was directly used for next step without further purification. MS (ESI) m/z 373.1 (M+H).

Step 10: 3-(5-chloro-2-cyanophenyl)-7-(ethoxycarbonyl)-7-hydroxy-4-methoxy-6,7-dihydro-5H-cyclopenta[b]pyridine-1-oxide To a round bottom flask was added ethyl 3-(5-chloro-2-cyanophenyl)-7-hydroxy-4-methoxy-6,7-dihydro-5H-cyclopenta[b]pyridine-7-carboxylate (50 mg, 0.13 mmol), DCM (2 mL) and m-CPBA (39.7 mg, 0.16 mmol). The reaction mixture was stirred for 12 h at 15° C. LCMS showed the reaction was complete. The mixture was diluted with DCM (5 mL). The organic layer was separated, washed with sat. sodium bicarbonate (aq.), dried over Na$_2$SO$_4$, filtered and concentrated in vacuo to give the title compound which was directly used for next step without further purification. MS (ESI) m/z 389.1 (M+H).

Step 11: lithium 3-(5-chloro-2-cyanophenyl)-7-hydroxy-4-methoxy-1-oxido-6,7-dihydro-5H-cyclopenta[b]pyridine-7-carboxylate To solution of 3-(5-chloro-2-cyanophenyl)-7-(ethoxycarbonyl)-7-hydroxy-4-methoxy-6,7-dihydro-5H-cyclopenta[b]pyridine-1-oxide (40 mg, 0.103 mmol) in MeOH (3 mL) and water (0.5 mL) was added lithium hydroxide hydrate (5.18 mg, 0.123 mmol) at 15° C. under N$_2$ in a round bottom flask. The mixture was stirred at 60° C. for 2 h under N$_2$. LCMS showed the reaction was complete. The mixture was concentrated in vacuo to give the title compound which was used for the next step without further purification. MS (ESI) m/z 361.0 (M+H).

3-(2-((tert-butoxycarbonyl)amino)-5-chlorophenyl)-7-(2-methoxyethyl)-6,7-dihydro-5H-cyclopenta[b]pyridine-7-carboxylic acid

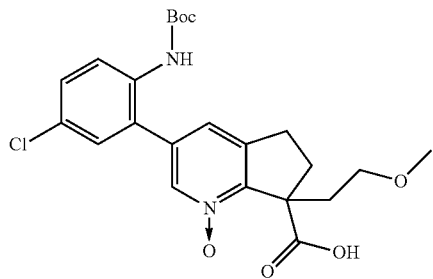 [SMILES: COCCC1(C(=O)O)CCc2cc(-c3cc(Cl)ccc3NC(=O)OC(C)(C)C)c[n+]([O-])c21]

Step 1: ethyl 3-bromo-7-(2-methoxyethyl)-6,7-dihydro-5H-cyclopenta[b]pyridine-7-carboxylate Ethyl 3-bromo-6,7-dihydro-5H-cyclopenta[b]pyridine-7-carboxylate (500 mg, 1.8 mmol) in DMF (4 ml) was mixed with 1-bromo-2-methoxyethane (360 mg, 2.59 mmol). NaH (90%, 74 mg, 2.7 mmol) was added. Mixture was stirred at 50° C. under nitrogen for 4 hours, then at 40° C. overnight. Mixture was poured into water (50 mL). Product was extracted with ethyl acetate (100 mL). The organic layer was further washed with brine. After being dried over anhydrous sodium sulfate, and filtered, the solution was concentrated. The crude was purified by column chromatography, eluting with 0-30% EtOAc/hexane gradient to give the title compound as an oil. MS (ESI) m/z 329.8 (M+H).

Step 2: ethyl 3-(2-((tert-butoxycarbonyl)amino)-5-chlorophenyl)-7-(2-methoxyethyl)-6,7-dihydro-5H-cyclopenta[b]pyridine-7-carboxylate 4,4,4',4',5,5,5',5'-Octamethyl-2,2'-bi(1,3,2-dioxaborolane) (460 mg, 1.8 mmol), PdCl$_2$(dppf) (268 mg, 0.36 mmol), and potassium acetate (538 mg, 5.48 mmol) were mixed in a microwave reaction vial. The vial was then capped. Air was removed by vacuum, and back-filled with nitrogen (×3). Ethyl 3-bromo-7-(2-methoxyethyl)-6,7-dihydro-5H-cyclopenta[b]pyridine-7-carboxylate (600 mg, 1.83 mmol) in 1,4-dioxane (7 ml) was introduced by syringe. Mixture was then heated to 110° C. for 1.5 hours. After cooled to rt, tert-butyl (4-chloro-2-iodophenyl)carbamate (646 mg, 1.8 mmol), PdCl$_2$(dppf) (134 mg, 0.183 mmol), and K$_2$CO$_3$ (1M, 5.48 ml, 5.48 mmol) were added. The vial was then capped. Air was removed by vacuum, and back-filled with nitrogen (×3), then heated to 100° C. for 1 hour.

Mixture was diluted with ethyl acetate, and filtered. The organic layer was separated and dried over anhydrous sodium sulfate. After being filtered and concentrated, the crude was purified by on silica gel, eluting with gradient 0-70% EtOAc/isohexane to give the titled compound as a liquid. MS (ESI) m/z 475.0 (M+H).

Step 3: 3-(2-((tert-butoxycarbonyl)amino)-5-chlorophenyl)-7-(2-methoxyethyl)-6,7-dihydro-5H-cyclopenta[b]pyridine-7-carboxylic acid Ethyl 3-(2-((tert-butoxycarbonyl)amino)-5-chlorophenyl)-7-(2-methoxyethyl)-6,7-dihydro-5H-cyclopenta[b]pyridine-7-carboxylate (780 mg, 1.64 mmol) in MeOH (5 ml) was mixed with LiOH solution (1M, 2.5 ml, 2.5 mmol) and heated to 50° C. for 2 hours. Mixture was concentrated on a rotary evaporator, then further dried in vacuum oven at 50° C. for 2 days. The lithium salt of the titled compound was used directly in the next step without further treatment. MS (ESI) m/z 446.9 (M+H).

3-Bromo-8-(ethoxycarbonyl)-8-hydroxy-5,6,7,8-tetrahydroquinoline 1-oxide

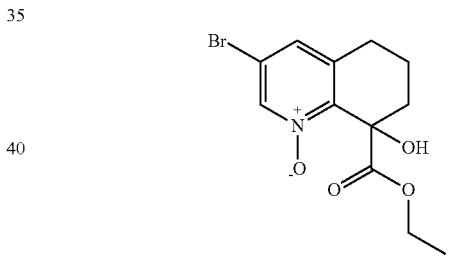

To a solution of ethyl 3-bromo-5,6,7,8-tetrahydroquinoline-8-carboxylate (1 g, 3.52 mmol), methyltrioxorhenium (VII) (0.219 g, 0.88 mmol) in DCM (20 ml) was added hydrogen peroxide (30%, 7.19 ml, 70.4 mmol). The mixture was stirred at 35° C. for 7 days. The mixture was then quenched with MnO$_2$ (50 mg), diluted with water (20 ml) and extracted with DCM (3×20 ml). The combined organic layer was concentrated to give the title compound as a solid. MS (ESI) m/z: 316.1 [M+H$^+$].

Methyl (4-(2-chloroacetyl)phenyl)carbamate

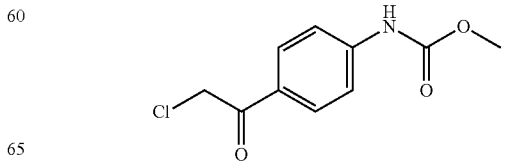

Step 1: Methyl phenylcarbamate

To a reaction mixture of aniline (500 g, 5.37 mol) in dioxane (2 L) and H$_2$O (2 L) was added NaOH (236 g, 5.91 mol). After stirring for 1 hour, methyl chloroformate (550 g, 5.91 mol) was added and the reaction mixture was stirred for 16 hours. The reaction mixture was concentrated and diluted with EA and H$_2$O. The organic layer was dried over Na$_2$SO$_4$ and concentrated to give the title compound. $^1$H NMR (400 MHz, CDCl$_3$) δ (ppm): 3.79 (s, 3H), 6.66 (m, 1H), 7.06-7.09 (m, 1H), 7.30-7.34 (m, 2H), 7.38-7.40 (m, 2H).

Step 2: Methyl (4-(2-chloroacetyl)phenyl)carbamate

A reaction mixture of methyl phenylcarbamate (500 g, 3.3 mol), 2-chloroacetyl chloride (556 g, 5 mol) and AlCl$_3$ (1.3 kg, 10 mol) in 1,2-dichloroethane (5 L) was heated at 70° C. for 2 hours. The reaction mixture was allowed to cool down and poured onto ice-H$_2$O. The aqueous layer was extracted with DCM 3 times. The combined organic layers were washed with H$_2$O, dried over Na$_2$SO$_4$ and concentrated. The residue was purified by column chromatography to give the title compound as a solid. $^1$H NMR (400 MHz, DMSO-d$_6$) δ (ppm): 3.71 (s, 3H), 5.09 (s, 2H), 7.62 (d, J=8.8 Hz, 2H), 7.94 (d, J=8.8 Hz, 2H), 10.12 (s, 1H).

Methyl (4-(2-bromopropanoyl)phenyl)carbamate

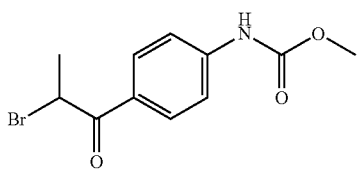

Step 1: Methyl (4-propionylphenyl)carbamate

To a mixture of 1-(4-aminophenyl)propan-1-one (1 g, 6.70 mmol) and sodium bicarbonate (620 mg, 7.37 mmol) in THF (33.5 mL) at 0° C. was added methyl chloroformate (571 µl, 7.37 mmol), dropwise. The reaction mixture was warmed to rt slowly and stirred at rt for 3 h. Water (40.0 mL) was added, and the THF was evaporated under vacuum. The residue was extracted twice with EtOAc (40 mL), and the combined extracts were dried over Na$_2$SO$_4$, filtered and concentrated under vacuum to give the title compound. MS (ESI) m/z 207.93 (M+H). The crude product was used directly in the next step without further purification.

Step 2: Methyl (4-(2-bromopropanoyl)phenyl)carbamate

To a solution of methyl (4-propionylphenyl)carbamate (1.3869 g, 6.69 mmol) in THF (19.12 mL) was added a solution of phenyltrimethylammonium tribromide (2.39 g, 6.36 mmol) in THF (19.00 mL), and the mixture was stirred at rt overnight. Water was added to the reaction mixture, and the volatile solvents were evaporated under vacuum. The aqueous layer was then extracted three times with EtOAc (50.0 mL), and the combined organic layers were dried over Na$_2$SO$_4$, filtered and concentrated under vacuum. The crude was triturated with hexanes to give the title compound. MS (ESI) m/z 286.05 (M+H).

1-(6-Aminopyridin-3-yl)-2-bromoethan-1-one, HBr salt

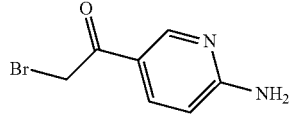 [SMILES: Nc1ccc(C(=O)CBr)cn1]

1-(6-Aminopyridin-3-yl)ethanone (4.0 g, 29 mmol) was dissolved in acetic acid (100 ml) and mixed with hydrobromic acid (33% in acetic acid, 10 ml, 59 mmol). The mixture was cooled in a cold water bath (−5° C.), and pyridinium tribromide (9.4 g, 29 mmol) was added. The mixture was stirred at this temperature for 2 hours, then at rt overnight. The mixture was concentrated. The product was washed with 1:1 acetone/isopropanol, then dried in vacuum oven at 50° C. overnight. MS (ESI) m/z 217 (M+H).

Methyl (4-(2-bromoacetyl)phenyl)carbamate

Step 1: methyl (4-acetylphenyl)carbamate

Methyl carbonochloridate (3.58 ml, 46.2 mmol) was added dropwise into a solution of 1-(4-aminophenyl)ethanone (5.0 g, 37.0 mmol) and pyridine (4.49 ml, 55.5 mmol) in CH$_2$Cl$_2$ (100 ml) at 0° C. and the mixture was stirred at 0° C. for 30 min. Then, the ice-bath was removed and the reaction was run at RT for 90 min. The solvent was removed under reduced pressure and the residue was purified by flash chromatography on a silica gel column with 0-45% EtOAc/hexane to give the title compound. MS (ESI) m/z 194.10 (M+H).

Step 2: methyl (4-(2-bromoacetyl)phenyl)carbamate

Bromine (0.850 ml, 16.50 mmol) was added dropwise slowly into a suspension of methyl (4-acetylphenyl)carbamate (2.90 g, 15 mmol) in CHCl$_3$ (100 ml) at rt. The reaction was stirred and monitored by LCMS. After 18 h, the solvent was removed under reduced pressure and the residue was taken up in MeOH/CH$_2$Cl$_2$ (30 ml, 6:1) and stirred for 15 min. The solid was filtered, washed with 5 ml of CH$_2$Cl$_2$ and dried in vacuo to give the title compound. MS (ESI) m/z 274.0 (M+H).

Methyl (4-(2-bromoacetyl)-3-methylphenyl)carbamate

Step 1: methyl (4-acetyl-3-methylphenyl)carbamate 1-(4-amino-2-methylphenyl)ethanone was used as starting material for the synthesis of the title compound by following the same procedure as in step 1 for the synthesis of methyl (4-acetylphenyl)carbamate. MS (ESI) m/z 208.06 (M+H).

Step 2: methyl (4-(2-bromoacetyl)-3-methylphenyl)carbamate

Phenyltrimethylammononium tribromide (1.0 g, 2.65 mmol) was added to a solution of methyl (4-acetyl-3-methylphenyl)carbamate (0.5 g, 2.41 mmol) in THF (15 ml) at RT, followed by stirring at RT overnight. The mixture was filtered and the solid was washed with THF. The filtrate was concentrated and the residue was purified by a flash chromatography on a silica gel column with 0-55% EtOAc/hexane to give the title compound. MS (ESI) m/z 285.99 (M+H).

Methyl (4-(2-bromoacetyl)-3-fluorophenyl)carbamate

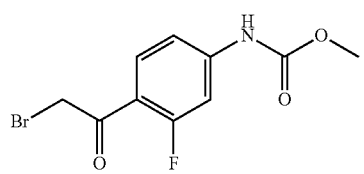

Step 1: methyl (4-acetyl-3-fluorophenyl)carbamate 1-(4-amino-2-fluorophenyl)ethanone was used as starting material for the synthesis of the title compound by following the same procedure as in step 1 for the synthesis of methyl (4-acetylphenyl)carbamate. MS (ESI) m/z 212.03 (M+H).

Step 2: methyl (4-(2-bromoacetyl)-3-fluorophenyl)carbamate

Methyl (4-acetyl-3-fluorophenyl)carbamate was used as starting material for the synthesis of the title compound by following the same procedure as in step 2 for the synthesis of methyl (4-(2-bromoacetyl)phenyl)carbamate. MS (ESI) m/z 292.01 (M+H).

Methyl (4-(2-bromoacetyl)-3-chlorophenyl)carbamate

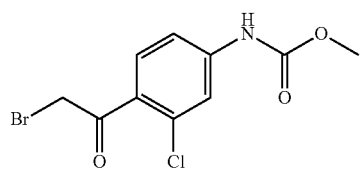

Step 1: methyl (4-acetyl-3-chlorophenyl)carbamate 1-(4-amino-2-chlorophenyl)ethanone was used as starting material for the synthesis of the title compound by following the same procedure as in step 1 for the synthesis of methyl (4-acetylphenyl)carbamate. MS (ESI) m/z 227.96 (M+H).

Step 2: methyl (4-(2-bromoacetyl)-3-chlorophenyl)carbamate

Methyl (4-acetyl-3-chlorophenyl)carbamate was used as starting material for the synthesis of the title compound by following the same procedure as in step 2 for the synthesis of methyl (4-(2-bromoacetyl)phenyl)carbamate. The reaction was run at RT for 3 h and the mixture was concentrated under reduced pressure and the residue was purified by a flash chromatography on a silica gel column with 0-45% EtOAc/hexane to give the title compound. MS (ESI) m/z 307.96 (M+H).

2-Methoxyethyl (4-(2-bromoacetyl)phenyl)carbamate

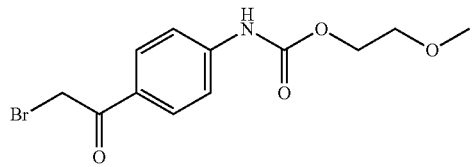 [SMILES: COCCOC(=O)Nc1ccc(C(=O)CBr)cc1]

Step 1: 2-methoxyethyl (4-acetylphenyl)carbamate 2-methoxyethyl carbonochloridate was reacted with 1-(4-aminophenyl)ethanone by following the same procedure as in step 1 for the synthesis of methyl (4-acetylphenyl)carbamate to give the title compound. MS (ESI) m/z 238.04 (M+H).

Step 2: 2-methoxyethyl (4-(2-bromoacetyl)phenyl)carbamate 2-methoxyethyl (4-acetylphenyl)carbamate was used as starting material for the synthesis of the title compound by following the same procedure as in step 2 for the synthesis of methyl (4-(2-bromoacetyl)phenyl)carbamate. The reaction was run at RT for 90 min. and the mixture was concentrated under reduced pressure and the residue was purified by a flash chromatography on a silica gel column with 0-70% EtOAc/hexane to give the title compound. MS (ESI) m/z 238.04 (M+H).

Methyl 5-(2-bromoacetyl)thiophene-2-carboxylate

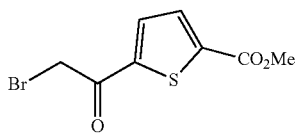 [SMILES: COC(=O)c1ccc(C(=O)CBr)s1]

Step 1: methyl 5-acetylthiophene-2-carboxylate

A mixture of 5-acetylthiophene-2-carboxylic acid (0.85 g, 5 mmol), iodomethane (0.38 ml, 6.00 mmol) and sodium carbonate (1.86 g, 17.50 mmol) in DMF (10 ml) was stirred at RT overnight. The mixture was concentrated under reduced pressure and the residue was taken up in EtOAc. The mixture was filtered through celite and washed with EtOAc. The filtrate was concentrated and the residue was purified by flash chromatography on a silica gel column with 0-30% EtOAc/hexane to give the title compound. MS (ESI) m/z 185.07 (M+H).

Step 2: methyl 5-(2-bromoacetyl)thiophene-2-carboxylate

Bromine (0.13 ml, 2.61 mmol) was added slowly to a solution of methyl 5-acetylthiophene-2-carboxylate (0.48 g, 2.61 mmol) in dioxane (5 ml) and the mixture was stirred at RT for 90 min. The solvent was removed under reduced pressure and the residue was purified by flash chromatography on a silica gel column with 0-30% EtOAc/hexane to give the title compound. MS (ESI) m/z 264.91 (M+H).

1-(6-Amino-2-chloropyridin-3-yl)-2-bromoethan-1-one

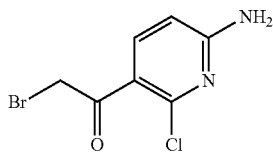 [SMILES: Nc1ccc(C(=O)CBr)c(Cl)n1]

Step 1: 1-(6-amino-2-chloropyridin-3-yl)ethanone

A flask was charged with tributyl(1-ethoxyvinyl)tin (3.43 g, 9.51 mmol), 6-chloro-5-iodopyridin-2-amine (2.20 g, 8.65 mmol), Tetrakis (0.50 g, 0.43 mmol) and exchanged air with $N_2$ by vacuum/backfilling with $N_2$. Then, toluene (50 ml) was added and the mixture was stirred at 110° C. for 16 h. After cooling down to RT, the reaction mixture was passed through a Celite® pad and washed with toluene. The filtrate was taken up in EtOAc (100 ml), mixed with 1N HCl aq. (20 ml) and neutralized with sat. $NaHCO_3$. The organic phase was separated, dried over $MgSO_4$, filtered, concentrated under reduced pressure and the residue was purified by column chromatography on silica gel with 0-75% EtOAc/hexane to give the title compound. MS (ESI) m/z 171.05 (M+H).

Step 2: Bis(tert-butyl) (5-(2-bromoacetyl)-6-chloropyridin-2-yl)carbamate

Hunig's Base (6.07 ml, 34.7 mmol) was added to a mixture of 1-(6-amino-2-chloropyridin-3-yl)ethanone (2.37 g, 13.89 mmol), BOC anhydride (7.10 ml, 30.6 mmol), DMAP (0.34 g, 2.78 mmol) in THF (75 ml), followed by stirring at RT for 3 h. The mixture was concentrated under reduced pressure and the residue was purified by flash chromatography on silica gel with 0-30% EtOAc/hexane to give the title compound. MS (ESI) m/z 471.06 (M+H).

Step 3: 1-(6-amino-5-bromo-2-chloropyridin-3-yl)ethanone

Bromine (0.46 ml, 8.90 mmol) was added to a solution of Bis(tert-butyl) (5-(2-bromoacetyl)-6-chloropyridin-2-yl)carbamate (3.3 g, 8.90 mmol) and 33 wt % HBr in acetic acid (2.20 ml, 13.35 mmol) in acetic acid (50 ml) at RT, followed by stirring for 1 h. Then, acetic acid was removed under reduced pressure and the residue was taken up in EtOAc and neutralized with sat. $NaHCO_3$ aq. The organic phase was separated and the aqueous phase was extracted with EtOAc. The combined organic phase was dried over $MgSO_4$, filtered, concentrated and the residue was purified by flash chromatography on silica gel with 0-80% EtOAc/hexane to give the title compound. MS (ESI) m/z 250.93 (M+H).

Methyl (4-carbamimidoylphenyl)carbamate

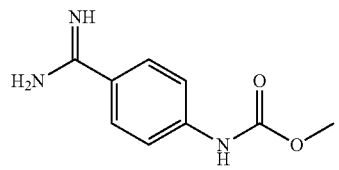

Step 1: methyl (4-cyanophenyl)carbamate

Methyl chloroformate (1.55 ml, 20.00 mmol) was added dropwise into a solution of 4-aminobenzonitrile (2.36 g, 20 mmol) and Hunig's base (4.37 ml, 25.00 mmol) in $CH_3CN$ (75 ml) at 0° C., followed by stirring for 30 min. Then, the ice-bath was removed and the reaction was run at RT overnight. The mixture was concentrated under reduced pressure and the residue was purified by flash chromatography on silica gel with 0-50% EtOAc/hexane to give the title compound. MS (ESI) m/z 177.08 (M+H).

Step 2: methyl (4-carbamimidoylphenyl)carbamate

Acetyl chloride (4.27 ml, 60.0 mmol) was added to a mixture of methyl (4-cyanophenyl)carbamate (0.53 g, 3.0 mmol) in EtOH (10 ml) at 0° C., followed by stirring at RT overnight and then and additional 3 h at 50° C. The mixture was concentrated under reduced pressure and the residue was taken up in EtOH (10 ml). To it was added ammonium carbonate (2.63 g, 15.00 mmol), and it was stirred at RT overnight. The solid was filtered and washed with EtOH. The filtrate was concentrated and the residue was dried in vacuo. MS (ESI) m/z 194.09 (M+H).

2-bromo-4-chloro-1-(difluoromethyl)-3-fluorobenzene

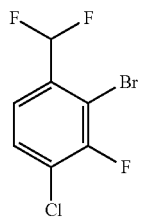

Step 1: 2-bromo-4-chloro-3-fluorobenzoic acid

A solution of 4-chloro-3-fluorobenzoic acid (2.0 g, 11.46 mmol) in THF (25 ml) was added by syringe pump to a solution of LDA (13.18 ml, 26.4 mmol) in THF (50 ml) at −78° C. over 30 min followed by stirring at −78° C. for 3 h. Then, to it was added a solution of 1,2-dibromotetrachloroethane (7.46 g, 22.92 mmol) in THF (25 ml). The reaction was run at −78° C. for 30 min, then slowly warmed up to RT and stirred overnight. The reaction mixture was quenched with water and extracted with $Et_2O$. The aqueous was neutralized with 4N HCl in dioxane (45.8 ml, 45.8 mmol) and extracted with EtOAc. The organic phase was dried over MgSO4, filtered and concentrated to give the title compound. MS (ESI) m/z 276.04 (M+H).

Step 2: (2-bromo-4-chloro-3-fluorophenyl)methanol $BH_3DMS$ (2.367 ml, 4.73 mmol) was added to a solution of 2-bromo-4-chloro-3-fluorobenzoic acid (1.0 g, 3.95 mmol) in THF (30 ml) at 0° C. After the mixture was stirred at 0° C. for 1 h, the ice-bath was removed and the reaction was run at RT for 5 h. The reaction was not complete. Then, additional $BH_3DMS$ (2.367 ml, 4.73 mmol) was added to the reaction mixture at 0° C. and continued stirring overnight with the temperature slowly rising to RT. Then, the mixture was treated with 1 N HCl (10 ml) and extracted with EtOAc (2×50 ml). The combined organic phase was dried over $MgSO_4$, filtered, concentrated and purified by flash chromatography on silica gel with 0-30% EtOAc/hexane to give the title compound. MS (ESI) m/z 240.25 (M+H).

Step 3: 2-bromo-4-chloro-3-fluorobenzaldehyde

PCC (0.57 g, 2.66 mmol) was added to a solution of (2-bromo-4-chloro-3-fluorophenyl)methanol (0.58 g, 2.42 mmol) in $CH_2Cl_2$ (10 ml) at 0° C. Then, the ice-bath was removed, and the reaction was run at RT for 2 h. The solvent was removed and the residue was purified by a flash chromatography on a silica gel column with 0-20% EtOAc/hexane to give the title compound. MS (ESI) m/z 238.31 (M+H).

Step 4: 2-bromo-4-chloro-1-(difluoromethyl)-3-fluorobenzene

DAST (0.31 ml, 2.37 mmol) was added to a solution of 2-bromo-4-chloro-3-fluorobenzaldehyde (0.45 g, 1.90 mmol) in $CH_2Cl_2$ (15 ml) at 0° C. After the mixture was stirred for 1 h, the ice-bath was removed and the reaction was run at RT for 5 h. The mixture was quenched with 1N HCl. The organic phase was separated. The aqueous was extracted with EtOAc. The combined organic phase was dried over $MgSO_4$, filtered, concentrated and purified by a flash chromatography on a silica gel column with 0-20% EtOAc/hexane. MS (ESI) m/z 397.25 (M+H).

N-(5-(2-bromoacetyl)-6-fluoropyridin-2-yl)acetamide

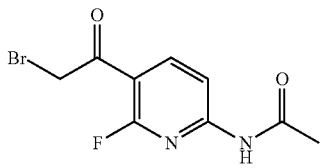

Step 1: 3-iodopyridine-2,6-diamine

To a solution of pyridine-2,6-diamine (10 g, 92 mmol) in HOAc (80 mL) and water (12 mL) was added $H_2SO_4$ (2.20 mL, 41.20 mmol). The reaction mixture was stirred at 50° C. for 1 h. $I_2$ (11.63 g, 45.80 mmol) was added at 25° C. and then $H_5IO_6$ (3.13 g, 13.75 mmol) was added, and the reaction mixture was stirred at 50° C. for 5 h. The reaction was mostly completed by TLC. Sat. sodium sulfite (15 mL) was added to the reaction mixture and the HOAc was then removed under high vacuum. The residue was dissolved in 200 mL of DCM and washed with 1M aq. sodium bicarbonate (2×100 mL). The organic fraction was separated, dried ($Na_2SO_4$), filtered and evaporated under reduced pressure. The residue was purified by column chromatography on silica gel (PE/EtOAc=5/1 to 1/1) to give the title compound. MS (ESI) m/z 235.9 (M+H).

Step 2: N-(6-amino-5-iodopyridin-2-yl)acetamide

To a solution of 3-iodopyridine-2,6-diamine (10 g, 42.50 mmol) in pyridine (80 mL) was added $Ac_2O$ (6.42 mL, 68.10 mmol) and DMAP (1.04 g, 8.51 mmol). The reaction mixture was stirred at 30° C. for 15 h. The reaction was mostly completed by LCMS. The solvent was evaporated under reduced pressure. The residue was purified by column chromatography ($SiO_2$; PE/EtOAc=5/1) to give the title compound. MS (ESI) m/z 278.0 (M+H).

Step 3: N-(6-fluoro-5-iodopyridin-2-yl)acetamide

A solution of N-(6-amino-5-iodopyridin-2-yl)acetamide (7.4 g, 26.7 mmol) in $HBF_4$ (400 mL, 26.7 mmol) (50% aqueous solution) was stirred at −5° C. for 1 h. Then sodium nitrite (3.69 g, 53.4 mmol) was added and the reaction mixture was stirred at −5° C. for 15 h. The reaction was complete as shown by TLC. The reaction mixture was quenched with sat. sodium bicarbonate (15 mL) and extracted with EtOAc (20 mL×3). The combined organic fractions were dried ($Na_2SO_4$), filtered and the solvent was evaporated under reduced pressure. The residue was purified by column chromatography on silica gel (PE/EtOAc=3/1 to 1/1) to give the title compound.

Step 4: N-(5-(2-bromoacetyl)-6-fluoropyridin-2-yl)acetamide

To a solution of N-(6-fluoro-5-iodopyridin-2-yl)acetamide (1.5 g, 5.36 mmol) and tributyl(1-ethoxyvinyl)stannane (1.81 mL, 5.36 mmol) in dioxane (20 mL) was added $Pd(Ph_3P)_4$ (0.309 g, 0.268 mmol). The reaction mixture was stirred at 100° C. for 15 h. The reaction was complete as shown by TLC. The solvent was evaporated under reduced pressure. To the solution in THF (15 mL) and water (5 mL) was added NBS (0.953 g, 5.35 mmol). The reaction mixture was then stirred at 25° C. for 5 h. TLC showed the reaction was complete. The mixture was cooled, sat. sodium bicarbonate (50 mL) was added and the mixture was extracted with DCM (100 mL×3). The combined organic fractions were dried ($Na_2SO_4$) and the solvent was evaporated under reduced pressure. The residue was purified by column chromatography on silica gel (PE/EtOAc=5/1) to give the title compound.

N-(5-(2-bromoacetyl)-6-chloropyridin-2-yl)acetamide

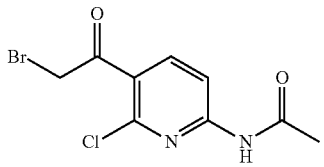

Step 1: 6-chloro-5-iodopyridin-2-amine

To a solution of 6-chloropyridin-2-amine (10 g, 78 mmol) in DMF (100 mL) was added 1-iodopyrrolidine-2,5-dione (17.50 g, 78 mmol). The reaction mixture was allowed to stir under $N_2$ balloon at 25° C. for 18 h. LCMS showed some of the desired product. The reaction was then diluted with EtOAc (100 mL) and water (200 mL). The aqueous layer was extracted with EtOAc (3×100 mL). The combined organic phases were dried over $Na_2SO_4$, and concentrated in vacuo. The residue was then washed with DCM (30 mL) and then dried to give the title compound. MS (ESI) m/z 254.8 (M+H).

Step 2: N-(6-chloro-5-iodopyridin-2-yl)acetamide

To a solution of 6-chloro-5-iodopyridin-2-amine (5 g, 19.65 mmol) in DCM (100 mL) was added acetyl chloride (4.21 mL, 58.90 mmol) and triethylamine (8.06 mL, 58.9 mmol). The reaction mixture was allowed to stir under $N_2$ balloon at 28° C. for 4 h. TLC showed SM was consumed and a new spot formed. The reaction was quenched with $H_2O$ (100 mL) and the aqueous layer was extracted with EtOAc (3×100 mL). The combined organic phases were dried over $Na_2SO_4$, and concentrated in vacuo. The residue was purified by column chromatography ($SiO_2$, PE:EtOAc=20:1 to 3:1) to give the title compound. MS (ESI) m/z 296.8 (M+H).

Step 3: N-(6-chloro-5-(1-ethoxyvinyl)pyridin-2-yl)acetamide

To a solution of N-(6-chloro-5-iodopyridin-2-yl)acetamide (4.80 g, 16.19 mmol) in dioxane (80 mL) was added tributyl(1-ethoxyvinyl)stannane (5.44 mL, 16.19 mmol) and $Pd(Ph_3P)_4$ (0.94 g, 0.81 mmol). The reaction mixture was degassed and refilled with $N_2$ for 3 times and allowed to stir under $N_2$ balloon at 90° C. for 5 h. TLC showed SM was consumed and a new spot formed. The reaction was treated with sat. KF (80 mL) and then stirred for 1 h. The mixture was filtered and the filtrate was concentrated. The aqueous layer was extracted with EtOAc (3×80 mL). The combined organic phases were dried over $Na_2SO_4$, and concentrated in vacuo. The residue was purified by column chromatography ($SiO_2$, PE:EtOAc=20:1 to 5:1) to give the title compound. MS (ESI) m/z 241.0 (M+H).

Step 4: N-(5-(2-bromoacetyl)-6-chloropyridin-2-yl)acetamide

To a solution of N-(6-chloro-5-(1-ethoxyvinyl)pyridin-2-yl)acetamide (1.70 g, 7.06 mmol) in THF (35 mL) and water (8 mL) was added NBS (1.26 g, 7.06 mmol). The reaction mixture was allowed to stir under $N_2$ balloon at 20° C. for 0.5 h. TLC showed SM was consumed and a new spot formed. The reaction was quenched with water (40 mL) and extracted with EtOAc (3×30 mL). The combined organic phases were dried over $Na_2SO_4$, and concentrated in vacuo. The residue was purified by column chromatography ($SiO_2$, PE:EtOAc=20:1 to 3:1) to give the title compound. MS (ESI) m/z 292.9 (M+H). $^1$H NMR (400 MHz, $CDCl_3$): δ 8.24 (d, J=8.5 Hz, 1H), 8.16 (br s, 1H), 8.07 (d, J=8.5 Hz, 1H), 4.55 (s, 2H), 2.25 (s, 3H).

7-(2-Bromoacetyl)-3,4-dihydroquinolin-2(1H)-one

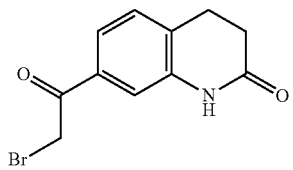 [SMILES: O=C1CCc2ccc(C(=O)CBr)cc2N1]

Step 1: 4-bromo-N-methoxy-N-methyl-3-nitrobenzamide

A solution of 4-bromo-3-nitrobenzoic acid (30 g, 122 mmol) in $SOCl_2$ (300 mL) was stirred at 100° C. for 2 h. The solvent was evaporated under reduced pressure. The residue was dissolved in DCM (200 mL) and added to a solution of N,O-dimethylhydroxylamine hydrochloride (23.79 g, 244 mmol) in DCM (200 mL) at 0° C. TEA (100 mL, 717 mmol) was added to the reaction mixture to pH=10. The reaction mixture was stirred at 0° C. for 1 h. The reaction was complete as shown by TLC. The solvent was evaporated under reduced pressure and the residue was dissolved in EtOAc (1 L) and washed with HCl (500 mL×3, 1N) and sat. sodium bicarbonate (500 mL×2). The organic fractions were dried ($Na_2SO_4$), filtered and the solvent was evaporated under reduced pressure to give 4-bromo-N-methoxy-N-methyl-3-nitrobenzamide.

Step 2: (E)-ethyl 3-(4-(methoxy(methyl)carbamoyl)-2-nitrophenyl)acrylate

To a solution of 4-bromo-N-methoxy-N-methyl-3-nitrobenzamide (30 g, 104 mmol) and $K_3PO_4$ (44.1 g, 208 mmol) in dioxane (500 mL) and water (100 mL) was added $PdCl_2(dppf)$ (3.80 g, 5.19 mmol). The reaction mixture was stirred at 110° C. for 18 h under $N_2$. The reaction was complete as shown by TLC. The solvent was evaporated under reduced pressure. The residue was diluted water (500 mL) and extracted with EtOAc (500 mL×3). The combined organic fractions were dried ($Na_2SO_4$), filtered and the solvent was evaporated under reduced pressure. The residue was purified by column chromatography ($SiO_2$; PE/EtOAc=5/1) to give the title compound.

Step 3: N-methoxy-N-methyl-2-oxo-1,2,3,4-tetrahydroquinoline-7-carboxamide

To a solution of (E)-ethyl 3-(4-(methoxy(methyl)carbamoyl)-2-nitrophenyl)acrylate (27 g, 88 mmol) in THF (500 mL) was added Pd/C (4.66 g, 4.38 mmol, 10% wt). The reaction mixture was stirred at 25° C. for 15 h under $H_2$. The reaction was complete as shown by LCMS. The mixture was filtered, washed with MeOH (500 mL) and the solvent was evaporated under reduced pressure. The residue was purified by column chromatography (SiO₂; PE/EtOAc=1/1) to give the title compound. MS (ESI) m/z 234.9 (M+H).

Step 4: 7-acetyl-3,4-dihydroquinolin-2(1H)-one

To a solution of N-methoxy-N-methyl-2-oxo-1,2,3,4-tetrahydroquinoline-7-carboxamide (5.60 g, 23.91 mmol) in THF (150 mL) was added CH₃MgBr (23.91 mL, 71.7 mmol, 3M). The reaction mixture was stirred at 0° C. for 2 h. The reaction was complete as shown by TLC. The reaction mixture was added to sat. NH₄Cl (200 mL) and extracted with DCM (200 mL×3). The combined organic fractions were dried (Na₂SO₄), filtered and the solvent was evaporated under reduced pressure to give the title compound. MS (ESI) m/z 234.9 (M+H).

Step 5: 7-(2-bromoacetyl)-3,4-dihydroquinolin-2(1H)-one

To a solution of 7-acetyl-3,4-dihydroquinolin-2(1H)-one (3.7 g, 19.55 mmol)) in THF (60 mL) was added pyridinium tribromide (6.25 g, 19.55 mmol). The reaction mixture was stirred at 25° C. for 15 h. The reaction was complete as shown by LCMS. The solvent was evaporated under reduced pressure. The residue was purified by column chromatography (SiO₂; PE/EtOAc=1/1) to give the title compound. MS (ESI) m/z 270.1 (M+H). ¹H NMR (CDCl₃, 400 MHz): δ 7.91-7.81 (m, 1H), 7.61 (d, J=7.8 Hz, 1H), 7.38 (s, 1H), 7.31 (d, J=7.8 Hz, 1H), 4.42 (s, 2H), 3.06 (t, J=7.4 Hz, 2H), 2.69 (t, J=7.4 Hz, 2H).

7-(2-Bromopropanoyl)-3,4-dihydroquinolin-2(1H)-one

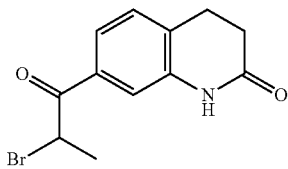 [SMILES: CC(Br)C(=O)c1ccc2c(c1)NC(=O)CC2]

Step 1: 7-propionyl-3,4-dihydroquinolin-2(1H)-one

To a solution of N-methoxy-N-methyl-2-oxo-1,2,3,4-tetrahydroquinoline-7-carboxamide (2 g, 8.54 mmol) in THF (30 mL) was added ethylmagnesium bromide (14.23 mL, 42.7 mmol) at 0° C. The reaction mixture was stirred at 0° C. for 5 h. The reaction was complete as shown by LCMS. The reaction mixture was added to sat. NH₄Cl (50 mL) and extracted with DCM (50 mL×3). The combined organic fractions were dried (Na₂SO₄), filtered and the solvent was evaporated under reduced pressure to give the title compound. MS (ESI) m/z 204.3 (M+H).

Step 2: 7-(2-bromopropanoyl)-3,4-dihydroquinolin-2(1H)-one

To a solution of 7-propionyl-3,4-dihydroquinolin-2(1H)-one (1.7 g, 8.36 mmol) in THF (40 mL) was added pyridinium tribromide (2.68 g, 8.36 mmol). The reaction mixture was stirred at 25° C. for 5 h. The reaction was complete as shown by LCMS. The solvent was evaporated under reduced pressure. The mixture was cooled, water (50 mL) was added and the mixture was extracted with EtOAc (50 mL×3). The combined organic fractions were dried (Na₂SO₄), filtered and the solvent was evaporated under reduced pressure. The residue was re-crystallized in PE/EtOAc=10/1 (100 mL) to give the title compound. MS (ESI) m/z 282.1 (M+H). ¹H NMR (CDCl₃, 400 MHz): δ 8.22 (br s, 1H), 7.65 (d, J=6.7 Hz, 1H), 7.44 (s, 1H), 7.30 (d, J=7.8 Hz, 1H), 5.25 (q, J=6.5 Hz, 1H), 3.06 (t, J=7.4 Hz, 2H), 2.69 (t, J=7.4 Hz, 2H), 1.91 (d, J=6.7 Hz, 3H).

tert-Butyl 4-(2-bromopropanoyl)thiophene-2-carboxylate

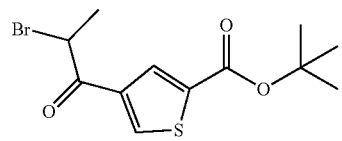 [SMILES: CC(Br)C(=O)c1csc(C(=O)OC(C)(C)C)c1]

Step 1: tert-butyl 4-vinylthiophene-2-carboxylate

To a solution of tert-butyl 4-bromothiophene-2-carboxylate (5 g, 19.00 mmol) and potassium trifluoro(vinyl)borate (2.55 g, 19.00 mmol) in toluene (50 mL) and water (10 mL) was added potassium phosphate tribasic (8.07 g, 38.00 mmol) and PdCl₂(dppf) (1.39 g, 1.90 mmol). The mixture was then degassed and refilled with N₂ 3 times and then stirred at 90° C. for 12 h under N₂ atmosphere. TLC showed the reaction was complete. The mixture was diluted with H₂O (80 mL) and extracted with EtOAc (50 mL×3), the combined organic layers were concentrated, and the residue was purified with flash silica gel chromatography (0-5% EtOAc/PE gradient) to give the title compound.

Step 2: tert-butyl 4-formylthiophene-2-carboxylate

A solution of tert-butyl 4-vinylthiophene-2-carboxylate (1.50 g, 7.13 mmol) in DCM (20 mL) was bubbled with O₃ until the mixture became blue. Then dimethylsulfane (8.86 g, 143 mmol) was added and the reaction mixture was stirred at 20° C. for 12 h. TLC showed the reaction was complete. Then H₂O (20 mL) was added and the mixture was extracted with DCM (20 mL×3). The combined organic phases were dried over Na₂SO₄, and concentrated in vacuo. The residue was purified by column chromatography (SiO₂, PE:EtOAc=50:1 to 20:1) to give the title compound.

Step 3: tert-butyl 4-(1-hydroxypropyl)thiophene-2-carboxylate

To a solution of tert-butyl 4-formylthiophene-2-carboxylate (2.5 g, 11.78 mmol) in THF (35 mL) was added ethylmagnesium bromide (17.67 mL, 17.67 mmol) at 0° C., and the mixture was stirred at 0° C. for 0.5 h. TLC showed the reaction was almost completed. Then the mixture was quenched with water (10 mL) and extracted with DCM (10 mL×3). The combined organic layers were dried over Na₂SO₄, filtered and the filtrated was concentrated to give the title compound.

Step 4: tert-butyl 4-propionylthiophene-2-carboxylate

To a solution of tert-butyl 4-(1-hydroxypropyl)thiophene-2-carboxylate (2 g, 8.25 mmol) in DCM (30 mL) was added DMP (5.25 g, 12.3 mmol) at 0° C., and the mixture was stirred at 20° C. for 1 h. TLC showed the reaction was complete. The reaction was diluted with a solution of sodium thiosulfate (20 mL) and sodium bicarbonate (20 mL), then the aqueous layer was extracted with DCM (20 mL×3). The combined organic phases were dried over $Na_2SO_4$, filtered and the filtrate was concentrated in vacuo. The residue was purified by column chromatography ($SiO_2$, PE:EtOAc=20:1 to 10:1) to give the title compound.

Step 5: tert-butyl 4-(2-bromopropanoyl)thiophene-2-carboxylate

To a solution of tert-butyl 4-propionylthiophene-2-carboxylate (1.50 g, 6.24 mmol) in THF (30 mL) was added pyridinium tribromide (2.00 g, 6.24 mmol). The reaction mixture was stirred at 25° C. for 2 h. TLC showed the SM was consumed. The reaction was diluted with water (20 mL) and extracted with DCM (20 mL×3). The combined organic layers were concentrated. The residue was purified by column chromatography ($SiO_2$, PE:EtOAc=10:1 to 6:1) to give the title compound. $^1$H NMR ($CDCl_3$, 400 MHz): δ8.29 (s, 1H) 8.11 (s, 1H) 5.05-5.00 (m, 1H) 1.86 (d, J=6.65 Hz, 3H) 1.57 (s, 9H).

tert-Butyl 4-(2-bromopropanoyl)-3-fluorothiophene-2-carboxylate

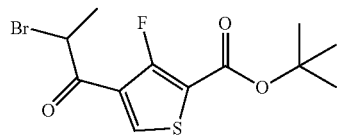 [SMILES: CC(Br)C(=O)c1csc(C(=O)OC(C)(C)C)c1F]

Step 1: methyl 3-fluorothiophene-2-carboxylate

To a solution of 3-fluorothiophene-2-carboxylic acid (10 g, 68.40 mmol) in MeOH (100 mL) was added $H_2SO_4$ (1 mL, 18.76 mmol), and the mixture was stirred at 100° C. for 12 h. TLC showed a new spot formed. The reaction mixture was quenched with sat. sodium bicarbonate, adjusted ~pH 7 and extracted with EtOAc (3×50 mL). The combined organic phases were dried over $Na_2SO_4$, and concentrated in vacuo to give the title compound.

Step 2: methyl 4-bromo-3-fluorothiophene-2-carboxylate

To a solution of methyl 3-fluorothiophene-2-carboxylate (13.2 g, 82 mmol) in $CHCl_3$ (400 mL) were added iron (III) bromide (2.436 g, 8.24 mmol) and aluminum trichloride (65.9 g, 494 mmol). Then a solution of bromine (19.76 g, 124 mmol) in chloroform (60 mL) was added dropwise into the mixture. The reaction mixture was allowed to stir under $N_2$ balloon at 28° C. for 15 h. TLC showed little starting material remained and a new spot formed. The reaction was poured into ice water (500 mL) and extracted with DCM (3×300 mL). The combined organic phases were washed successively with sat. sodium sulfite (500 mL) and sat. NaCl (500 mL), dried over $Na_2SO_4$, and concentrated in vacuo. The residue was purified by flash silica gel chromatography (0-2% EtOAc/PE gradient) to give the title compound.

Step 3: 4-bromo-3-fluorothiophene-2-carboxylic acid

To a solution of methyl 4-bromo-3-fluorothiophene-2-carboxylate (4.5 g, 18.82 mmol) in MeOH (15 mL) and water (5 mL) was added lithium hydroxide hydrate (0.90 g, 37.60 mmol). The reaction mixture was allowed to stir under $N_2$ balloon at 28° C. for 8 h. TLC showed little starting material remained and a new spot formed. The reaction was quenched with $H_2O$ (40 mL) and extracted with EtOAc (3×70 mL). The combined organic phases were dried over $Na_2SO_4$, and concentrated in vacuo to give the title compound which was used for the next step without further purification.

Step 4: tert-butyl 4-bromo-3-fluorothiophene-2-carboxylate

To a solution of 4-bromo-3-fluorothiophene-2-carboxylic acid (4 g, 17.77 mmol) in THF (100 mL) was added di-tert-butyl dicarbonate (8.25 mL, 35.50 mmol) and DMAP (0.43 g, 3.55 mmol). The reaction mixture was allowed to stir under $N_2$ balloon at 28° C. for 8 h. TLC showed little starting material remained and a new spot formed. The reaction was quenched with $H_2O$ (80 mL) and extracted with EtOAc (3×80 mL). The combined organic phases were dried over $Na_2SO_4$, and concentrated in vacuo. The residue was purified by column chromatography ($SiO_2$, PE:EtOAc=10:1) to give the title compound.

Step 5: tert-butyl 3-fluoro-4-vinylthiophene-2-carboxylate

To a solution of tert-butyl 4-bromo-3-fluorothiophene-2-carboxylate (3.20 g, 11.38 mmol) in toluene (60 mL) and water (15 mL) was added potassium trifluoro(vinyl)borate (1.601 g, 11.95 mmol), potassium phosphate tribasic (7.25 g, 34.1 mmol) and $PdCl_2$(dppf) (0.416 g, 0.569 mmol). The reaction mixture was allowed to stir under $N_2$ balloon at 90° C. for 8 h. TLC showed little starting material remained and a new spot formed. The reaction was quenched with $H_2O$ (50 mL) and extracted with EtOAc (3×60 mL). The combined organic phases were dried over $Na_2SO_4$, and concentrated in vacuo. The residue was purified by column chromatography ($SiO_2$, PE:EtOAc=20:1 to 10:1) to give the title compound.

Step 6: tert-butyl 3-fluoro-4-formylthiophene-2-carboxylate

A solution of tert-butyl 3-fluoro-4-vinylthiophene-2-carboxylate (2.10 g, 9.20 mmol) in DCM (40 mL) was treated with ozone (excess) at −78° C. The reaction turned from colorless to blue. The reaction mixture was flushed with $N_2$ for 0.5 h and dimethylsulfane (11.43 g, 184 mmol) was added to the mixture and it was stirred for 12 h at 28° C. TLC showed little starting material remained and a new spot formed. The mixture was concentrated and the residue was purified by column chromatography ($SiO_2$, PE:EtOAc=20:1 to 10:1) to give the title compound.

Step 7: tert-butyl 3-fluoro-4-(1-hydroxypropyl)thiophene-2-carboxylate

To a solution of tert-butyl 3-fluoro-4-formylthiophene-2-carboxylate (1.4 g, 6.08 mmol) in THF (30 mL) was added ethylmagnesium bromide (2.027 mL, 6.08 mmol) at 0° C. The reaction mixture was allowed to stir under $N_2$ balloon at 0° C. for 2 h. TLC showed little starting material remained and a new spot formed. The reaction was quenched with sat. NH$_4$Cl (50 mL) and extracted with EtOAc (3×50 mL). The combined organic phases were dried over Na$_2$SO$_4$, and concentrated in vacuo. The residue was purified by column chromatography (SiO$_2$, PE:EtOAc=10:1) to give the title compound.

Step 8: tert-butyl 3-fluoro-4-propionylthiophene-2-carboxylate

To a solution of tert-butyl 3-fluoro-4-(1-hydroxypropyl) thiophene-2-carboxylate (1.5 g, 5.76 mmol) in DCM (50 mL) was added Dess-Martin Periodinane (3.05 g, 7.20 mmol). The reaction mixture was allowed to stir under N$_2$ balloon at 0° C. for 2 h. TLC showed little starting material remained and a new spot formed. The reaction was quenched with sat. sodium sulfite (20 mL) and water (80 mL), and extracted with DCM (3×80 mL). The combined organic phases were dried over Na$_2$SO$_4$, and concentrated in vacuo. The residue was purified by column chromatography (SiO$_2$, PE:EtOAc=10:1) to give the title compound.

Step 9: tert-butyl 4-(2-bromopropanoyl)-3-fluorothiophene-2-carboxylate

To a solution of tert-butyl 3-fluoro-4-propionylthiophene-2-carboxylate (1 g, 3.87 mmol) in THF (40 mL) was added pyridinium tribromide (1.24 g, 3.87 mmol) at 25° C., and the mixture was stirred at 25° C. for 10 h. TLC showed the reaction was complete. The reaction was diluted with H$_2$O (60 mL) and extracted with DCM (3×80 mL). The combined organic phases were dried over Na$_2$SO$_4$, and concentrated in vacuo. The residue was purified by column chromatography (SiO$_2$, PE:EtOAc=20:1) to give the title compound. $^1$H NMR (CDCl$_3$, 400 MHz): 8.24 (d, J=4.0 Hz, 1H), 5.08 (q, J=6.8 Hz, 1H), 1.86 (d, J=6.8 Hz, 3H), 1.58 (s, 9H).

tert-Butyl 5-(2-bromoacetyl)thiophene-2-carboxylate

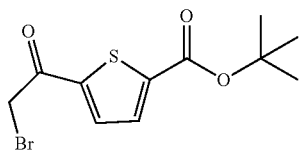 [SMILES: CC(C)(C)OC(=O)c1ccc(C(=O)CBr)s1]

Step 1: tert-butyl-5-acetylthiophene-2-carboxylate

To a solution of 5-acetylthiophene-2-carboxylic acid (10 g, 58.80 mmol) and pivalic anhydride (28 g, 58.80 mmol) in THF (100 mL) was added di-tert-butyl dicarbonate (27 mL, 117 mmol) DMAP (1.43 g, 11.72 mmol). The reaction mixture was stirred at 20° C. for 16 h. The reaction was mostly completed by TLC. Then the solution was diluted with water (100 mL) and extracted with EtOAc (50 mL×3). The combined organic fractions were dried (Na$_2$SO$_4$), filtered and the solvent was evaporated under reduced pressure. The residue was purified by column chromatography (SiO$_2$; PE/EtOAc=20/1 to 10/1) to give the title compound.

Step 2: tert-butyl 5-(2-bromoacetyl)thiophene-2-carboxylate

To a solution of tert-butyl-5-acetylthiophene-2-carboxylate (12 g, 53 mmol) in THF (100 mL) was added pyridinium tribromide (16.7 g, 53 mmol). The reaction mixture was stirred at 20° C. for 3 h. The reaction was mostly completed based on TLC. Then the solution was diluted with water (100 mL) and extracted with EtOAc (50 mL×3). The combined organic fractions were dried (Na$_2$SO$_4$), filtered and the solvent was evaporated under reduced pressure. The residue was purified by column chromatography (SiO$_2$; PE/EtOAc=20/1 to 10/1) to give the title compound. $^1$H NMR (CDCl$_3$, 400 MHz): 7.69-7.72 (m, 2H), 4.33 (s, 2H), 1.57 (s, 9H).

tert-butyl 5-(2-chloropropanoyl)thiophene-2-carboxylate

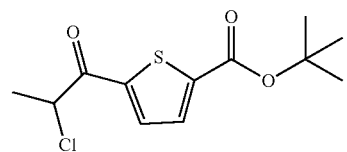 [SMILES: CC(Cl)C(=O)c1ccc(C(=O)OC(C)(C)C)s1]

Step 1: 2-chloro-N-methoxy-N-methylpropanamide

To a solution of N,O-dimethylhydroxylamine hydrochloride (6.15 g, 63.00 mmol) in water (60 mL) was added a solution of 2-chloropropanoyl chloride (10 g, 79 mmol) in DCM (60 mL) and potassium carbonate (27.20 g, 197 mmol), and the mixture was allowed to stir under N$_2$ balloon at 28° C. for 12 h. The reaction was diluted with DCM (50 mL) and water (50 mL), and extracted with DCM (50 mL×3). The combined organic phases were dried over Na$_2$SO$_4$, and concentrated in vacuo to give the title compound.

Step 2: tert-butyl 5-(2-chloropropanoyl)thiophene-2-carboxylate

To a solution of tert-butyl 5-bromothiophene-2-carboxylate (2.2 g, 8.36 mmol) in THF (40 mL) was added butyllithium (3.34 mL, 8.36 mmol). The reaction mixture was allowed to stir under N$_2$ balloon at −68° C. for 0.5 h and then 2-chloro-N-methoxy-N-methylpropanamide (1.267 g, 8.36 mmol) was added. The mixture was stirred at −68° C. for 2 h. TLC showed little starting material remained and a new spot formed. The reaction was quenched with sat. NH$_4$Cl (20 mL), diluted with EtOAc (20 mL) and water (10 mL), and extracted with EtOAc (3×10 mL). The combined organic phases were dried over Na$_2$SO$_4$, and concentrated in vacuo. The residue was purified by column chromatography (SiO$_2$, PE/EtOAc=50:1) to give the title compound. $^1$H NMR (CDCl$_3$, 400 MHz): 7.76 (d, J=3.9 Hz, 1H), 7.70 (d, J=3.9 Hz, 1H), 5.07-5.01 (m, 1H), 1.75 (d, J=6.7 Hz, 3H), 1.58 (s, 9H).

Methyl 4-(2-bromoacetyl)-3-fluorothiophene-2-carboxylate

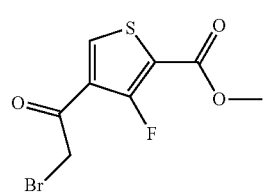

Step 1: methyl 4-(2-bromoacetyl)-3-fluorothiophene-2-carboxylate

To a solution of methyl 4-bromo-3-fluorothiophene-2-carboxylate (10 g, 41.80 mmol) in dioxane (100 mL) was added tributyl(1-ethoxyvinyl)stannane (14.13 mL, 41.80 mmol) and Pd(Ph$_3$P)$_4$ (2.42 g, 2.09 mmol). The reaction mixture was allowed to stir under N$_2$ balloon at 95° C. for 8 h. TLC showed little starting material remained and a new spot formed. The reaction was quenched with sat. KF (100 mL) and stirred at 26° C. for 1 h. Then the mixture was filtered and the filtrate was concentrated. The residue was dissolved in THF (100 mL) and 1M HCl (100 mL) was added. The mixture was stirred at 26° C. for another 1 h and then extracted with EtOAc (3×100 mL). The combined organic phases were dried over Na$_2$SO$_4$, and concentrated in vacuo. The residue was purified by column chromatography (SiO$_2$, PE:EtOAc=5:1) to give the title compound.

Step 2: methyl 4-(2-bromoacetyl)-3-fluorothiophene-2-carboxylate

To a solution of methyl 4-acetyl-3-fluorothiophene-2-carboxylate (7.60 g, 37.60 mmol) in THF (150 mL) was added pyridinium tribromide (12.02 g, 37.60 mmol). The reaction mixture was allowed to stir under N$_2$ balloon at 28° C. for 8 h. TLC showed little starting material remained and a new spot formed. The reaction was quenched with H$_2$O (40 mL) and extracted with EtOAc (3×50 mL). The combined organic phases were dried over Na$_2$SO$_4$, and concentrated in vacuo. The residue was purified by column chromatography (SiO$_2$, PE:EtOAc=10:1 to 5:1) to give the title compound. $^1$H NMR (CDCl$_3$, 400 MHz): 8.30 (d, J=4.0 Hz, 1H), 4.34 (s, 2H), 3.93 (s, 3H).

2-(3-Chloro-2,6-difluorophenyl)-4,4,5,5-tetramethyl-1,3,2-dioxaborolane

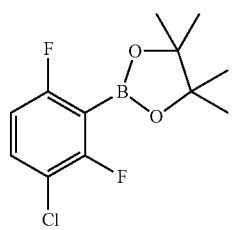 [SMILES: CC1(C)OB(c2c(F)ccc(Cl)c2F)OC1(C)C]

To a solution of 1-chloro-2,4-difluorobenzene (6 g, 40.4 mmol) in THF (150 mL) was added butyllithium (16.16 mL, 40.40 mmol) dropwise at −78° C., and the temperature was controlled below −65° C. After the addition was completed, the mixture was further stirred at −78° C. for 1.5 h. Then 2-isopropoxy-4,4,5,5-tetramethyl-1,3,2-dioxaborolane (15.03 g, 81 mmol) was added dropwise at this temperature. The mixture was warmed to rt (25° C.) and stirred for 16 h. TLC showed that the SM was consumed. The mixture was quenched with water (50 mL), and filtered. The filtrate was concentrated to remove the organic solvent and then extracted with EtOAc (150 mL×2). The combined organic layers were dried over Na$_2$SO$_4$, filtered and concentrated to afford the crude product. The crude product was diluted with PE (100 mL) and stirred vigorously at 25° C. for 1 h. The mixture was filtered, and the filter cake was dried to afford the title compound.

Methyl 4-(2-bromoacetyl)thiophene-2-carboxylate

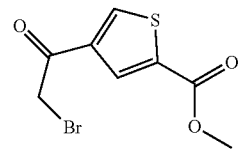

Step 1: methyl 4-acetylthiophene-2-carboxylate

To a solution of methyl 4-bromothiophene-2-carboxylate (8 g, 36.20 mmol) in toluene (100 mL) was added tributyl (1-ethoxyvinyl)stannane (15.68 g, 43.40 mmol) and PdCl$_2$(PPh$_3$)$_2$ (1.27 g, 1.81 mmol). The reaction mixture was degassed and refilled with N$_2$ 3 times and allowed to stir under N$_2$ balloon at 70° C. for 7 h. TLC showed the SM was consumed; the reaction was treated with sat. potassium fluoride (20 mL), then stirred for 1 h. The mixture was filtered and the filtrate was concentrated. The residue was dissolved in THF (40 mL) and 1M HCl (40 mL) was added. The mixture was stirred at 26° C. for another 1 h and concentrated. The residue was purified by column chromatography (SiO$_2$, PE: EtOAc=10:1 to 6:1) to afford the title compound.

Step 2: methyl 4-(2-bromoacetyl)thiophene-2-carboxylate

To a solution of methyl 4-acetylthiophene-2-carboxylate (6 g, 32.60 mmol) in THF (60 mL) was added pyridinium tribromide (10.42 g, 32.60 mmol). The reaction mixture was stirred at 25° C. for 7 h. TLC showed the SM was consumed. The reaction was diluted with water (20 mL), extracted with DCM (20 mL×3) and the combined organic layer was concentrated. The residue was purified by column chromatography (SiO$_2$, PE:EtOAc=10:1 to 6:1) to give the title compound. $^1$H NMR (CDCl3, 400 MHz): 8.33 (s, 1H) 8.19 (d, J=0.78 Hz, 1H) 4.30 (s, 2H) 3.92 (s, 3H).

2-Bromo-4-chloro-3-fluoroaniline

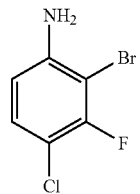

Step 1: tert-butyl (4-chloro-3-fluorophenyl)carbamate

To a solution of 4-chloro-3-fluoroaniline (7.50 g, 51.50 mmol) in DCM (150 mL) was added di-tert-butyl dicarbonate (11.96 mL, 51.5 mmol) dropwise. The reaction mixture was stirred at 25° C. for 16 h under N$_2$ atmosphere (balloon). TLC showed a new spot and the SM was consumed. The mixture was diluted with water (200 mL) and extracted with EtOAc (150 mL×2). The combined organic layers were dried over Na$_2$SO$_4$, filtered and the filtrate was concentrated. The residue was purified by flash silica gel chromatography (0-18% EtOAc/PE gradient) to afford the title compound.

Step 2: tert-butyl (2-bromo-4-chloro-3-fluorophenyl)carbamate

To a solution of tert-butyl (4-chloro-3-fluorophenyl)carbamate (1.00 g, 4.07 mmol) in THF (30 mL) was added isobutyllithium (10.18 mL, 10.18 mmol) dropwise at −78° C. The reaction mixture was stirred for 2 h. Then 1,2-dibromoethane (1.30 g, 6.92 mmol) was added dropwise. After 30 min, the mixture was stirred at 21° C. for 16 h under N$_2$ atmosphere (balloon). TLC showed still some SM remained and a new spot formed. The mixture was poured into water (30 mL), and extracted with EtOAc (20 mL×4). The combined organic layers were dried over Na$_2$SO$_4$, filtered and the filtrate was concentrated to afford the crude title compound which was used for next step without further purification.

Step 3: 2-bromo-4-chloro-3-fluoroaniline

To a solution of tert-butyl (2-bromo-4-chloro-3-fluorophenyl)carbamate (970 mg, 2.99 mmol) in DCM (20 mL) was added TFA (0.69 mL, 8.97 mmol), and the mixture was stirred for 4 h at 25° C. under N$_2$ atmosphere (balloon). TLC showed a new spot and SM was consumed. The mixture was concentrated. The residue was diluted with water (10 mL) and extracted with DCM (15 mL×3). The combined organic layers were dried over Na$_2$SO$_4$, filtered and the filtrate was concentrated to afford the title compound. $^1$HNMR (CDCl$_3$, 400 MHz): δ 7.07 (d, J=8.8 Hz, 1H), 6.48 (d, J=8.8 Hz, 1H).

EXAMPLE 1

Methyl [4-(2-{3-[5-chloro-2-(1H-tetrazol-1-yl)phenyl]-1-oxido-6,7-dihydro-5H-cyclopenta[b]pyridin-7-yl}-1H-imidazol-4-yl)phenyl]carbamate

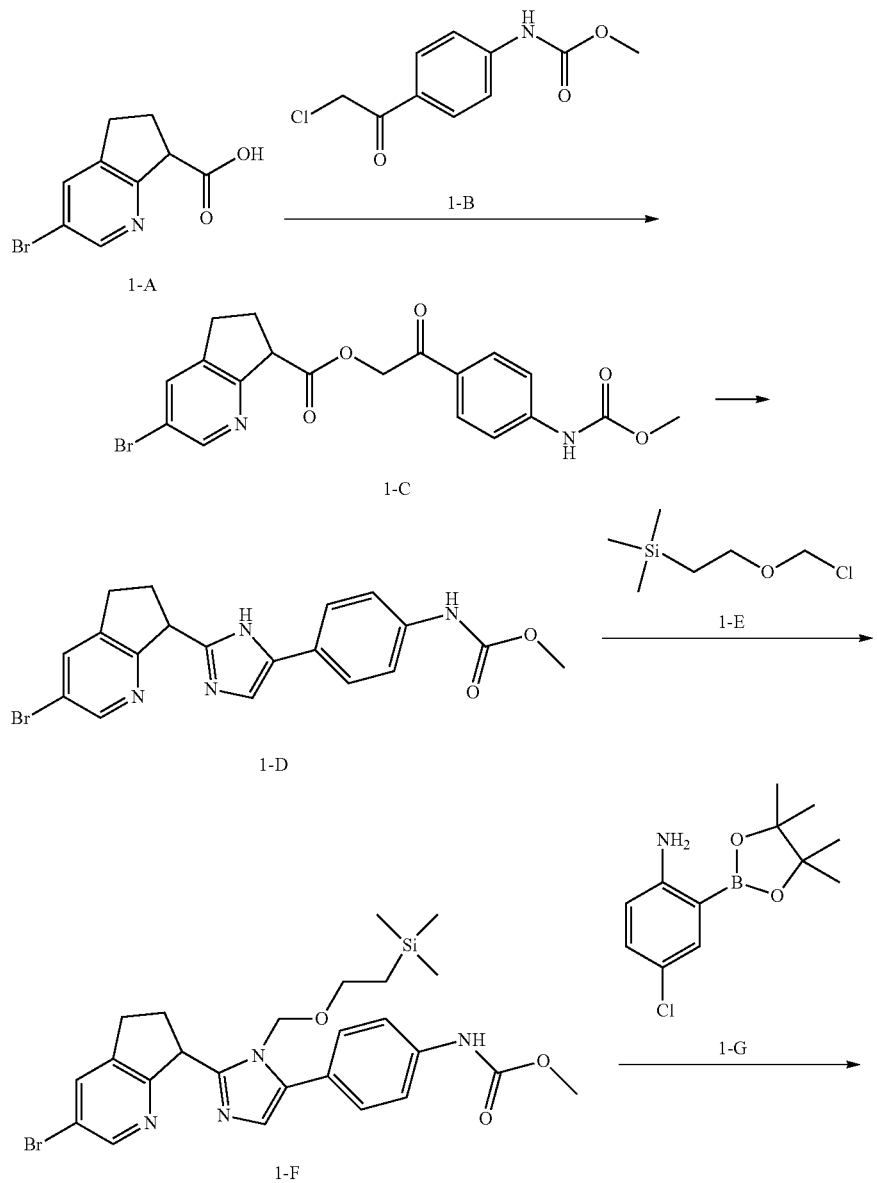

-continued
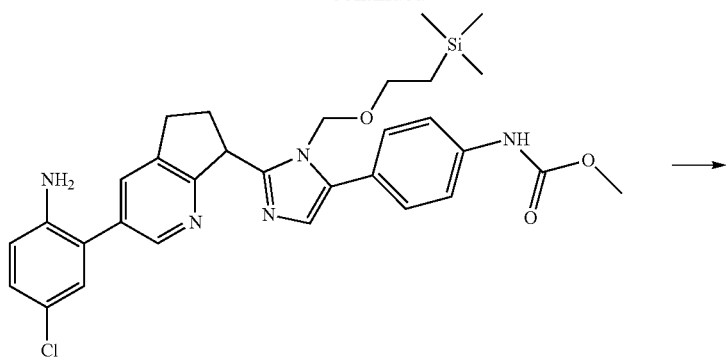
1-H
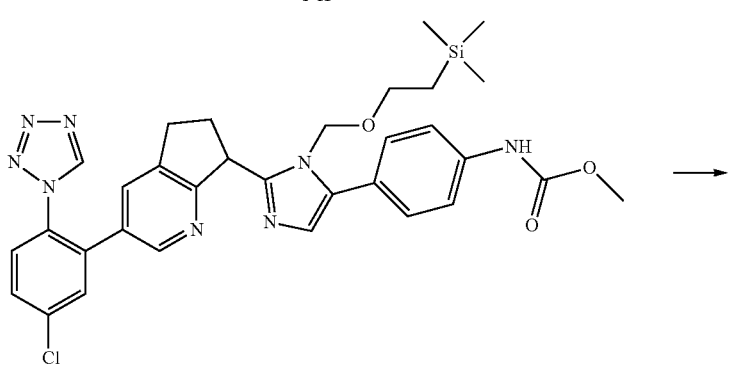
1-I
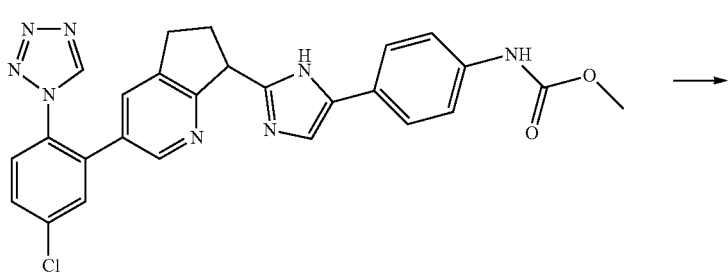
1-J
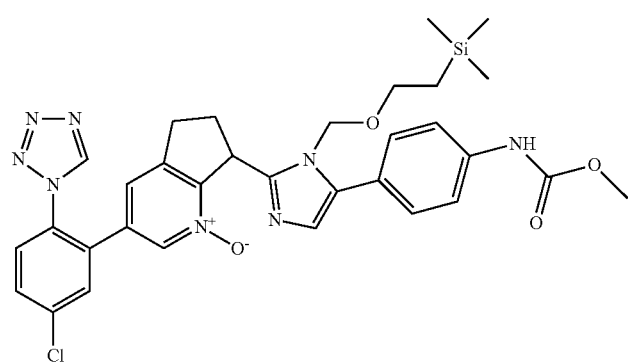
Example 1

Step 1: 2-(4-((methoxycarbonyl)amino)phenyl)-2-oxoethyl-3-bromo-6,7-dihydro-5H-cyclopenta-[b]pyridine-7-carboxylate (1-C)

To a solution the lithium salt of 3-bromo-6,7-dihydro-5H-cyclopenta[b]pyridine-7-carboxylic acid (1-A) in DMF (10 mL) was added methyl (4-(2-chloroacetyl)phenyl)carbamate (1-B) (1.685 g, 7.40 mmol). The reaction mixture was stirred overnight at rt and then at 90° C. for 3 hours until the reaction appeared complete by LCMS. The mixture was quenched with water and extracted with EtOAc. The organic phase was washed with brine, dried over $Na_2SO_4$ and concentrated. The residue was purified by column chromatography on silica gel (80 g), eluting with EtOAc/hexane to afford the title compound. MS (ESI) m/z 435.11 (M+H).

Step 2: Methyl (4-(2-(3-bromo-6,7-dihydro-5H-cyclopenta[b]pyridin-7-yl)-1H-imidazol-4-yl)-phenyl)carbamate (1-D)

2-(4-((methoxycarbonyl)amino)phenyl)-2-oxoethyl-3-bromo-6,7-dihydro-5H-cyclopenta[b]-pyridine-7-carboxylate (1-C) (1900 mg, 4.39 mmol) and ammonium acetate (1352 mg, 17.54 mmol) in toluene (10 mL) were heated to 150° C. using microwave irradiation for 30 min. The reaction mixture was cooled to rt, diluted with EtOAc, washed with brine, dried over $Na_2SO_4$, filtered and concentrated under vacuum. The crude product was purified by silica gel chromatography (0-100% EtOAc in hexane) to give recovered starting material and the title compound. MS (ESI) m/z 415.19 (M+H).

Step 3: Methyl (4-(2-(3-bromo-6,7-dihydro-5H-cyclopenta[b]pyridin-7-yl)-1-((2-(trimethylsilyl)-ethoxy)methyl)-1H-imidazol-4-yl)phenyl)carbamate (1-F)

To a solution of methyl (4-(2-(3-bromo-6,7-dihydro-5H-cyclopenta[b]pyridin-7-yl)-1H-imidazol-4-yl)-phenyl)carbamate (1-D) (420 mg, 1.02 mmol) in $CH_2Cl_2$ (10 mL) was added DIPEA (0.355 mL, 2.033 mmol) followed by SEM-Cl (1-E) (0.216 mL, 1.220 mmol). The reaction mixture was stirred at rt for 1 hr. After this time, the reaction was complete by LCMS. The mixture was diluted with water and extracted by EtOAc. The EtOAc layer was dried with $Na_2SO_4$, filtered, and concentrated. The residue was purified by column chromatography on silica gel (40 g), eluting with EtOAc/hexane (0-70%) to give the title compound. MS (ESI) m/z 545.31 (M+H). The product consisted of two regioisomers which were combined and used immediately in the next step.

Step 4: Methyl (4-(2-(3-(2-amino-5-chlorophenyl)-6,7-dihydro-5H-cyclopenta[b]pyridin-7-yl)-1-((2-(trimethylsilyl)ethoxy)methyl)-1H-imidazol-4-yl)phenyl)carbamate (1-H)

A mixture of 4-chloro-2-(4,4,5,5-tetramethyl-1,3,2-dioxaborolan-2-yl)aniline (1-G) (143 mg, 0.563 mmol), methyl (4-(2-(3-bromo-6,7-dihydro-5H-cyclopenta[b]pyridin-7-yl)-1-((2-(trimethylsilyl)-ethoxy)methyl)-1H-imidazol-4-yl)phenyl)carbamate (255 mg, 0.47 mmol), $PdCl_2$(dppf) (68.7 mg, 0.094 mmol) and cesium fluoride (143 mg, 0.938 mmol) in dioxane (5 mL) in a microwave tube was heated at 110° C. for 1 hr in an oil bath with vigorous stirring. The reaction mixture was diluted with water and extracted with EtOAc. The organic phase was washed by brine then concentrated. The residue was purified by column chromatography on silica gel (24 g), eluting with EtOAc/hexane (0-70%) to give the title compound. MS (ESI) m/z 590.44 (M+H).

Step 5: Methyl-(4-(2-(3-(5-chloro-2-(1H-tetrazol-1-yl)phenyl)-6,7-dihydro-5H-cyclopenta-[b]pyridin-7-yl)-1-((2-(trimethylsilyl)ethoxy)methyl)-1H-imidazol-4-yl)phenyl)carbamate (1-I)

A reaction vial was charged with methyl (4-(2-(3-(2-amino-5-chlorophenyl)-6,7-dihydro-5H-cyclopenta[b]pyridin-7-yl)-1-((2-(trimethylsilyl)ethoxy)methyl)-1H-imidazol-4-yl)phenyl)-carbamate (1-H) (270 mg, 0.457 mmol), followed by sodium azide (89 mg, 1.372 mmol) trimethoxymethane (146 mg, 1.372 mmol) and acetic acid. The reaction mixture was heated at rt overnight. The mixture was cooled, and the solvent was removed under vacuum. The residue was dissolved with ethyl acetate (50 mL), washed with water, brine, dried ($Na_2SO_4$), filtered, and the solvent was evaporated under reduced pressure. The residue was purified by column chromatography on silica gel (40 g), eluting with EtOAc/hexane (0-70%) to give the title compound. MS (ESI) m/z 643.43 (M+H).

Step 6: Methyl (4-(2-(3-(5-chloro-2-(1H-tetrazol-1-yl)phenyl)-6,7-dihydro-5H-cyclopenta[b]-pyridin-7-yl)-1H-imidazol-4-yl)phenyl)carbamate (1-J)

Methyl-(4-(2-(3-(5-chloro-2-(1H-tetrazol-1-yl)phenyl)-6,7-dihydro-5H-cyclopenta[b]pyridin-7-yl)-1-((2-(trimethylsilyl)ethoxy)methyl)-1H-imidazol-4-yl)phenyl)carbamate (1-I) (220 mg, 0.342 mmol) was dissolved in 1:1 DCM/TFA and the mixture was stirred at 50° C. for 1 hour. The reaction mixture was concentrated and purified by flash chromatography (24 g $SiO_2$, 0-10% MeOH in DCM) to provide the title compound. MS (ESI) m/z 513.31 (M+H).

Step 7: Methyl [4-(2-{3-[5-chloro-2-(1H-tetrazol-1-yl)phenyl]-1-oxido-6,7-dihydro-5H-cyclopenta[b]pyridin-7-yl}-1H-imidazol-4-yl)phenyl]carbamate (Example 1)

Methyl (4-(2-(3-(5-chloro-2-(1H-tetrazol-1-yl)phenyl)-6,7-dihydro-5H-cyclopenta[b]-pyridin-7-yl)-1H-imidazol-4-yl)phenyl)carbamate (1-J) (105.6 mg, 0.206 mmol) was dissolved in 5 mL of acetic acid, and peracetic acid (0.162 mL, 1.03 mmol) was added. The reaction mixture was stirred at rt for 4 hours. The reaction mixture was dried under vacuum and purified using RP-HPLC (Waters SunFire™ Prep $C_{18}$ OBD™ 5 μm 19×100 mm column, 0-100% MeCN in water with 0.05% TFA) to give the title compound as its TFA salt form. MS (ESI) m/z 529.46 (M+H). $^1$H NMR ($CD_3OD$) δ (ppm): 2.42 (m, 1H), 2.65 (m, 1H), 2.95 (m, 1H), 3.20 (m, 1H), 3.86 (s, 3H), 5.10 (t, 1H), 7.31 (d, 1H), 7.60 (m, 4H), 7.70-7.90 (m, 4H), 8.10 (s, 1H), 9.45 (s, 1H).

The following compounds were prepared following procedures similar to those described above using appropriate starting materials and characterized by LCMS.

| Example | Compound Name | Structure | LCMS [M + 1] |
|---|---|---|---|
| 2 (racemic) | methyl [4-(2-{3-[5-chloro-2-(1H-tetrazol-1-yl)phenyl]-1-oxido-6,7-dihydro-5H-cyclopenta[b]pyridin-7-yl}-4-methyl-1H-imidazol-5-yl)phenyl]carbamate | 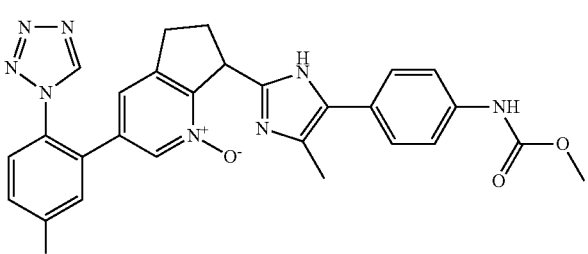 | 543.40 |
| 3 (racemic) | 3-[5-chloro-2-(1H-tetrazol-1-yl)phenyl]-7-[4-(3-fluorophenyl)-1H-imidazol-2-yl]-6,7-dihydro-5H-cyclopenta[b]pyridine-1-oxide | 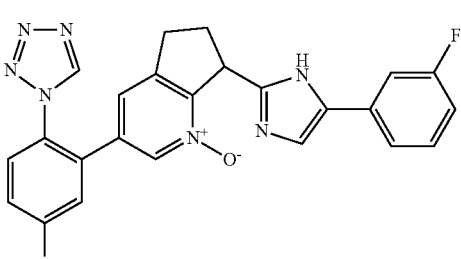 | 474.34 |
| 4 (racemic) | methyl 4-(2-{3-[5-chloro-2-(1H-tetrazol-1-yl)phenyl]-1-oxido-6,7-dihydro-5H-cyclopenta[b]pyridin-7-yl}-1H-imidazol-4-yl)-3-fluorothiophene-2-carboxylate | 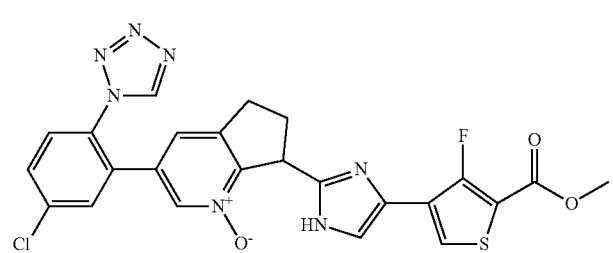 [SMILES: COC(=O)c1scc(-c2c[nH]c(C3CCc4cc(-c5cc(Cl)ccc5-n5cnnn5)c[n+]([O-])c43)n2)c1F] | 538.43 |
| 5 (racemic) | 3-[5-chloro-2-(1H-tetrazol-1-yl)phenyl]-7-[4-(3-fluorophenyl)-1H-imidazol-2-yl]-7-methyl-6,7-dihydro-5H-cyclopenta[b]pyridine-1-oxide | 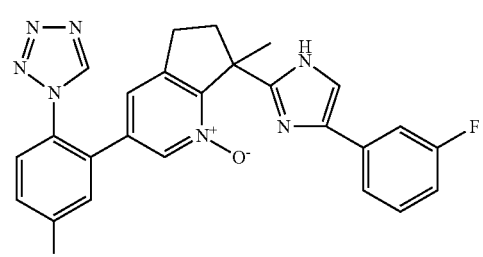 | 488.36 |
| 6 (racemic) | methyl [4-(2-{3-[5-chloro-2-(1H-tetrazol-1-yl)phenyl]-7-methyl-1-oxido-6,7-dihydro-5H-cyclopenta[b]pyridin-7-yl}-1H-imidazol-4-yl)phenyl]carbamate | 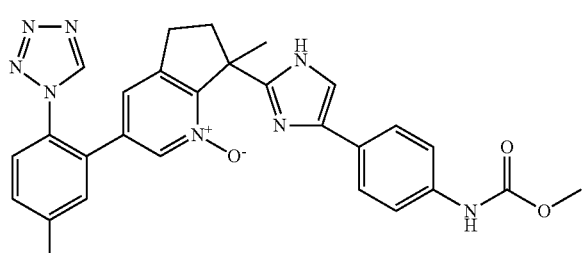 | 543.45 |

EXAMPLES 7-10

Methyl [4-(5-chloro-2-{3-[5-chloro-2-(1H-tetrazol-1-yl)phenyl]-1-oxido-6,7-dihydro-5H-cyclopenta[b]pyridin-7-yl}-1H-imidazol-4-yl)phenyl]carbamate (Example 7)   5

Methyl [4-(5-chloro-2-{3-[5-chloro-2-(1H-tetrazol-1-yl)phenyl]-7-hydroxy-1-oxido-6,7-dihydro-5H-cyclopenta[b]pyridin-7-yl}-1H-imidazol-4-yl)phenyl]carbamate (Example 8—racemic)   10

Methyl [4-(5-chloro-2-{3-[5-chloro-2-(1H-tetrazol-1-yl)phenyl]-7-hydroxy-1-oxido-6,7-dihydro-5H-cyclopenta[b]pyridin-7-yl}-1H-imidazol-4-yl)phenyl]carbamate   15

Example 9—Chiral, Non-Racemic

Methyl [4-(5-chloro-2-{3-[5-chloro-2-(1H-tetrazol-1-yl)phenyl]-7-hydroxy-1-oxido-6,7-dihydro-5H-cyclopenta[b]pyridin-7-yl}-1H-imidazol-4-yl)phenyl]carbamate   20

Example 10—Chiral, Non-Racemic

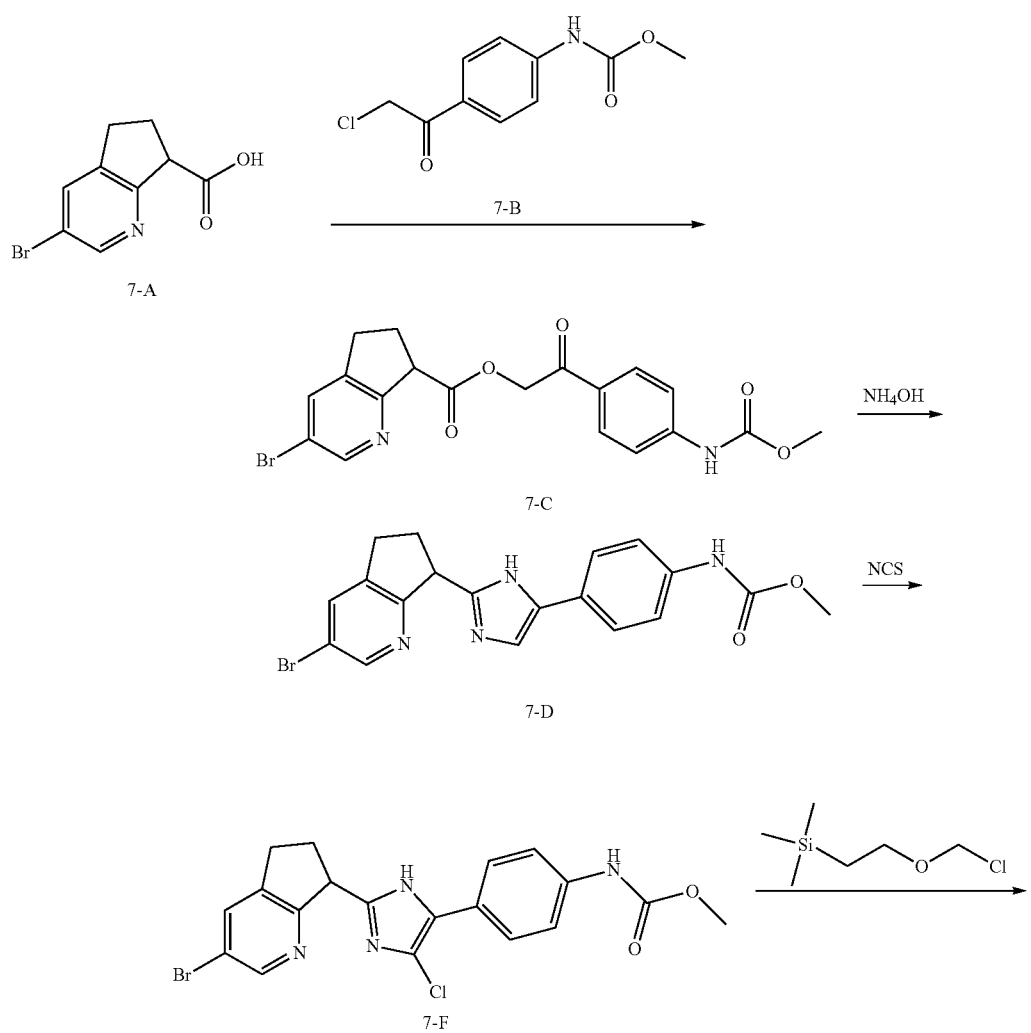

-continued
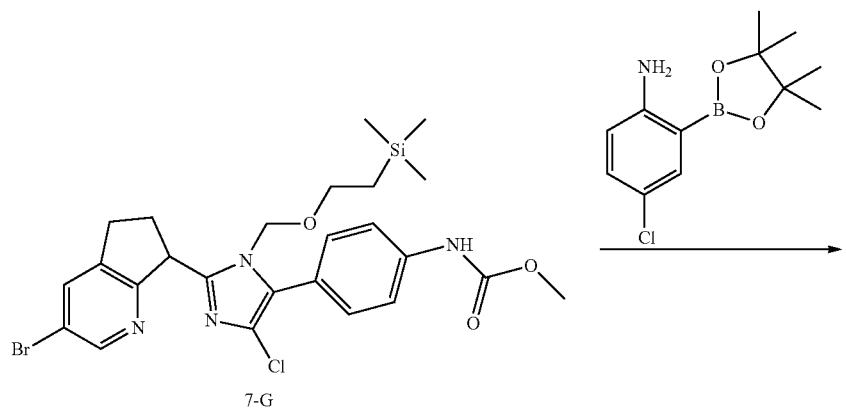
7-G
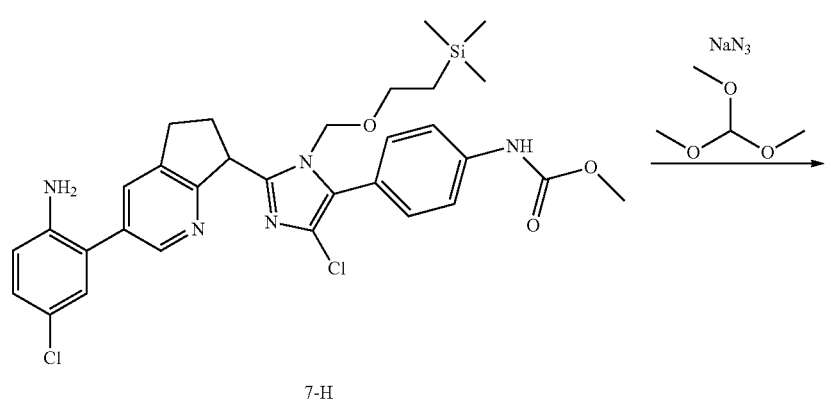
7-H
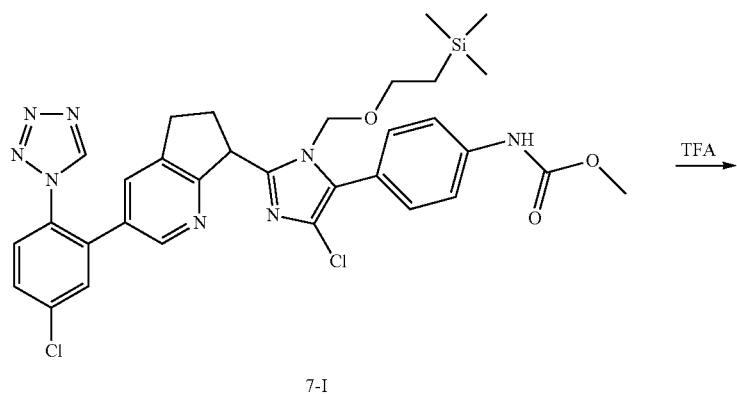
7-I
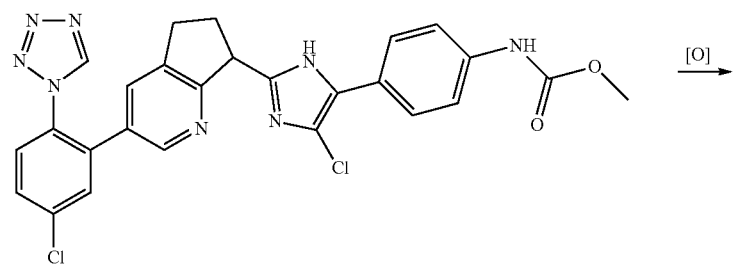
7-J

-continued

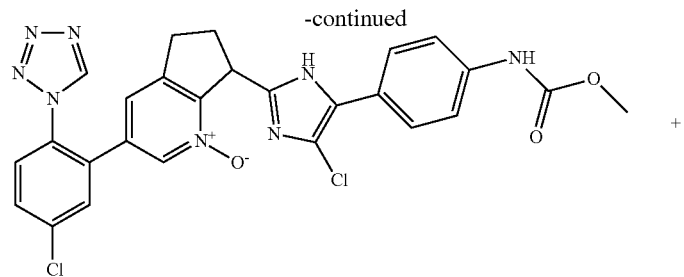

Example 7
(racemic)

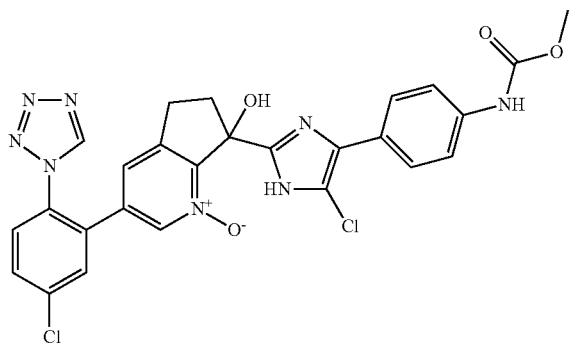

Example 8
(racemic)

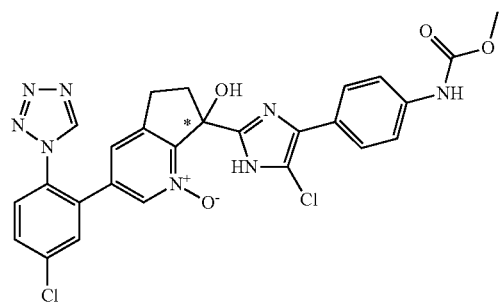

Example 9
(chiral, non-racemic)

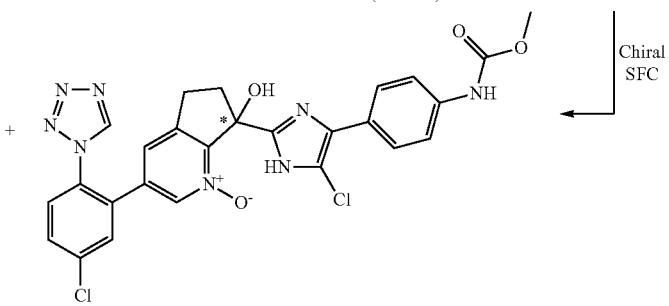

Example 10
(chiral, non-racemic)

Chiral SFC

Step 1: 2-(4-((methoxycarbonyl)amino)phenyl)-2-oxoethyl-3-bromo-6,7-dihydro-5H-cyclopenta-[b]pyridine-7-carboxylate (7-C)

To a solution the lithium salt of 3-bromo-6,7-dihydro-5H-cyclopenta[b]pyridine-7-carboxylic acid (7-A) in DMF (10 mL) was added methyl (4-(2-chloroacetyl)phenyl)carbamate (7-B) (1.685 g, 7.40 mmol). The reaction mixture was stirred overnight at rt and then at 90° C. for 3 hours until the reaction appeared complete by LCMS. The mixture was quenched with water and extracted with EtOAc. The organic phase was washed with brine, dried over $Na_2SO_4$ and concentrated. The residue was purified by column chromatography on silica gel (80 g), eluting with EtOAc/hexane to afford the title compound. MS (ESI) m/z 435.11 (M+H).

Step 2: Methyl (4-(2-(3-bromo-6,7-dihydro-5H-cyclopenta[b]pyridin-7-yl)-1H-imidazol-4-yl)-phenyl)carbamate (7-D)

2-(4-((methoxycarbonyl)amino)phenyl)-2-oxoethyl-3-bromo-6,7-dihydro-5H-cyclopenta[b]-pyridine-7-carboxylate (7-C) (1900 mg, 4.39 mmol) and ammonium acetate (1352 mg, 17.54 mmol) in toluene (10 mL) were heated to 150° C. using microwave irradiation for 30 min. The reaction mixture was cooled to rt, diluted with EtOAc, washed with brine, dried over $Na_2SO_4$, filtered and concentrated under vacuum. The crude product was purified by silica gel chromatography (0-100% EtOAc in hexane) to give recovered starting material and the title compound. MS (ESI) m/z 415.19 (M+H).

Step 3: methyl (4-(2-(3-bromo-6,7-dihydro-5H-cyclopenta[b]pyridin-7-yl)-4-chloro-1H-imidazol-5-yl)phenyl)carbamate (7-F)

Methyl (4-(2-(3-bromo-6,7-dihydro-5H-cyclopenta[b]pyridin-7-yl)-1H-imidazol-4-yl)-phenyl)carbamate (7-D) (2200 mg, 5.32 mmol) was dissolved in 100 mL of anhydrous DCM. To this solution at 0° C. was added N-chlorosuccinimide (853 mg, 6.39 mmol). The reaction mixture was stirred at rt for 4 hours until completion and then filtered and concentrated.

The crude product was purified by silica gel chromatography (0-100% EtOAc in hexane) to give the title compound. MS (ESI) m/z 447.30 (M+H).

Step 4: methyl (4-(2-(3-bromo-6,7-dihydro-5H-cyclopenta[b]pyridin-7-yl)-4-chloro-1-((2-(trimethylsilyl)ethoxy)methyl)-1H-imidazol-5-yl)phenyl)carbamate (7-G)

To a solution of methyl (4-(2-(3-bromo-6,7-dihydro-5H-cyclopenta[b]pyridin-7-yl)-4-chloro-1H-imidazol-5-yl)phenyl)carbamate (7-F) (1380 mg, 3.08 mmol) in $CH_2Cl_2$ (100 mL) was added DIPEA (1.077 mL, 6.160 mmol) followed by SEM-Cl (0.656 mL, 3.700 mmol) at 0° C. The reaction mixture was stirred at rt for 3 hr. After this time, the reaction was complete by LCMS. The mixture was diluted with water and extracted by DCM. The DCM layer was dried with $Na_2SO_4$, filtered, and concentrated. The residue was purified by column chromatography on silica gel (120 g), eluting with EtOAc/hexane (0-70%) to give the title compound as a gum. MS (ESI) m/z 577.00 (M+H). The product consisted of two regioisomers which were combined and used immediately in the next step.

Step 5: methyl (4-(2-(3-(2-amino-5-chlorophenyl)-6,7-dihydro-5H-cyclopenta[b]pyridin-7-yl)-4-chloro-1-((2-(trimethylsilyl)ethoxy)methyl)-1H-imidazol-5-yl)phenyl)carbamate (7-H)

A mixture of 4-chloro-2-(4,4,5,5-tetramethyl-1,3,2-dioxaborolan-2-yl)aniline (7-G) (432 mg, 1.703 mmol), methyl (4-(2-(3-bromo-6,7-dihydro-5H-cyclopenta[b]pyridin-7-yl)-4-chloro-1-((2-(trimethylsilyl)ethoxy)methyl)-1H-imidazol-5-yl)phenyl)carbamate (7-G) (820 mg, 1.42 mmol), $PdCl_2(dppf)$ (104 mg, 0.142 mmol) and cesium fluoride (431 mg, 2.84 mmol) in dioxane (20 mL) in a microwave tube was heated at 110° C. for 2 hrs in an oil bath with vigorous stirring. The reaction mixture was diluted with water and extracted with EtOAc. The organic phase was washed with brine then concentrated. The residue was purified by column chromatography on silica gel (80 g), eluting with EtOAc/hexane (0-70%) to give the title compound. MS (ESI) m/z 624.61 (M+H).

Step 6: methyl (4-(4-chloro-2-(3-(5-chloro-2-(1H-tetrazol-1-yl)phenyl)-6,7-dihydro-5H-cyclopenta[b]pyridin-7-yl)-1-((2-(trimethylsilyl)ethoxy)methyl)-1H-imidazol-5-yl)phenyl)carbamate (7-I)

A reaction vial was charged with methyl (4-(2-(3-(2-amino-5-chlorophenyl)-6,7-dihydro-5H-cyclopenta[b]pyridin-7-yl)-4-chloro-1-((2-(trimethylsilyl)ethoxy)methyl)-1H-imidazol-5-yl)phenyl)carbamate (7-H) (670 mg, 1.073 mmol), followed by sodium azide (418 mg, 6.44 mmol), trimethoxymethane (683 mg, 6.44 mmol) and acetic acid (2 mL). The reaction mixture was stirred at rt overnight. The mixture was cooled, and the solvent was removed under vacuum. The residue was dissolved with ethyl acetate (50 mL), washed with water, brine, dried ($Na_2SO_4$), filtered and the solvent was evaporated under reduced pressure. The residue was purified by column chromatography on silica gel (40 g), eluting with EtOAc/hexane (0-70%) to give the title compound. MS (ESI) m/z 677.59 (M+H).

Step 7: methyl (4-(4-chloro-2-(3-(5-chloro-2-(1H-tetrazol-1-yl)phenyl)-6,7-dihydro-5H-cyclopenta[b]pyridin-7-yl)-1H-imidazol-5-yl)phenyl)carbamate (7-J)

Methyl (4-(4-chloro-2-(3-(5-chloro-2-(1H-tetrazol-1-yl)phenyl)-6,7-dihydro-5H-cyclopenta[b]pyridin-7-yl)-1-((2-(trimethylsilyl)ethoxy)methyl)-1H-imidazol-5-yl)phenyl)carbamate (7-I) (300 mg, 0.443 mmol) was dissolved in 1:2 DCM/TFA and the mixture was stirred at rt for 2 hours. The reaction mixture was concentrated and purified by flash chromatography (24 g $SiO_2$, 0-10% MeOH in DCM) to provide the title compound. MS (ESI) m/z 457.43 (M+H).

Step 8: Methyl [4-(5-chloro-2-{3-[5-chloro-2-(1H-tetrazol-1-yl)phenyl]-1-oxido-6,7-dihydro-5H-cyclopenta[b]pyridin-7-yl}-1H-imidazol-4-yl)phenyl]carbamate (Example 7) and methyl [4-(5-chloro-2-{3-[5-chloro-2-(1H-tetrazol-1-yl)phenyl]-7-hydroxy-1-oxido-6,7-dihydro-5H-cyclopenta[b]pyridin-7-yl}-1H-imidazol-4-yl)phenyl]carbamate (Example 8)

Methyl (4-(4-chloro-2-(3-(5-chloro-2-(1H-tetrazol-1-yl)phenyl)-6,7-dihydro-5H-cyclopenta[b]pyridin-7-yl)-1H-imidazol-5-yl)phenyl)carbamate (5-J) (210 mg, 0.284 mmol) was dissolved in 3 mL of acetic acid, and peracetic acid (0.364 mL, 1.918 mmol) was added. The reaction mixture was stirred at rt for 16 hrs. The reaction mixture was dried under vacuum and purified by flash chromatography (24 g $SiO_2$, 20-100% EtOAc in hexane) to provide the title compounds Example 7, MS (ESI) m/z 563.37 (M+H) and Example 8 MS (ESI) m/z 579.50 (M+H) in approximately a 1:1 ratio.

Step 9: methyl [4-(5-chloro-2-{3-[5-chloro-2-(1H-tetrazol-1-yl)phenyl]-7-hydroxy-1-oxido-6,7-dihydro-5H-cyclopenta[b]pyridin-7-yl}-1H-imidazol-4-yl)phenyl]carbamate (Example 9) methyl [4-(5-chloro-2-{3-[5-chloro-2-(1H-tetrazol-1-yl)phenyl]-7-hydroxy-1-oxido-6,7-dihydro-5H-cyclopenta[b]pyridin-7-yl}-1H-imidazol-4-yl)phenyl]carbamate (Example 10)

The racemic mixture of 3-(5-chloro-2-(1H-tetrazol-1-yl)phenyl)-7-(5-chloro-4-(4-((methoxycarbonyl)amino)phenyl)-1H-imidazol-2-yl)-7-hydroxy-6,7-dihydro-5H-cyclopenta[b]pyridine-1-oxide from above (30 mg, 0.052 mmol) was separated using chiral SFC (IC (2×15 cm column) using 40% (2:1) methanol:MeCN (0.1% DEA)/$CO_2$ at 100 bar and 60 mL/min). The separation yielded Example 9 (SFC retention time=4.58 min. chemical purity>99%, ee>99%) and Example 10 (SFC retention time=6.95 min. chemical purity>99%, ee>98%). The absolute configurations of Examples 9 and 10 were not assigned.

EXAMPLE 11

4-(2-{3-[5-chloro-2-(1H-tetrazol-1-yl)phenyl]-1-oxido-6,7-dihydro-5H-cyclopenta[b]pyridin-7-yl}-1H-imidazol-4-yl)-3-fluorothiophene-2-carboxylic acid

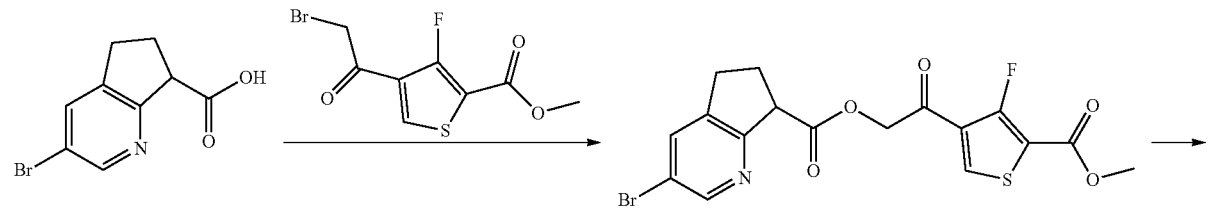

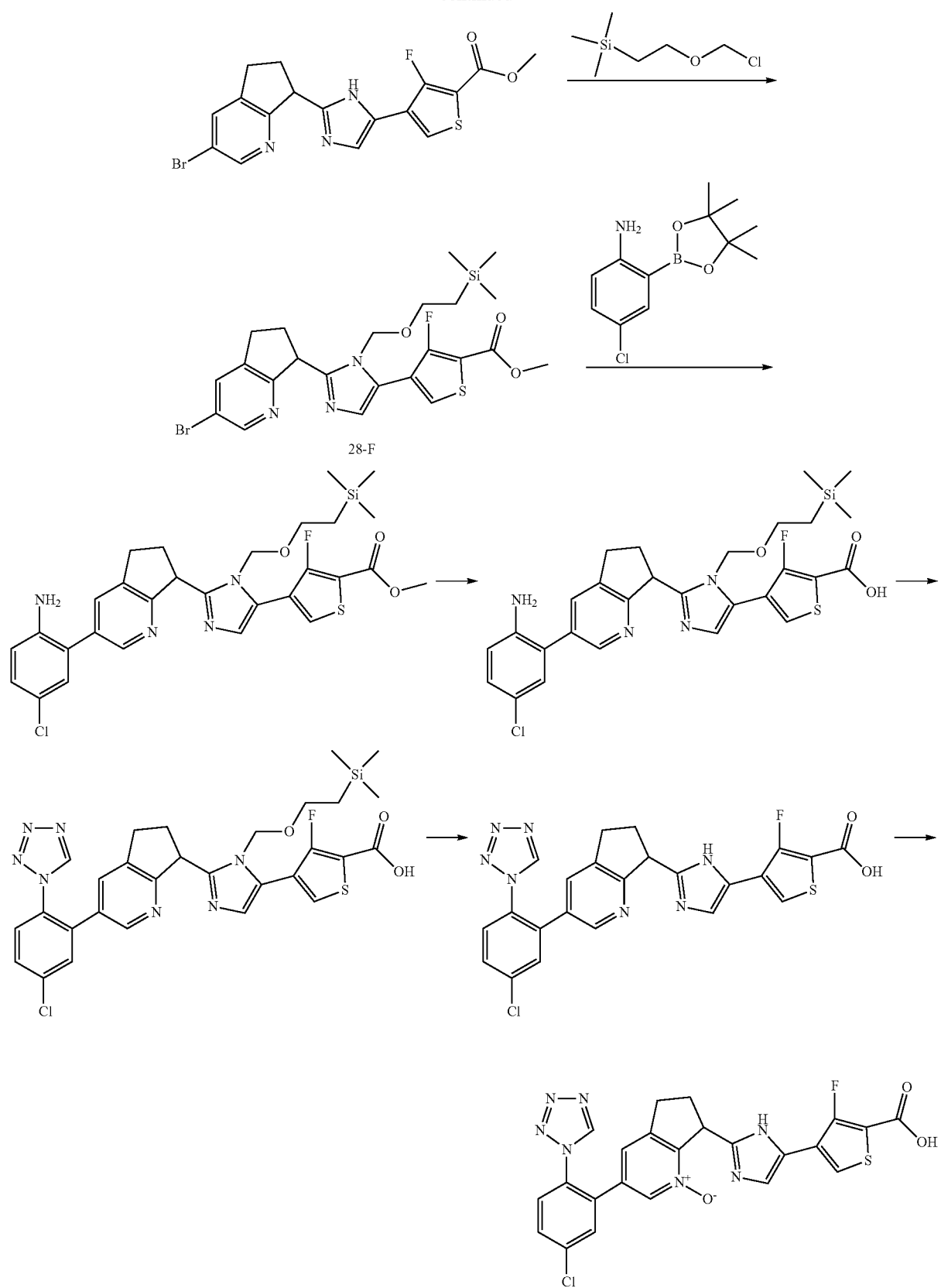
28-F
Example 11

Step 1: 2-(4-Fluoro-5-(methoxycarbonyl)thiophen-3-yl)-2-oxoethyl-3-bromo-6,7-dihydro-5H-cyclopenta[b]pyridine-7-carboxylate A mixture of cesium carbonate (234 mg, 0.717 mmol), 3-bromo-6,7-dihydro-5H-cyclopenta[b]pyridine-7-carboxylic acid (347 mg, 1.43 mmol), and methyl 4-(2-bromoacetyl)-3-fluorothiophene-2-carboxylate (403 mg, 1.43 mmol) in DMF (10 mL) was stirred at rt over the weekend. The mixture was quenched with water and extracted with EtOAc. The organic phase was washed with brine, dried over $MgSO_4$, and then concentrated. The residue was purified by column chromatography on silica gel (80 g), eluting with EtOAc/hexane to afford the title compound. MS (ESI) m/z 444.22 (M+H).

Step 2: Methyl 4-(2-(3-bromo-6,7-dihydro-5H-cyclopenta[b]pyridin-7-yl)-1H-imidazol-4-yl)-3-fluorothiophene-2-carboxylate A mixture of 2-(4-fluoro-5-(methoxycarbonyl)thiophen-3-yl)-2-oxoethyl-3-bromo-6,7-dihydro-5H-cyclopenta-[b]pyridine-7-carboxylate (405 mg, 0.916 mmol) and ammonium acetate (353 mg, 4.58 mmol) in toluene (8 mL) was heated at 148° C. under microwave irradiation for 25 min. By LCMS, 40% of the starting material had been converted to the title compound. The reaction mixture was cooled to rt and toluene was evaporated off. The residue was partitioned between EtOAc and water. The organic layer was washed with brine, dried over $MgSO_4$ and concentrated. A second reaction was carried out as described above. The crude products from the two reactions were combined, and the residue was purified by column chromatography on silica gel (120 g), eluting with 0-40% (1:3 EtOH/EtOAc) in hexane to give the title compound. MS (ESI) m/z 424.25 (M+H).

Step 3: Methyl 4-(2-(3-bromo-6,7-dihydro-5H-cyclopenta[b]pyridin-7-yl)-1H-imidazol-4-yl)-3-fluorothiophene-2-carboxylate To a solution of methyl 4-(2-(3-bromo-6,7-dihydro-5H-cyclopenta[b]pyridin-7-yl)-1H-imidazol-4-yl)-3-fluorothiophene-2-carboxylate in DCM (7 mL) was added DIEA (0.210 mL, 1.204 mmol) followed by 2-(trimethylsilyl) ethoxymethyl chloride (0.128 mL, 0.722 mmol). The reaction mixture was stirred at RT for 1 hr, diluted with water and extracted by EtOAc. The organic phase was dried with $MgSO_4$ then concentrated. The residue was purified by column chromatography on silica gel (40 g), eluting with 0-30% (1:3 EtOH/EtOAc) in hexane to give the title compound. MS (ESI) m/z 552.5 (M+H).

Step 4: Methyl 4-(2-(3-(2-amino-5-chlorophenyl)-6,7-dihydro-5H-cyclopenta[b]pyridin-7-yl)-1-((2-(trimethylsilyl)ethoxy)methyl)-1H-imidazol-4-yl)-3-fluorothiophene-2-carboxylate A mixture of methyl 4-(2-(3-bromo-6,7-dihydro-5H-cyclopenta[b]pyridin-7-yl)-1H-imidazol-4-yl)-3-fluorothiophene-2-carboxylate (163 mg, 0.295 mmol), 4-chloro-2-(4,4,5,5-tetramethyl-1,3,2-dioxaborolan-2-yl)aniline (90 mg, 0.354 mmol), PdCl2(dppf)$PdCl_2$(dppf) (43.2 mg, 0.059 mmol) and cesium fluoride (134 mg, 0.885 mmol) was mixed in a 20 mL microwave vial. The mixture was evacuated and purged with nitrogen gas, and this process was repeated three times. The reaction mixture was heated to 100° C. for 1 hr. After cooling to rt, the reaction mixture was filtered through a pad of celite, and the celite pad was washed with EtOAc. The combined filtrates were concentrated under vacuum. The crude product was purified by silica gel chromatography, eluting with 0-50% (1:3 EtOH/EtOAc) in hexane to give the title compound. MS (ESI) m/z 599.53 (M+H).

Step 5: 4-(2-(3-(2-Amino-5-chlorophenyl)-6,7-dihydro-5H-cyclopenta[b]pyridin-7-yl)-1-((2-(trimethylsilyl)ethoxy)methyl)-1H-imidazol-4-yl)-3-fluorothiophene-2-carboxylic acid A mixture of methyl 4-(2-(3-(2-amino-5-chlorophenyl)-6,7-dihydro-5H-cyclopenta[b]pyridin-7-yl)-1-((2-(trimethylsilyl)ethoxy)methyl)-1H-imidazol-4-yl)-3-fluorothiophene-2-carboxylate (132 mg, 0.220 mmol), 2 M aqueous lithium hydroxide (220 µL, 0.441 mmol), and 2.2 mL THF was heated at 50° C. for 2 hours. The mixture was cooled then stored in the refrigerator over the weekend, then heated at 50° C. for another 3 hours. The reaction mixture was concentrated to remove THF. The residue was combined with water to make a solution. The solution was combined with 1 N aqueous HCl to achieve pH~5. A precipitate formed. The suspension was extracted with ethyl acetate two times. The combined organic layers were washed with brine, dried over $MgSO_4$, filtered, and concentrated to afford the title compound. MS (ESI) m/z 585.50 (M+H). The crude product was used in the next step without additional purification.

Step 6: 4-(2-(3-(5-Chloro-2-(1H-tetrazol-1-yl)phenyl)-6,7-dihydro-5H-cyclopenta[b]pyridin-7-yl)-1-((2-(trimethylsilyl)ethoxy)methyl)-1H-imidazol-4-yl)-3-fluorothiophene-2-carboxylic acid A mixture of 4-(2-(3-(2-amino-5-chlorophenyl)-6,7-dihydro-5H-cyclopenta[b]pyridin-7-yl)-1-((2-(tri-methylsilyl)ethoxy)methyl)-1H-imidazol-4-yl)-3-fluorothiophene-2-carboxylic acid (129 mg, 0.215 mmol), sodium azide (42.0 mg, 0.646 mmol) and trimethyl orthoformate (0.071 mL, 0.646 mmol) was stirred at RT overnight. A saturated, aqueous solution of $NaHCO_3$ was added carefully with cooling in an ice bath. The resulting mixture was extracted with EtOAc. The organic phase was washed with brine, dried and concentrated in vacuo. The residue was purified by prep TLC (7% MeOH/DCM+1% HOAc) to give the title compound. MS (ESI) m/z 638.54 (M+H).

Step 7: 4-(2-(3-(5-Chloro-2-(1H-tetrazol-1-yl)phenyl)-6,7-dihydro-5H-cyclopenta[b]pyridin-7-yl)-1H-imidazol-4-yl)-3-fluorothiophene-2-carboxylic acid A mixture of 4-(2-(3-(5-chloro-2-(1H-tetrazol-1-yl)phenyl)-6,7-dihydro-5H-cyclopenta-[b]-pyridin-7-yl)-1-((2-(trimethylsilyl)ethoxy)methyl)-1H-imidazol-4-yl)-3-fluorothiophene-2-carboxylic acid (65 mg, 0.102 mmol), 0.5 mL DCM, and 1.0 mL TFA was stirred at rt for 2.5 hr. The reaction mixture was stored in the refrigerator over the weekend. After this time, the reaction mixture was concentrated. The residue was combined with DCM, and the mixture was concentrated again. This process was repeated three times to afford the title compound as a trifluoroacetate salt which was used in the next step without additional purification. MS (ESI) m/z 508.41 (M+H).

Step 8: 4-(2-{3-[5-chloro-2-(1H-tetrazol-1-yl)phenyl]-1-oxido-6,7-dihydro-5H-cyclopenta[b]-pyridin-7-yl}-1H-imidazol-4-yl)-3-fluorothiophene-2-carboxylic acid (Example 11)

A mixture of 4-(2-(3-(5-chloro-2-(1H-tetrazol-1-yl)phenyl)-6,7-dihydro-5H-cyclopenta[b]pyridin-7-yl)-1H-imidazol-4-yl)-3-fluorothiophene-2-carboxylic acid, peracetic acid (0.099 mL, 0.523 mmol), and acetic acid (1.5 mL) was stirred at rt for 5 hr. The mixture was stored in the refrigerator overnight, and then stirred again at rt for 7 hr. The reaction was cooled over an ice bath and quenched with 10% aqueous NaHSO$_3$/Na$_2$S$_2$O$_4$. Water was added, and the mixture was extracted with EtOAc three times. A grey solid suspended between the organic and aqueous layers was removed. The organic layer was washed with brine, dried over MgSO$_4$, filtered and concentrated in vacuo. The crude product was purified by preparative C18 RP-HPLC, eluting with 0-100% MeCN in water with 0.1% TFA, to give the title compound in its TFA salt form. MS (ESI) m/z 524.43 (M+H).

The following compound was prepared following procedures similar to those described above using appropriate starting materials and characterized by LCMS.

| Example | Compound Name | Structure | LCMS [M + 1] | FXIa Ki (nM) |
|---|---|---|---|---|
| 12 | 5-(2-{3-[5-chloro-2-(1H-tetrazol-1-yl)phenyl]-1-oxido-6,7-dihydro-5H-cyclopenta[b]pyridin-7-yl}-1H-imidazol-5-yl)thiophene-2-carboxylic acid | 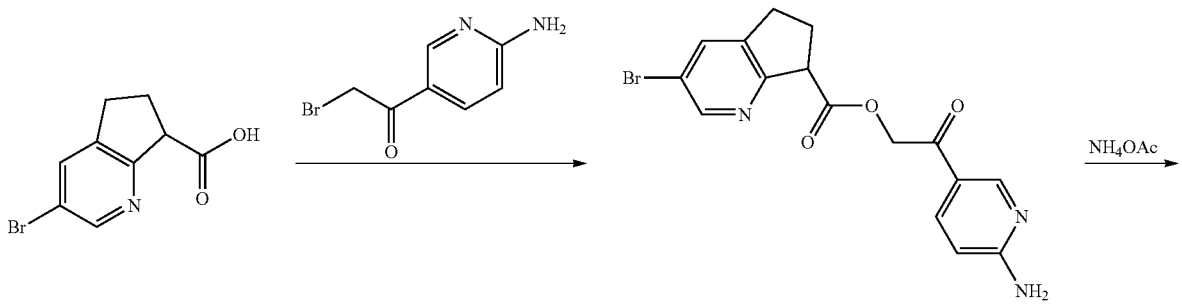 | 506.16 | 3.08 |

EXAMPLES 13-14

7-(5-(6-aminopyridin-3-yl)-1H-imidazol-2-yl)-3-(5-chloro-2-(1H-tetrazol-1-yl)phenyl)-6,7-dihydro-5H-cyclopenta[b]pyridine-1-oxide (Example 13)

7-(5-(6-aminopyridin-3-yl)-1H-imidazol-2-yl)-3-(5-chloro-2-(1H-tetrazol-1-yl)phenyl)-7-hydroxy-6,7-dihydro-5H-cyclopenta[b]pyridine-1-oxide (Example 14)

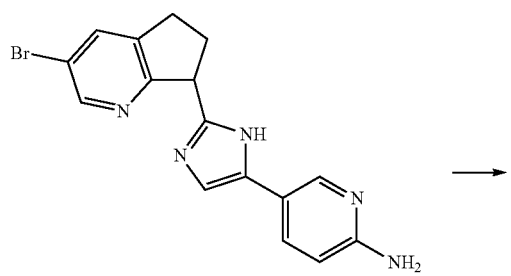

-continued
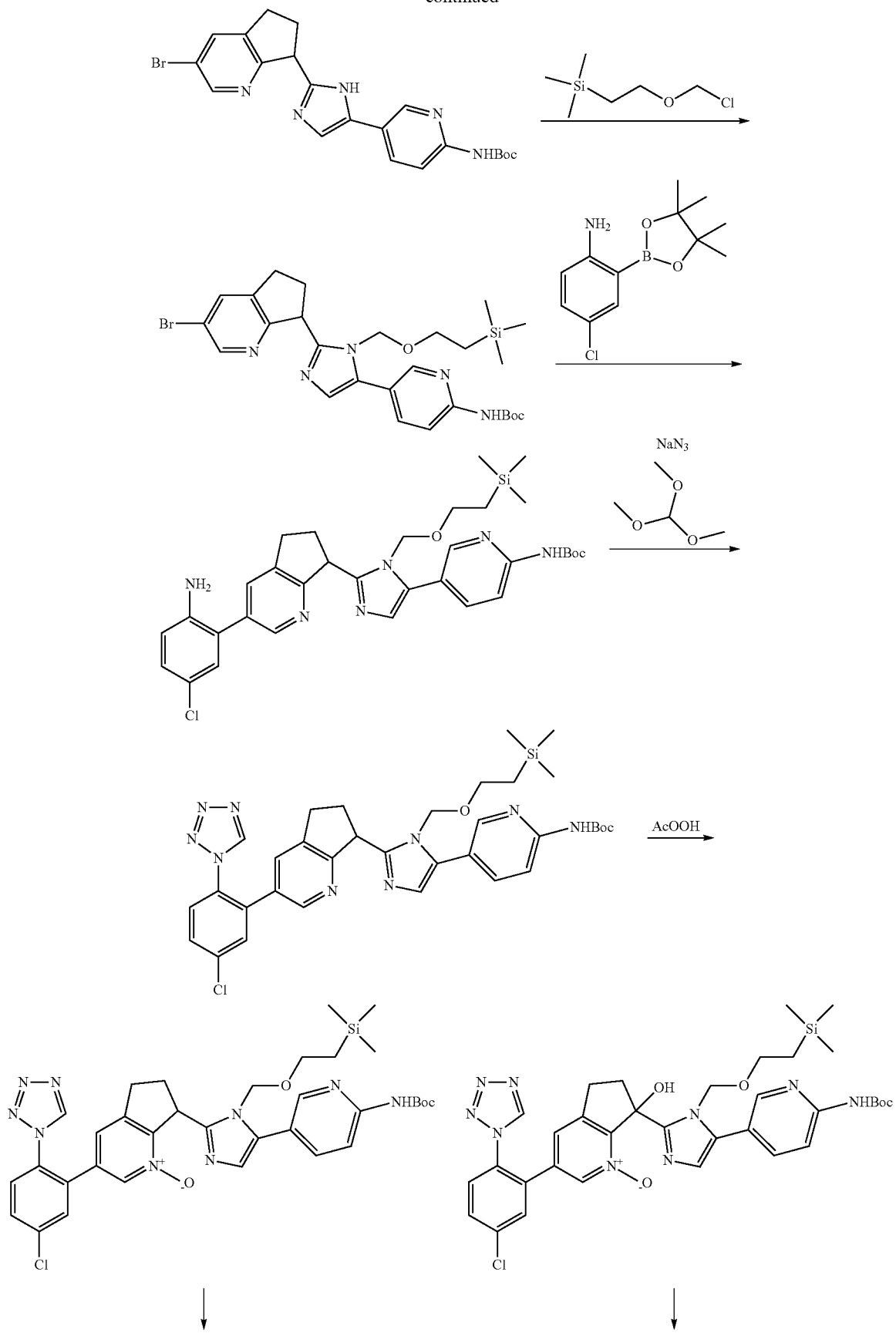

81                                                               82

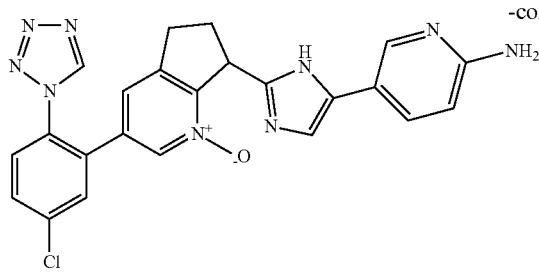

Example 13

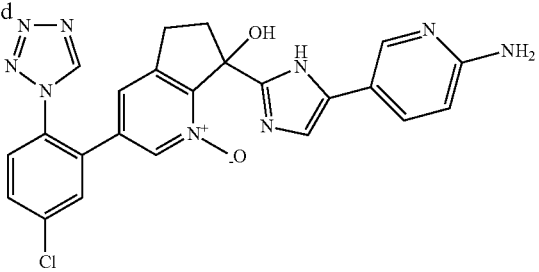

Example 14

Step 1: 2-(6-aminopyridin-3-yl)-2-oxoethyl 3-bromo-6,7-dihydro-5H-cyclopenta[b]pyridine-7-carboxylate Lithium 3-bromo-6,7-dihydro-5H-cyclopenta[b]pyridine-7-carboxylate (2700 mg, 11 mmol), 1-(6-aminopyridin-3-yl)-2-bromoethanone HBr (3900 mg, 13 mmol), and Hunig's base (4.27 ml, 24 mmol) were mixed in DMF (50 ml). The mixture was stirred at 50° C. for 2 hour. DMF was removed under vacuum. The residue was diluted with 300 mL of ethyl acetate and 50 mL of methanol, and washed with diluted sodium bicarbonate solution. The aq. layer was extracted with ethyl acetate/methanol. The combined organic solution was dried over anhydrous sodium sulfate. After it was concentrated, the crude was dissolved in THF/Methanol and mixed with silica gel. After it was concentrated to dryness, the silica gel powder was dry-loaded, and purified by column chromatography on silica gel eluting with 50~100% EtOAc/isohexane to give the product. MS (ESI) m/z 378 (M+H).

Step 2: 5-(2-(3-bromo-6,7-dihydro-5H-cyclopenta[b]pyridin-7-yl)-1H-imidazol-5-yl)pyridin-2-amine 2-(6-aminopyridin-3-yl)-2-oxoethyl 3-bromo-6,7-dihydro-5H-cyclopenta[b]pyridine-7-carboxylate (1000 mg, 2.66 mmol) and ammonium acetate (2049 mg, 26.6 mmol) were mixed in toluene (22 ml) and acetic acid (2.2 ml). The mixture was put in a capped microwave vial was heated at 120° C. for 30 minutes. The mixture was concentrated to remove toluene and acetic acid, then dissolved in methanol (50 mL). A solution of 4 N NH$_3$ in methanol was added to free up the product as free base. Silica gel powder was added. The slurry was concentrated to dryness, then dry-loaded to a silica gel pad, which was connected to a 80-gram silica gel column. The product was eluted with gradient 3 to 10% MeOH in DCM, then 10% MeOH in DCM to give the title product. MS (ESI) m/z 358 (M+H).

Step 3: tert-butyl (5-(2-(3-bromo-6,7-dihydro-5H-cyclopenta[b]pyridin-7-yl)-1H-imidazol-5-yl)pyridin-2-yl)carbamate 5-(2-(3-bromo-6,7-dihydro-5H-cyclopenta[b]pyridin-7-yl)-1H-imidazol-5-yl)pyridin-2-amine (600 mg, 1.7 mmol) in THF (6 ml) was mixed with (BOC)$_2$O (1.1 ml, 5.0 mmol). Acetonitrile (6 ml) and DMAP (206 mg, 1.684 mmol) were added. The mixture was then stirred at rt overnight and then concentrated. The residue was dissolved in 10 mL of methanol and concentrated ammonium hydroxide (2 mL) was added. The mixture was then stirred at rt overnight. The mixture was concentrated, the residue was dissolved in a mixed solvent of methanol and acetone. Silica gel powder was added. After it was concentrated to dryness, the silica gel with crude product was dry-loaded and to a 40 g column, and eluting with 0~8% gradient methanol/DCM gave a 1:1 mixture of mono-Boc- and di-Boc-protected products. MS (ESI) m/z 458 (M+H for mono-Boc). 558 (M+H for di-Boc).

Step 4: tert-butyl (5-(2-(3-bromo-6,7-dihydro-5H-cyclopenta[b]pyridin-7-yl)-1-((2-(trimethylsilyl)ethoxy)methyl)-1H-imidazol-5-yl)pyridin-2-yl)carbamate Tert-butyl (5-(2-(3-bromo-6,7-dihydro-5H-cyclopenta[b]pyridin-7-yl)-1H-imidazol-4-yl)pyridin-2-yl)carbamate (274 mg, 0.6 mmol) and its di-Boc derivative (334 mg, 0.600 mmol) in DCM (9 ml) was cooled in an ice-water bath. SEM-Cl (0.24 ml, 1.3 mmol) was added, followed by Hunig's base (0.692 ml, 3.96 mmol). The mixture was stirred overnight, while the mixture slowly warmed up to rt. The mixture was diluted with ethyl acetate, and washed with 1N HCl solution, and brine. The organic layer was separated, and dried over anhydrous sodium sulfate. After it was filtered and concentrated, the crude was purified by column chromatography on silica gel eluting with gradient 0~100% EtOAc/isohexane to give the product. MS (ESI) m/z 588 (M+H for mono-Boc). 688 (M+H for di-Boc).

Step 5: tert-butyl (5-(2-(3-(2-amino-5-chlorophenyl)-6,7-dihydro-5H-cyclopenta[b]pyridin-7-yl)-1-((2-(trimethylsilyl)ethoxy)methyl)-1H-imidazol-5-yl)pyridin-2-yl)carbamate The mixture of tert-butyl (5-(2-(3-bromo-6,7-dihydro-5H-cyclopenta[b]pyridin-7-yl)-1-((2-(trimethylsilyl)ethoxy)methyl)-1H-imidazol-4-yl)pyridin-2-yl)carbamate (0.11 g, 0.188 mmol) and its di-Boc derivative (0.129 g, 0.188 mmol) was mixed with 4-chloro-2-(4,4,5,5-tetramethyl-1,3,2-dioxaborolan-2-yl)aniline (0.114 g, 0.450 mmol), PdCl$_2$(dppf) (0.055 g, 0.075 mmol), and CsF (0.171 g, 1.125 mmol) in a microwave reaction vial. The vial was capped. Air was removed and it was back-filled with nitrogen (×3). 1,4-Dioxane (4 ml) was introduced with syringe. Air was removed again and back-filled with nitrogen. The mixture was then heated to 100° C. for 1 hour. The mixture was filtered through a celite pad, and further washed with ethyl acetate. The solution was concentrated, and purified by column chromatography on silica gel eluting with gradient 0~100% EtOAc/isohexane to give the product. MS (ESI) m/z 633 (M+H for mono-Boc), 733 (M+H for di-Boc).

Step 6: tert-butyl (5-(2-(3-(5-chloro-2-(1H-tetrazol-1-yl)phenyl)-6,7-dihydro-5H-cyclopenta[b]pyridin-7-yl)-1-((2-(trimethylsilyl)ethoxy)methyl)-1H-imidazol-5-yl)pyridin-2-yl)carbamate Tert-butyl (5-(2-(3-(2-amino-5-chlorophenyl)-6,7-dihydro-5H-cyclopenta[b]pyridin-7-yl)-1-((2-(trimethylsilyl)ethoxy)methyl)-1H-imidazol-4-yl)pyridin-2-yl)carbamate (0.101 g, 0.16 mmol) and its di-Boc derivative (0.11 g, 0.16 mmol) were mixed with sodium azide (0.062 g, 0.960 mmol) and trimethyl orthoformate (0.106 ml, 0.960 mmol) in acetic acid (2 ml). The vial was capped and stirred at rt overnight. Toluene (20 mL) was added, and the mixture was concentrated to dryness. The crude was then purified by column chromatography on silica gel eluting with gradient 0~100% EtOAc/isohexane to give the product. MS (ESI) m/z 686 (M+H for mono-Boc), 786 (M+H for di-Boc).

Step 7: 7-(5-(6-((tert-butoxycarbonyl)amino)pyridin-3-yl)-1-((2-(trimethylsilyl)ethoxy)methyl)-1H-imidazol-2-yl)-3-(5-chloro-2-(1H-tetrazol-1-yl)phenyl)-6,7-dihydro-5H-cyclopenta[b]pyridine-1-oxide and 7-(5-(6-(((tert-butoxycarbonyl)amino)pyridin-3-yl)-1-((2-(trimethylsilyl)ethoxy)methyl)-1H-imidazol-2-yl)-3-(5-chloro-2-(1H-tetrazol-1-yl)phenyl)-7-hydroxy-6,7-dihydro-5H-cyclopenta[b]pyridine-1-oxide The product from step 6 (110 mg, 0.140 mmol) was mixed with peracetic acid (0.290 ml, 1.399 mmol) in acetic acid (1.5 ml). The resulting mixture was stirred at rt overnight.
Toluene (10 mL) was added. The mixture was concentrated. The crude was purified by column chromatography on silica gel eluting with 0~100% EtOAc/isohexane to give the two title products. MS (ESI) m/z 702.5 (M+H for mono-Boc), 802.5 (M+H for di-Boc) for mono-oxidation products. MS (ESI) m/z 718.6 (M+H for mono-Boc), 816.6 (M+H for di-Boc) for bis-oxidation products

Step 8: 7-(5-(6-aminopyridin-3-yl)-1H-imidazol-2-yl)-3-(5-chloro-2-(1H-tetrazol-1-yl)phenyl)-6,7-dihydro-5H-cyclopenta[b]pyridine-1-oxide (Example 13)

The mono-oxidation product from step 7 (20 mg, 0.025 mmol) was dissolved in DCM (0.3 ml). TFA (0.6 ml) was added. The mixture was stirred at rt overnight, then the mixture was diluted with 5 mL of toluene, and then evaporated to dryness using rotary evaporator. The crude was purified by preparative RP-HPLC (C-18), eluting with acetonitrile/water+0.1% TFA. The fractions were lyophilized to give the title product. MS (ESI) m/z 472.

Step 9: 7-(5-(6-aminopyridin-3-yl)-1H-imidazol-2-yl)-3-(5-chloro-2-(1H-tetrazol-1-yl)phenyl)-7-hydroxy-6,7-dihydro-5H-cyclopenta[b]pyridine-1-oxide (Example 14)

The di-oxidation product from step 7 (18 mg, 0.022 mmol) was stirred in TFA (0.4 ml) and DCM (0.20 ml) at rt overnight. Toluene was added to the reaction mixture, and the mixture was concentrated under vacuum. The crude was purified by preparative RP-HPLC (C-18), eluting with acetonitrile/water+0.1% TFA, to give the title product. MS (ESI) m/z 488.

EXAMPLE 15

Methyl [4-(2-{3-[5-chloro-2-(1H-tetrazol-1-yl)phenyl]-5-hydroxy-1-oxido-6,7-dihydro-5H-cyclopenta[b]pyridin-7-yl}-1H-imidazol-5-yl)phenyl]carbamate (four stereoisomers)

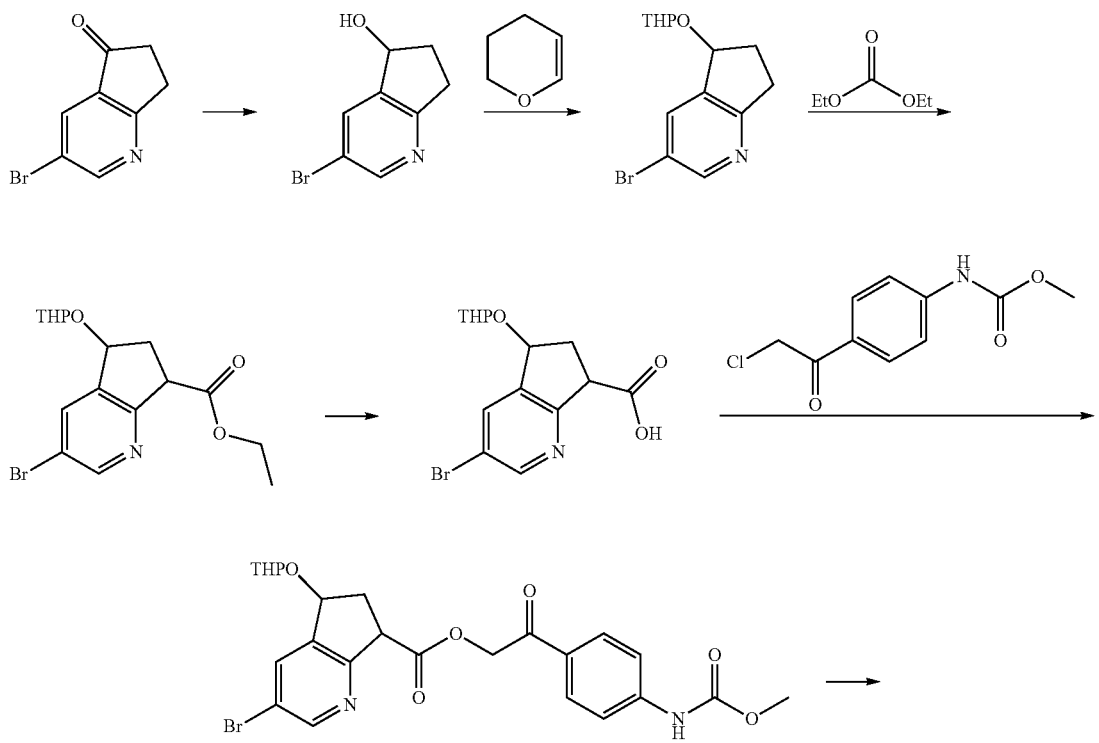

-continued
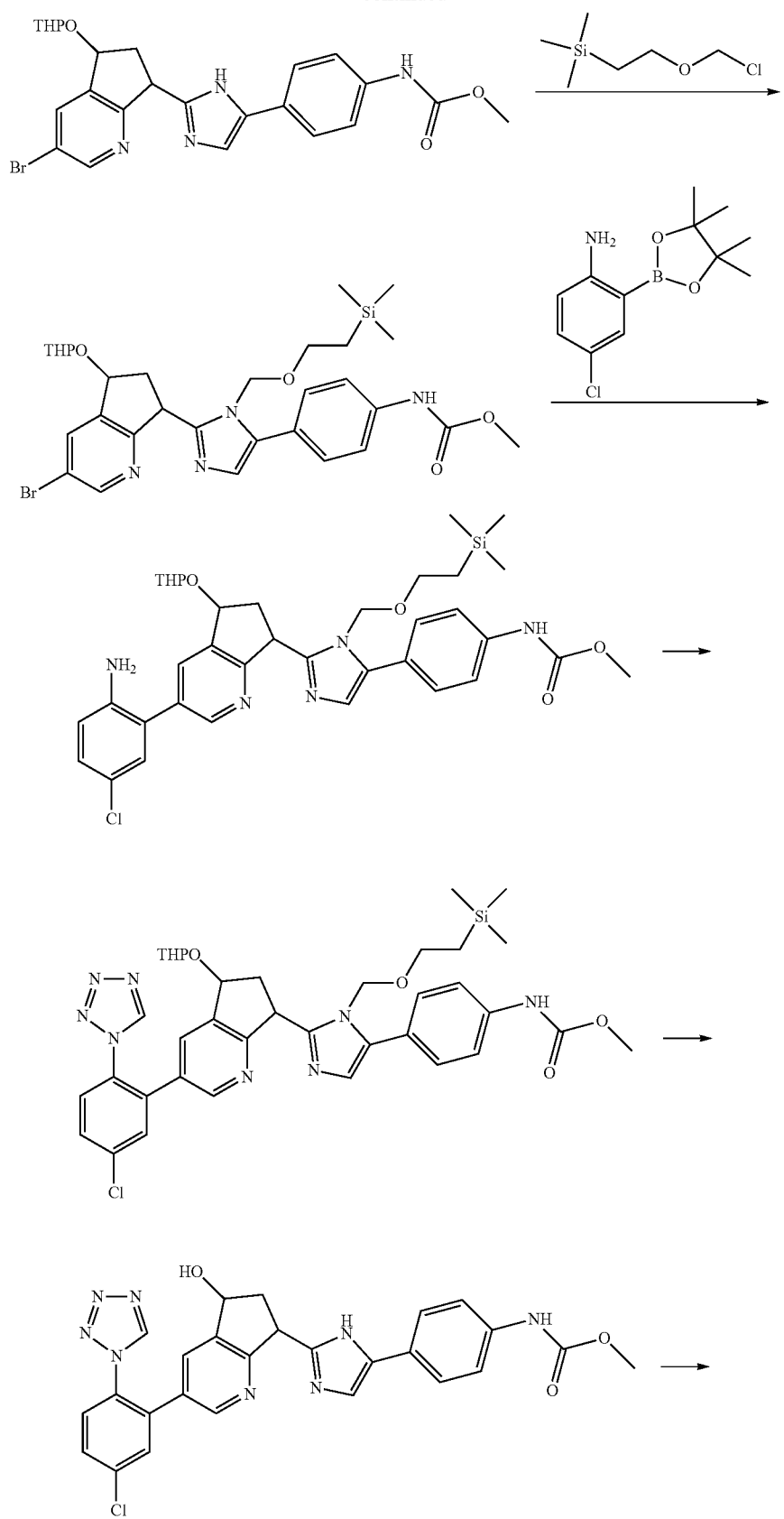

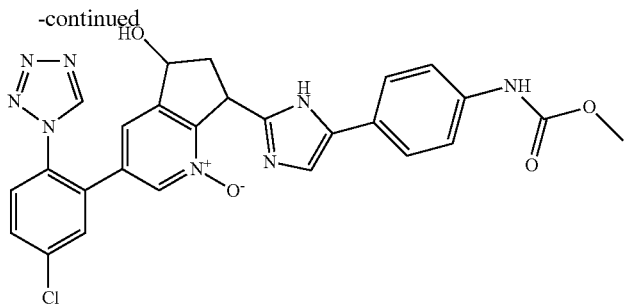

Example 15
(four stereoisomers)

Step 1: 3-Bromo-6,7-dihydro-5H-cyclopenta[b]pyridin-5-ol

To 3-bromo-6,7-dihydro-5H-cyclopenta[b]pyridin-5-one (300 mg, 1.415 mmol) in ethanol (14 mL) was added sodium borohydride (107 mg, 2.83 mmol) portionwise at rt. The reaction mixture was stirred at rt for 2.5 h before 10% aqueous HCl was added. The volatiles were evaporated under vacuum, and the aqueous layer was treated with 1 N aqueous NaOH. It was then extracted twice with EtOAc (40 mL), and the combined organic layers were dried over $Na_2SO_4$, filtered and concentrated under vacuum to provide the title compound. MS (ESI) m/z 216.0 (M+H). The crude product was used directly in the next step.

Step 2: 3-Bromo-5-((tetrahydro-2H-pyran-2-yl)oxy)-6,7-dihydro-5H-cyclopenta[b]pyridine A solution of 3-bromo-6,7-dihydro-5H-cyclopenta[b]pyridin-5-ol (3350 mg, 15.65 mmol), 3,4-dihydro-2H-pyran (2284 µl, 25.04 mmol) and pyridinium p-toluenesulfonate (787 mg, 3.13 mmol) in DCM (41 mL) was stirred at rt overnight. The reaction mixture was poured into a saturated $NaHCO_3$ solution and then extracted with DCM. The extract was washed with brine, dried over $Na_2SO_4$, filtered and concentrated under vacuum. The residue was purified by silica gel chromatography eluting with 0-90% EtOAc in hexanes to give the title compound. MS (ESI) m/z 297.0 (M+H).

Step 3: Ethyl-3-bromo-5-((tetrahydro-2H-pyran-2-yl)oxy)-6,7-dihydro-5H-cyclopenta[b]-pyridine-7-carboxylate To 3-bromo-5-((tetrahydro-2H-pyran-2-yl)oxy)-6,7-dihydro-5H-cyclopenta[b]pyridine, (1930 mg, 6.47 mmol) in THF (65 mL) at −78° C. was added 1.0 M LHMDS (16.2 mL, 16.2 mmol) slowly via a syringe. The reaction mixture was stirred at the same temperature for 1 h, then diethyl carbonate (1971 µl, 16.18 mmol) was added dropwise via a syringe. The dry-ice/acetone bath was removed, and the reaction mixture was warmed to rt and stirred overnight. Saturated aqueous $NH_4Cl$ was added to quench the reaction, and the solvent was evaporated under vacuum. To the residue was added EtOAc, and the mixture was washed with brine. The organic layer was dried over $Na_2SO_4$, filtered and concentrated under vacuum. The crude was purified by silica gel chromatography (0-40% EtOAc in hexanes) to give the title compound as two separated diastereomeric mixtures. For each mixture, MS (ESI) m/z 369.0 (M+H).

Step 4: 3-Bromo-5-((tetrahydro-2H-pyran-2-yl)oxy)-6,7-dihydro-5H-cyclopenta[b]pyridine-7-carboxylic acid The less polar isomer of ethyl-3-bromo-5-((tetrahydro-2H-pyran-2-yl)oxy)-6,7-dihydro-5H-cyclopenta[b]pyridine-7-carboxylate (1254 mg, 3.39 mmol) in THF (16.9 mL) was treated with 2.0 M aqueous LiOH (6774 µl, 13.55 mmol). The reaction mixture was stirred at rt overnight, and then the volatiles were evaporated under vacuum. The residue was diluted with EtOAc, acidified with 1 N aqueous HCl until pH 4 was achieved. The organic layer was washed with water and then dried over $Na_2SO_4$, filtered and concentrated under vacuum to afford the title compound. MS (ESI) m/z 344.3 (M+H). The crude product was used directly in the next step. A second hydrolysis reaction was carried out as described above using the more polar isomer of ethyl-3-bromo-5-((tetrahydro-2H-pyran-2-yl)oxy)-6,7-dihydro-5H-cyclopenta[b]pyridine-7-carboxylate as the starting material.

Step 5: 2-(4-((Methoxycarbonyl)amino)phenyl)-2-oxoethyl 3-bromo-5-((tetrahydro-2H-pyran-2-yl)oxy)-6,7-dihydro-5H-cyclopenta[b]pyridine-7-carboxylate The isomer of 3-bromo-5-((tetrahydro-2H-pyran-2-yl)oxy)-6,7-dihydro-5H-cyclopenta[b]pyridine-7-carboxylic acid derived from the less polar isomer in Step 3 (1159 mg, 3.39 mmol), methyl (4-(2-chloroacetyl)phenyl)carbamate (771 mg, 3.39 mmol) and cesium carbonate (1104 mg, 3.39 mmol) were mixed in DMF (16.9 mL) and stirred at rt overnight. The mixture was concentrated under vacuum, diluted with water and extracted twice with EtOAc (50.0 mL). The combined organic layers were washed with water, brine, dried over $Na_2SO_4$, filtered and concentrated under vacuum. The crude was purified by silica gel chromatography to give the title compound. MS (ESI) m/z 535.3 (M+H). A second reaction was carried out as described above using the isomer of 3-bromo-5-((tetrahydro-2H-pyran-2-yl)oxy)-6,7-dihydro-5H-cyclopenta[b]pyridine-7-carboxylic acid from the more polar isomer in Step 3 as the starting material.

Step 6: Methyl (4-(2-(3-bromo-5-((tetrahydro-2H-pyran-2-yl)oxy)-6,7-dihydro-5H-cyclopenta-[b]pyridin-7-yl)-1H-imidazol-5-yl)phenyl)carbamate The combined isomers of 2-(4-((methoxycarbonyl)amino)phenyl)-2-oxoethyl 3-bromo-5-((tetrahydro-2H-pyran-2-yl)oxy)-6,7-dihydro-5H-cyclopenta[b]pyridine-7-carboxylate (515 mg, 0.966 mmol) and ammonium acetate (298 mg, 3.86 mmol) in toluene (9.7 mL) were heated at 150° C. using microwave irradiation for 30 min. The reaction mixture was diluted with EtOAc, washed with brine, dried over $Na_2SO_4$, filtered and concentrated under vacuum. The crude was purified by silica gel chromatography (24 g $SiO_2$) eluting with 0-100% EtOAc in hexanes to give the title compound. MS (ESI) m/z 515.3 (M+H).

Step 7: Methyl (4-(2-(3-bromo-5-((tetrahydro-2H-pyran-2-yl)oxy)-6,7-dihydro-5H-cyclopenta-[b]pyridin-7-yl)-1-((2-(trimethylsilyl)ethoxy)methyl)-1H-imidazol-5-yl)phenyl)carbamate To a solution of methyl (4-(2-(3-bromo-5-((tetrahydro-2H-pyran-2-yl)oxy)-6,7-dihydro-5H-cyclopenta[b]-pyridin-7-yl)-1H-imidazol-5-yl)phenyl)carbamate (493 mg, 0.960 mmol) in DCM (9.6 mL) was added DIPEA (335 µl, 1.92 mmol) followed by 2-(trimethylsilyl)ethoxymethyl chloride (204 µl, 1.15 mmol). The reaction mixture was stirred at rt for 2 h before brine was added. The mixture was extracted twice with DCM (30.0 mL), and the combined organic layers were dried over $Na_2SO_4$, filtered and concentrated under vacuum. The crude was purified by silica gel chromatography (24 g $SiO_2$) eluting with 0-100% EtOAc in hexanes to give methyl (4-(2-(3-bromo-5-((tetrahydro-2H-pyran-2-yl)oxy)-6,7-dihydro-5H-cyclopenta[b]pyridin-7-yl)-1-((2-(tri-methylsilyl)ethoxy)methyl)-1H-imidazol-5-yl)-phenyl)carbamate. MS (ESI) m/z 645.5 (M+H).

Step 8: Methyl (4-(2-(3-(2-amino-5-chlorophenyl)-5-((tetrahydro-2H-pyran-2-yl)oxy)-6,7-dihydro-5H-cyclopenta[b]pyridin-7-yl)-1-((2-(trimethylsilyl)ethoxy)methyl)-1H-imidazol-5-yl)-phenyl)carbamate A mixture of methyl (4-(2-(3-bromo-5-((tetrahydro-2H-pyran-2-yl)oxy)-6,7-dihydro-5H-cyclopenta[b]pyridin-7-yl)-1-((2-(trimethylsilyl)ethoxy)methyl)-1H-imidazol-5-yl)phenyl)-carbamate (244 mg, 0.379 mmol), 4-chloro-2-(4,4,5,5-tetramethyl-1,3,2-dioxaborolan-2-yl)aniline (96 mg, 0.379 mmol), $PdCl_2$(dppf) (41.6 mg, 0.057 mmol) and cesium fluoride (173 mg, 1.137 mmol) in a round-bottom flask was evacuated under vacuum and purged with $N_2$. This process was repeated three times. Dioxane (3.8 mL) was then added, and the slurry mixture was heated at 110° C. for 1 h. After cooling to rt, the reaction mixture was filtered through a pad of celite, rinsed with EtOAc, and the filtrate was concentrated under vacuum. The crude product was purified by silica gel chromatography (24 g $SiO_2$) eluting with 0-100% EtOAc in hexanes to give methyl (4-(2-(3-(2-amino-5-chlorophenyl)-5-((tetrahydro-2H-pyran-2-yl)oxy)-6,7-dihydro-5H-cyclopenta[b]-pyridin-7-yl)-1-((2-(trimethylsilyl)ethoxy)-methyl)-1H-imidazol-5-yl)phenyl)carbamate. MS (ESI) m/z 690.6 (M+H).

Step 9: (4-(2-(3-(5-Chloro-2-(1H-tetrazol-1-yl)phenyl)-5-((tetrahydro-2H-pyran-2-yl)oxy)-6,7-dihydro-5H-cyclopenta[b]pyridin-7-yl)-1-((2-(trimethylsilyl)ethoxy)methyl)-1H-imidazol-5-yl)phenyl)carbamate A mixture of methyl (4-(2-(3-(2-amino-5-chlorophenyl)-5-((tetrahydro-2H-pyran-2-yl)oxy)-6,7-dihydro-5H-cyclopenta[b]pyridin-7-yl)-1-((2-(trimethylsilyl)ethoxy)methyl)-1H-imidazol-5-yl)phenyl)carbamate (545 mg, 0.790 mmol), trimethyl orthoformate (262 µl, 2.37 mmol) and sodium azide (154 mg, 2.37 mmol) in AcOH (7.9 mL) was stirred at rt overnight. The solvent was evaporated under vacuum, and to the crude product was added EtOAc. The organic layer was washed with saturated aqueous $NaHCO_3$, dried over $Na_2SO_4$, filtered and concentrated under vacuum. The crude product was purified by silica gel chromatography (24 g $SiO_2$) eluting with 0-85% EtOAc in hexane to give methyl (4-(2-(3-(5-chloro-2-(1H-tetrazol-1-yl)phenyl)-5-((tetrahydro-2H-pyran-2-yl)oxy)-6,7-dihydro-5H-cyclopenta[b]pyridin-7-yl)-1-((2-(trimethyl-silyl)ethoxy)methyl)-1H-imidazol-5-yl)phenyl)carbamate. MS (ESI) m/z 743.7 (M+H).

Step 10: Methyl (4-(2-(3-(5-chloro-2-(1H-tetrazol-1-yl)phenyl)-5-hydroxy-6,7-dihydro-5H-cyclopenta[b]pyridin-7-yl)-1H-imidazol-5-yl)phenyl)carbamate Methyl (4-(2-(3-(5-chloro-2-(1H-tetrazol-1-yl)phenyl)-5-((tetrahydro-2H-pyran-2-yl)oxy)-6,7-dihydro-5H-cyclopenta[b]pyridin-7-yl)-1-((2-(trimethylsilyl)ethoxy)methyl)-1H-imidazol-5-yl)phenyl)carbamate (304 mg, 0.409 mmol) was dissolved in DCM (1.5 mL) and TFA (3 mL, 38.9 mmol) was added dropwise via a syringe. The reaction was stirred at rt for 3 h before being concentrated under vacuum. The residue was dissolved in EtOAc and washed with saturated aqueous $NaHCO_3$. The organic layer was dried over $Na_2SO_4$, filtered and concentrated under vacuum to afford the title compound. MS (ESI) m/z 529.5 (M+H). The crude product was used directly in the next step without purification.

Step 11: Methyl [4-(2-{3-[5-chloro-2-(1H-tetrazol-1-yl)phenyl]-5-hydroxy-1-oxido-6,7-dihydro-5H-cyclopenta[b]pyridin-7-yl}-1H-imidazol-5-yl)phenyl]carbamate (Example 15)

To a mixture of methyl (4-(2-(3-(5-chloro-2-(1H-tetrazol-1-yl)phenyl)-5-hydroxy-6,7-dihydro-5H-cyclopentah-[b]pyridin-7-yl)-1H-imidazol-5-yl)phenyl)carbamate (216 mg, 0.408 mmol) in AcOH (4.0 mL) was added ethaneperoxoic acid (232 µl, 1.23 mmol). The reaction mixture was stirred at rt overnight and concentrated under vacuum. The crude residue was purified by RPHPLC (19×100 mm Waters) (Bridge C18 column, 5µ particle size, linear gradient, 1% to 100% ACN in $H_2O$ buffering with 0.05% TFA) to give a mixture of four isomers of the title compound. MS (ESI) m/z 545.5 (M+H).

EXAMPLES 16-19

Methyl [4-(2-{3-[5-chloro-2-(1H-tetrazol-1-yl)phenyl]-5,7-dihydroxy-1-oxido-6,7-dihydro-5H-cyclopenta[b]pyridin-7-yl}-1H-imidazol-5-yl)phenyl]carbamate

Example 16—Chiral, Non-Racemic

Methyl [4-(2-{3-[5-chloro-2-(1H-tetrazol-1-yl)phenyl]-5,7-dihydroxy-1-oxido-6,7-dihydro-5H-cyclopenta[b]pyridin-7-yl}-1H-imidazol-5-yl)phenyl]carbamate

Example 17—Chiral, Non-Racemic

Methyl [4-(2-{3-[5-chloro-2-(1H-tetrazol-1-yl)phenyl]-5,7-dihydroxy-1-oxido-6,7-dihydro-5H-cyclopenta[b]pyridin-7-yl}-1H-imidazol-5-yl)phenyl]carbamate

Example 18—Chiral, Non-Racemic

Methyl [4-(2-{3-[5-chloro-2-(1H-tetrazol-1-yl)phenyl]-5,7-dihydroxy-1-oxido-6,7-dihydro-5H-cyclopenta[b]pyridin-7-yl}-1H-imidazol-5-yl)phenyl]carbamate

Example 19—Chiral, Non-Racemic

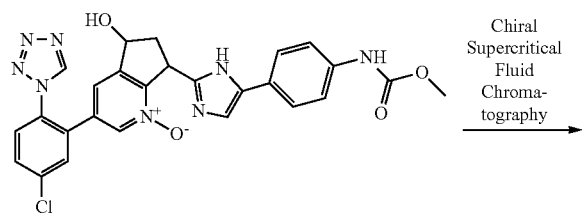

Example 15

Chiral Supercritical Fluid Chromatography →

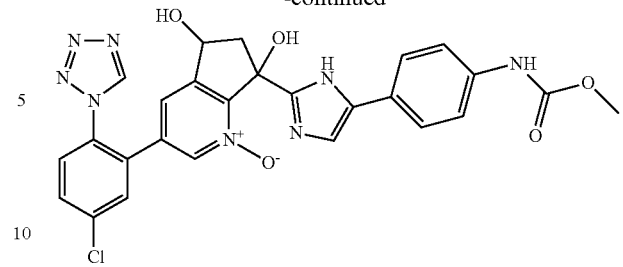

Examples 16-19

Step 1: Methyl [4-(2-{3-[5-chloro-2-(1H-tetrazol-1-yl)phenyl]-5,7-dihydroxy-1-oxido-6,7-dihydro-5H-cyclopenta[b]pyridin-7-yl}-1H-imidazol-5-yl)phenyl]carbamate A sample of Example 15 was subjected to chiral SFC (step 1 separation of peak 1—OD-H (2×25 cm), 35% MeOH (0.1% DEA)/CO$_2$, 100 bar, 60 mL/min; step 2 separation of peak 2, 3 and 4—AD-H (2×15 cm), 45-60% gradient MeOH/CO$_2$, 100 bar, 50 mL/min) to give four enantiomerically pure isomers of the title compound with the following SFC retention times: (Example 16 Rt=7.20 min, Example 17 Rt=5.38 min, Example 18 Rt=8.03 min, Example 19 Rt=11.4 min). LCMS: m/z 561 [M+H]$^+$.

EXAMPLE 20

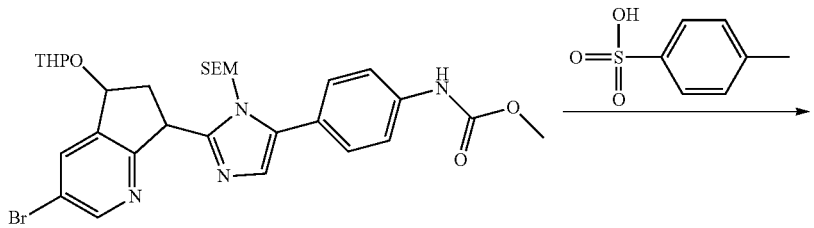

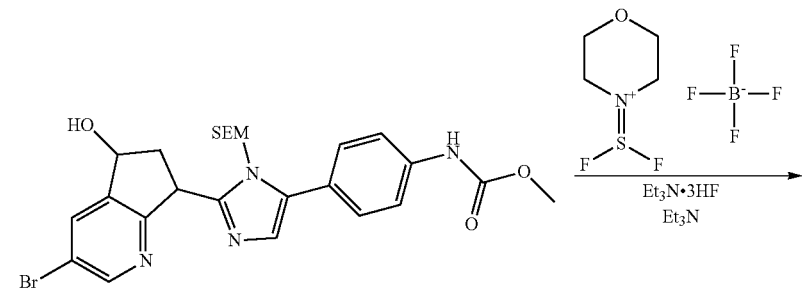

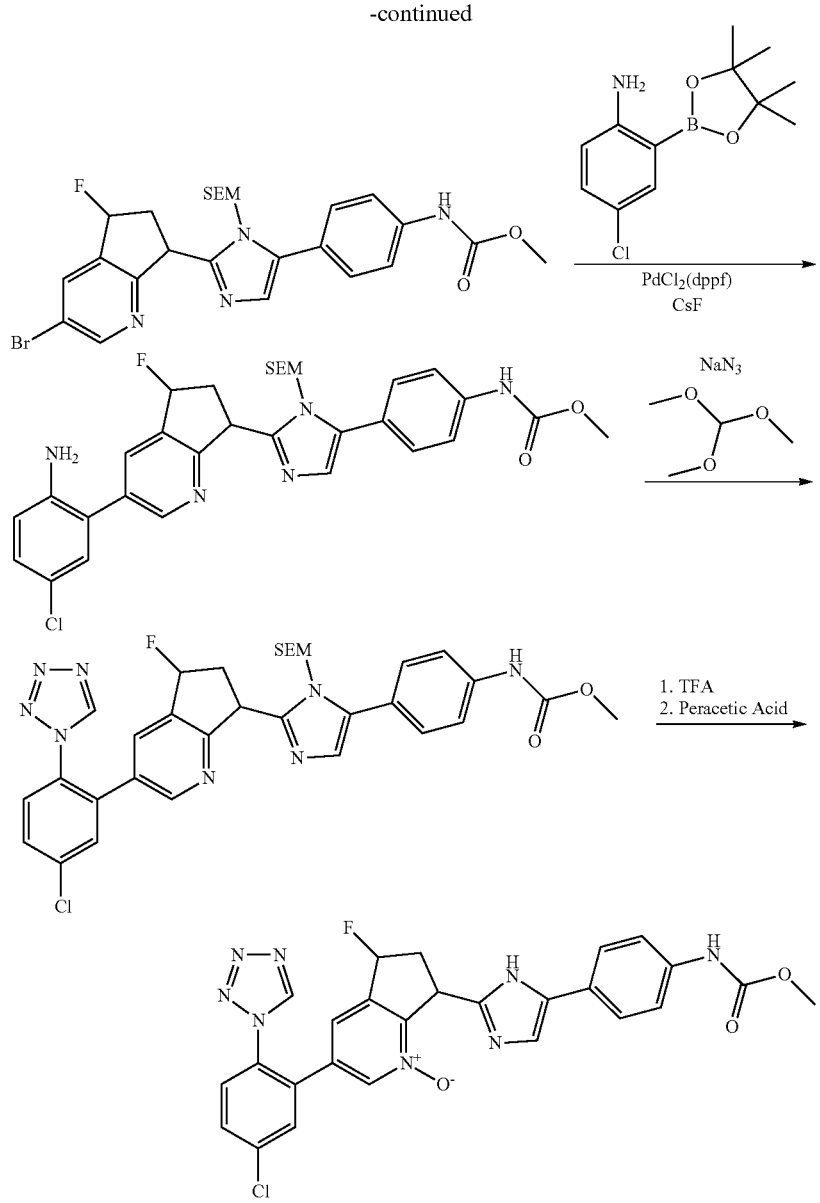

Example 20

Step 1: methyl (4-(2-(3-bromo-5-hydroxy-6,7-dihydro-5H-cyclopenta[1])]pyridin-7-yl)-1-((2-(trimethyl silyl)ethoxy)methyl)-1H-imidazol-5-yl)phenyl) carbamate To methyl(4-(2-(3-bromo-5-((tetrahydro-2H-pyran-2-yl)oxy)-6,7-dihydro-5H-cyclopenta[1)]-pyridin-7-yl)-1-((2-(trimethylsilyl)ethoxy)methyl)-1H-imidazol-5-yl)phenyl) carbamate (401 mg, 0.623 mmol) in MeOH (6.2 mL) was added p-toluenesulfonic acid (237 mg, 1.25 mmol), and the mixture was stirred at rt for 1 h before the solvent was evaporated under vacuum. The residue was dissolved in EtOAc and washed with sat. aqueous NaHCO₃. The organic layer was dried over Na₂SO₄, filtered and concentrated under vacuum. The crude was purified by silica gel chromatography, eluting with 0-95% EtOAc/hexanes, to give the title compound. LCMS: m/z 559 [M+H]⁺.

Step 2: Methyl (4-(2-(3-bromo-5-fluoro-6,7-dihydro-5H-cyclopenta[b]pyridin-7-yl)-1-((2-(trimethyl silyl)ethoxy)methyl)-1H-imidazol-5-yl)phenyl) carbamate To a solution of triethylamine trihydrofluoride (187 µl, 1.12 mmol) and TEA (78 µl, 0.558 mmol) in DCM (5.6 mL) at rt was successively added difluoro(morpholino)sulfonium tetrafluoroborate (203 mg, 0.836 mmol) and methyl (4-(2-(3-bromo-5-hydroxy-6,7-dihydro-5H-cyclopenta[b]pyridin-7-yl)-1-((2-(trimethylsilyl)ethoxy)methyl)-1H-imidazol-5-yl)phenyl)-carbamate (312 mg, 0.558 mmol) in DCM (3.00 mL). The reaction mixture was stirred at rt for 24 h, quenched with 5% aqueous NaHCO₃, and stirred for an additional 15 min. The mixture was then extracted with DCM (2×, 20.0 mL), and the combined organic layers were dried over Na₂SO₄, filtered and concentrated under vacuum.

The crude was purified by silica gel chromatography, eluting with 0-45% EtOAc/hexanes, to give the title compound. LCMS: m/z 561 [M+H]+.

Step 3: methyl (4-(2-(3-(2-amino-5-chlorophenyl)-5-fluoro-6,7-dihydro-5H-cyclopenta[b]-pyridin-7-yl)-1-((2-(trimethylsilyl)ethoxy)methyl)-1H-imidazol-5-yl)phenyl)carbamate A mixture of methyl (4-(2-(3-bromo-5-fluoro-6,7-dihydro-5H-cyclopenta[b]pyridin-7-yl)-1-((2-(trimethylsilyl)ethoxy)methyl)-1H-imidazol-5-yl)phenyl)carbamate (297 mg, 0.529 mmol), 4-chloro-2-(4,4,5,5-tetramethyl-1,3,2-dioxaborolan-2-yl)aniline (268 mg, 1.058 mmol), PdCl$_2$(dppf) (116 mg, 0.159 mmol) and cesium fluoride (241 mg, 1.587 mmol) in a round bottom flask was evacuated under vacuum and purged with N$_2$. This process was repeated three times. Dioxane (5.3 mL) was then added, and the slurry mixture was heated to 110° C. for 1 h. After cooling to rt, the reaction mixture was filtered through a pad of celite, rinsed with EtOAc, and the filtrate was concentrated under vacuum. The crude was purified by silica gel chromatography, eluting with 0-100% EtOAc/hexanes, to give the title compound. LCMS: m/z 608 [M+H]+.

Step 4: Methyl (4-(2-(3-(5-chloro-2-(1H-tetrazol-1-yl)phenyl)-5-fluoro-6,7-dihydro-5H-cyclopenta[b]pyridin-7-yl)-1-((2-(trimethylsilyl)ethoxy)methyl)-1H-imidazol-5-yl)phenyl)-carbamate A mixture of methyl (4-(2-(3-(2-amino-5-chlorophenyl)-5-fluoro-6,7-dihydro-5H-cyclopenta[b]pyridin-7-yl)-1-((2-(trimethylsilyl)ethoxy)methyl)-1H-imidazol-5-yl)phenyl) carbamate (252 mg, 0.414 mmol), trimethyl orthoformate (137 μl, 1.243 mmol) and sodium azide (81 mg, 1.243 mmol) in AcOH (4.1 mL) was stirred at rt overnight. The solvent was evaporated under vacuum, and to the crude was added EtOAc. The organic layer was washed with sat aqueous NaHCO$_3$, dried over Na$_2$SO$_4$, filtered and concentrated under vacuum. The crude was purified by silica gel chromatography, eluting with 0-70% EtOAc/hexanes, to give the title compound. LCMS: m/z 661 [M+H]+.

Step 5: Methyl [4-(2-{3-[5-chloro-2-(1H-tetrazol-1-yl)phenyl]-5-fluoro-1-oxido-6,7-dihydro-5H-cyclopenta[b]pyridin-7-yl}-1H-imidazol-5-yl)phenyl] carbamate (Example 20)

To a solution of methyl (4-(2-(3-(5-chloro-2-(1H-tetrazol-1-yl)phenyl)-5-fluoro-6,7-dihydro-5H-cyclopenta[b]pyridin-7-yl)-1-((2-(trimethylsilyl)ethoxy)methyl)-1H-imidazol-5-yl)phenyl)carbamate (35-E) (231 mg, 0.349 mmol) in DCM (1.00 mL) was added TFA (2.00 mL, 26.0 mmol), and the reaction was stirred at rt for 3 h. Upon completion based on LCMS, sat aqueous NaHCO$_3$ was added carefully, and the resulting mixture was extracted with DCM (2×, 30.0 mL). The combined organic layers were dried over Na$_2$SO$_4$, filtered and concentrated under vacuum. The crude was used directly in the next step without further purification. LCMS: m/z 531 [M+H]+. The crude product methyl (4-(2-(3-(5-chloro-2-(1H-tetrazol-1-yl)phenyl)-5-fluoro-6,7-dihydro-5H-cyclopenta[b]-pyridin-7-yl)-1H-imidazol-5-yl)phenyl) carbamate in acetic acid (3.50 mL) was added ethaneperoxoic acid (0.200 mL, 1.048 mmol). The reaction mixture was stirred at rt overnight and concentrated under vacuum. The crude residue was purified by RP HPLC (19×100 mm, Waters)(Bridge C18 column, 5μ particle size, 1% to 100% ACN in H$_2$O buffering with 0.05% TFA) to give a mixture of 4 isomers of the title compound. LCMS: m/z 547 [M+H]+.

EXAMPLE 21 and 22

(S)-3-(5-chloro-2-(1H-tetrazol-1-yl)phenyl)-7-hydroxy-7-(5-(4-((methoxycarbonyl)amino)phenyl)-1H-imidazol-2-yl)-6,7-dihydro-5H-cyclopenta[b]pyridine-1-oxide and (R)-3-(5-chloro-2-(1H-tetrazol-1-yl)phenyl)-7-hydroxy-7-(5-(4-((methoxycarbonyl)amino)phenyl)-1H-imidazol-2-yl)-6,7-dihydro-5H-cyclopenta[b]pyridine-1-oxide

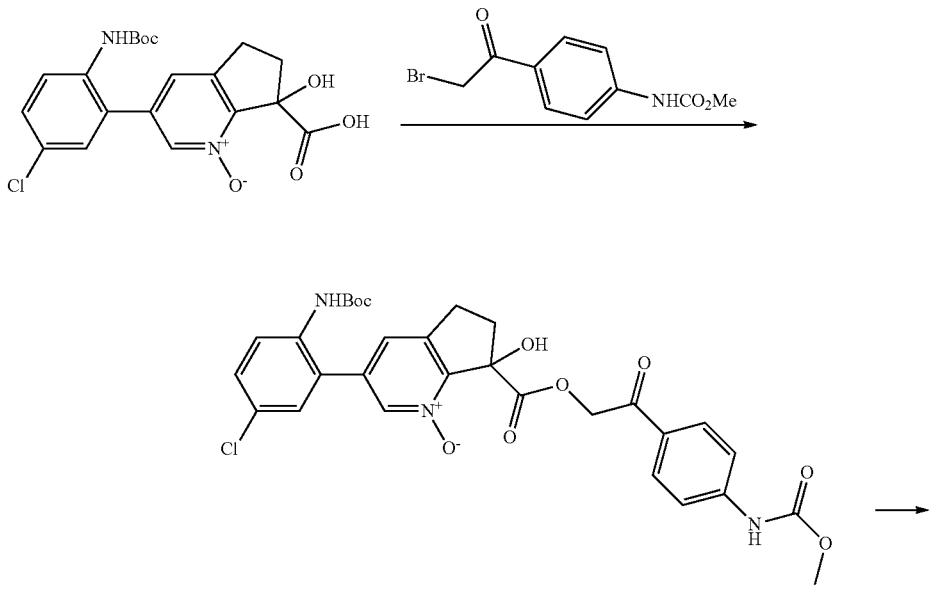

-continued

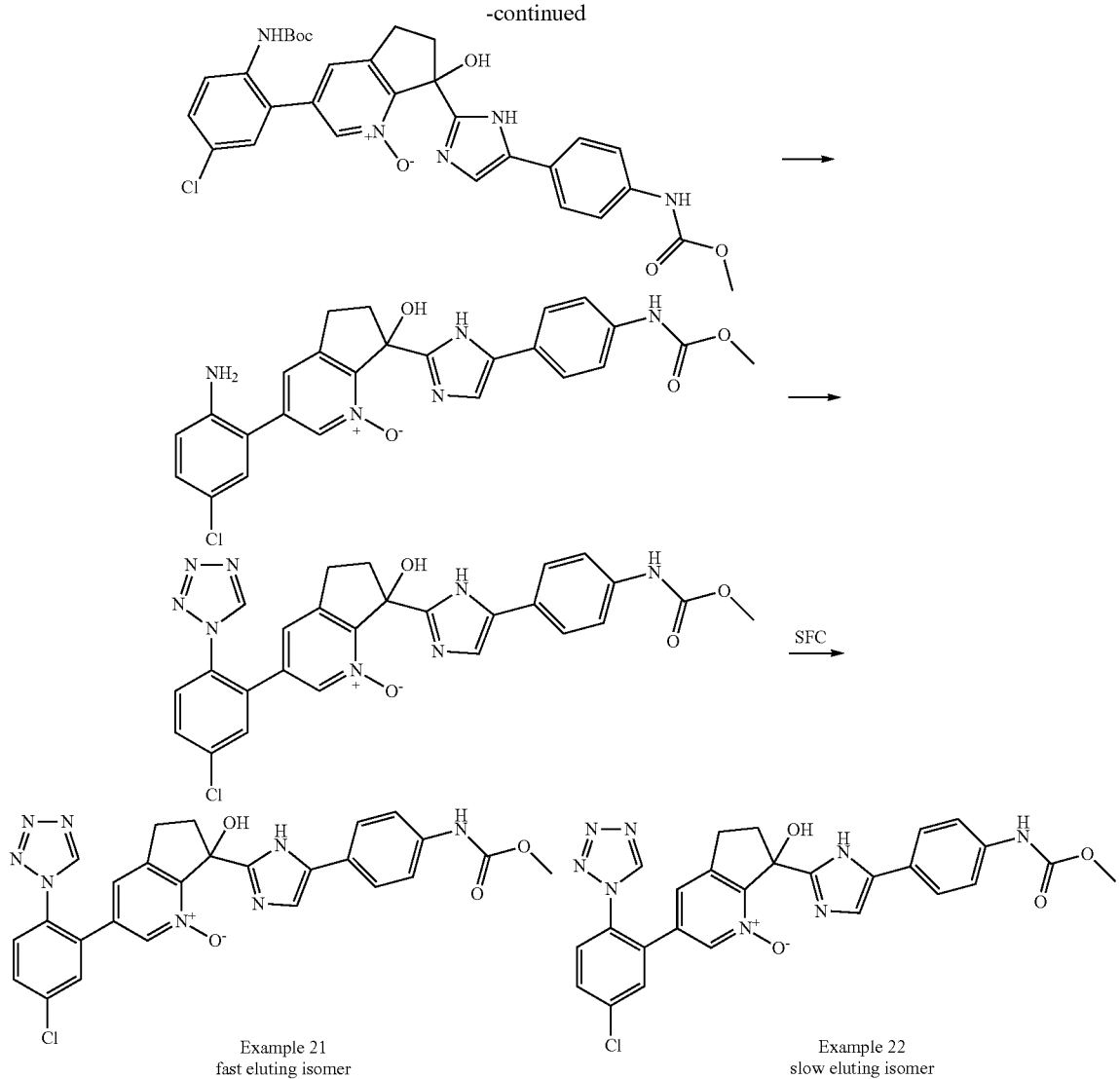

Example 21
fast eluting isomer

Example 22
slow eluting isomer

Step 1: 3-(2-((tert-butoxycarbonyl)amino)-5-chlorophenyl)-7-hydroxy-7-((2-(4-((methoxycarbonyl)amino)phenyl)-2-oxoethoxy)carbonyl)-6,7-dihydro-5H-cyclopenta[b]pyridine-1-oxide To a solution of 3-(2-((tert-butoxycarbonyl)amino)-5-chlorophenyl)-7-carboxy-7-hydroxy-6,7-dihydro-5H-cyclopenta[b]pyridine-1-oxide (300 mg, 0.71 mmol) and methyl (4-(2-bromoacetyl)phenyl)carbamate (237 mg, 0.71 mmol) in DMF (4 mL) was added cesium carbonate (232 mg, 0.71 mmol). After addition, the mixture was stirred at 25° C. for 16 h. TLC showed that the starting material was consumed. The mixture was diluted with water (5 mL). The precipitate was collected by filtration and dried to afford the crude title compound, which was used for the next step without further purification. MS (ESI) m/z 612.1 (M+H).

Step 2: 3-(2-((tert-butoxycarbonyl)amino)-5-chlorophenyl)-7-hydroxy-7-(5-(4-((methoxycarbonyl)amino)phenyl)-1H-imidazol-2-yl)-6,7-dihydro-5H-cyclopenta[b]pyridine-1-oxide To a solution of 3-(2-((tert-butoxycarbonyl)amino)-5-chlorophenyl)-7-hydroxy-7-((2-(4-((methoxycarbonyl) amino)phenyl)-2-oxoethoxy)carbonyl)-6,7-dihydro-5H-cyclopenta[b]pyridine-1-oxide (360 mg, 0.59 mmol) in toluene (15 mL) was added ammonium acetate (453 mg, 5.88 mmol). After addition, the mixture was reacted in a microwave reactor at 130° C. for 1 h. TLC showed that the starting material was consumed. The reaction mixture was diluted with EtOAc (20 mL) and washed with water (20 mL). The organic phase was dried over $Na_2SO_4$, filtered and the filtrate was concentrated to afford the title compound, which was used for the next step without further purification. MS (ESI) m/z 592.1 (M+H).

Step 3: 3-(2-amino-5-chlorophenyl)-7-hydroxy-7-(5-(4-((methoxycarbonyl)amino)phenyl)-1H-imidazol-2-yl)-6,7-dihydro-5H-cyclopenta[b]pyridine-1-oxide A mixture of 3-(2-((tert-butoxycarbonyl)amino)-5-chlorophenyl)-7-hydroxy-7-(5-(4-((methoxycarbonyl)amino)phenyl)-1H-imidazol-2-yl)-6,7-dihydro-5H-cyclopenta[b] pyridine-1-oxide (360 mg, 0.61 mmol) and HCl in dioxane (4 M, 8 mL) was stirred at 25° C. for 1 h. LCMS showed the desired product and that the starting material was consumed.

The mixture was concentrated to afford the crude product which was purified by prep-HPLC (TFA method) to afford the title compound. MS (ESI) m/z 492.2 (M+H).

Step 4: 3-(5-chloro-2-(1H-tetrazol-1-yl)phenyl)-7-hydroxy-7-(5-(4-((methoxycarbonyl)-amino)phenyl)-1H-imidazol-2-yl)-6,7-dihydro-5H-cyclopenta[b]pyridine-1-oxide To a mixture of 3-(2-amino-5-chlorophenyl)-7-hydroxy-7-(5-(4-((methoxycarbonyl)-amino)phenyl)-1H-imidazol-2-yl)-6,7-dihydro-5H-cyclopenta[b]pyridine-1-oxide (130 mg, 0.26 mmol), trimethoxymethane (400 mg, 3.77 mmol) and sodium azide (200 mg, 3.08 mmol) was added HOAc (4 mL) drop-wise at 0° C. After addition, the mixture was stirred at 25° C. for 16 h. LCMS showed the desired product and that the starting material was consumed. The mixture was cooled to 0° C. Water (2 mL) and aqueous HCl (0.6 mL, 6 mol/L) was added to the mixture and then saturated aqueous sodium nitrite (0.6 mL) was added dropwise, and air escaped. After addition, the mixture was stirred at 0° C. for 1.5 h, diluted with EtOAc (15 mL) and washed with water (15 mL). The organic phase was dried over Na$_2$SO$_4$, filtered and concentrated to afford the crude product which was purified by prep-HPLC (TFA method) to afford the title compound. MS (ESI) m/z 545.1 (M+H).

Step 5: 3-(5-chloro-2-(1H-tetrazol-1-yl)phenyl)-7-hydroxy-7-(5-(4-((methoxycarbonyl)-amino)phenyl)-1H-imidazol-2-yl)-6,7-dihydro-5H-cyclopenta[b]pyridine-1-oxide (Example 21) and 3-(5-chloro-2-(1H-tetrazol-1-yl)phenyl)-7-hydroxy-7-(5-(4-((methoxycarbonyl)amino)-phenyl)-1H-imidazol-2-yl)-6,7-dihydro-5H-cyclopenta[b]pyridine-1-oxide (Example 22)

Racemic compound 3-(5-chloro-2-(1H-tetrazol-1-yl)phenyl)-7-hydroxy-7-(5-(4-((methoxycarbonyl)amino)phenyl)-1H-imidazol-2-yl)-6,7-dihydro-5H-cyclopenta[b]pyridine-1-oxide (58 mg, 0.106 mmol) was separated by SFC with Chiralpak OD column 250×30 mm I.D., 10 um, eluting with supercritical 50/50 CO$_2$/MeOH (0.1% NH$_3$H$_2$O) at 80 mL/min, to afford 3-(5-chloro-2-(1H-tetrazol-1-yl)phenyl)-7-hydroxy-7-(5-(4-((methoxycarbonyl)amino)phenyl)-1H-imidazol-2-yl)-6,7-dihydro-5H-cyclopenta[b]pyridine-1-oxide (Example 21, fast eluting isomer). MS (ESI) m/z 545.0 (M+H), and 3-(5-chloro-2-(1H-tetrazol-1-yl)phenyl)-7-hydroxy-7-(5-(4-((methoxycarbonyl)amino)phenyl)-1H-imidazol-2-yl)-6,7-dihydro-5H-cyclopenta[b]pyridine-1-oxide (Example 22, slow eluting isomer). MS (ESI) m/z 545.1 (M+H).

Example 21: $^1$HNMR (MeOH-d$_4$, 400 MHz): δ 9.36 (s, 1H), 7.97 (s, 1H), 7.76-7.74 (m, 2H), 7.69-7.67 (m, 1H), 7.54 (d, J=8.0 Hz, 2H), 7.41-7.40 (m, 2H), 7.22-7.20 (m, 2H), 3.71 (s, 3H), 3.08-3.07 (m, 2H), 2.93-2.88 (m, 1H), 2.50-2.45 (m, 1H).

Example 22: $^1$HNMR (MeOH-d$_4$, 400 MHz): δ 9.39 (s, 1H), 7.99 (s, 1H), 7.78-7.76 (m, 2H), 7.71-7.69 (m, 1H), 7.56 (d, J=8.0 Hz, 2H), 7.42 (d, J=7.6 Hz, 2H), 7.25-7.22 (m, 2H), 3.74 (s, 3H), 3.12-3.09 (m, 2H), 2.95-2.90 (m, 1H), 2.51-2.48 (m, 1H).

EXAMPLE 23 and 24

3-[5-chloro-2-(1H-tetrazol-1-yl)phenyl]-7-{5-[4-(trifluoromethyl)phenyl]-1H-imidazol-2-yl}-6,7-dihydro-5H-cyclopenta[b]pyridin-7-ol 1-oxide (Example 23, fast eluting isomer)

3-[5-chloro-2-(1H-tetrazol-1-yl)phenyl]-7-{5-[4-(trifluoromethyl)phenyl]-1H-imidazol-2-yl}-6,7-dihydro-5H-cyclopenta[b]pyridin-7-ol 1-oxide (Example 24, slow eluting isomer)

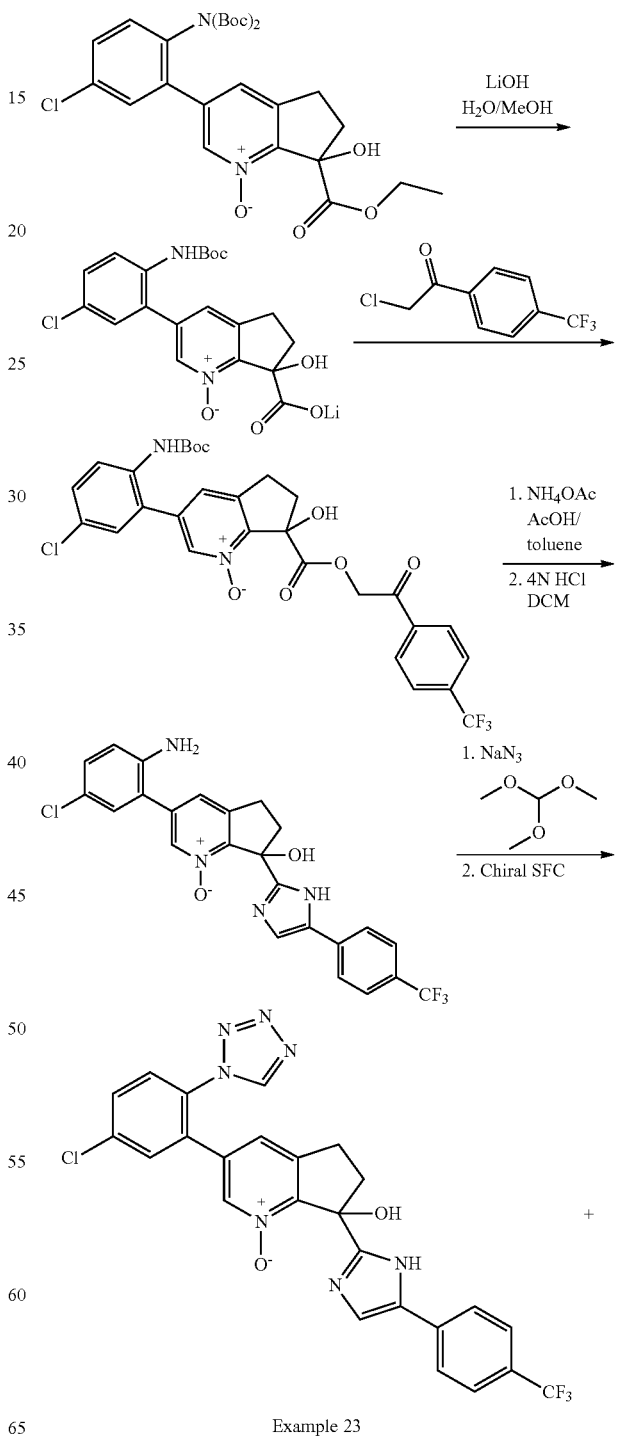

Example 23
fast eluting isomer

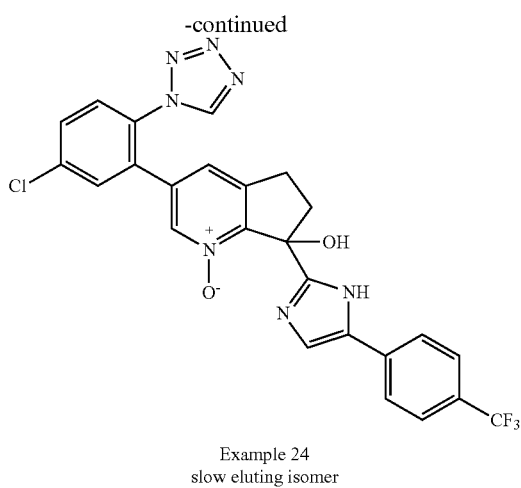

Example 24
slow eluting isomer

Step 1: Lithium 3-(2-((tert-butoxycarbonyl)amino)-5-chlorophenyl)-7-hydroxy-1-oxido-6,7-dihydro-5H-cyclopenta[b]pyridine-7-carboxylate A mixture of intermediate (1.35 g, 2.5 mmol) and LiOH hydrate (0.12 g, 3.0 mmol) in MeOH (10 mL) and water (3 mL) was stirred at 50° C. for 30 min. The solvent was removed and the residue was dried in vacuum to give crude lithium 3-(2-((tert-butoxycarbonyl)amino)-5-chlorophenyl)-7-hydroxy-1-oxido-6,7-dihydro-5H-cyclopenta[b]pyridine-7-carboxylate, which was used in the next step without further purification. LCMS: m/z 421 [M+H]$^+$.

Step 2: 3-(2-((tert-Butoxycarbonyl)amino)-5-chlorophenyl)-7-hydroxy-7-((2-oxo-2-(4-(trifluoromethyl)phenyl)ethoxy)carbonyl)-6,7-dihydro-5H-cyclopenta[b]pyridine-1-oxide A mixture of lithium 3-(2-((tert-butoxycarbonyl)amino)-5-chlorophenyl)-7-hydroxy-1-oxido-6,7-dihydro-5H-cyclopenta[b]pyridine-7-carboxylate (0.19 g, 0.2 mmol) and 2-bromo-1-(4-(trifluoromethyl)phenyl)ethanone (0.12 g, 0.44 mmol) in DMF (3 mL) was stirred at rt overnight. DMF was removed under vacuum and the residue was purified by flash chromatography on a silica gel column with 0-65% EtOAc/CH$_2$Cl$_2$ to give the title compound.

Step 3: 3-(2-amino-5-chlorophenyl)-7-hydroxy-7-(5-(4-(trifluoromethyl)phenyl)-1H-imidazol-2-yl)-6,7-dihydro-5H-cyclopenta[b]pyridine-1-oxide The mixture obtained from step 2 above (0.14 g, 0.11 mmol) and ammonium acetate (0.082 g, 1.1 mmol) in toluene (1.5 mL) and acetic acid (0.15 mL) was stirred at 130° C. for 45 min. Solvent was removed, and the residue was dissolved in CH$_2$Cl$_2$ (1.5 mL) and treated with 4N HCl in dioxane at rt for 2 hours. The mixture was concentrated and the residue was purified by preparative C-18 RP-HPLC, eluting with gradient acetonitrile/water+0.1% TFA to give the title compound. LCMS: m/z 487 [M+H]$^+$.

Step 4: 3-[5-chloro-2-(1H-tetrazol-1-yl)phenyl]-7-{5-[4-(trifluoromethyl)phenyl]-1H-imidazol-2-yl}-6,7-dihydro-5H-cyclopenta[b]pyridin-7-ol 1-oxide (Example 23) and 3-[5-chloro-2-(1H-tetrazol-1-yl)phenyl]-7-{5-[4-(trifluoromethyl)phenyl]-1H-imidazol-2-yl}-6,7-dihydro-5H-cyclopenta[b]pyridin-7-ol 1-oxide (Example 24)

Sodium azide (11.6 mg, 0.18 mmol) was added to a solution of 3-(2-amino-5-chlorophenyl)-7-hydroxy-7-(5-(4-(trifluoromethyl)phenyl)-1H-imidazol-2-yl)-6,7-dihydro-5H-cyclopenta-[b]-pyridine-1-oxide (29 mg, 0.060 mmol) and trimethyl orthoformate (0.020 mL, 0.18 mmol) in acetic acid (0.5 mL), followed by stirring at rt overnight. Additional trimethyl orthoformate (2 eq.) and sodium azide (1 eq.) were added and then stirred for 5 hours. The mixture was concentrated, and purified by preparative RP-HPLC (C-18), eluting with acetonitrile/water+0.1% TFA to give the racemic product. The racemic mixture was resolved using chiral SFC (30×250 mm OD column, 65% MeOH with 0.2% NH$_4$OH/CO$_2$, 70 mL/min at 100 bar and 35° C.) to afford Example 23 (SFC retention time=4.29 min) and Example 24 (SFC retention time=8.36 min). LCMS: m/z 540 [M+H]$^+$. The absolute configuration of these enantiomers was not assigned.

The following compound was prepared following procedures similar to those described above using appropriate starting materials and characterized by LCMS. In cases where a racemic compound is indicated, resolution by chiral SFC was not performed.

| Ex # | Compound Name | Structure | Chiral Separation | LCMS [M + 1] |
|---|---|---|---|---|
| 25 | 3-[5-chloro-2-(1H-tetrazol-1-yl)phenyl]-7-[5-(3-fluorophenyl)-1H-imidazol-2-yl]-6,7-dihydro-5H-cyclopenta[b]pyridin-7-ol 1-oxide | 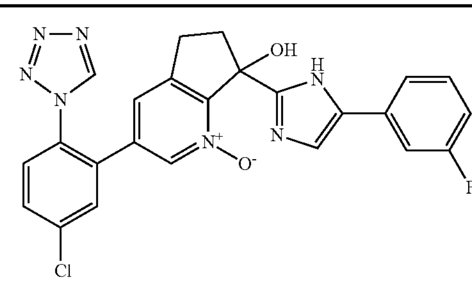 | racemic | 490.2 |

| Ex # | Compound Name | Structure | Chiral Separation | LCMS [M + 1] |
|---|---|---|---|---|
| 26 | 3-[5-chloro-2-(1H-tetrazol-1-yl)phenyl]-7-[5-(4-fluorophenyl)-1H-imidazol-2-yl]-6,7-dihydro-5H-cyclopenta[b]pyridin-7-ol 1-oxide | 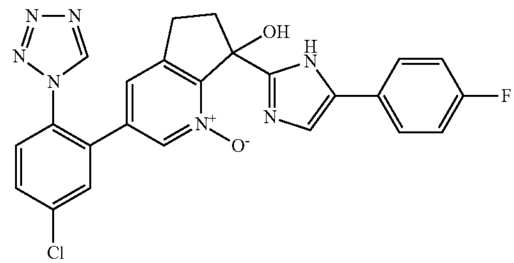 [SMILES: [O-][n+]1cc(-c2cc(Cl)ccc2-n2cnnn2)cc2c1C(O)(c1ncc(-c3ccc(F)cc3)[nH]1)CC2] | racemic | 490.2 |
| 27 | methyl [4-(2-{3-[5-chloro-2-(1H-tetrazol-1-yl)phenyl]-7-methoxy-1-oxido-6,7-dihydro-5H-cyclopenta[b]pyridin-7-yl}-1H-imidazol-5-yl)phenyl]carbamate | 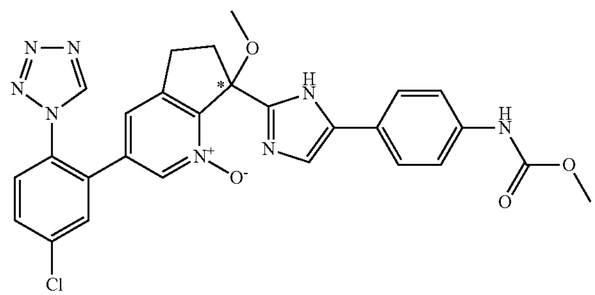 [SMILES: COC(=O)Nc1ccc(-c2cnc(C3(OC)CCc4cc(-c5cc(Cl)ccc5-n5cnnn5)c[n+]([O-])c43)[nH]2)cc1] | AS column, fast eluting isomer | 559 |
| 28 | methyl [4-(2-{3-[5-chloro-2-(1H-tetrazol-1-yl)phenyl]-7-methoxy-1-oxido-6,7-dihydro-5H-cyclopenta[b]pyridin-7-yl}-1H-imidazol-5-yl)phenyl]carbamate | 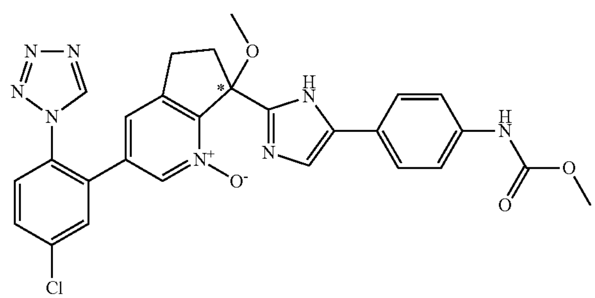 [SMILES: COC(=O)Nc1ccc(-c2cnc(C3(OC)CCc4cc(-c5cc(Cl)ccc5-n5cnnn5)c[n+]([O-])c43)[nH]2)cc1] | AS column, slow eluting isomer | 559 |
| 29 | methyl [3-chloro-4-(2-{3-[5-chloro-2-(1H-tetrazol-1-yl)phenyl]-7-hydroxy-1-oxido-6,7-dihydro-5H-cyclopenta[b]pyridin-7-yl}-1H-imidazol-5-yl)phenyl]carbamate | 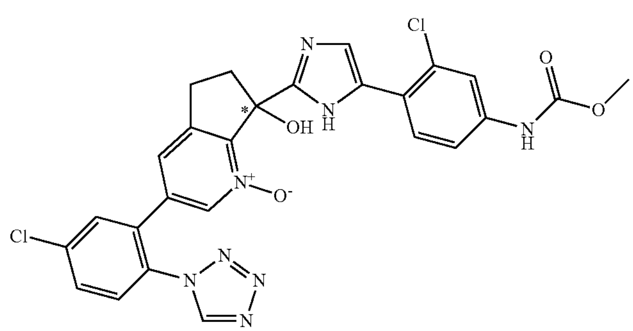 [SMILES: COC(=O)Nc1ccc(-c2cnc(C3(O)CCc4cc(-c5cc(Cl)ccc5-n5cnnn5)c[n+]([O-])c43)[nH]2)c(Cl)c1] | MAS column, fast eluting isomer | 579.0 |
| 30 | methyl [3-chloro-4-(2-{3-[5-chloro-2-(1H-tetrazol-1-yl)phenyl]-7-hydroxy-1-oxido-6,7-dihydro-5H-cyclopenta[b]pyridin-7-yl}-1H-imidazol-5-yl)phenyl]carbamate | 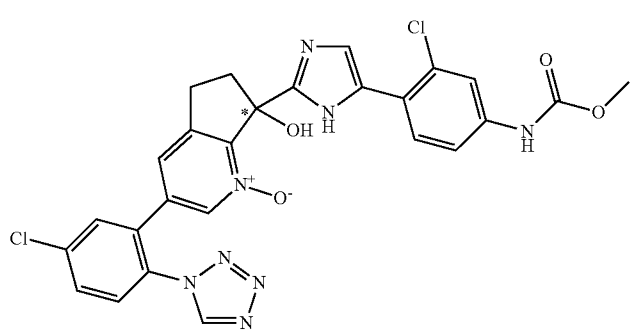 [SMILES: COC(=O)Nc1ccc(-c2cnc(C3(O)CCc4cc(-c5cc(Cl)ccc5-n5cnnn5)c[n+]([O-])c43)[nH]2)c(Cl)c1] | MAS column, slow eluting isomer | 579.0 |

| Ex # | Compound Name | Structure | Chiral Separation | LCMS [M + 1] |
|---|---|---|---|---|
| 31 | (S)-methyl [4-(2-{3-[5-chloro-2-(1H-tetrazol-1-yl)phenyl]-7-hydroxy-1-oxido-6,7-dihydro-5H-cyclopenta[b]pyridin-7-yl}-1H-imidazol-5-yl)-3-fluorophenyl]carbamate | 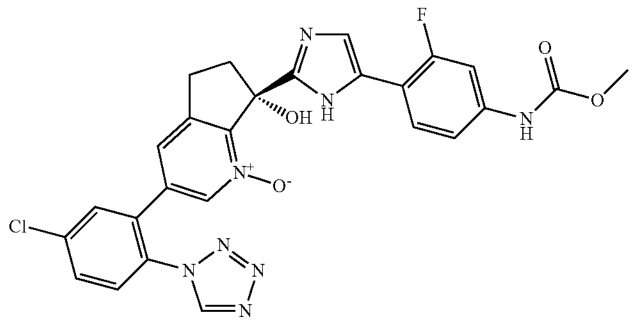 [SMILES: COC(=O)Nc1ccc(-c2cnc([C@]3(O)CCc4cc(-c5cc(Cl)ccc5-n5cnnn5)c[n+]([O-])c43)[nH]2)c(F)c1] | From chiral intermediate | 563.0 |
| 32 | methyl [4-(2-{3-[5-chloro-2-(1H-tetrazol-1-yl)phenyl]-7-hydroxy-1-oxido-6,7-dihydro-5H-cyclopenta[b]pyridin-7-yl}-1H-imidazol-5-yl)-3-methylphenyl]carbamate | 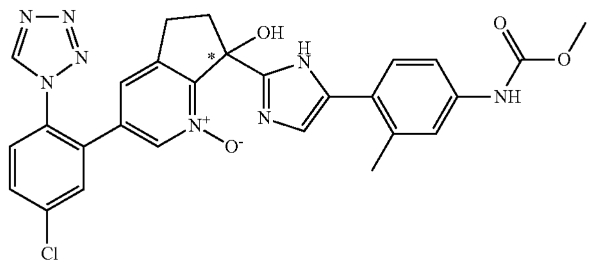 [SMILES: COC(=O)Nc1ccc(-c2cnc(C3(O)CCc4cc(-c5cc(Cl)ccc5-n5cnnn5)c[n+]([O-])c43)[nH]2)c(C)c1] | AS column, fast eluting isomer | 559 |
| 33 | methyl [4-(2-{3-[5-chloro-2-(1H-tetrazol-1-yl)phenyl]-7-hydroxy-1-oxido-6,7-dihydro-5H-cyclopenta[b]pyridin-7-yl}-1H-imidazol-5-yl)-3-methylphenyl]carbamate | 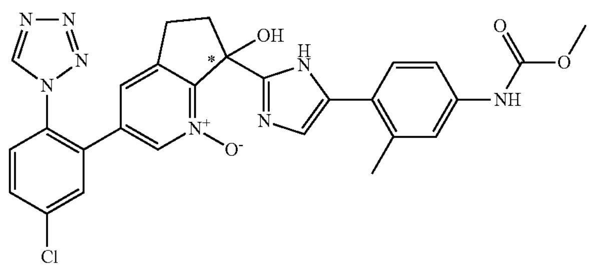 [SMILES: COC(=O)Nc1ccc(-c2cnc(C3(O)CCc4cc(-c5cc(Cl)ccc5-n5cnnn5)c[n+]([O-])c43)[nH]2)c(C)c1] | AS column, slow eluting isomer | 559 |
| 34 | methyl 4-(2-{3-[5-chloro-2-(1H-tetrazol-1-yl)phenyl]-7-hydroxy-1-oxido-6,7-dihydro-5H-cyclopenta[b]pyridin-7-yl}-1H-imidazol-4-yl)-3-fluorothiophene-2-carboxylate | 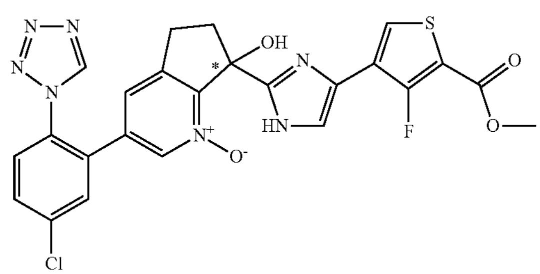 [SMILES: COC(=O)c1scc(-c2c[nH]c(C3(O)CCc4cc(-c5cc(Cl)ccc5-n5cnnn5)c[n+]([O-])c43)n2)c1F] | OD column, fast eluting isomer | 554 |
| 35 | methyl 4-(2-{3-[5-chloro-2-(1H-tetrazol-1-yl)phenyl]-7-hydroxy-1-oxido-6,7-dihydro-5H-cyclopenta[b]pyridin-7-yl}-1H-imidazol-4-yl)-3-fluorothiophene-2-carboxylate | 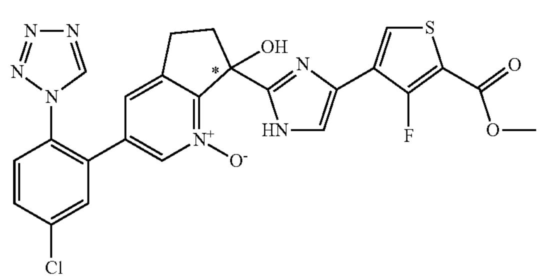 [SMILES: COC(=O)c1scc(-c2c[nH]c(C3(O)CCc4cc(-c5cc(Cl)ccc5-n5cnnn5)c[n+]([O-])c43)n2)c1F] | OD column, slow eluting isomer | 554 |

| Ex # | Compound Name | Structure | Chiral Separation | LCMS [M + 1] |
|---|---|---|---|---|
| 36 | 7-(2-{3-[5-chloro-2-(1H-tetrazol-1-yl)phenyl]-7-hydroxy-1-oxido-6,7-dihydro-5H-cyclopenta[b]pyridin-7-yl}-1H-imidazol-5-yl)-3,4-dihydroquinolin-2(1H)-one | 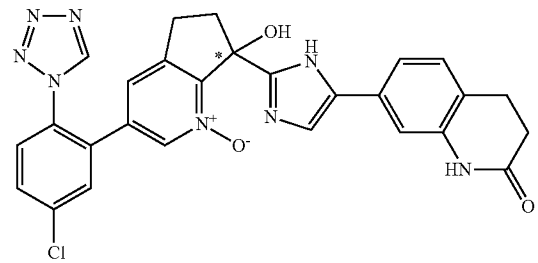 [SMILES: O=C1CCc2ccc(-c3cnc(C4(O)CCc5cc(-c6cc(Cl)ccc6-n6cnnn6)c[n+]([O-])c54)[nH]3)cc2N1] | OD column, fast eluting isomer | 541 |
| 37 | 7-(2-{3-[5-chloro-2-(1H-tetrazol-1-yl)phenyl]-7-hydroxy-1-oxido-6,7-dihydro-5H-cyclopenta[b]pyridin-7-yl}-1H-imidazol-5-yl)-3,4-dihydroquinolin-2(1H)-one | 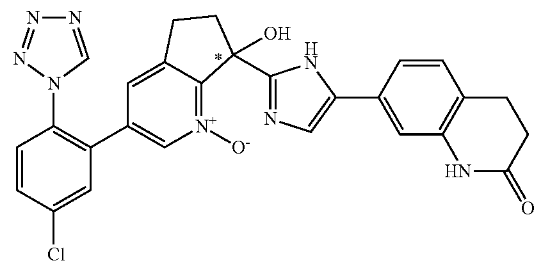 [SMILES: O=C1CCc2ccc(-c3cnc(C4(O)CCc5cc(-c6cc(Cl)ccc6-n6cnnn6)c[n+]([O-])c54)[nH]3)cc2N1] | OD column, slow eluting isomer | 541 |
| 38 | 2-methoxyethyl [4-(2-{3-[5-chloro-2-(1H-tetrazol-1-yl)phenyl]-7-hydroxy-1-oxido-6,7-dihydro-5H-cyclopenta[b]pyridin-7-yl}-1H-imidazol-5-yl)phenyl]carbamate | 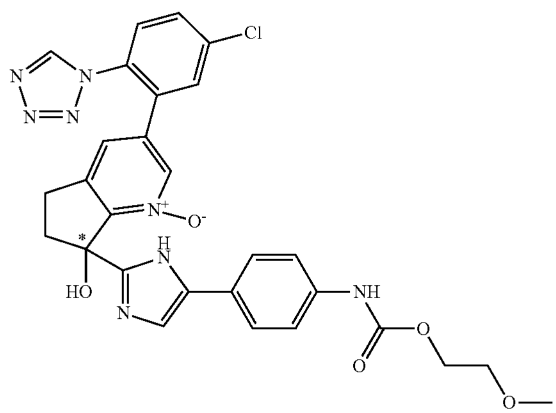 [SMILES: COCCOC(=O)Nc1ccc(-c2cnc(C3(O)CCc4cc(-c5cc(Cl)ccc5-n5cnnn5)c[n+]([O-])c43)[nH]2)cc1] | OD column, fast eluting isomer | 589 |
| 39 | 2-methoxyethyl [4-(2-{3-[5-chloro-2-(1H-tetrazol-1-yl)phenyl]-7-hydroxy-1-oxido-6,7-dihydro-5H-cyclopenta[b]pyridin-7-yl}-1H-imidazol-5-yl)phenyl]carbamate | 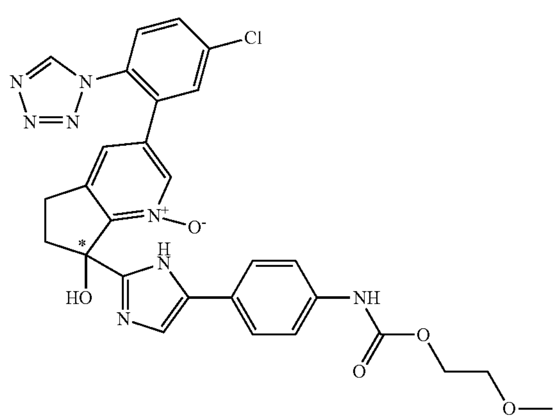 [SMILES: COCCOC(=O)Nc1ccc(-c2cnc(C3(O)CCc4cc(-c5cc(Cl)ccc5-n5cnnn5)c[n+]([O-])c43)[nH]2)cc1] | OD column, slow eluting isomer | 589 |

EXAMPLES 40 and 41

7-(5-(6-amino-2-fluoropyridin-3-yl)-1H-imidazol-2-yl)-3-(5-chloro-2-(1H-tetrazol-1-yl)phenyl)-7-hydroxy-6,7-dihydro-5H-cyclopenta[b]pyridine-1-oxide

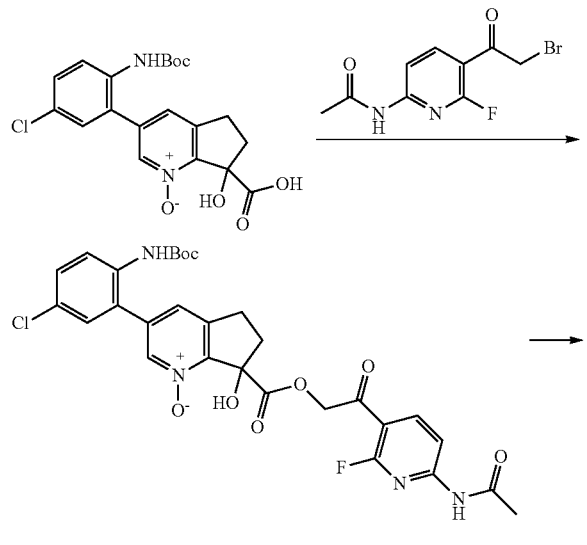

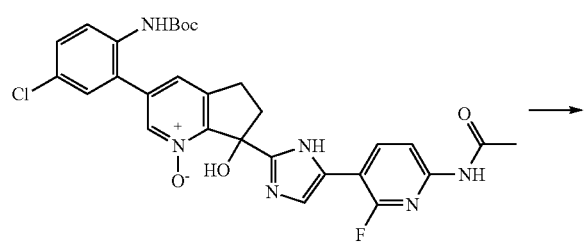

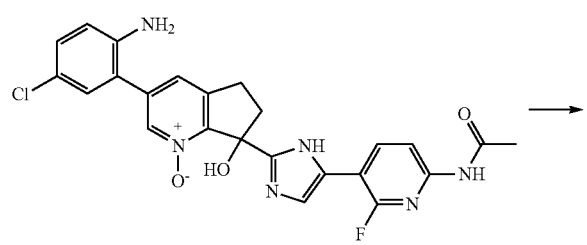

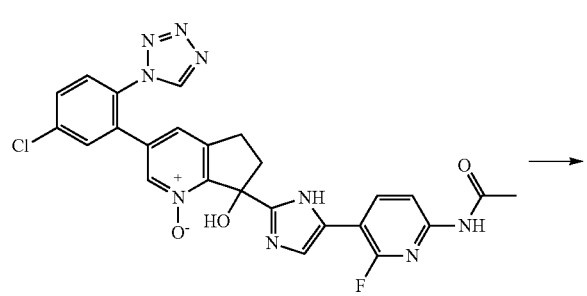

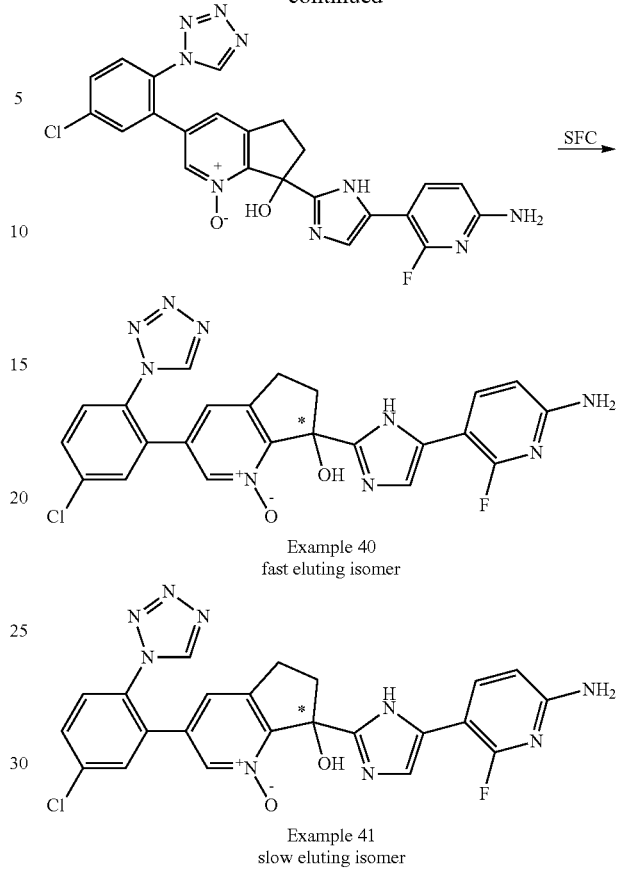

Example 40
fast eluting isomer

Example 41
slow eluting isomer

Step 1: 7-((2-(6-acetamido-2-fluoropyridin-3-yl)-2-oxoethoxy)carbonyl)-3-(2-((tert-butoxycarbonyl)amino)-5-chlorophenyl)-7-hydroxy-6,7-dihydro-5H-cyclopenta[b]pyridine-1-oxide To a solution of 3-(2-((tert-butoxycarbonyl)amino)-5-chlorophenyl)-7-carboxy-7-hydroxy-6,7-dihydro-5H-cyclopenta[b]pyridine-1-oxide (612 mg, 1.45 mmol)) and N-(5-(2-bromoacetyl)-6-fluoropyridin-2-yl)acetamide (800 mg, 1.45 mmol) in DMF (15 mL) was added cesium carbonate (474 mg, 1.45 mmol). The reaction mixture was stirred at 20° C. for 2 h. The reaction was complete based on TLC. Water (100 mL) was added to the reaction mixture and the mixture was extracted with EtOAc (100 mL×3). The combined organic fractions were washed with water (200 mL×3), dried (Na$_2$SO$_4$), filtered and the solvent was evaporated under reduced pressure. The residue was purified by column (SiO$_2$; PE/EtOAc=1/1) to give the title compound. MS (ESI) m/z 615.0 (M+H).

Step 2: 7-(5-(6-acetamido-2-fluoropyridin-3-yl)-1H-imidazol-2-yl)-3-(2-((tert-butoxycarbonyl)amino)-5-chlorophenyl)-7-hydroxy-6,7-dihydro-5H-cyclopenta[b]pyridine-1-oxide To a solution of 7-((2-(6-acetamido-2-fluoropyridin-3-yl)-2-oxoethoxy)carbonyl)-3-(2-((tert-butoxycarbonyl)amino)-5-chlorophenyl)-7-hydroxy-6,7-dihydro-5H-cyclopenta[b]pyridine-1-oxide (550 mg, 80% purity, 0.72 mmol) in toluene (1.5 mL) was added NH$_4$Cl (1103 mg, 14.31 mmol). The reaction mixture was stirred at 150° C. for 50 min under microwave. The reaction was complete based on LCMS. The mixture was cooled, diluted with water (50 mL) and extracted with EtOAc (50 mL×3). The combined organic fractions were dried (Na$_2$SO$_4$), filtered and the solvent was evaporated under reduced pressure. The residue was purified (SiO$_2$, DCM/MeOH=10/1) to give the title compound. MS (ESI) m/z 595.2 (M+H).

Step 3: 7-(5-(6-acetamido-2-fluoropyridin-3-yl)-1H-imidazol-2-yl)-3-(2-amino-5-chlorophenyl)-7-hydroxy-6,7-dihydro-5H-cyclopenta[b]pyridine-1-oxide To a solution of 7-(5-(6-acetamido-2-fluoropyridin-3-yl)-1H-imidazol-2-yl)-3-(2-((tert-butoxycarbonyl)amino)-5-chlorophenyl)-7-hydroxy-6,7-dihydro-5H-cyclopenta[b]pyridine-1-oxide (140 mg, 0.24 mmol) in DCM (2.5 mL) was added TFA (0.5 mL). The reaction mixture was stirred at 25° C. for 2 h. The reaction was complete based on LCMS. The solvent was evaporated under reduced pressure to give the title compound. MS (ESI) m/z 495.2 (M+H).

Step 4: 7-(5-(6-acetamido-2-fluoropyridin-3-yl)-1H-imidazol-2-yl)-3-(5-chloro-2-(1H-tetrazol-1-yl)phenyl)-7-hydroxy-6,7-dihydro-5H-cyclopenta[b]pyridine-1-oxide To a solution of 7-(5-(6-acetamido-2-fluoropyridin-3-yl)-1H-imidazol-2-yl)-3-(2-amino-5-chlorophenyl)-7-hydroxy-6,7-dihydro-5H-cyclopenta[b]pyridine-1-oxide (116 mg, 0.23 mmol) in trimethoxymethane (497 mg, 4.69 mmol) was added sodium azide (305 mg, 4.69 mmol) and HOAc (2 mL). The reaction mixture was stirred at 60° C. for 15 h. The reaction was complete based on LCMS. The reaction mixture was adjusted with sat. Na$_2$CO$_3$ to pH=9 and extracted with EtOAc (10 mL×4). The combined organic fractions were dried (Na$_2$SO$_4$), filtered and the solvent was evaporated under reduced pressure to give the crude title compound. MS (ESI) m/z 458.2 (M+H).

Step 5: 7-(5-(6-acetamido-2-fluoropyridin-3-yl)-1H-imidazol-2-yl)-3-(5-chloro-2-(1H-tetrazol-1-yl)phenyl)-7-hydroxy-6,7-dihydro-5H-cyclopenta[b]pyridine-1-oxide To a solution of 7-(5-(6-acetamido-2-fluoropyridin-3-yl)-1H-imidazol-2-yl)-3-(5-chloro-2-(1H-tetrazol-1-yl)phenyl)-7-hydroxy-6,7-dihydro-5H-cyclopenta[b]pyridine-1-oxide (crude) in MeOH (5 mL) and H$_2$O (5 mL) was added 1 mL of H$_2$SO$_4$ (98%), and the reaction mixture was stirred at 20° C. for 5 h. After quenching with sodium bicarbonate (20 mL), it was extracted with EtOAc (10 mL×3), the combined organic layers were washed with brine (10 mL), dried over Na$_2$SO$_4$, filtered and concentrated. The residue was purified by p-HPLC under HCl conditions to give the title compound. MS (ESI) m/z 506.1 (M+H). $^1$H NMR (MeOH-d$_4$, 400 MHz): δ 9.43 (s, 1H), 8.07 (s, 1H), 7.67-7.92 (m, 4H), 7.52 (d, J=1.2 Hz, 1H), 7.29 (s, 1H), 6.47 (d, J=7.4 Hz, 1H), 3.30-3.35 (m, 1H), 3.13 (dd, J=17.2, 7.8 Hz, 1H), 2.57-2.75 (m, 2H).

Step 6: 7-(5-(6-acetamido-2-fluoropyridin-3-yl)-1H-imidazol-2-yl)-3-(5-chloro-2-(1H-tetrazol-1-yl)phenyl)-7-hydroxy-6,7-dihydro-5H-cyclopenta[b]pyridine-1-oxide (Example 40) and 7-(5-(6-acetamido-2-fluoropyridin-3-yl)-1H-imidazol-2-yl)-3-(5-chloro-2-(1H-tetrazol-1-yl)phenyl)-7-hydroxy-6,7-dihydro-5H-cyclopenta[b]pyridine-1-oxide (Example 41)

Racemic 7-(5-(6-amino-2-fluoropyridin-3-yl)-1H-imidazol-2-yl)-3-(5-chloro-2-(1H-tetrazol-1-yl)phenyl)-7-hydroxy-6,7-dihydro-5H-cyclopenta[b]pyridine-1-oxide (55 mg, 0.109 mmol) was resolved by SFC on a chiral OD column (250×30 mm, 10 um) to give the title compounds Example 40 (fast eluting isomer), MS (ESI) m/z 506.1 (M+H) and Example 41 slow eluting isomer) MS (ESI) m/z 506.1 (M+H).

The following compounds were prepared following procedures similar to those described above using appropriate starting materials and characterized by LCMS.

| Ex # | Compound Name | Structure | Chiral Separation | LCMS [M + 1] |
|---|---|---|---|---|
| 42 | 7-[5-(6-amino-2-chloropyridin-3-yl)-1H-imidazol-2-yl]-3-[5-chloro-2-(1H-tetrazol-1-yl)phenyl]-6,7-dihydro-5H-cyclopenta[b]pyridin-7-ol 1-oxide | 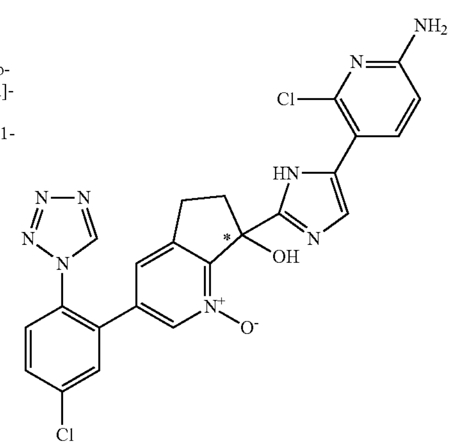 | AD column, fast eluting isomer | 522 |

| Ex # | Compound Name | Structure | Chiral Separation | LCMS [M + 1] |
|---|---|---|---|---|
| 43 | 7-[5-(6-amino-2-chloropyridin-3-yl)-1H-imidazol-2-yl]-3-[5-chloro-2-(1H-tetrazol-1-yl)phenyl]-6,7-dihydro-5H-cyclopenta[b]pyridin-7-ol 1-oxide | 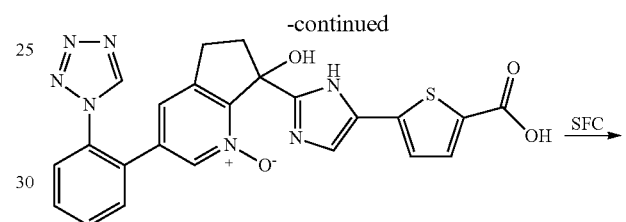 | AD column, slow eluting isomer | 522 |

EXAMPLE 44 and 45

7-(5-(5-carboxythiophen-2-yl)-1H-imidazol-2-yl)-3-(5-chloro-2-(1H-tetrazol-1-yl)phenyl)-7-hydroxy-6,7-dihydro-5H-cyclopenta[b]pyridine-1-oxide

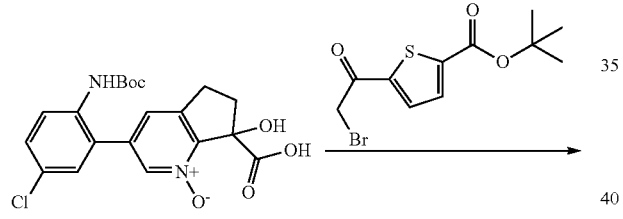

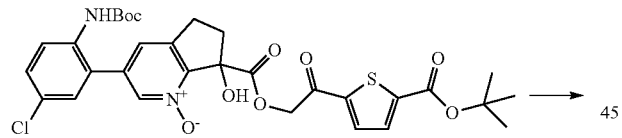

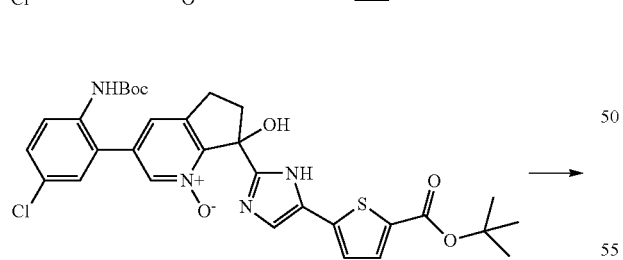

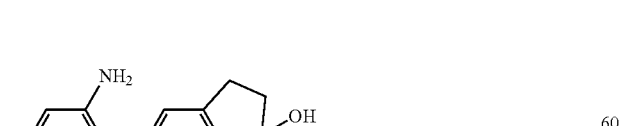

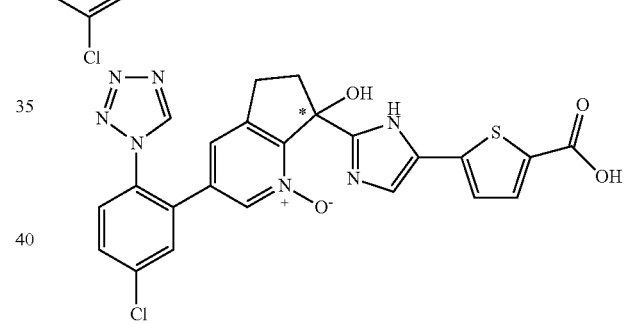

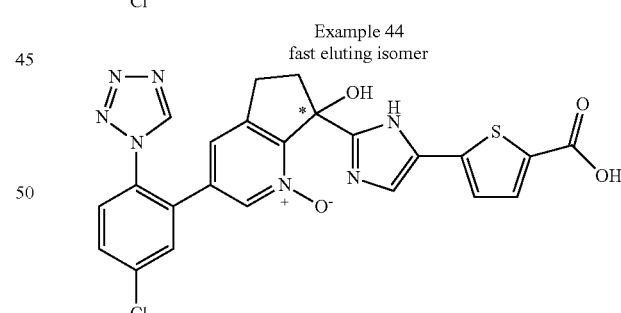

Example 44
fast eluting isomer

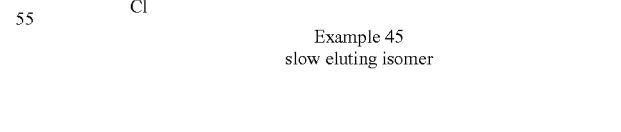

Example 45
slow eluting isomer

Step 1: 3-(2-((tert-butoxycarbonyl)amino)-5-chlorophenyl)-7-((2-(5-(tert-butoxycarbonyl)thiophen-2-yl)-2-oxoethoxy)carbonyl)-7-hydroxy-6,7-dihydro-5H-cyclopenta[b]pyridine-1-oxide To a solution of methyl tert-butyl-5-acetylthiophene-2-carboxylate (866 mg, 2.85 mmol) in DMF (10 mL) was added 3-(2-(((tert-butoxycarbonyl)amino)-5-chlorophenyl)-

7-carboxy-7-hydroxy-6,7-dihydro-5H-cyclopenta[b]pyridine-1-oxide (1200 mg, 2.85 mmol) and cesium carbonate (929 mg, 2.85 mmol) and the mixture was stirred at 20° C. for 12 h. LCMS showed the reaction was complete. The reaction was diluted with H₂O (20 mL) and extracted with EtOAc (3×20 mL). The combined organic phases were dried over Na₂SO₄, and concentrated in vacuo. The residue was purified by column chromatography (SiO₂, PE:EtOAc=5:1 to 1:1) to give the title compound. LCMS (ESI) m/z 645.1 (M+H).

Step 2: 3-(2-((tert-butoxycarbonyl)amino)-5-chlorophenyl)-7-(5-(5-(tert-butoxycarbonyl)thiophen-2-yl)-1H-imidazol-2-yl)-7-hydroxy-6,7-dihydro-5H-cyclopenta[b]pyridine-1-oxide To a solution of 3-(2-((tert-butoxycarbonyl)amino)-5-chlorophenyl)-7-((2-(5-(tert-butoxycarbonyl)thiophen-2-yl)-2-oxoethoxy)carbonyl)-7-hydroxy-6,7-dihydro-5H-cyclopenta[b]pyridine-1-oxide (1 g, 1.55 mmol) in toluene (10 mL) was added ammonium acetate (2.81 g, 36.50 mmol) and the mixture was stirred at 150° C. under microwave for 30 min. LCMS showed the reaction was complete. Then the mixture was treated with water (10 mL) and extracted with EtOAc (10 mL×3). The combined organic layers were dried over Na₂SO₄, filtered and concentrated. The residue was purified by prep-HPLC to give the title compound. LCMS (ESI) m/z 625.1 (M+H).

Step 3: 3-(2-amino-5-chlorophenyl)-7-(5-(5-carboxythiophen-2-yl)-1H-imidazol-2-yl)-7-hydroxy-6,7-dihydro-5H-cyclopenta[b]pyridine-1-oxide To a solution of 3-(2-((tert-butoxycarbonyl)amino)-5-chlorophenyl)-7-(5-(5-(tert-butoxycarbonyl)thiophen-2-yl)-1H-imidazol-2-yl)-7-hydroxy-6,7-dihydro-5H-cyclopenta[b]pyridine-1-oxide (150 mg, 0.24 mmol) in MeOH (8 mL) was added TFA (2 mL) and the mixture was stirred at 20° C. for 1 hr. LCMS showed the reaction was complete. The solvent was evaporated under reduced pressure to give the title compound. LCMS (ESI) m/z 469.0 (M+H).

Step 4: 7-(5-(5-carboxythiophen-2-yl)-1H-imidazol-2-yl)-3-(5-chloro-2-(1H-tetrazol-1-yl)phenyl)-7-hydroxy-6,7-dihydro-5H-cyclopenta[b]pyridine-1-oxide To a mixture of 3-(2-amino-5-chlorophenyl)-7-(5-(5-carboxythiophen-2-yl)-1H-imidazol-2-yl)-7-hydroxy-6,7-dihydro-5H-cyclopenta[b]pyridine-1-oxide (100 mg, 0.21 mmol) and trimethoxymethane (632 mg, 5.96 mmol) was added sodium azide (258 mg, 3.97 mmol) and HOAc (2 mL), and the mixture was stirred at 50° C. for 15 h. LCMS showed the reaction was complete. The reaction mixture was treated with HCl (6N) and sat. sodium nitrite (4 mL) at ice bath temperature and stirred for 0.5 h. The mixture was then concentrated and purified by prep-HPLC to give the title compound. LCMS (ESI) m/z 522.0 (M+H).

Step 5: 7-(5-(5-carboxythiophen-2-yl)-1H-imidazol-2-yl)-3-(5-chloro-2-(1H-tetrazol-1-yl)phenyl)-7-hydroxy-6,7-dihydro-5H-cyclopenta[b]pyridine-1-oxide (Example 44) and 7-(5-(5-carboxythiophen-2-yl)-1H-imidazol-2-yl)-3-(5-chloro-2-(1H-tetrazol-1-yl)phenyl)-7-hydroxy-6,7-dihydro-5H-cyclopenta[b]pyridine-1-oxide (Example 45)

Racemic 7-(5-(5-carboxythiophen-2-yl)-1H-imidazol-2-yl)-3-(5-chloro-2-(1H-tetrazol-1-yl)phenyl)-7-hydroxy-6,7-dihydro-5H-cyclopenta[b]pyridine-1-oxide (60 mg, 0.115 mmol) was resolved by SFC on chiral OD column, to give Example 44 (fast eluting isomer); LCMS (ESI) m/z 522.0 (M+H) and Example 45 (slow eluting isomer) LCMS (ESI) m/z 522.0 (M+H). Example 44: ¹H NMR (MeOH-d₄, 400 MHz): δ 9.40 (s, 1H), 7.99 (s, 1H), 7.87-7.74 (m, 2H), 7.73-7.66 (m, 1H), 7.59 (d, J=3.5 Hz, 1H), 7.39 (s, 1H), 7.29-7.15 (m, 2H), 3.12 (t, J=6.8 Hz, 2H), 2.91 (td, J=14.0, 6.9 Hz, 1H), 2.49 (td, J=13.9, 7.1 Hz, 1H). Example 45: ¹H NMR (MeOH-d₄, 400 MHz): δ 9.44 (s, 1H), 8.08 (br s, 1H), 7.88 (s, 1H), 7.83-7.61 (m, 4H), 7.50 (d, J=3.9 Hz, 1H), 7.31 (br s, 1H), 3.33 (br s, 1H), 3.15 (dd, J=16.8, 8.2 Hz, 1H), 2.76-2.59 (m, 2H).

EXAMPLE 46 and 47

7-(5-(5-carboxythiophen-2-yl)-4-chloro-1H-imidazol-2-yl)-3-(5-chloro-2-(1H-tetrazol-1-yl)phenyl)-7-hydroxy-6,7-dihydro-5H-cyclopenta[b]pyridine

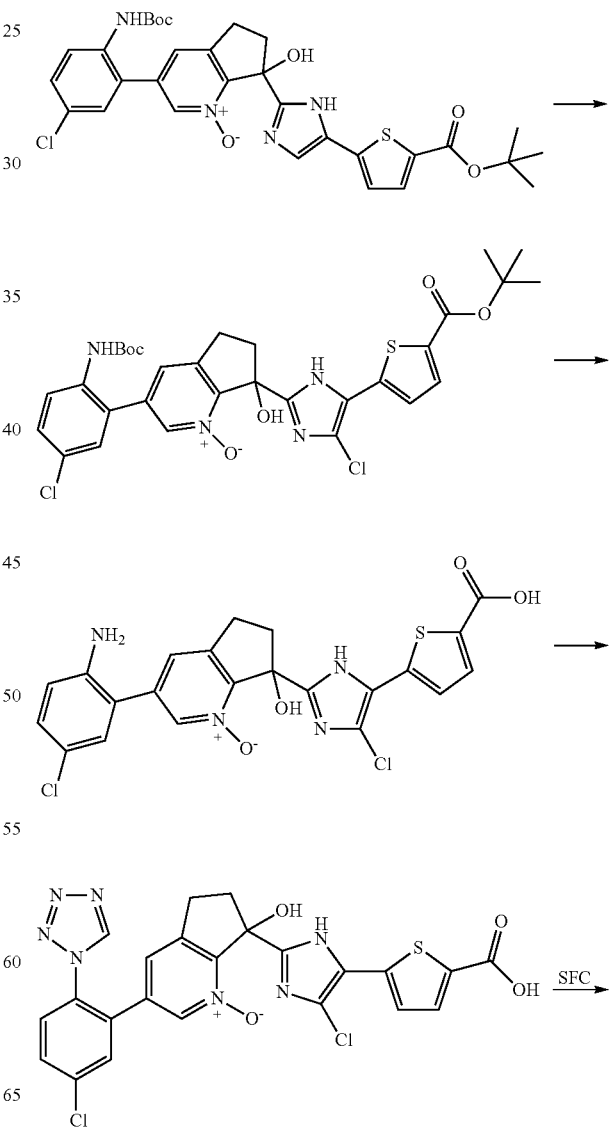

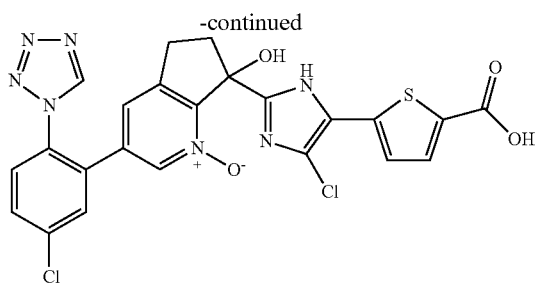

Example 46
fast eluting isomer

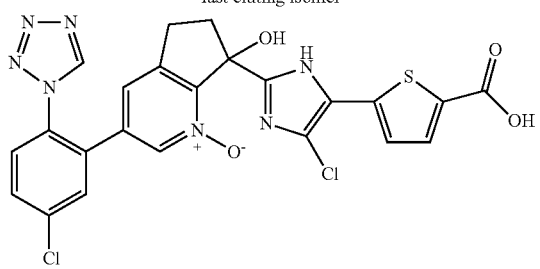

Example 47
slow eluting isomer

Step 1: 3-(2-((tert-butoxycarbonyl)amino)-5-chlorophenyl)-7-(5-(5-(tert-butoxycarbonyl)thiophen-2-yl)-4-chloro-1H-imidazol-2-yl)-7-hydroxy-6,7-dihydro-5H-cyclopenta[b]pyridine-1-oxide To a solution of 3-(2-((tert-butoxycarbonyl)amino)-5-chlorophenyl)-7-(5-(5-(tert-butoxycarbonyl)thiophen-2-yl)-1H-imidazol-2-yl)-7-hydroxy-6,7-dihydro-5H-cyclopenta[b]pyridine-1-oxide (100 mg, 0.16 mmol) in DCM (10 mL) was added 1,3-dichloro-5,5-dimethylimidazolidine-2,4-dione (31.5 mg, 0.16 mmol). The solution was then stirred for 30 min at ice bath temperature. TLC showed the reaction was almost complete. Then the reaction was quenched with saturated sodium bicarbonate and extracted with EtOAc (20 mL×3). The combined organic layers were washed with water (20 mL), dried, filtered and concentrated to give the title compound which was used for the next reaction without further purification.

Step 2: 3-(2-amino-5-chlorophenyl)-7-(5-(5-carboxythiophen-2-yl)-1H-imidazol-2-yl)-7-hydroxy-6,7-dihydro-5H-cyclopenta[b]pyridine-1-oxide To a solution of 3-(2-((tert-butoxycarbonyl)amino)-5-chlorophenyl)-7-(5-(5-(tert-butoxycarbonyl)thiophen-2-yl)-1H-imidazol-2-yl)-7-hydroxy-6,7-dihydro-5H-cyclopenta[b]pyridine-1-oxide (100 mg, 0.16 mmol) in DCM (4 mL) was added TFA (1 mL, 12.98 mmol). The reaction mixture was stirred at 20° C. for 2 h. LCMS showed the reaction was complete. The mixture was then concentrated to give the title compound, which was used for next reaction without further purification. MS (ESI) m/z 503.1 (M+H).

Step 3: 7-(5-(5-carboxythiophen-2-yl)-4-chloro-1H-imidazol-2-yl)-3-(5-chloro-2-(1H-tetrazol-1-yl)phenyl)-7-hydroxy-6,7-dihydro-5H-cyclopenta[b]pyridine-1-oxide To a mixture of 3-(2-amino-5-chlorophenyl)-7-(5-(5-carboxythiophen-2-yl)-4-chloro-1H-imidazol-2-yl)-7-hydroxy-6,7-dihydro-5H-cyclopenta[b]pyridine-1-oxide (100 mg, 0.199 mmol) and trimethoxymethane (632 mg, 5.96 mmol) was added sodium azide (258 mg, 3.97 mmol) and HOAc (2 mL) and then stirred at 50° C. for 15 h. LCMS showed the reaction was complete. The reaction was treated with HCl (6N) and sat. sodium nitrite (4 mL) dropwise at ice bath temperature and stirred for 0.5 h.

The mixture was then concentrated and purified by prep-HPLC (acidic condition) to give the title compound. MS (ESI) m/z 556.1 (M+H).

Step 4: 7-(5-(5-carboxythiophen-2-yl)-4-chloro-1H-imidazol-2-yl)-3-(5-chloro-2-(1H-tetrazol-1-yl)phenyl)-7-hydroxy-6,7-dihydro-5H-cyclopenta[b]pyridine-1-oxide (Example 46) and 7-(5-(5-carboxythiophen-2-yl)-4-chloro-1H-imidazol-2-yl)-3-(5-chloro-2-(1H-tetrazol-1-yl)phenyl)-7-hydroxy-6,7-dihydro-5H-cyclopenta[b]pyridine-1-oxide (Example 47)

The racemic compound 7-(5-(5-carboxythiophen-2-yl)-4-chloro-1H-imidazol-2-yl)-3-(5-chloro-2-(1H-tetrazol-1-yl)phenyl)-7-hydroxy-6,7-dihydro-5H-cyclopenta[b]pyridine-1-oxide (40 mg, 0.07 mmol) was resolved by SFC on a chiral OD column, to give Example 46 (fast eluting isomer), MS (ESI) m/z 556.0 (M+H); and Example 47 (slow eluting isomer). MS (ESI) m/z 556.0 (M+H). Example 46: $^1$H NMR (MeOH-d$_4$, 400 MHz): δ 9.41 (s, 1H), 8.05 (s, 1H), 7.85-7.77 (m, 2H), 7.76-7.70 (m, 1H), 7.66 (d, J=3.5 Hz, 1H), 7.46 (d, J=3.5 Hz, 1H), 7.23 (s, 1H), 3.12 (t, J=6.8 Hz, 2H), 2.85 (td, J=13.6, 6.8 Hz, 1H), 2.58-2.47 (m, 1H). Example 47: $^1$H NMR (MeOH-d$_4$, 400 MHz): δ9.37 (s, 1H), 8.07-7.96 (m, 1H), 7.86-7.66 (m, 3H), 7.63 (d, J=3.1 Hz, 1H), 7.42 (d, J=3.3 Hz, 1H), 7.19 (br s, 1H), 3.08 (t, J=6.6 Hz, 2H), 2.89-2.75 (m, 1H), 2.48 (td, J=13.9, 7.2 Hz, 1H)

EXAMPLE 48 and 49

7-(5-(5-carboxythiophen-3-yl)-4-chloro-1H-imidazol-2-yl)-3-(5-chloro-2-(1H-tetrazol-1-yl)phenyl)-7-hydroxy-6,7-dihydro-5H-cyclopenta[b]pyridine-1-oxide

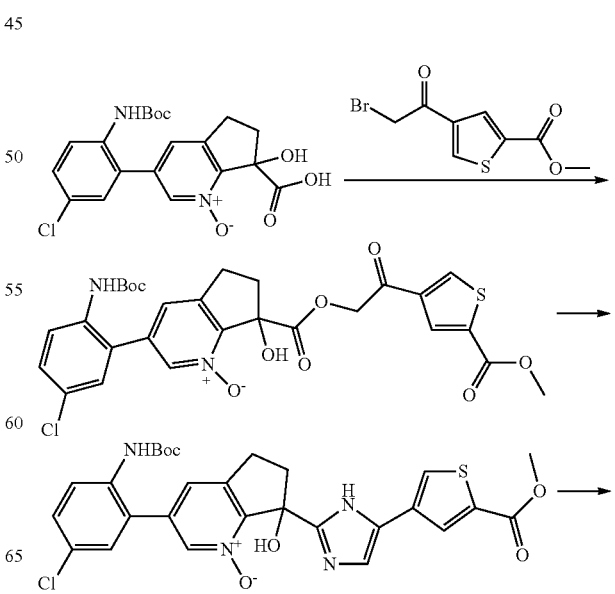

-continued

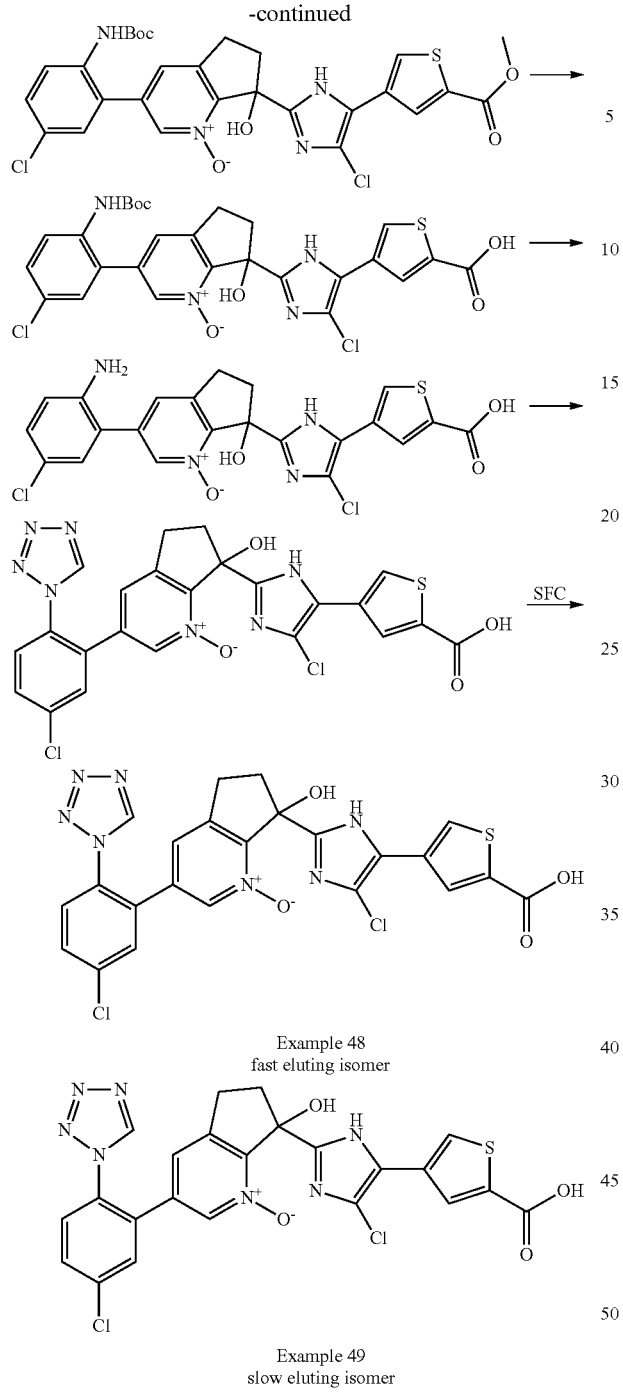

Example 48
fast eluting isomer

Example 49
slow eluting isomer

Step 1: 3-(2-((tert-butoxycarbonyl)amino)-5-chlorophenyl)-7-hydroxy-7-((2-(5-(methoxycarbonyl)thiophen-3-yl)-2-oxoethoxy)carbonyl)-6,7-dihydro-5H-cyclopenta[b]pyridine-1-oxide To a solution of methyl 4-(2-bromoacetyl)thiophene-2-carboxylate (750 mg, 2.85 mmol)) in DMF (10 mL) was added 3-(2-((tert-butoxycarbonyl)amino)-5-chlorophenyl)-7-carboxy-7-hydroxy-6,7-dihydro-5H-cyclopenta[b]pyridine-1-oxide (1.2 g, 2.85 mmol) and cesium carbonate (929 mg, 2.85 mmol). The mixture was stirred at 20° C. for 12 h. TLC showed the reaction was complete. The reaction was diluted with H$_2$O (20 mL) and extracted with EtOAc (3×20 mL). The combined organic phases were dried over Na$_2$SO$_4$, filtered and the filtrate was concentrated in vacuo. The residue was purified by column chromatography (SiO$_2$, PE:EtOAc=5:1 to 1:1) to afford the title compound.

Step 2: 3-(2-((tert-butoxycarbonyl)amino)-5-chlorophenyl)-7-hydroxy-7-(5-(5-(methoxycarbonyl)thiophen-3-yl)-1H-imidazol-2-yl)-6,7-dihydro-5H-cyclopenta[b]pyridine-1-oxide To a solution of 3-(2-((tert-butoxycarbonyl)amino)-5-chlorophenyl)-7-hydroxy-7-((2-(5-(methoxycarbonyl)thiophen-3-yl)-2-oxoethoxy)carbonyl)-6,7-dihydro-5H-cyclopenta[b]pyridine-1-oxide (1.1 g, 1.82 mmol) in toluene (10 mL) was added ammonium acetate (2.81 g, 36.50 mmol) and the mixture was stirred at 140° C. under microwave for 50 mins. LCMS showed the reaction was nearly complete. Then the mixture was treated with water (10 mL) and extracted with DCM (10 mL×3). The combined organic layers were dried over Na$_2$SO$_4$, filtered and concentrated. The residue was purified by silica gel chromatography (0-70% EtOAc/PE gradient) to give the title compound. MS (ESI) m/z 483.2 (M+H).

Step 3: 3-(2-((tert-butoxycarbonyl)amino)-5-chlorophenyl)-7-(4-chloro-5-(5-(methoxycarbonyl)thiophen-3-yl)-1H-imidazol-2-yl)-7-hydroxy-6,7-dihydro-5H-cyclopenta[b]pyridine-1-oxide To a solution of 3-(2-((tert-butoxycarbonyl)amino)-5-chlorophenyl)-7-hydroxy-7-(5-(5-(methoxycarbonyl)thiophen-3-yl)-1H-imidazol-2-yl)-6,7-dihydro-5H-cyclopenta[b]pyridine-1-oxide (140 mg, 0.24 mmol) in DCM (5 mL) was added 1,3-dichloro-5,5-dimethylimidazolidine-2,4-dione (47.3 mg, 0.24 mmol) and the reaction mixture was stirred at 0° C. for 20 min. TLC showed the reaction was complete. The mixture was concentrated and purified by TLC (EtOAc/PE=2/1) to give the title compound. MS (ESI) m/z 617.0 (M+H).

Step 4: 3-(2-((tert-butoxycarbonyl)amino)-5-chlorophenyl)-7-(5-(5-carboxythiophen-3-yl)-4-chloro-1H-imidazol-2-yl)-7-hydroxy-6,7-dihydro-5H-cyclopenta[b]pyridine-1-oxide To a solution of 3-(2-((tert-butoxycarbonyl)amino)-5-chlorophenyl)-7-(4-chloro-5-(5-(methoxycarbonyl)thiophen-3-yl)-1H-imidazol-2-yl)-7-hydroxy-6,7-dihydro-5H-cyclopenta[b]pyridine-1-oxide (120 mg, 0.19 mmol) in MeOH (4 mL) and water (4 mL) was added lithium hydroxide hydrate (46.50 mg, 1.94 mmol) and the reaction mixture was stirred at 25° C. for 3 h. LCMS show the reaction was complete. The mixture was then diluted with H$_2$O (10 mL), adjusted pH=6 with HCl (1M) and extracted with DCM (10 mL×3). The combined organic layers were concentrated to give the title compound. MS (ESI) m/z 602.9 (M+H).

Step 5: 3-(2-amino-5-chlorophenyl)-7-(5-(5-carboxythiophen-3-yl)-4-chloro-1H-imidazol-2-yl)-7-hydroxy-6,7-dihydro-5H-cyclopenta[b]pyridine-1-oxide To a solution of 3-(2-((tert-butoxycarbonyl)amino)-5-chlorophenyl)-7-(5-(5-carboxythiophen-3-yl)-4-chloro-1H-imidazol-2-yl)-7-hydroxy-6,7-dihydro-5H-cyclopenta[b]pyridine-1-oxide (110 mg, 0.18 mmol) in DCM (10 mL) was added TFA (2 mL, 26 mmol), and the mixture was stirred at 20° C. for 1 h. LCMS showed the reaction was complete. The mixture was concentrated to give the title compound. MS (ESI) m/z 503.1 (M+H).

Step 6: 7-(5-(5-carboxythiophen-3-yl)-4-chloro-1H-imidazol-2-yl)-3-(5-chloro-2-(1H-tetrazol-1-yl)phenyl)-7-hydroxy-6,7-dihydro-5H-cyclopenta[b]pyridine-1-oxide To a mixture of 3-(2-amino-5-chlorophenyl)-7-(5-(5-carboxythiophen-3-yl)-4-chloro-1H-imidazol-2-yl)-7-hydroxy-6,7-dihydro-5H-cyclopenta[b]pyridine-1-oxide (90 mg, 0.18 mmol) and trimethoxymethane (190 mg, 1.79 mmol) was added sodium azide (116 mg, 1.79 mmol) and HOAc (3 mL). The mixture was stirred at 50° C. for 15 h. LCMS showed the reaction was nearly complete. Then the mixture was treated with water (2 mL), 6N HCl (2 mL) and saturated sodium nitrite (15 mL), and extracted with DCM (10 mL×3). The combined organic layers were dried over $Na_2SO_4$, filtered and concentrated. The residue was purified by HPLC (HCl method) to give the title compound. MS (ESI) m/z 556.1 (M+H). $^1$H NMR (MeOH-$d_4$, 400 MHz): δ 9.44 (s, 1H), 8.22 (s, 1H), 8.13 (d, J=15.26 Hz, 2H), 7.81-7.76 (m, 2H), 7.74-7.70 (m, 1H), 7.32 (s, 1H), 3.26 (br s, 1H), 3.19-3.09 (m, 1H), 2.78-2.58 (m, 2H).

Step 8: 7-(5-(5-carboxythiophen-3-yl)-4-chloro-1H-imidazol-2-yl)-3-(5-chloro-2-(1H-tetrazol-1-yl)phenyl)-7-hydroxy-6,7-dihydro-5H-cyclopenta[b]pyridine-1-oxide (Example 48) and 7-(5-(5-carboxythiophen-3-yl)-4-chloro-1H-imidazol-2-yl)-3-(5-chloro-2-(1H-tetrazol-1-yl)phenyl)-7-hydroxy-6,7-dihydro-5H-cyclopenta[b]pyridine-1-oxide (Example 49)

The racemic compound 7-(5-(5-carboxythiophen-3-yl)-4-chloro-1H-imidazol-2-yl)-3-(5-chloro-2-(1H-tetrazol-1-yl)phenyl)-7-hydroxy-6,7-dihydro-5H-cyclopenta[b]pyridine-1-oxide (50 mg, 0.09 mmol) was resolved by SFC on Chiralcel OD-3 column (50×4.6 mm), 3 μm, eluting with 40% of methanol (0.05% DEA) in $CO_2$, to give Example 48 (fast eluting isomer), MS (ESI) m/z 556.0 (M+H); and Example 49 (slow eluting isomer). MS (ESI) m/z 556.0 (M+H).

EXAMPLE 50 and 51

7-(4-(5-carboxy-4-fluorothiophene-3-yl)-1H-imidazol-2-yl)-3-(5-chloro-2-(1H-tetrazol-1-yl)phenyl)-7-hydroxy-6,7-dihydro-5H-cyclopenta[b]pyridine-1-oxide

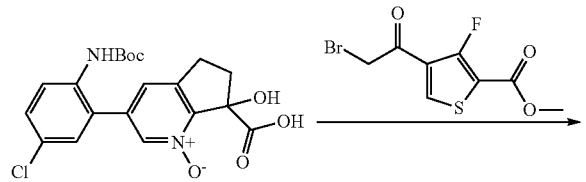

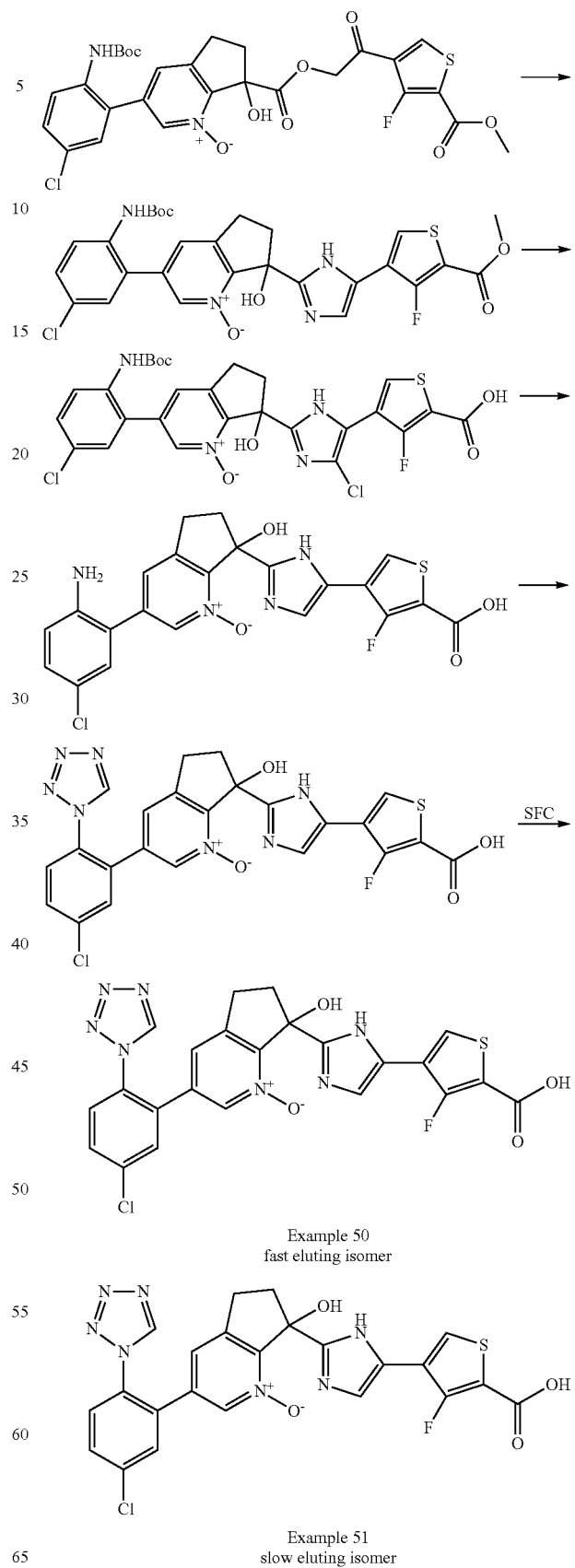

Example 50
fast eluting isomer

Example 51
slow eluting isomer

Step 1: 3-(2-((tert-butoxycarbonyl)amino)-5-chlorophenyl)-7-((2-(4-fluoro-5-(methoxycarbonyl)thiophen-3-yl)-2-oxoethoxy)carbonyl)-7-hydroxy-6,7-dihydro-5H-cyclopenta[b]pyridine-1-oxide To a solution of 3-(2-((tert-butoxycarbonyl)amino)-5-chlorophenyl)-7-carboxy-7-hydroxy-6,7-dihydro-5H-cyclopenta[b]pyridine-1-oxide (350 mg, 0.83 mmol) in DMF (20 ml) was added methyl 4-(2-bromoacetyl)-3-fluorothiophene-2-carboxylate (250 mg, 0.89 mmol) and the mixture was stirred at 28° C. for 12 h. The reaction was quenched with water (40 mL) and the aqueous layer was extracted with EtOAc (3×50 mL). The combined organic phase was dried over Na$_2$SO$_4$, and concentrated in vacuo. The residue was purified by column chromatography (SiO$_2$, PE:EtOAc=10:1 to 3:1) to give the title compound.

Step 2: 3-(2-((tert-butoxycarbonyl)amino)-5-chlorophenyl)-7-(5-(4-fluoro-5-(methoxycarbonyl)thiophen-3-yl)-1H-imidazol-2-yl)-7-hydroxy-6,7-dihydro-5H-cyclopenta[b]pyridine-1-oxide To a solution of 3-(2-((tert-butoxycarbonyl)amino)-5-chlorophenyl)-7-((2-(4-fluoro-5-(methoxycarbonyl)thiophen-3-yl)-2-oxoethoxy)carbonyl)-7-hydroxy-6,7-dihydro-5H-cyclopenta[b]pyridine-1-oxide (360 mg, 0.580 mmol) in toluene (10 ml) was added ammonium acetate (894 mg, 11.59 mmol) and the mixture was stirred at 150° C. in a microwave reactor for 0.5 h. Then the mixture was treated with water (50 mL) and extracted with EtOAc (50 mL×3). The combined organic layers were dried over Na$_2$SO$_4$, filtered and concentrated. The residue was purified by flash silica gel chromatography, eluting with gradient 0-70% EA/PE to give the title compound. MS (ESI) m/z 601 (M+H).

Step 3: 3-(2-((tert-butoxycarbonyl)amino)-5-chlorophenyl)-7-(4-(4-fluoro-5-(methoxycarbonyl)thiophen-3-yl)-1H-imidazol-2-yl)-7-hydroxy-6,7-dihydro-5H-cyclopenta[b]pyridine-1-oxide To a solution of 3-(2-((tert-butoxycarbonyl)amino)-5-chlorophenyl)-7-(4-(4-fluoro-5-(methoxycarbonyl)thiophen-3-yl)-1H-imidazol-2-yl)-7-hydroxy-6,7-dihydro-5H-cyclopenta[b]pyridine-1-oxide (3 g, 5 mmol) in MeOH (80 ml) and water (20 ml) was added lithium hydroxide hydrate (0.63 g, 15 mmol), and the mixture was stirred at 23° C. for 10 h. LCMS showed the reaction was complete. The reaction was diluted with water (10 mL) and adjusted to a pH about 5 with saturated citric acid solution. The aqueous layer was extracted with EtOAc (3×50 mL). The combined organic phase was dried over Na$_2$SO$_4$, and concentrated in vacuo to give the title compound. MS (ESI) m/z: 586.9[M+H±].

Step 4: 3-(2-amino-5-chlorophenyl)-7-(4-(5-carboxy-4-fluorothiophen-3-yl)-1H-imidazol-2-yl)-7-hydroxy-6,7-dihydro-5H-cyclopenta[b]pyridine-1-oxide To a solution of 3-(2-((tert-butoxycarbonyl)amino)-5-chlorophenyl)-7-(4-(5-carboxy-4-fluorothiophen-3-yl)-1H-imidazol-2-yl)-7-hydroxy-6,7-dihydro-5H-cyclopenta[b]pyridine-1-oxide (3 g, 5.0 mmol) in DCM (50 ml) was added TFA (4 ml, 51 mmol), and the mixture was stirred at 20° C. for 2 h. The reaction was concentrated in vacuo to give 3-(2-amino-5-chlorophenyl)-7-(4-(5-carboxy-4-fluorothiophen-3-yl)-1H-imidazol-2-yl)-7-hydroxy-6,7-dihydro-5H-cyclopenta[b]pyridine-1-oxide. MS (ESI) m/z: 487.0[M+H$^+$].

Step 5: 7-(4-(5-carboxy-4-fluorothiophen-3-yl)-1H-imidazol-2-yl)-3-(5-chloro-2-(1H-tetrazol-1-yl)phenyl)-7-hydroxy-6,7-dihydro-5H-cyclopenta[b]pyridine-1-oxide To a solution of 3-(2-amino-5-chlorophenyl)-7-(4-(5-carboxy-4-fluorothiophen-3-yl)-1H-imidazol-2-yl)-7-hydroxy-6,7-dihydro-5H-cyclopenta[b]pyridine-1-oxide (2.5 g, 5.13 mmol) in AcOH (50 ml) was added trimethoxymethane (8.17 g, 77 mmol) and sodium azide (3.34 g, 51.3 mmol). The mixture was stirred at 30° C. under N$_2$ conditions for 12 h. LCMS showed the reaction was complete. The reaction was diluted with water (30 mL), and the aqueous layer was extracted with DCM (3×30 mL). The combined organic phase was dried over Na$_2$SO$_4$, and concentrated in vacuo. The residue was purified by prep-HPLC (TFA) to give the title compound. MS(ESI) m/z: 540.0[M+H$^+$].

Step 6: 7-(4-(5-carboxy-4-fluorothiophen-3-yl)-1H-imidazol-2-yl)-3-(5-chloro-2-(1H-tetrazol-1-yl)phenyl)-7-hydroxy-6,7-dihydro-5H-cyclopenta[b]pyridine-1-oxide Example 50 and 51)

The racemic 7-(4-(5-carboxy-4-fluorothiophen-3-yl)-1H-imidazol-2-yl)-3-(5-chloro-2-(1H-tetrazol-1-yl)phenyl)-7-hydroxy-6,7-dihydro-5H-cyclopenta[b]pyridine-1-oxide from above was subjected to chiral SFC using a OD-H (2×25 cm) column eluting with 35% methanol (0.1% TFA)/CO$_2$, (100 bar, flow rate 60 mL/min, 220 nm), to afford Example 50 (fast eluting isomer), and Example 51 (slow eluting isomer). For each isomer, MS (ESI) m/z 540.4 (M+H).

The following compounds were prepared following procedures similar to those described above using appropriate starting materials and characterized by LCMS.

| EX | IUPAC Name | Structure | Chiral Separation | LCMS [M + 1] |
|---|---|---|---|---|
| 52 | 4-(2-{3-[5-chloro-2-(1H-tetrazol-1-yl)phenyl]-7-hydroxy-1-oxido-6,7-dihydro-5H-cyclopenta[b]pyridin-7-yl}-4-methyl-1H-imidazol-5-yl)thiophene-2-carboxylic acid | 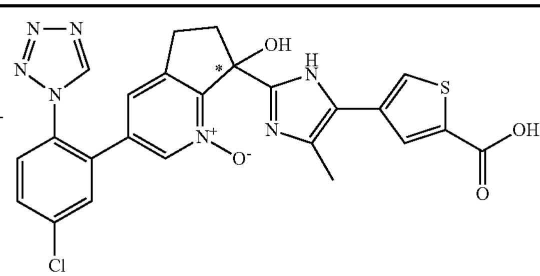 | OD column, fast eluting isomer | 536 |

-continued

| EX | IUPAC Name | Structure | Chiral Separation | LCMS [M + 1] |
|----|------------|-----------|-------------------|--------------|
| 53 | 4-(2-{3-[5-chloro-2-(1H-tetrazol-1-yl)phenyl]-7-hydroxy-1-oxido-6,7-dihydro-5H-cyclopenta[b]pyridin-7-yl}-4-methyl-1H-imidazol-5-yl)thiophene-2-carboxylic acid | 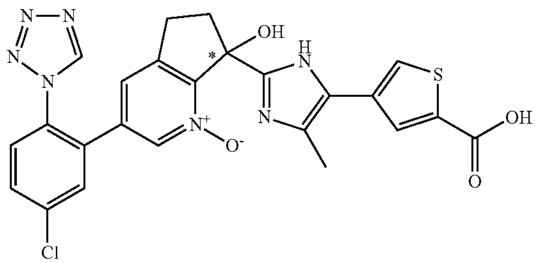 | OD column, slow eluting isomer | 536 |
| 54 | 4-(2-{3-[5-chloro-2-(1H-tetrazol-1-yl)phenyl]-7-hydroxy-1-oxido-6,7-dihydro-5H-cyclopenta[b]pyridin-7-yl}-4-methyl-1H-imidazol-5-yl)-3-fluorothiophene-2-carboxylic acid | 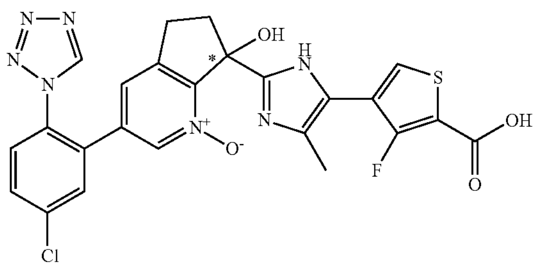 [SMILES: Cc1nc(C2(O)CCc3cc(-c4cc(Cl)ccc4-n4cnnn4)c[n+]([O-])c32)[nH]c1-c1csc(C(=O)O)c1F] | OD column, fast eluting isomer | 554 |
| 55 | 4-(2-{3-[5-chloro-2-(1H-tetrazol-1-yl)phenyl]-7-hydroxy-1-oxido-6,7-dihydro-5H-cyclopenta[b]pyridin-7-yl}-4-methyl-1H-imidazol-5-yl)-3-fluorothiophene-2-carboxylic acid | 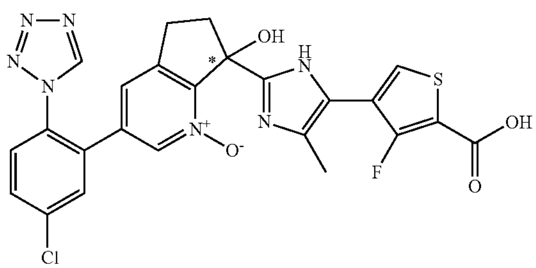 [SMILES: Cc1nc(C2(O)CCc3cc(-c4cc(Cl)ccc4-n4cnnn4)c[n+]([O-])c32)[nH]c1-c1csc(C(=O)O)c1F] | OD column, slow eluting isomer | 554 |

EXAMPLE 56 and 57

3-(5-chloro-2-(1H-tetrazol-1-yl)phenyl)-7-(5-(4-fluoro-5-(hydroxymethyl)thiophen-3-yl)-1H-imidazol-2-yl)-7-hydroxy-6,7-dihydro-5H-cyclopenta[b]pyridine-1-oxide

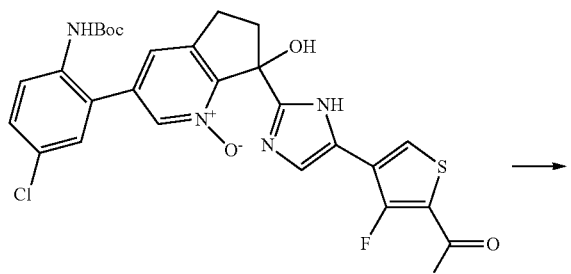

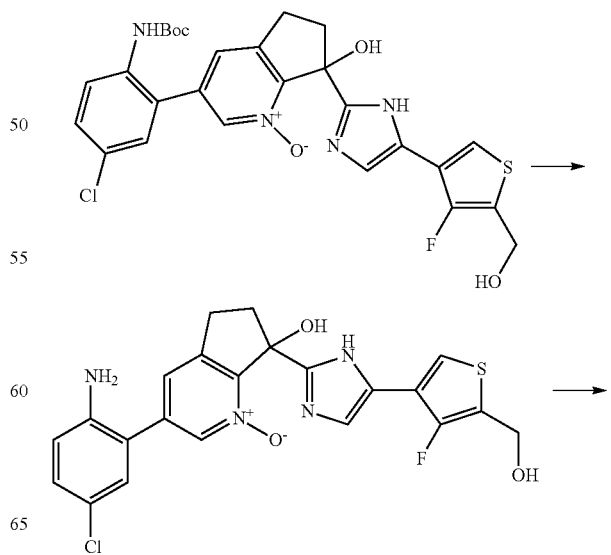

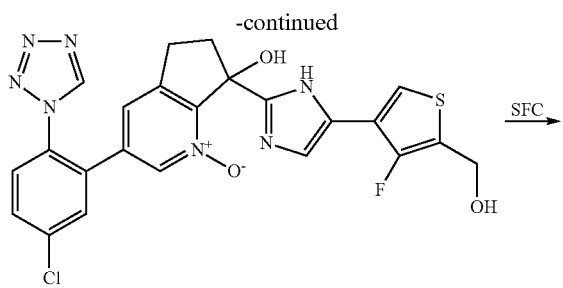

Example 56
fast eluting isomer

Example 57
slow eluting isomer

Step 1: 3-(2-((tert-butoxycarbonyl)amino)-5-chlorophenyl)-7-(4-(4-fluoro-5-(hydroxymethyl)thiophen-3-yl)-1H-imidazol-2-yl)-7-hydroxy-6,7-dihydro-5H-cyclopenta[b]pyridine-1-oxide To a solution of 3-(2-((tert-butoxycarbonyl)amino)-5-chlorophenyl)-7-(4-(4-fluoro-5-(methoxycarbonyl)thiophen-3-yl)-1H-imidazol-2-yl)-7-hydroxy-6,7-dihydro-5H-cyclopenta[b]pyridine-1-oxide (0.05 g, 0.08 mmol) in DCM (3 mL) was added DIBAL-H (0.83 mL, 0.83 mmol), and the mixture was stirred at −78° C. under for 3 h and then at 20° C. for 8 h. LCMS showed the reaction was complete. The mixture was quenched with $H_2O$ (30 mL) and extracted with EtOAc (3×30 mL). The combined organic layers were dried over $Na_2SO_4$, and concentrated in vacuo. The residue was purified by prep-TLC (DCM: MeOH=10:1) to give the title compound. MS (ESI) m/z 573.2 (M+H).

Step 2: 3-(2-amino-5-chlorophenyl)-7-(4-(4-fluoro-5-(hydroxymethyl)thiophen-3-yl)-1H-imidazol-2-yl)-7-hydroxy-6,7-dihydro-5H-cyclopenta[b]pyridine-1-oxide 2,2,2-trifluoroacetate To a solution of 3-(2-((tert-butoxycarbonyl)amino)-5-chlorophenyl)-7-(4-(4-fluoro-5-(hydroxymethyl)thiophen-3-yl)-1H-imidazol-2-yl)-7-hydroxy-6,7-dihydro-5H-cyclopenta[b]pyridine-1-oxide (35 mg, 0.061 mmol) in DCM (3 mL) was added TFA (0.5 mL), and the mixture was stirred at −20° C. under for 3 h. LCMS showed the reaction was complete. The reaction was concentrated in vacuo to give the title compound, which was used for next step without further purification. MS (ESI) m/z 473.1 (M+H).

Step 3: 3-(5-chloro-2-(1H-tetrazol-1-yl)phenyl)-7-(4-(4-fluoro-5-(hydroxylmethyl)thiophen-3-yl)-1H-imidazol-2-yl)-7-hydroxy-6,7-dihydro-5H-cyclopenta[b]pyridine-1-oxide To a solution of 3-(2-amino-5-chlorophenyl)-7-(4-(4-fluoro-5-(hydroxymethyl)thiophen-3-yl)-1H-imidazol-2-yl)-7-hydroxy-6,7-dihydro-5H-cyclopenta[b]pyridine-1-oxide 2,2,2-trifluoroacetate (40 mg, 0.07 mmol) in HOAc (3 mL) was added trimethoxymethane (289 mg, 2.73 mmol) and sodium azide (89 mg, 1.363 mmol), and the mixture was stirred at 30° C. under $N_2$ for 12 h. LCMS showed the corresponding acetate ester was obtained. The reaction mixture was diluted with $H_2O$ (10 mL) and extracted with EtOAc (3×10 mL). The combined organic layers were dried over $Na_2SO_4$ and concentrated in vacuo. Then lithium hydroxide hydrate (32.6 mg, 1.363 mmol), MeOH (10 mL) and $H_2O$ (4 mL) was added, the mixture was stirred at 50° C. for 2 h. The reaction was diluted with $H_2O$ (10 mL). The aqueous layer was extracted with EtOAc (3×10 mL). The combined organic layers were dried over $Na_2SO_4$, and concentrated in vacuo, the residue was purified by prep-HPLC (TFA) to give the title compound. MS (ESI) m/z 526.0 (M+H). $^1$H NMR (MeOH-$d_4$, 400 MHz): δ 9.43 (s, 1H), 8.06 (s, 1H), 7.81-7.69 (m, 4H), 7.62 (s, 1H), 7.29 (s, 1H), 4.72 (s, 2H), 3.35-3.31 (m, 1H), 3.15 (d, J=7.9 Hz, 1H), 2.76-2.59 (m, 2H).

Step 4: 3-(5-chloro-2-(1H-tetrazol-1-yl)phenyl)-7-(4-(4-fluoro-5-(hydroxylmethyl)thiophen-3-yl)-1H-imidazol-2-yl)-7-hydroxy-6,7-dihydro-5H-cyclopenta[b]pyridine-1-oxide (Example 56) and 3-(5-chloro-2-(1H-tetrazol-1-yl)phenyl)-7-(4-(4-fluoro-5-(hydroxylmethyl)thiophen-3-yl)-1H-imidazol-2-yl)-7-hydroxy-6,7-dihydro-5H-cyclopenta[b]pyridine-1-oxide (Example 57)

The racemic compound was separated by SFC on a chiral AD column to give Example 56 (fast eluting isomer); MS (ESI) m/z 526.1 (M+H); and Example 57 (slow eluting isomer); MS (ESI) m/z 526.0 (M+H).

EXAMPLE 58 and 59

3-(5-chloro-2-(1H-tetrazol-1-yl)phenyl)-7-hydroxy-7-(4-methyl-5-(2-oxo-1,2,3,4-tetrahydroquinolin-7-yl)-1H-imidazol-2-yl)-6,7-dihydro-5H-cyclopenta[b]pyridine-1-oxide

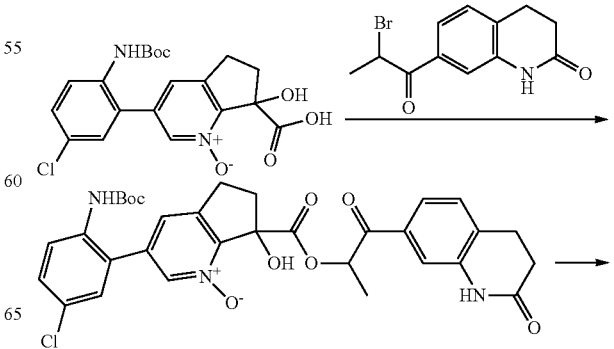

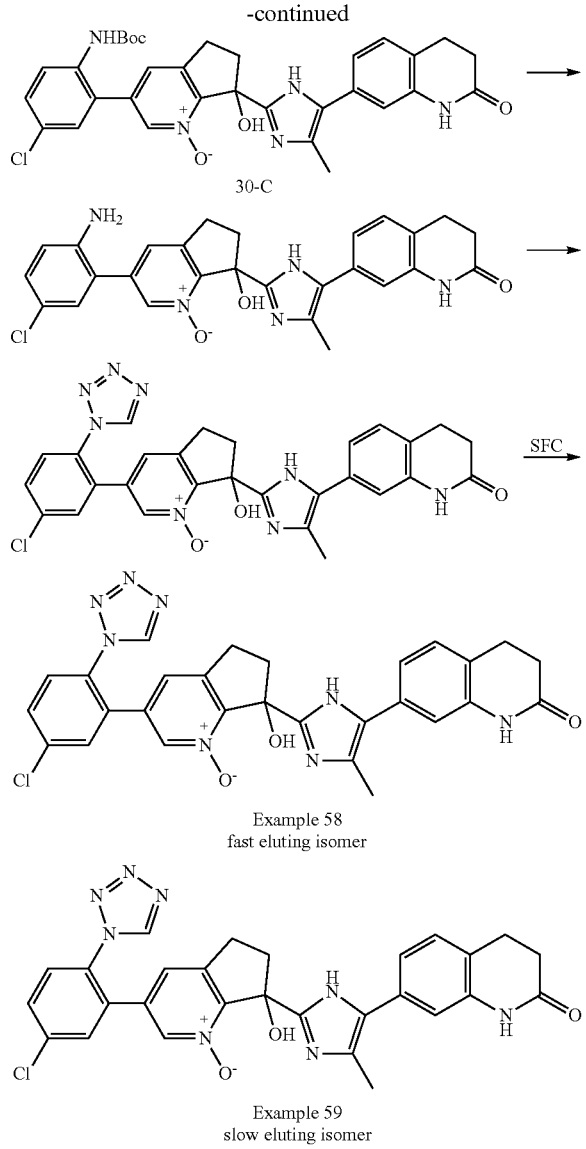

Example 58
fast eluting isomer

Example 59
slow eluting isomer

Step 1: 3-(2-((tert-butoxycarbonyl)amino)-5-chlorophenyl)-7-hydroxy-7-(((1-oxo-1-(2-oxo-1,2,3,4-tetrahydroquinolin-7-yl)propan-2-yl)oxy)carbonyl)-6,7-dihydro-5H-cyclopenta[b]pyridine-1-oxide To a solution of 7-(2-bromopropanoyl)-3,4-dihydroquinolin-2(1H)-one (369 mg, 1.307 mmol) and 3-(2-((tert-butoxycarbonyl)amino)-5-chlorophenyl)-7-carboxy-7-hydroxy-6,7-dihydro-5H-cyclopenta[b]pyridine-1-oxide (550 mg, 1.31 mmol) in DMF (5 mL) was added cesium carbonate (426 mg, 1.31 mmol). The reaction mixture was stirred at 25° C. for 15 h. The reaction was complete based on LCMS. Water (100 mL) was added and the mixture was extracted with EtOAc (100 mL×3). The combined organic fractions were washed with water (200 mL×3), dried (Na$_2$SO$_4$), filtered and the solvent was evaporated under reduced pressure to give the title compound. MS (ESI) m/z 622.2 (M+H).

Step 2: 3-(2-((tert-butoxycarbonyl)amino)-5-chlorophenyl)-7-hydroxy-7-(4-methyl-5-(2-oxo-1,2,3,4-tetrahydroquinolin-7-yl)-1H-imidazol-2-yl)-6,7-dihydro-5H-cyclopenta[b]pyridine-1-oxide To a solution of 3-(2-((tert-butoxycarbonyl)amino)-5-chlorophenyl)-7-hydroxy-7-(((1-oxo-1-(2-oxo-1,2,3,4-tetrahydroquinolin-7-yl)propan-2-yl)oxy)carbonyl)-6,7-dihydro-5H-cyclopenta[b]pyridine-1-oxide (850 mg, 1.366 mmol) in toluene (10 mL) was added NH$_4$Cl (2107 mg, 27.30 mmol). The reaction mixture was stirred at 150° C. for 50 min under microwave. The reaction was complete based on LCMS. The mixture was cooled, water (50 mL) was added and the mixture was extracted with DCM (50 mL×3). The combined organic fractions were dried (Na$_2$SO$_4$), filtered and evaporated under reduced pressure. The residue was purified by preparative HPLC (HCl method) to give the title compound. MS (ESI) m/z 602.2 (M+H).

Step 3: 3-(2-amino-5-chlorophenyl)-7-hydroxy-7-(4-methyl-5-(2-oxo-1,2,3,4-tetrahydroquinolin-7-yl)-1H-imidazol-2-yl)-6,7-dihydro-5H-cyclopenta[b]pyridine-1-oxide To a solution of 3-(2-((tert-butoxycarbonyl)amino)-5-chlorophenyl)-7-hydroxy-7-(4-methyl-5-(2-oxo-1,2,3,4-tetrahydroquinolin-7-yl)-1H-imidazol-2-yl)-6,7-dihydro-5H-cyclopenta[b]pyridine-1-oxide (140 mg, 0.233 mmol) in DCM (2.5 mL) was added TFA (0.5 mL). The reaction mixture was stirred at 25° C. for 2 h. The reaction was complete based on LCMS. The solvent was evaporated under reduced pressure to give the title compound. MS (ESI) m/z 502.2 (M+H).

Step 4: 3-(5-chloro-2-(1H-tetrazol-1-yl)phenyl)-7-hydroxy-7-(4-methyl-5-(2-oxo-1,2,3,4-tetrahydroquinolin-7-yl)-1H-imidazol-2-yl)-6,7-dihydro-5H-cyclopenta[b]pyridine-1-oxide To a solution of 3-(2-amino-5-chlorophenyl)-7-hydroxy-7-(4-methyl-5-(2-oxo-1,2,3,4-tetrahydroquinolin-7-yl)-1H-imidazol-2-yl)-6,7-dihydro-5H-cyclopenta[b]pyridine-1-oxide (117 mg, 0.233 mmol) in trimethoxymethane (495 mg, 4.66 mmol) and HOAc (2 mL) was added NaN$_3$ (303 mg, 4.66 mmol). The reaction mixture was stirred at 60° C. for 15 h and was complete based on LCMS. The mixture was treated with 6N HCl (0.5 mL) and saturated sodium nitrite (2 mL) and stirred at 20° C. for 1 h. The solvent was evaporated under reduced pressure and the residue was purified by preparative HPLC (HCl method) to give the title compound. MS (ESI) m/z 555.2 (M+H).

Step 5: 3-(5-chloro-2-(1H-tetrazol-1-yl)phenyl)-7-hydroxy-7-(4-methyl-5-(2-oxo-1,2,3,4-tetrahydroquinolin-7-yl)-1H-imidazol-2-yl)-6,7-dihydro-5H-cyclopenta[b]pyridine-1-oxide (Example 58) and 3-(5-chloro-2-(1H-tetrazol-1-yl)phenyl)-7-hydroxy-7-(4-methyl-5-(2-oxo-1,2,3,4-tetrahydroquinolin-7-yl)-1H-imidazol-2-yl)-6,7-dihydro-5H-cyclopenta[b]pyridine-1-oxide (Example 59)

The racemic compound 3-(5-chloro-2-(1H-tetrazol-1-yl)phenyl)-7-hydroxy-7-(4-methyl-5-(2-oxo-1,2,3,4-tetrahydroquinolin-7-yl)-1H-imidazol-2-yl)-6,7-dihydro-5H-cyclopenta[b]pyridine-1-oxide (30 mg) was separated by SFC to give Example 58 (fast eluting isomer); MS (ESI) m/z 555.1 (M+H); and Example 59 (slow eluting isomer); MS (ESI)

m/z 555.3 (M+H). Example 58: ¹H NMR (MeOH-d₄, 400 MHz): δ 9.39 (s, 1H), 7.98 (br s, 1H), 7.80-7.74 (m, 2H), 7.74-7.68 (m, 1H), 7.23 (s, 1H), 7.17 (br s, 1H), 7.14-7.09 (m, 1H), 7.01 (br s, 1H), 3.09 (br s, 2H), 2.95 (t, J=7.0 Hz, 2H), 2.91-2.81 (m, 1H), 2.57 (t, J=7.2 Hz, 2H), 2.48 (td, J=13.7, 7.2 Hz, 1H), 2.34 (br s, 3H). Example 59: ¹H NMR (MeOH-d₄, 400 MHz): δ 9.39 (s, 1H), 7.99 (s, 1H), 7.80-7.75 (m, 2H), 7.73-7.68 (m, 1H), 7.23 (s, 1H), 7.19 (d, J=7.4 Hz, 1H), 7.14-7.09 (m, 1H), 7.02 (br s, 1H), 3.10 (br s, 2H), 2.95 (t, J=7.2 Hz, 2H), 2.88 (dd, J=13.1, 5.7 Hz, 1H), 2.57 (t, J=7.4 Hz, 2H), 2.53-2.44 (m, 1H), 2.34 (br s, 3H)

EXAMPLE 60

Methyl [4-(2-{3-[5-chloro-2-(1H-tetrazol-1-yl)phenyl]-1-oxido-6,7-dihydro-5H-cyclopenta[b]pyridin-7-yl}-1H-imidazol-4-yl)phenyl]carbamate (racemic)

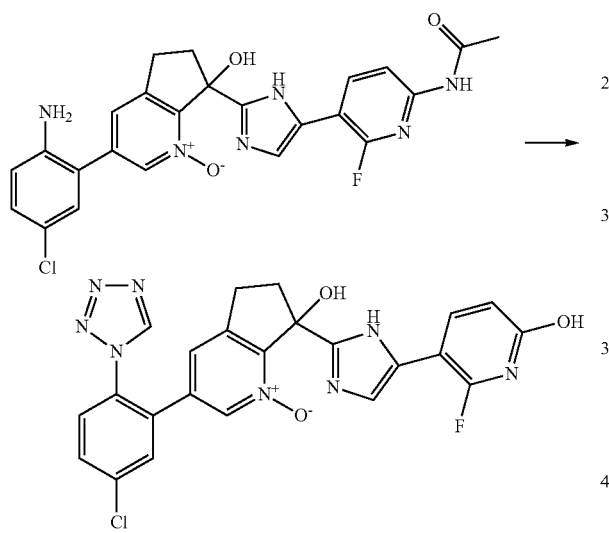

Example 60

Step 1: 3-(5-chloro-2-(1H-tetrazol-1-yl)phenyl)-7-(5-(2-fluoro-6-hydroxypyridin-3-yl)-1H-imidazol-2-yl)-7-hydroxy-6,7-dihydro-5H-cyclopenta[b]pyridine-1-oxide (Example 60)

To a solution of 7-(5-(6-acetamido-2-fluoropyridin-3-yl)-1H-imidazol-2-yl)-3-(2-amino-5-chlorophenyl)-7-hydroxy-6,7-dihydro-5H-cyclopenta[b]pyridine-1-oxide (67 mg, 0.14 mmol) in trimethoxymethane (287 mg, 2.71 mmol)) was added sodium azide (176 mg, 2.71 mmol) and HOAc (2 mL). The reaction mixture was stirred at 60° C. for 15 h. The reaction was complete based on LCMS. The mixture was then treated with 6N HCl (0.5 mL) and sat. sodium nitrite (2 mL) at 20° C. and stirred for 1 h. The solvent was evaporated under reduced pressure and the residue was purified by preparative HPLC (HCl condition) to give the title compound. MS (ESI) m/z 507.1 (M+H). ¹H NMR (MeOH-d₄, 400 MHz): δ 9.47 (s, 1H), 8.10-8.15 (m, 2H), 7.54-7.81 (m, 4H), 7.37 (s, 1H), 6.69 (d, J=7.6 Hz, 1H), 3.50-3.52 (m, 1H), 3.16-3.20 (m, 1H), 2.67-2.76 (m, 2H).

EXAMPLE 61

Methyl [4-(5-{3-[5-chloro-2-(1H-tetrazol-1-yl)phenyl]-7-hydroxy-1-oxido-6,7-dihydro-5H-cyclopenta[b]pyridin-7-yl}-1H-imidazol-2-yl)phenyl]carbamate

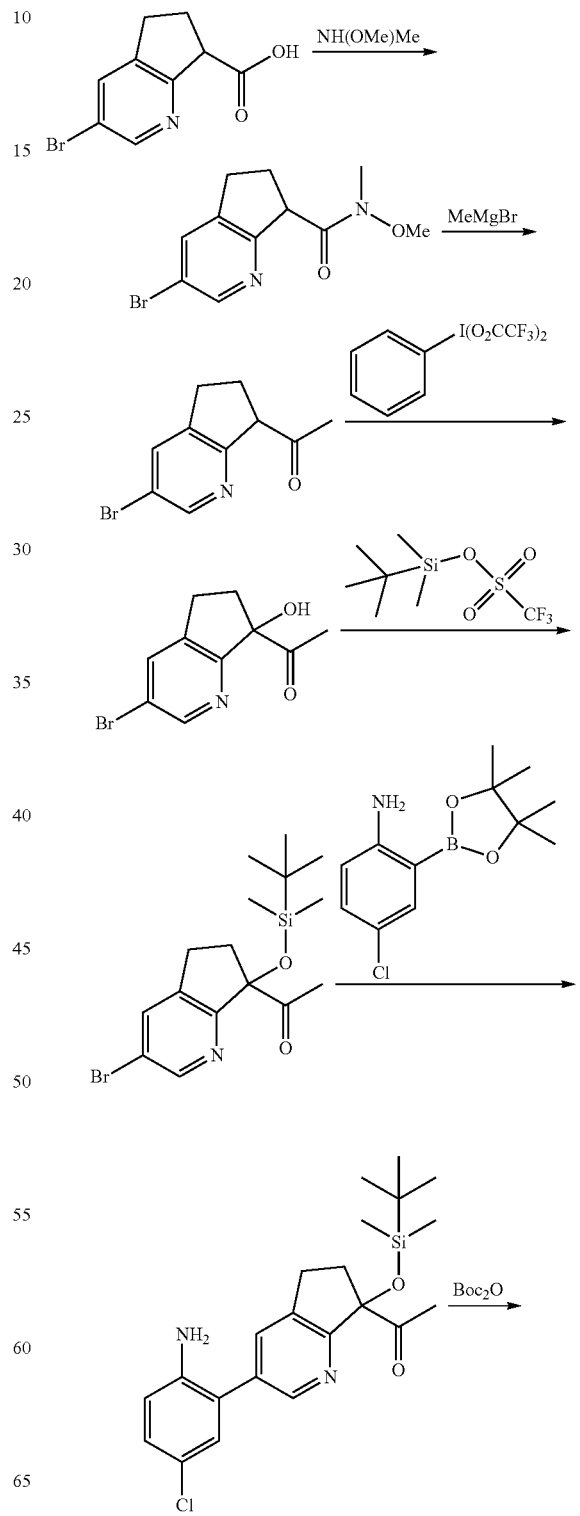

-continued

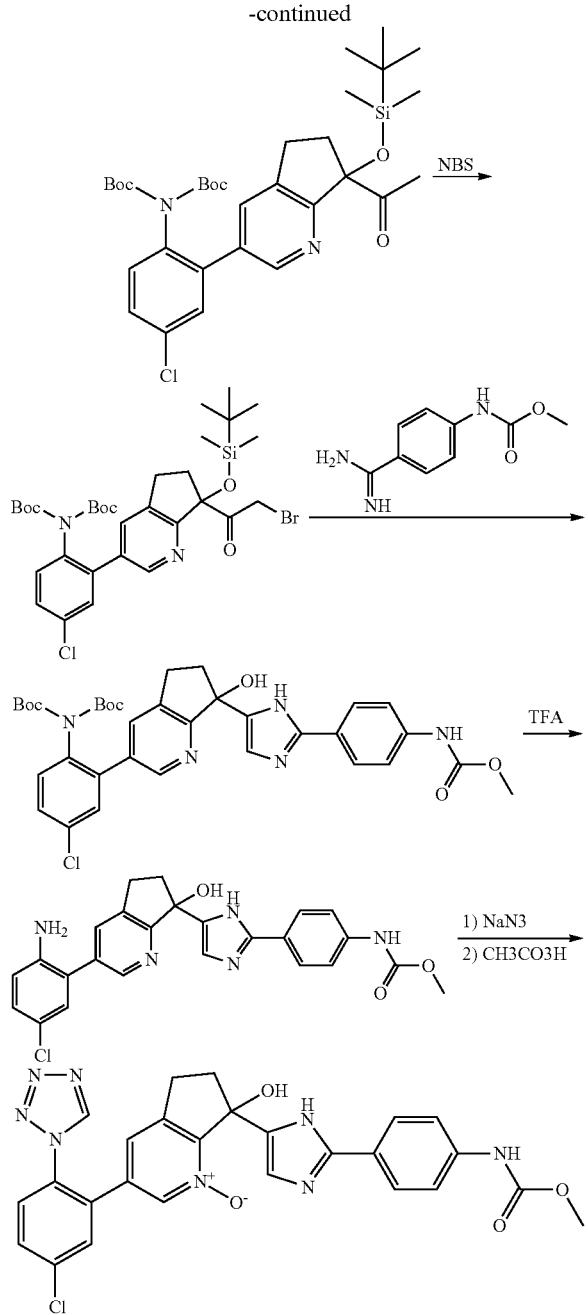

Example 61

Step 1: 3-bromo-N-methoxy-N-methyl-6,7-dihydro-5H-cyclopenta[b]pyridine-7-carboxamide Hunig's base (4.98 ml, 28.5 mmol) was added to a mixture of 3-bromo-6,7-dihydro-5H-cyclopenta[b]pyridine-7-carboxylic acid (2.30 g, 9.5 mmol), N,O-dimethylhydroxylamine hydrochloride (1.11 g, 11.40 mmol) and HATU (4.52 g, 11.88 mmol) in $CH_2Cl_2$ (50 ml), followed by stirring at RT for 2 h. The mixture was diluted with $CH_2Cl_2$ and water. The $CH_2Cl_2$ phase was separated, dried over $MgSO_4$, filtered, concentrated and the residue was purified by flash chromatography on a silica gel column with 0-50% EtOAc/hexane to give the title compound. MS (ESI) m/z 241.98 (M+H).

Step 2: 1-(3-bromo-6,7-dihydro-5H-cyclopenta[b]pyridin-7-yl)ethanone

Methylmagnesium bromide (4.03 ml, 12.10 mmol) was added dropwise into a solution of 3-bromo-N-methoxy-N-methyl-6,7-dihydro-5H-cyclopenta[b]pyridine-7-carboxamide (2.3 g, 8.07 mmol) in THF (100 ml) at −50° C. The mixture was stirred for 2 h with the temperature slowly rising up to 0° C. Then, the mixture was quenched with 1N HCl (30 ml), neutralized with sat. $NaHCO_3$ and extracted with ethyl ether (2×50 ml). The combined organic phase was dried over $MgSO_4$, filtered, concentrated and purified by flash chromatography on silica gel with 0-40% EtOAc/hexane to give the title compound. MS (ESI) m/z 424.25 (M+H).

Step 3: 1-(3-bromo-7-hydroxy-6,7-dihydro-5H-cyclopenta[b]pyridin-7-yl)ethanone 1-(3-bromo-6,7-dihydro-5H-cyclopenta[b]pyridin-7-yl)ethanone (1.30 g, 5.41 mmol) was added to a solution of [bis(trifluoroacetoxyiodo]benzene (4.66 g, 10.83 mmol), $H_2O$ (4.39 ml, 244 mmol) and TFA (0.83 ml, 10.83 mmol) in acetonitrile (20 ml) at RT, followed by stirring at 85° C. for 4 h. Then, $CH_3CN$ was removed under reduced pressure, the residue was diluted with $H_2O$, and extracted with ethyl ether (2×50 ml). The organic phase was dried over $MgSO_4$, filtered, concentrated and purified by flash chromatography on silica gel with 0-45% EtOAc/hexane to give the title compound. MS (ESI) m/z 258.02 (M+H).

Step 4: 1-(3-bromo-7-((tert-butyldimethylsilyl)oxy)-6,7-dihydro-5H-cyclopenta[b]pyridin-7-yl)ethanone To a solution of 1-(3-bromo-7-hydroxy-6,7-dihydro-5H-cyclopenta[b]pyridin-7-yl)ethanone (0.83 g, 3.24 mmol) in $CH_2Cl_2$ (20 ml) was added tert-butyldimethylsilyl trifluoromethanesulfonate (2.142 g, 8.10 mmol) at 0° C., followed by stirring at 0° C. for 1 h and RT for 1 h, respectively. Then, the mixture was diluted with water and $CH_2Cl_2$. The organic phase was separated and dried over $MgSO_4$, filtered, concentrated and purified by flash chromatography on silica gel with 0-25% EtOAc/hexane to give the title compound. MS (ESI) m/z 371.98 (M+H).

Step 5: 4-(2-(3-(2-Amino-5-chlorophenyl)-6,7-dihydro-5H-cyclopenta[b]pyridin-7-yl)-1-((2-(trimethylsilyl)ethoxy)methyl)-1H-imidazol-4-yl)-3-fluorothiophene-2-carboxylic acid A pressure release vial was charged with 1-(3-bromo-7-((tert-butyldimethylsilyl)oxy)-6,7-dihydro-5H-cyclopenta[b]pyridin-7-yl)ethanone (0.32 g, 0.86 mmol), 4-chloro-2-(4,4,5,5-tetramethyl-1,3,2-dioxaborolan-2-yl)aniline (0.33 g, 1.30 mmol), tetrakis (0.20 g, 0.17 mmol) and $K_2CO_3$ (0.24 g, 1.73 mmol), capped, degassed and backfilled with $N_2$. Then, dioxane (5 ml) and water (1 ml) was added, and the mixture was heated at 100° C. for 2 h. After cooling, the mixture was diluted with water and extracted with $CH_2Cl_2$/iPrOH (5:1, 2×50 ml). The organic phase was separated, dried over $MgSO_4$, filtered, concentrated and purified by flash chromatography on a silica gel column with 0-45% EtOAc/hexane to give the title compound. MS (ESI) m/z 417.25 (M+H).

Step 6: Bis(tert-butyl) (2-(7-acetyl-7-((tert-butyldimethylsilyl)oxy)-6,7-dihydro-5H-cyclopenta[b]pyridin-3-yl)-4-chlorophenyl)carbamate Hunig's base (0.20 ml, 1.15 mmol) was added to a solution of 1-(3-(2-amino-5-chlorophenyl)-7-((tert-butyldimethylsilyl)oxy)-6,7-dihydro-5H-cyclopenta[b]pyridin-7-yl) (0.4 g, 0.96 mmol), Boc-anhydride (0.27 ml, 1.15 mmol) and DMAP (0.02 g, 0.19 mmol) in CH$_2$Cl$_2$ (5 ml), and the mixture was stirred at 50° C. for 90 min. The mixture was diluted with water and EtOAc and extracted with EtOAc (50 ml). The organic phase was separated, dried over MgSO$_4$, filtered, concentrated and purified by flash chromatography on a silica gel column with 0-20% EtOAc/hexane to give the title compound. MS (ESI) m/z 617.31 (M+H).

Step 7: Bis(tert-butyl) (2-(7-(2-bromoacetyl)-7-((tert-butyldimethylsilyl)oxy)-6,7-dihydro-5H-cyclopenta[b]pyridin-3-yl)-4-chlorophenyl)carbamate NBS (0.10 g, 0.55 mmol) was added to a solution of the product from step 6 (0.31 g, 0.28 mmol) in THF (2.5 ml) at 0° C., then, the ice-bath was removed and the mixture was stirred at RT overnight. The reaction was monitored by LCMS. Additional NBS (0.20 g, 1.11 mmol) was added and it was stirred at RT for 3 days. Then, the solvent was removed and the residue was purified by flash chromatography on a silica gel column with 0-15% EtOAc/hexane to give the title compound. MS (ESI) m/z 697.42 (M+H).

Step 8: Methyl (4-(5-(3-(2-(bis(tert-butoxycarbonyl)amino)-5-chlorophenyl)-7-hydroxy-6,7-dihydro-5H-cyclopenta[b]pyridin-7-yl)-1H-imidazol-2-yl)phenyl)carbamate A pressure released microwave vial was charged the product from step 7 (0.20 g, 0.16 mmol), methyl (4-carbamimidoylphenyl)carbamate (0.06 g, 0.31 mmol), K$_2$CO$_3$ (0.09 g, 0.62 mmol), THF (2.5 ml) and water (0.5 ml) and capped. The mixture was stirred at 90° C. for 2 h. After cooling, the mixture was diluted with water and EtOAc and extracted with EtOAc. The organic phase was combined, dried over MgSO$_4$, filtered, concentrated and purified by flash chromatography on a silica gel column with 0-40% EtOAc/hexane and then, 0-12% MeOH/CH$_2$Cl$_2$ to give the title compound. MS (ESI) m/z 676.52 (M+H).

Step 9: methyl (4-(5-(3-(2-amino-5-chlorophenyl)-7-hydroxy-6,7-dihydro-5H-cyclopenta[b]pyridin-7-yl)-1H-imidazol-2-yl)phenyl)carbamate TFA (0.5 ml) was added to a solution of the product from step 8 (0.19 g, 0.15 mmol) in CH$_2$Cl$_2$ (1 ml) followed by stirring at RT for 2 h. The solvent was removed and the residue was dried in a vacuum to give de-Boc intermediate. The crude intermediate was used for the next reaction without further purification. MS (ESI) m/z 476.16 (M+H).

Step 10: 3-(5-chloro-2-(1H-tetrazol-1-yl)phenyl)-7-hydroxy-7-(2-(4-((methoxycarbonyl)amino)phenyl)-1H-imidazol-5-yl)-6,7-dihydro-5H-cyclopenta[b]pyridine-1-oxide (Example 61)

The intermediate from step 9 (71 mg, 0.15 mmol) in acetic acid (2.0 ml) was mixed with sodium azide (29 mg, 0.45 mmol) and trimethyl orthoformate (0.05 ml, 0.45 mmol). The mixture was stirred at RT for 24 h. Then, peracetic acid (0.12 ml, 0.75 mmol) was added and the mixture was stirred at RT for 6 h. Some of SM was still not consumed. Then, additional peracetic acid (0.12 ml, 0.75 mmol) was added, and it was stirred at RT overnight. The solvent was removed and the residue was purified by preparative RP-HPLC (C-18), eluting with acetonitrile/water, to give the title compound. MS (ESI) m/z 545.31 (M+H).

EXAMPLE 62

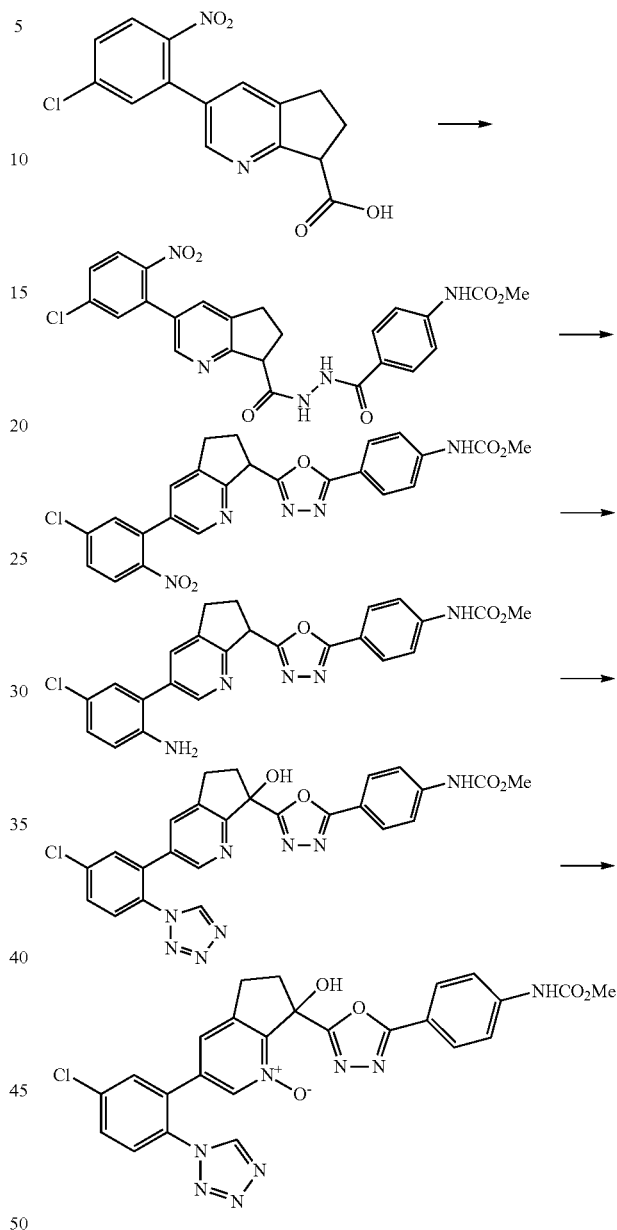

Example 62

Step 1: Methyl (4-(2-(3-(5-chloro-2-nitrophenyl)-6,7-dihydro-5H-cyclopenta[1]]pyridine-7-carbonyl)hydrazine-1-carbonyl)phenyl)carbamate The title compound was prepared following the HATU coupling procedures similar to those described in Example 61, step 1, by substituting methyl (4-(hydrazinecarbonyl)phenyl)carbamate for tert-butyl 4-aminobenzoate. MS (ESI) m/z 510 (M+H)$^+$.

Step 2: Methyl (4-(5-(3-(5-chloro-2-nitrophenyl)-6,7-dihydro-5H-cyclopenta[1]]pyridin-7-yl)-1,3,4-oxadiazol-2-yl)phenyl)carbamate A microwave vial was charged with methyl (4-(5-(3-(5-chloro-2-nitrophenyl)-6,7-dihydro-5H-cyclopenta[1]]pyridin-7-yl)-1,3,4-oxadiazol-2-yl)phenyl)carbamate (500 mg, 0.98 mmol), Burgess' Reagent (350 mg, 1.47 mmol), and THF (6.5 mL). The reaction mixture was heated at 120° C. under microwave irradiation for 10 min. The mixture was cooled, and the reaction mixture was partitioned between EtOAc and water. The organic phase was washed with brine, dried over sodium sulfate, and concentrated. The resulting crude residue was purified by flash chromatography on silica gel (gradient elution; 20%-70% EtOAc/hexanes) to afford the title compound. m/z (ES) 492 (M+H)$^+$.

Step 3: Methyl (4-(5-(3-(2-amino-5-chlorophenyl)-6,7-dihydro-5H-cyclopenta[b]pyridin-7-yl)-1,3,4-oxadiazol-2-yl)phenyl)carbamate The title compound was prepared by stirring methyl (4-(5-(3-(5-chloro-2-nitrophenyl)-6,7-dihydro-5H-cyclopenta[b]pyridin-7-yl)-1,3,4-oxadiazol-2-yl)phenyl)carbamate and PtO$_2$ in EtOAc/MeOH (3:1) under a hydrogen balloon for 4 hours, followed by filtration and concentration. MS (ESI) m/z 462 (M+H)$^+$.

Step 4: Methyl (4-(5-(3-(5-chloro-2-(1H-tetrazol-1-yl)phenyl)-7-hydroxy-6,7-dihydro-5H-cyclopenta[b]pyridin-7-yl)-1,3,4-oxadiazol-2-yl)phenyl)carbamate Trimethyl orthoformate (34 μL, 0.31 mmol), followed by sodium azide (20 mg, 0.31 mmol), was added to a solution of methyl (4-(5-(3-(2-amino-5-chlorophenyl)-6,7-dihydro-5H-cyclopenta[b]pyridin-7-yl)-1,3,4-oxadiazol-2-yl)phenyl)carbamate (47 mg, 0.10 mmol) in acetic acid (1.0 mL), and the reaction mixture was stirred at RT overnight. The reaction mixture was partitioned between EtOAc and water. The layers were separated, and the organic layer was washed with satd. aq. NaHCO$_3$, dried over sodium sulfate, filtered and concentrated. The resulting crude residue was purified by flash chromatography on silica gel (gradient elution; 10%-100% EtOAc/hexanes) to afford the title compound. m/z (ES) 531 (M+H)$^+$.

Step 5: 3-(5-Chloro-2-(1H-tetrazol-1-yl)phenyl)-7-hydroxy-7-(5-(4-((methoxycarbonyl)amino)phenyl)-1,3,4-oxadiazol-2-yl)-6,7-dihydro-5H-cyclopenta[b]pyridine-1-oxide (Example 62)

Example 62 was prepared following procedures similar to those described in Example 1, step 7. MS (ESI) m/z 547 (M+H)$^+$.

The following compound was prepared following procedures similar to those described above using appropriate starting materials and characterized by LCMS.

EXAMPLE 64 AND 65

3-(5-chloro-2-(1H-tetrazol-1-yl)phenyl)-7-(1-(2-chloro-4-((methoxycarbonyl)amino)phenyl)-1H-pyrazol-4-yl)-7-hydroxy-6,7-dihydro-5H-cyclopenta[b]pyridine-1-oxide

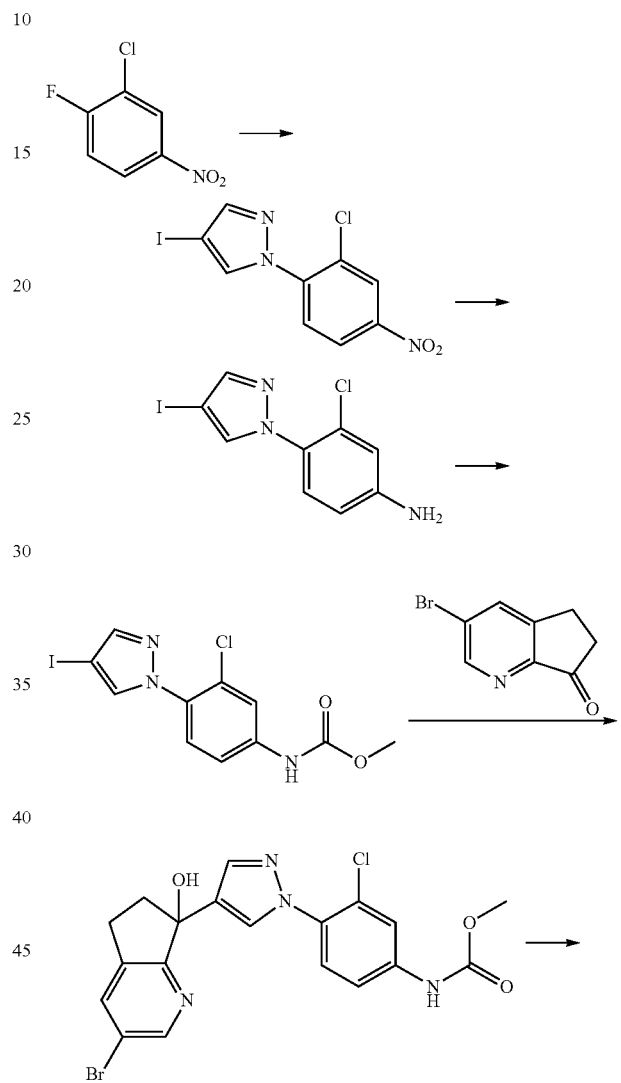

| Example | Compound Name | Structure | LCMS [M + 1] |
|---|---|---|---|
| 63 (racemic) | 7-[5-(4-chlorophenyl)-1,3,4-oxadiazol-2-yl]-3-[5-chloro-2-(1H-tetrazol-1-yl)phenyl]-6,7-dihydro-5H-cyclopenta[b]pyridin-7-ol 1-oxide | 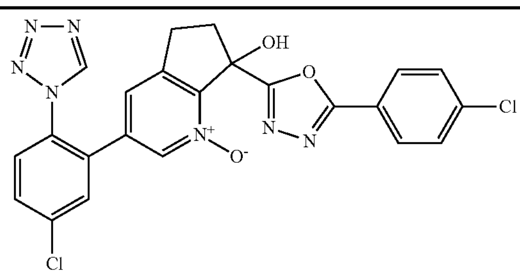 | 508.27 |

-continued

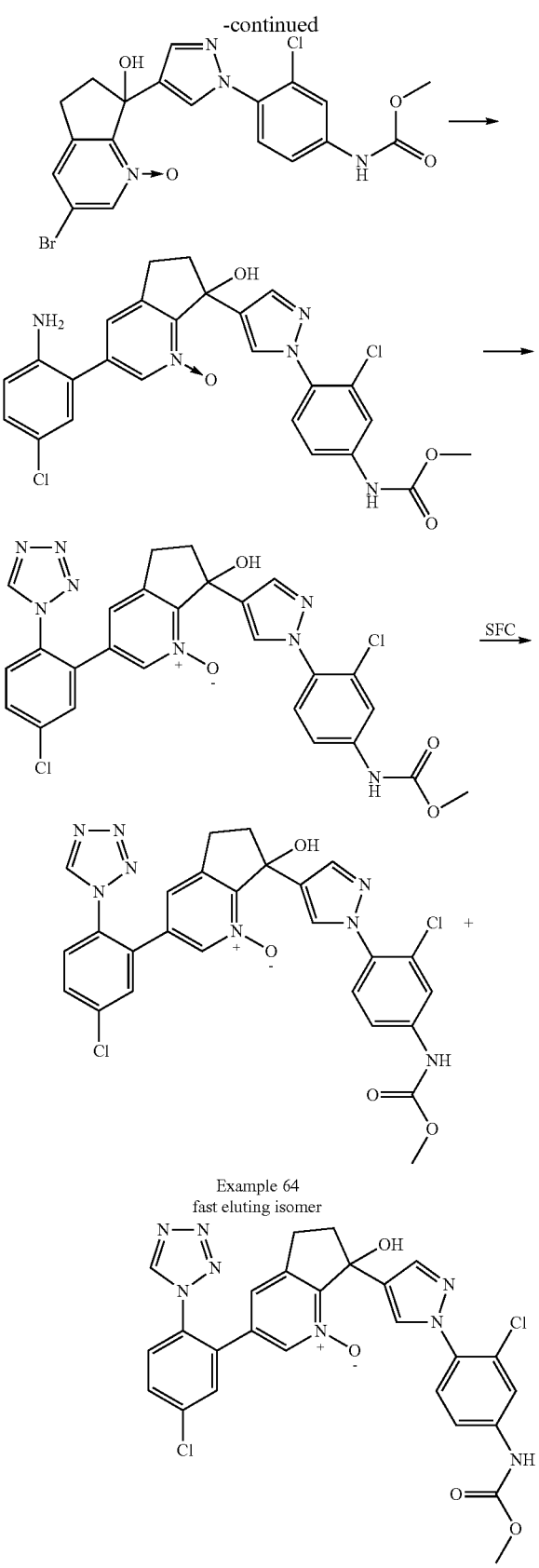

Example 64
fast eluting isomer

Example 65
slow eluting isomer

Step 1:
1-(2-chloro-4-nitrophenyl)-4-iodo-1H-pyrazole

To a mixture of 2-chloro-1-fluoro-4-nitrobenzene (1 g, 5.70 mmol) and 4-iodo-1H-pyrazole (1.11 g, 5.70 mmol) in DMF (10 mL) was added potassium carbonate (0.87 g, 6.27 mmol), and the mixture was stirred at 60° C. for 12 h. TLC indicated that the reaction was complete. The mixture was diluted with water (50 mL) and extracted with EtOAc (50 mL×3). The combined organic layers were washed with brine (50 mL), dried over magnesium sulfate, filtered, and concentrated in vacuo. The residue was purified by chromatography (SiO$_2$, petroleum ether: ethyl acetate=10:1) to give the title compound.

Step 2: 3-chloro-4-(4-iodo-1H-pyrazol-1-yl)aniline

To a mixture of 1-(2-chloro-4-nitrophenyl)-4-iodo-1H-pyrazole (1.70 g, 4.86 mmol) in ethanol (50 mL) and water (5 mL) was added iron powder (2.72 g, 48.60 mmol) and NH$_4$Cl (2.60 g, 48.60 mmol). The mixture was stirred at 20° C. for 12 h. TLC indicated that the reaction was complete. The residue was concentrated in a vacuum to give the title compound, which was used for next step without further purification.

Step 3: methyl (3-chloro-4-(4-iodo-1H-pyrazol-1-yl)phenyl)carbamate

To a mixture of 3-chloro-4-(4-iodo-1H-pyrazol-1-yl)aniline (650 mg, 2.03 mmol) in THF (10 mL) was added methyl chloroformate (288 mg, 3.05 mmol) and triethylamine (0.85 mL, 6.10 mmol). The mixture was stirred at 20° C. for 12 h. LCMS indicated some SM still remained. More methyl chloroformate (288 mg, 3.05 mmol) was added and the mixture was further stirred for 16 h. TLC indicated that the reaction was complete. The mixture was concentrated in vacuo. The residue was purified by chromatography (SiO$_2$, petroleum ether: ethyl acetate=2:1) to give the title compound. MS (ESI) m/z 378.0 (M+H).

Step 4: methyl (4-(4-(3-bromo-7-hydroxy-6,7-dihydro-5H-cyclopenta[b]pyridin-7-yl)-1H-pyrazol-1-yl)-3-chlorophenyl)carbamate To a mixture of methyl (3-chloro-4-(4-iodo-1H-pyrazol-1-yl)phenyl)carbamate (600 mg, 1.59 mmol) in THF (15 mL) was added isopropylmagnesium chloride (2.45 mL, 3.18 mmol) at 0° C. The mixture was stirred at 0° C. for 0.5 h. Then 3-bromo-5H-cyclopenta[b]pyridin-7(6H)-one (236 mg, 1.12 mmol) was added at 0° C., and the mixture was stirred at 20° C. for 14 h. LCMS indicated the reaction was complete. The mixture was quenched with water (50 mL), and extracted with EtOAc (50 mL×3). The combined organic layers were dried over sodium sulfate, filtered and the filtrate was concentrated in vacuo. The residue was purified by chromatography (petroleum ether: ethyl acetate=2:1) to give the title compound. MS (ESI) m/z 464.9 (M+H).

Step 5: 3-bromo-7-(1-(2-chloro-4-((methoxycarbonyl)amino)phenyl)-1H-pyrazol-4-yl)-7-hydroxy-6,7-dihydro-5H-cyclopenta[b]pyridine-1-oxide To a mixture of methyl (4-(4-(3-bromo-7-hydroxy-6,7-dihydro-5H-cyclopenta[b]pyridin-7-yl)-1H-pyrazol-1-yl)-3-chlorophenyl)carbamate (220 mg, 0.47 mmol) in DCM (5 mL) was added mCPBA (129 mg, 0.52 mmol), and the mixture was stirred at 10° C. for 16 h. LCMS indicated that the reaction was complete. The resulting mixture was quenched with sat. sodium thiosulfate (20 mL) and extracted with DCM (30 mL×3). The combined organic phase was washed with sat. sodium bicarbonate to pH>7, dried over $Na_2SO_4$ and filtered. The filtrate was concentrated in vacuo to give the title compound, which was used for next step without further purification. MS (ESI) m/z 480.9 (M+H).

Step 6: 3-(2-amino-5-chlorophenyl)-7-(1-(2-chloro-4-((methoxycarbonyl)amino)phenyl)-1H-pyrazol-4-yl)-7-hydroxy-6,7-dihydro-5H-cyclopenta[b]pyridine-1-oxide To a mixture of 4-chloro-2-(4,4,5,5-tetramethyl-1,3,2-dioxaborolan-2-yl)aniline (127 mg, 0.50 mmol), 3-bromo-7-(1-(2-chloro-4-((methoxycarbonyl)amino)phenyl)-1H-pyrazol-4-yl)-7-hydroxy-6,7-dihydro-5H-cyclopenta[b]pyridine-1-oxide (200 mg, 0.42 mmol) and potassium phosphate tribasic (265 mg, 1.25 mmol) in THF (2 mL) and water (0.5 mL) was added $PdCl_2$(dtbpf) (54.3 mg, 0.083 mmol). The mixture was stirred at 15° C. for 15 h. LCMS indicated that the reaction was complete. The residue was diluted with water (10 mL) and extracted with EtOAc (10 mL×3). The combined organic layers were washed with brine (10 mL), dried over magnesium sulfate, filtered, and concentrated in vacuo. The residue was purified by p-TLC (ethyl acetate) to give the title compound. MS (ESI) m/z 526.0 (M+H).

Step 7: 3-(5-chloro-2-(1H-tetrazol-1-yl)phenyl)-7-(1-(2-chloro-4-((methoxycarbonyl)amino)phenyl)-1H-pyrazol-4-yl)-7-hydroxy-6,7-dihydro-5H-cyclopenta[b]pyridine-1-oxide A mixture of 3-(2-amino-5-chlorophenyl)-7-(1-(2-chloro-4-((methoxycarbonyl)amino)phenyl)-1H-pyrazol-4-yl)-7-hydroxy-6,7-dihydro-5H-cyclopenta[b]pyridine-1-oxide (100 mg, 0.19 mmol), sodium azide (247 mg, 3.80 mmol) and trimethyl orthoformate (403 mg, 3.80 mmol) in HOAc (2 mL) was stirred at 30° C. for 15 h. LCMS indicated that the reaction was complete. The mixture was diluted with sat. sodium bicarbonate to pH>7, and extracted with EtOAc (20 mL×3). The combined organic layers were dried over magnesium sulfate, filtered and concentrated in vacuo. The residue was purified with p-HPLC (TFA conditions) to give the title compound. MS (ESI) m/z 579.1 (M+H).

Step 8: 3-(5-chloro-2-(1H-tetrazol-1-yl)phenyl)-7-(1-(2-chloro-4-((methoxycarbonyl)amino)phenyl)-1H-pyrazol-4-yl)-7-hydroxy-6,7-dihydro-5H-cyclopenta[b]pyridine-1-oxide (Example 64) and 3-(5-chloro-2-(1H-tetrazol-1-yl)phenyl)-7-(1-(2-chloro-4-((methoxycarbonyl)amino)phenyl)-1H-pyrazol-4-yl)-7-hydroxy-6,7-dihydro-5H-cyclopenta[b]pyridine-1-oxide (Example 65)

The racemic compound (50 mg, 0.09 mmol) was resolved with SFC on a chiral AD column: to give Example 64 (fast eluting isomer); MS (ESI) m/z 579.1 (M+H); and Example 65 (slow eluting isomer); MS (ESI) m/z 579.1 (M+H). Example 64: $^1$H NMR (MeOH-$d_4$, 400 MHz): δ 9.36 (s, 1H), 7.99 (s, 1H), 7.93 (s, 1H), 7.65-7.83 (m, 5H), 7.36-7.46 (m, 2H), 7.15 (s, 1H), 3.74 (s, 3H), 2.91-3.02 (m, 2H), 2.68-2.76 (m, 1H), 2.53 (d, J=13.0 Hz, 1H).

Example 65: $^1$H NMR (MeOH-$d_4$, 400 MHz): δ 9.36 (s, 1H), 8.09 (s, 1H), 7.99 (s, 1H), 7.66-7.85 (m, 5H), 7.33-7.48 (m, 2H), 7.15 (s, 1H), 3.74 (s, 3H), 2.97 (dd, J=18.4, 9.2 Hz, 2H), 2.68-2.77 (m, 1H), 2.47-2.57 (m, 1H).

EXAMPLE 66

3-(3-chloro-2-fluoro-6-(1H-tetrazol-1-yl)phenyl)-7-hydroxy-7-(5-(4-((methoxycarbonyl)amino)phenyl)oxazol-2-yl)-6,7-dihydro-5H-cyclopenta[b]pyridine-1-oxide

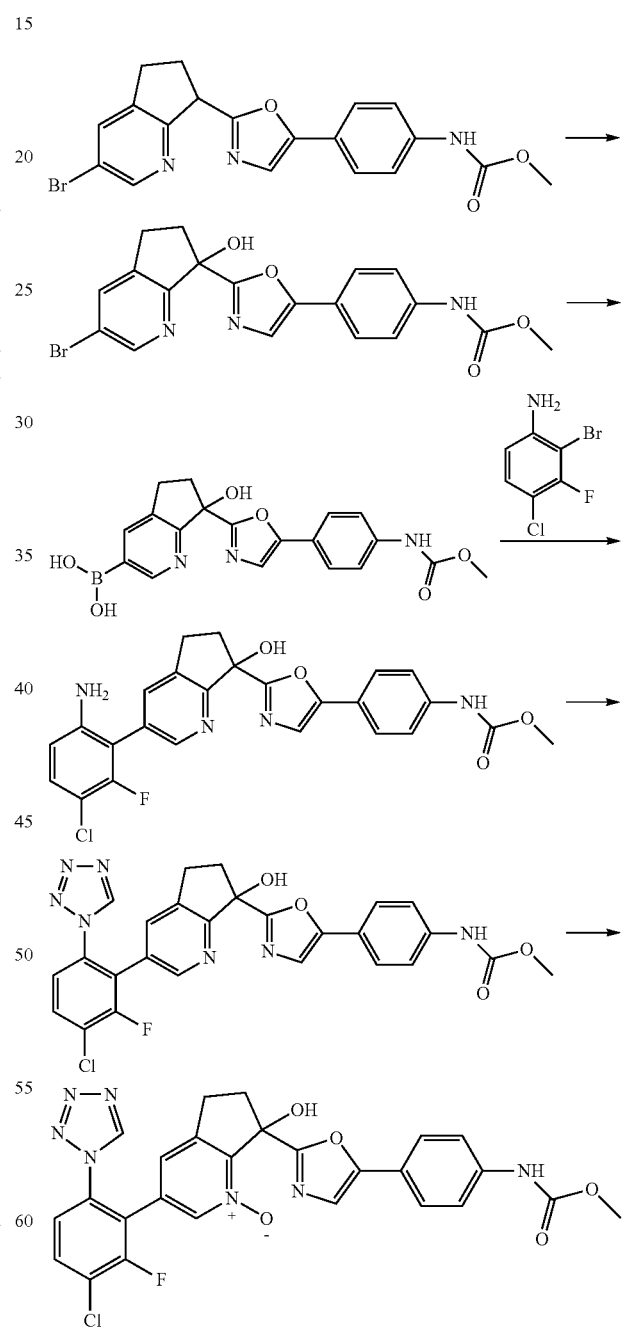

Example 66

Step 1: methyl (4-(2-(3-bromo-7-hydroxy-6,7-di-hydro-5H-cyclopenta[b]pyridin-7-yl)oxazol-5-yl)phenyl)carbamate To a solution of methyl (4-(2-(3-bromo-6,7-dihydro-5H-cyclopenta[b]pyridin-7-yl)oxazol-5-yl)phenyl)carbamate (side-product from step 2 of Example 1, 700 mg, 1.69 mmol) in DMSO (20 mL) and t-BuOH (5 mL) was added potassium tert-butoxide (379 mg, 3.38 mmol), and the mixture was stirred for 16 h at 25° C. under $N_2$ atmosphere (balloon). The mixture was concentrated, diluted with water (100 mL) and extracted with DCM (100 mL×3). The combined organic layers were washed with water (150 mL×3), dried over $Na_2SO_4$, filtered and concentrated to afford the title compound. MS (ESI) m/z 429.8 (M+H).

Step 2: methyl (4-(2-(3-bromo-7-hydroxy-6,7-di-hydro-5H-cyclopenta[b]pyridin-7-yl)oxazol-5-yl)phenyl)carbamate To a solution of methyl (4-(2-(3-bromo-7-hydroxy-6,7-dihydro-5H-cyclopenta[b]pyridin-7-yl)oxazol-5-yl)phenyl)carbamate (670 mg, 1.56 mmol) in THF (20 mL) and water (4 mL) was added 4,4,4',4',5,5,5',5'-octamethyl-2,2'-bi(1,3,2-dioxaborolane) (1186 mg, 4.67 mmol), potassium acetate (458 mg, 4.67 mmol) and $PdCl_2(dppf)$ (228 mg, 0.31 mmol) and the mixture was stirred for 16 h at 100° C. under $N_2$ atmosphere (balloon). LCMS showed SM was consumed. The mixture was extracted with EtOAc (50 mL×3). The combined organic layers were dried over $Na_2SO_4$, filtered and concentrated to afford a crude residue which was purified by silica gel flash chromatography, eluting with MeOH/DCM=1:10 to give the title compound. MS (ESI) m/z 395.9 (M+H).

Step 3: methyl (4-(2-(3-(6-amino-3-chloro-2-fluoro-phenyl)-7-hydroxy-6,7-dihydro-5H-cyclopenta[b]pyridin-7-yl)oxazol-5-yl)phenyl)carbamate To a mixture of (7-hydroxy-7-(5-(4-((methoxycarbonyl)amino)-phenyl)oxazol-2-yl)-6,7-dihydro-5H-cyclopenta[b]pyridin-3-yl)boronic acid (520 mg, 1.32 mmol), 2-bromo-4-chloro-3-fluoroaniline (266 mg, 1.18 mmol) in THF (6 mL) and water (1 mL) was added Pd(dtbpf)Cl₂ (86 mg, 0.13 mmol). The reaction mixture was stirred under $N_2$ protection for 18 h at 15° C. The mixture was quenched with water (50 mL), and extracted with EtOAc (25 mL×3). The combined organic layers were dried over $Na_2SO_4$, filtered and concentrated in vacuo. The residue was purified by silica gel column chromatography, eluting with gradient 0-80% EtOAc/PE, to give the title compound. MS (ESI) m/z 495.1 (M+H).

Step 4: methyl (4-(2-(3-(3-chloro-2-fluoro-6-(1H-tetrazol-1-yl)phenyl)-7-hydroxy-6,7-dihydro-5H-cyclopenta[b]pyridin-7-yl)oxazol-5-yl)phenyl)carbamate To a mixture of methyl (4-(2-(3-(6-amino-3-chloro-2-fluoro-phenyl)-7-hydroxy-6,7-dihydro-5H-cyclopenta[b]pyridin-7-yl)oxazol-5-yl)phenyl)carbamate (160 mg, 0.32 mmol) in HOAc (8 mL) was added trimethoxymethane (1029 mg, 9.70 mmol) and sodium azide (631 mg, 9.70 mmol). The reaction mixture was stirred for 18 h at 45° C. LCMS showed the reaction was complete. The mixture was adjusted with sat. sodium bicarbonate solution to pH 8-9, diluted with water (40 mL) and extracted with EtOAc (20 mL×3). The combined organic layers were dried over $Na_2SO_4$, filtered and concentrated in vacuo. The residue was purified by prep-TLC ($SiO_2$, PE:EtOAc=1:5) to give the title compound. MS (ESI) m/z 548.1 (M+H).

$^1$H NMR (MeOH-$d_4$, 400 MHz): δ 9.25 (s, 1H), 8.18 (d, J=17.4 Hz, 2H), 7.84 (d, J=7.63 Hz, 1H), 7.62-7.71 (m, 3H), 7.57 (d, J=8.6 Hz, 1H), 7.45 (d, J=8.2 Hz, 2H), 3.72 (s, 3H), 2.96-3.14 (m, 3H), 2.42-2.52 (m, 1H).

Step 5: 3-(3-chloro-2-fluoro-6-(1H-tetrazol-1-yl)phenyl)-7-hydroxy-7-(5-(4-((methoxycarbonyl)amino)phenyl)oxazol-2-yl)-6,7-dihydro-5H-cyclopenta[b]pyridine-1-oxide (Example 66)

To a round bottom flask was added methyl (4-(2-(3-(3-chloro-2-fluoro-6-(1H-tetrazol-1-yl)phenyl)-7-hydroxy-6,7-dihydro-5H-cyclopenta[b]pyridin-7-yl)oxazol-5-yl)phenyl)carbamate (70 mg, 0.13 mmol), DCM (8 mL) and 3-chlorobenzoperoxoic acid (113 mg, 0.51 mmol). The reaction mixture was stirred for 4 h at 15° C. The mixture was quenched with sat. sodium sulfite solution (10 mL), diluted with water (20 mL) and extracted with DCM (20 mL×3). The combined organic layers were dried over $Na_2SO_4$, filtered and concentrated in vacuo. The residue was purified by prep-HPLC (TFA condition) to give the title compound. MS (ESI) m/z 564.1 (M+H).

$^1$H NMR (MeOH-$d_4$, 400 MHz): δ 9.43 (s, 1H), 8.17 (d, J=16.4 Hz, 2H), 7.91 (t, J=8.0 Hz, 1H), 7.65-7.69 (m, 3H), 7.49 (d, J=8.4 Hz, 2H), 7.38 (s, 1H), 3.76 (s, 3H), 3.12-3.21 (m, 2H), 2.79-2.81 (m, 1H), 2.55-2.61 (m, 1H).

EXAMPLE 67 and 68

3-(5-chloro-2-(1H-tetrazol-1-yl)phenyl)-7-(6-fluoro-1H-benzo[d]imidazol-2-yl)-7-hydroxy-6,7-dihydro-5H-cyclopenta[b]pyridine-1-oxide

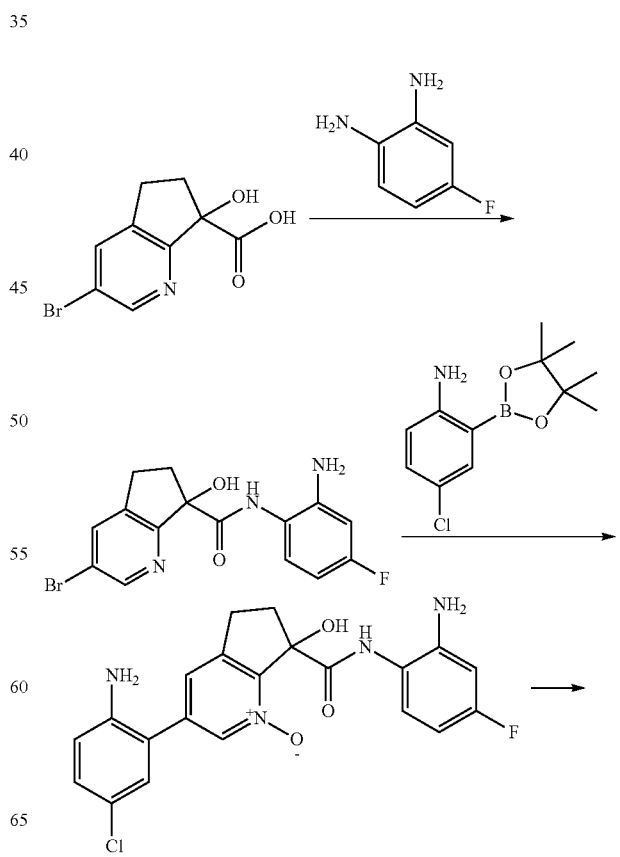

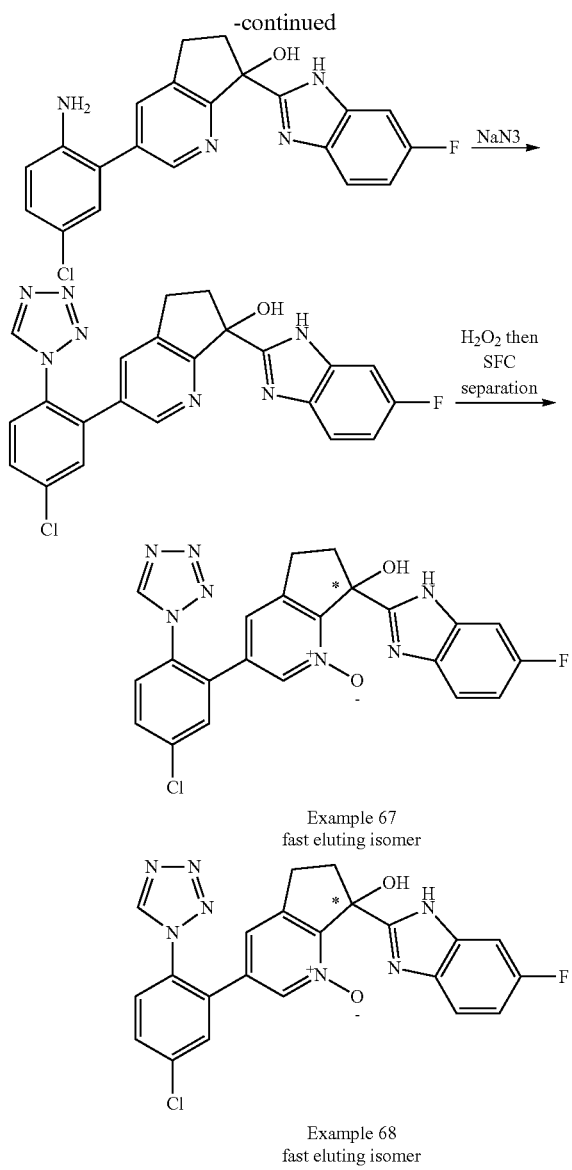

Example 67
fast eluting isomer

Example 68
fast eluting isomer

Step 1: N-(2-amino-4-fluorophenyl)-3-bromo-7-hydroxy-6,7-dihydro-5H-cyclopenta[b]pyridine-7-carboxamide A solution of 4-fluorobenzene-1,2-diamine (0.24 g, 1.88 mmol) in 2 ml of DMF was added to a solution of 3-bromo-7-hydroxy-6,7-dihydro-5H-cyclopenta[b]pyridine-7-carboxylic acid (0.39 g, 1.50 mmol), Hunig's base (0.33 ml, 1.88 mmol) and HATU (0.71 g, 1.88 mmol) in DMF (5 ml) at 0° C., followed by stirring at RT for 1 h. The solvent was removed under reduced pressure and the residue was purified by a flash chromatography on a silica gel column with 12% MeOH/DCM to give the title compound. MS (ESI) m/z 350.03 (M+H).

Step 2: 7-((2-amino-4-fluorophenyl)carbamoyl)-3-(2-amino-5-chlorophenyl)-7-hydroxy-6,7-dihydro-5H-cyclopenta[b]pyridine-1-oxide A pressure release vial was charged with 4-fluoro-2-(4,4,5,5-tetramethyl-1,3,2-dioxaborolan-2-yl)aniline (0.30 g, 1.26 mmol), N-(2-amino-4-fluorophenyl)-3-bromo-7-hydroxy-6,7-dihydro-5H-cyclopenta[b]pyridine-7-carboxamide (0.37 g, 1.01 mmol), tetrakis (0.23 g, 0.20 mmol) and sodium carbonate (0.16 g, 1.52 mmol), capped, degassed and backfilled with $N_2$. Dioxane (5 ml) and water (1 ml) were added, and it was stirred at 110° C. for 1 h. The mixture was diluted with $CH_2Cl_2$/MeOH (5:1, 5 ml), stirred and filtered. The filtrate was concentrated under reduced pressure and the residue was purified on a silica gel column with 0-12% MeOH/$CH_2Cl_2$ to give the title compound. MS (ESI) m/z 242.30 (M+H).

Step 3: 3-(2-amino-5-chlorophenyl)-7-(6-fluoro-1H-benzo[d]imidazol-2-yl)-6,7-dihydro-5H-cyclopenta[b]pyridin-7-ol A solution of 7-((2-amino-4-fluorophenyl)carbamoyl)-3-(2-amino-5-chlorophenyl)-7-hydroxy-6,7-dihydro-5H-cyclopenta[b]pyridine-1-oxide (0.10 g, 0.24 mmol) in acetic acid (0.5 ml) was heated at 70° C. for 3 h. After cooling, the solvent was removed under reduced pressure and the residue was purified by preparative RP-HPLC (C-18), eluting with acetonitrile/water+0.1% TFA to give the title compound. MS (ESI) m/z 395.20 (M+H).

Step 4: 3-(5-chloro-2-(1H-tetrazol-1-yl)phenyl)-7-(6-fluoro-1H-benzo[d]imidazol-2-yl)-6,7-dihydro-5H-cyclopenta[b]pyridin-7-ol Trimethyl orthoformate (0.045 ml, 0.41 mmol) was added to a solution of 3-(2-amino-5-chlorophenyl)-7-(6-fluoro-1H-benzo[d]imidazol-2-yl)-6,7-dihydro-5H-cyclopenta[b]pyridin-7-ol (54 mg, 0.14 mmol) in acetic acid (1.0 ml), followed by stirring at RT for 30 min. Then sodium azide (27 mg, 0.41 mmol) was added and it was stirred at RT overnight. Then, the mixture was concentrated and dried in a vacuum to give the crude title compound, which was used in the next step without further purification. MS (ESI) m/z 448.86 (M+H).

Step 5: 3-(5-chloro-2-(1H-tetrazol-1-yl)phenyl)-7-(6-fluoro-1H-benzo[d]imidazol-2-yl)-7-hydroxy-6,7-dihydro-5H-cyclopenta[b]pyridine-1-oxide (Example 67, fast eluting isomer) and 3-(5-chloro-2-(1H-tetrazol-1-yl)phenyl)-7-(6-fluoro-1H-benzo[d]imidazol-2-yl)-7-hydroxy-6,7-dihydro-5H-cyclopenta[b]pyridine-1-oxide (Example 68, slow eluting isomer)

Peracetic acid (0.24 ml, 1.36 mmol) was added to the mixture of 3-(5-chloro-2-(1H-tetrazol-1-yl)phenyl)-7-(6-fluoro-1H-benzo[d]imidazol-2-yl)-6,7-dihydro-5H-cyclopenta[b]pyridin-7-ol in acetic acid (2 ml) and stirred at RT overnight. The solvent was removed under reduced pressure and the residue was purified by preparative RP-HPLC (C-18), eluting with acetonitrile/water, to give the racemic title compound. MS (ESI) m/z 464.15 (M+H).

The racemic compound above was separated by SFC on chiral AD-H column (2×15 cm), eluting with 45% (2:1) MeOH:MeCN (0.05% NH4OH)/CO2, 100 bar, 45 mL/min, to give the title compounds Example 67 (fast eluting isomer) and Example 68 (slow eluting isomer).

The following compounds were prepared following procedures similar to those described above using appropriate starting materials and characterized by LCMS.

| Ex | Compound Name | Structure | Chiral Separation | LCMS [M + 1] |
|---|---|---|---|---|
| 69 | 7-(6-carboxy-1H-benzo[d]imidazol-2-yl)-3-(5-chloro-2-(1H-tetrazol-1-yl)phenyl)-7-hydroxy-6,7-dihydro-5H-cyclopenta[b]pyridine-1-oxide | 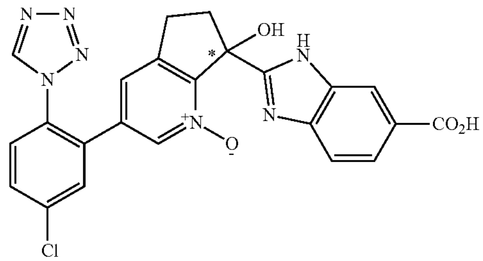 [SMILES: O=C(O)c1ccc2nc(C3(O)CCc4cc(-c5cc(Cl)ccc5-n5cnnn5)c[n+](O)c43)[nH]c2c1] | IA column, fast eluting isomer | 490.20 |
| 70 | 7-(6-carboxy-1H-benzo[d]imidazol-2-yl)-3-(5-chloro-2-(1H-tetrazol-1-yl)phenyl)-7-hydroxy-6,7-dihydro-5H-cyclopenta[b]pyridine-1-oxide | 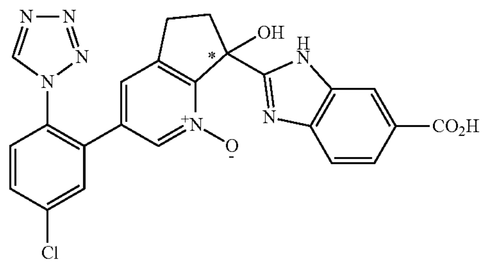 [SMILES: O=C(O)c1ccc2nc(C3(O)CCc4cc(-c5cc(Cl)ccc5-n5cnnn5)c[n+](O)c43)[nH]c2c1] | IA column, fast eluting isomer | 490.20 |
| 71 | 3-(5-chloro-2-(1H-tetrazol-1-yl)phenyl)-7-hydroxy-7-(6-(trifluoromethyl)-1H-benzo[d]imidazol-2-yl)-6,7-dihydro-5H-cyclopenta[b]pyridine-1-oxide | 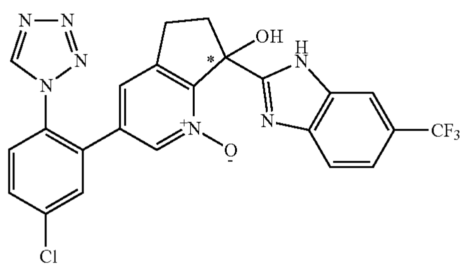 [SMILES: O[n+]1cc(-c2cc(Cl)ccc2-n2cnnn2)cc2c1C(O)(c1nc3ccc(C(F)(F)F)cc3[nH]1)CC2] | AD column, slow eluting isomer | 514.23 |

EXAMPLE 72

7-(5-(6-amino-2-chloropyridin-3-yl)-1H-imidazol-2-yl)-3-(3-chloro-6-(difluoromethyl)-2-fluorophenyl)-7-hydroxy-6,7-dihydro-5H-cyclopenta[b]pyridine-1-oxide

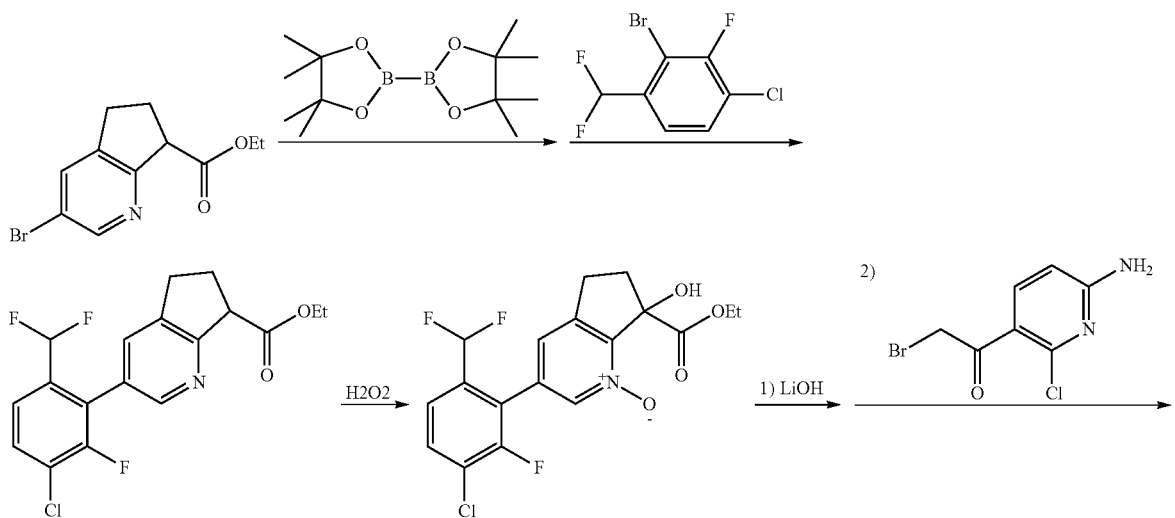

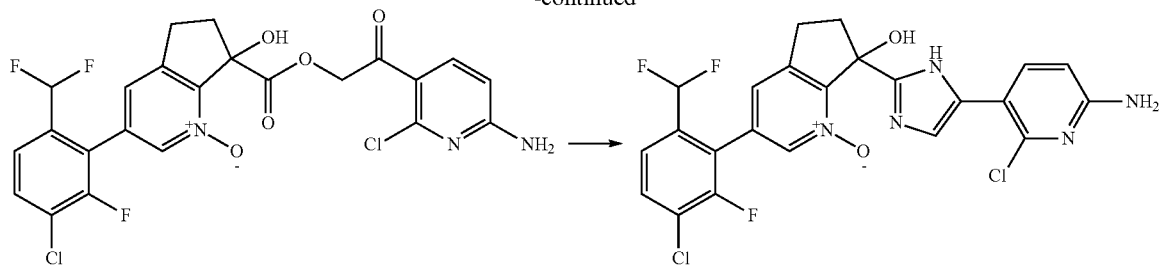

Example 72

Step 1: ethyl 3-(3-chloro-6-(difluoromethyl)-2-fluorophenyl)-6,7-dihydro-5H-cyclopenta[b]pyridine-7-carboxylate A pressure release vial was charged with ethyl 3-bromo-6,7-dihydro-5H-cyclopenta[b]pyridine-7-carboxylate (0.40 g), bis(pinacolato)diboron (0.38 g), potassium acetate (0.30 g), PdCl$_2$(dppf)dichloromethane complex (0.17 g) and dioxane (10 ml) and capped. The mixture was degassed by freeze-vacuum-thaw and back-filling with N$_2$ two times. Then, mixture was heated at 120° C. for 1 h. After cooling, the vial was charged with 2-bromo-4-chloro-1-(difluoromethyl)-3-fluorobenzene (0.39 g), PdCl$_2$(dppf) dichloromethane complex (0.17 g), potassium acetate (0.30 g) and water (2 ml), capped and degassed by freeze-vacuum-thaw and back-filling with N$_2$. Then, mixture was heated at 90° C. for 2 h. The reaction mixture was diluted with water and EtOAc. The organic phase was filtered, washed with EtOAc, concentrated and purified by flash chromatography on a silica gel column with 0-40% EtOAc/hexane to give the title compound. MS (ESI) m/z 369.92 (M+H).

Step 2: 3-(3-chloro-6-(difluoromethyl)-2-fluorophenyl)-7-(ethoxycarbonyl)-7-hydroxy-6,7-diydro-5H-cyclopenta[b]pyridine-1-oxide A pressure release vial was charged with ethyl 3-(3-chloro-6-(difluoromethyl)-2-fluorophenyl)-6,7-dihydro-5H-cyclopenta[b]pyridine-7-carboxylate (0.36 g, 0.974 mmol), methyltrioxorhenium (VII) (0.049 g, 0.195 mmol), H$_2$O$_2$ (0.85 ml, 9.74 mmol) and CH$_2$Cl$_2$ (5 ml) and capped. The reaction mixture was stirred at RT for 3 days. The CH$_2$Cl$_2$ phase was separated and the aqueous phase was extracted with CH$_2$Cl$_2$. The combined organic phase was dried over MgSO$_4$, filtered, concentrated and purified by flash chromatography on a silica gel column with 0-70% EtOAc/CH$_2$Cl$_2$ to give the title compound. MS (ESI) m/z 401.93 (M+H).

Step 3: 7-((2-(6-amino-2-chloropyridin-3-yl)-2-oxoethoxy)carbonyl)-3-(3-chloro-6-(difluoromethyl)-2-fluorophenyl)-7-hydroxy-6,7-dihydro-5H-cyclopenta[b]pyridine-1-oxide LiOH monohydrate (15 mg, 0.36 mmol) was added to a mixture of 3-(3-chloro-6-(difluoromethyl)-2-fluorophenyl)-7-(ethoxycarbonyl)-7-hydroxy-6,7-dihydro-5H-cyclopenta[b]pyridine-1-oxide (0.12 g, 0.30 mmol) in MeOH (2.0 ml) and water (0.50 ml) and the reaction was run at 50° C. for 30 min. Then, the solvent was removed under reduced pressure and the residue was dried in a vacuum to give an intermediate of lithium 3-(3-chloro-6-(difluoromethyl)-2-fluorophenyl)-7-hydroxy-1-oxido-6,7-dihydro-5H-cyclopenta[b]pyridine-7-carboxylate for the next reaction. The intermediate was taken up in DMF (2 ml) and to it was added cesium carbonate (24 mg, 0.075 mmol) and 1-(6-amino-2-chloropyridin-3-yl)-2-bromoethanone (82 mg, 0.33 mmol), and the mixture was stirred at RT overnight. DMF was removed and the residue was purified by flash chromatography on a silica gel column with 0-75% EtOAc/CH$_2$Cl$_2$ to give the title compound. MS (ESI) m/z 541.95 (M+H).

Step 4: 7-(5-(6-amino-2-chloropyridin-3-yl)-1H-imidazol-2-yl)-3-(3-chloro-6-(difluoromethyl)-2-fluorophenyl)-7-hydroxy-6,7-dihydro-5H-cyclopenta[b]pyridine-1-oxide (Example 72)

A pressure release vial was charged with 7-((2-(6-amino-2-chloropyridin-3-yl)-2-oxoethoxy)carbonyl)-3-(3-chloro-6-(difluoromethyl)-2-fluorophenyl)-7-hydroxy-6,7-dihydro-5H-cyclopenta[b]pyridine-1-oxide (0.10 g, 0.18 mmol), ammonium acetate (0.14 g, 1.84 mmol) and toluene (7 ml) and capped. The mixture was heated at 130° C. for 2 h. After cooling, the mixture was diluted with EtOAc and water, the organic layer was separated, washed with brine, dried over MgSO$_4$, filtered and the solvent was evaporated under reduced pressure. The residue was purified by column chromatography on silica gel and eluting with 0-85% EtOAc/CH$_2$Cl$_2$ to give the title compound. MS (ESI) m/z 521.78 (M+H).

EXAMPLE 73, 74, and 75

7-(5-(5-carboxy-4-fluorothiophen-3-yl)-1H-imidazol-2-yl)-3-(3-chloro-2,6-difluorophenyl)-7-hydroxy-6,7-dihydro-5H-cyclopenta[1)]pyridine-1-oxide

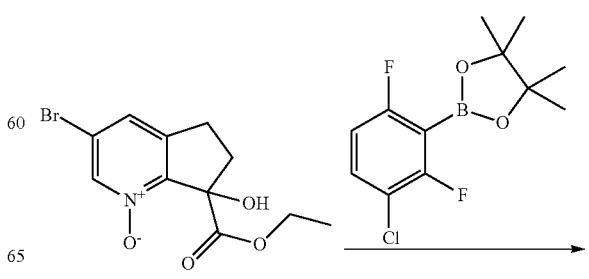

-continued

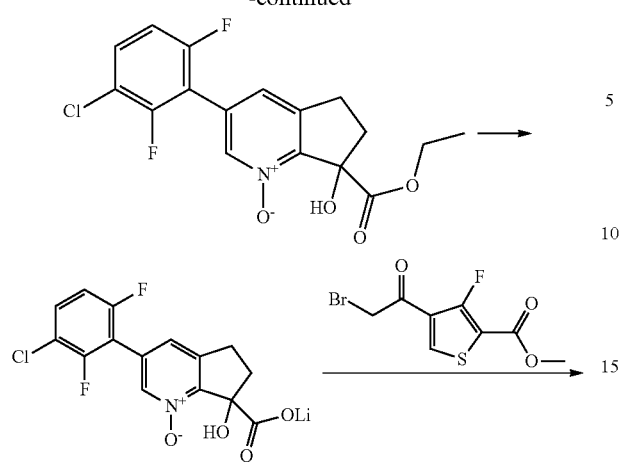

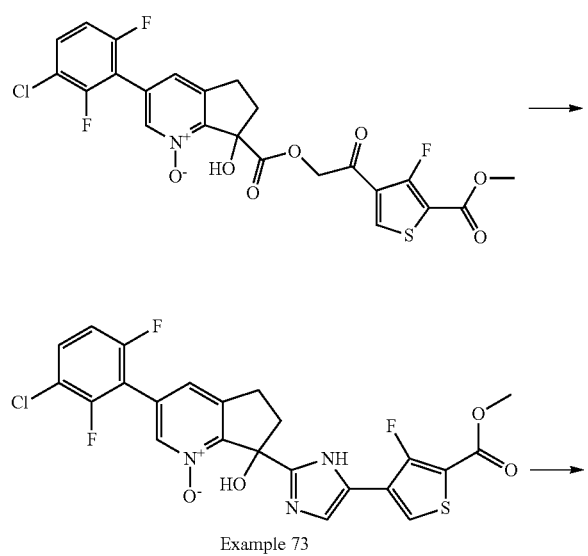

Example 73

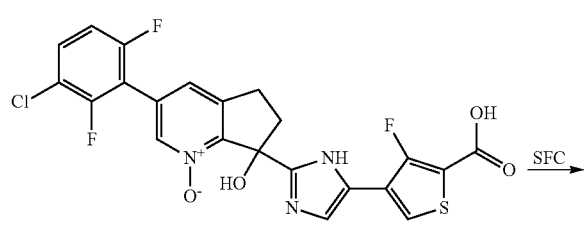

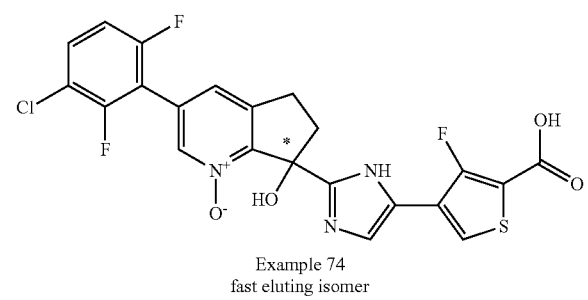

Example 74
fast eluting isomer

-continued

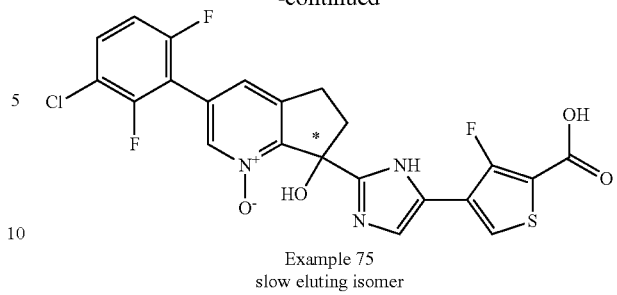

Example 75
slow eluting isomer

Step 1: 3-(3-chloro-2,6-difluorophenyl)-7-(ethoxycarbonyl)-7-hydroxy-6,7-dihydro-5H-cyclopenta[b]pyridine-1-oxide To a solution of 3-bromo-7-(ethoxycarbonyl)-7-hydroxy-6,7-dihydro-5H-cyclopenta[b]pyridine-1-oxide (500 mg, 1.66 mmol) in THF (10 mL) and water (3 mL) was added 2-(3-chloro-2,6-difluorophenyl)-4,4,5,5-tetramethyl-1,3,2-dioxaborolane (909 mg, 3.31 mmol), PdCl$_2$(dppf) (86 mg, 0.13 mmol) and potassium carbonate (686 mg, 4.96 mmol) and the mixture was stirred at 90° C. under microwave conditions for 0.5 h. TLC showed the reaction was complete. The reaction was diluted with H$_2$O (30 mL) and extracted with DCM (3×30 mL). The combined organic phases were dried over Na$_2$SO$_4$, and concentrated in vacuo. The residue was purified by column chromatography (SiO$_2$, PE:EtOAc=10:1 to 1:1) to give the title compound. MS (ESI) m/z: 370.2 (M+H).

Step 2: lithium 3-(3-chloro-2,6-difluorophenyl)-7-hydroxy-1-oxido-6,7-dihydro-5H-cyclopenta[b]pyridine-7-carboxylate To a solution of 3-(3-chloro-2,6-difluorophenyl)-7-(ethoxycarbonyl)-7-hydroxy-6,7-dihydro-5H-cyclopenta[b]pyridine-1-oxide (450 mg, 1.22 mmol) in MeOH (10 mL) and water (3 mL) was added lithium hydroxide hydrate (30.6 mg, 1.278 mmol). The mixture was stirred at 50° C. for 0.5 h. LCMS showed the reaction was complete. The reaction was concentrated in vacuo to give the title compound. MS (ESI) m/z: 342.1 (M+H).

Step 3: 3-(3-chloro-2,6-difluorophenyl)-7-((2-(4-fluoro-5-(methoxycarbonyl)thiophen-3-yl)-2-oxoethoxy)carbonyl)-7-hydroxy-6,7-dihydro-5H-cyclopenta[b]pyridine-1-oxide To a solution of lithium 3-(3-chloro-2,6-difluorophenyl)-7-hydroxy-1-oxido-6,7-dihydro-5H-cyclopenta[b]pyridine-7-carboxylate (423 mg, 1.22 mmol) in DMF (10 mL) was added methyl 4-(2-bromoacetyl)-3-fluorothiophene-2-carboxylate (380 mg, 1.35 mmol), and it was stirred at 25° C. for 15 h. LCMS and TLC showed the reaction was complete. The reaction was diluted with H$_2$O (40 mL) and extracted with EtOAc (3×40 mL). The combined organic phases were dried over Na$_2$SO$_4$, and concentrated in vacuo. The residue was purified by column chromatography (SiO$_2$, PE:EtOAc=10:1 to EtOAc) to give the title compound. MS (ESI) m/z: 542.0 (M+H).

Step 4: 3-(3-chloro-2,6-difluorophenyl)-7-(5-(4-fluoro-5-(methoxycarbonyl)thiophen-3-yl)-1H-imidazol-2-yl)-7-hydroxy-6,7-dihydro-5H-cyclopenta[b]pyridine-1-oxide (Example 73)

To a solution of 3-(3-chloro-2,6-difluorophenyl)-7-((2-(4-fluoro-5-(methoxycarbonyl)thiophen-3-yl)-2-oxoethoxy)

carbonyl)-7-hydroxy-6,7-dihydro-5H-cyclopenta[b]pyridine-1-oxide (400 mg, 0.74 mmol) in toluene (8 mL) was added ammonium acetate (1138 mg, 14.76 mmol). The mixture was stirred at 150° C. under microwave conditions for 0.5 h. LCMS and TLC showed the reaction was complete. The reaction was diluted with H$_2$O (30 mL) and extracted with EtOAc (3×50 mL). The combined organic phases were dried over Na$_2$SO$_4$, and concentrated in vacuo. The residue was purified by column chromatography (SiO$_2$, PE:EtOAc=10:1 to EtOAc) to give the title compound. MS (ESI) m/z: 522.1 (M+H).

Step 5: 7-(5-(5-carboxy-4-fluorothiophen-3-yl)-1H-imidazol-2-yl)-3-(3-chloro-2,6-difluorophenyl)-7-hydroxy-6,7-dihydro-5H-cyclopenta[b]pyridine-1-oxide To a solution of 3-(3-chloro-2,6-difluorophenyl)-7-(5-(4-fluoro-5-(methoxycarbonyl)thiophen-3-yl)-1H-imidazol-2-yl)-7-hydroxy-6,7-dihydro-5H-cyclopenta[b]pyridine-1-oxide (110 mg, 0.211 mmol) in MeOH (3 mL) and water (1 mL) as added lithium hydroxide hydrate (15.14 mg, 0.63 mmol) and the mixture was stirred at 20° C. for 15 h. LCMS showed the reaction was complete. The reaction mixture was diluted with H$_2$O (20 mL), and adjusted to pH 4-5 with 1N HCl and extracted with DCM (3×30 mL). The combined organic phases were dried over Na$_2$SO$_4$, and concentrated in vacuo. The residue was purified by prep-HPLC (neutral method) to give the title compound. MS (ESI) m/z: 508.0 (M+H).

$^1$H NMR (MeOH-d$_4$, 400 MHz): δ 8.25 (s, 1H), 7.70-7.55 (m, 3H), 7.34-7.29 (m, 1H), 7.23-7.14 (m, 1H), 3.27-3.21 (m, 2H), 2.92 (td, J=13.8, 7.0 Hz, 1H), 2.56 (td, J=14.0, 6.9 Hz, 1H).

Step 7: 7-(5-(5-carboxy-4-fluorothiophen-3-yl)-1H-imidazol-2-yl)-3-(3-chloro-2,6-difluorophenyl)-7-hydroxy-6,7-dihydro-5H-cyclopenta[b]pyridine-1-oxide (Example 74) and 7-(5-(5-carboxy-4-fluorothiophen-3-yl)-1H-imidazol-2-yl)-3-(3-chloro-2,6-difluorophenyl)-7-hydroxy-6,7-dihydro-5H-cyclopenta[b]pyridine-1-oxide (Example 75)

The racemic compound 3-(3-chloro-2,6-difluorophenyl)-7-(5-(4-fluoro-5-(methoxycarbonyl)thiophen-3-yl)-1H-imidazol-2-yl)-7-hydroxy-6,7-dihydro-5H-cyclopenta[b]pyridine-1-oxide (40 mg, 0.08 mmol) was separated by SFC on a chiral AD column, to give Example 74 (fast eluting isomer), MS (ESI) m/z: 508.0 (M+H and Example 75 (slow eluting isomer); MS (ESI) m/z: 508.0 (M+H).

The following compounds were prepared following procedures similar to those described above using appropriate starting materials and characterized by LCMS.

| EX | IUPAC Name | Structure | Chiral Separation | LCMS [M + 1] |
|---|---|---|---|---|
| 76 | methyl [3-chloro-4-(2-{3-[3-chloro-6-(difluoromethyl)-2-fluorophenyl]-7-hydroxy-1-oxido-6,7-dihydro-5H-cyclopenta[b]pyridin-7-yl}-1H-imidazol-5-yl)phenyl]carbamate | 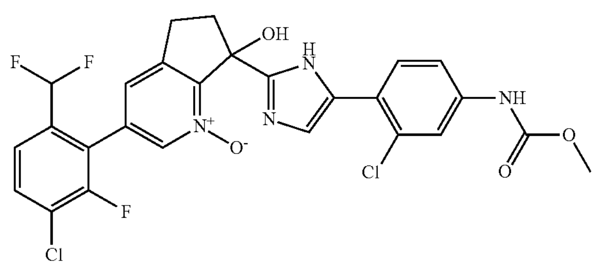 [SMILES: COC(=O)Nc1ccc(-c2cnc(C3(O)CCc4cc(-c5c(C(F)F)ccc(Cl)c5F)c[n+]([O-])c43)[nH]2)c(Cl)c1] | racemic | 579 |
| 77 | 7-[5-(6-amino-2-chloropyridin-3-yl)-1H-imidazol-2-yl]-3-[5-chloro-2-(difluoromethyl)phenyl]-6,7-dihydro-5H-cyclopenta[b]pyridin-7-ol 1-oxide | 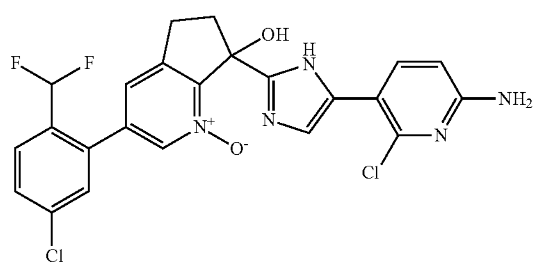 [SMILES: Nc1ccc(-c2cnc(C3(O)CCc4cc(-c5cc(Cl)ccc5C(F)F)c[n+]([O-])c43)[nH]2)c(Cl)n1] | racemic | 504 |
| 78 | methyl (4-{2-[3-(3-chloro-2,6-difluorophenyl)-1-oxido-6,7-dihydro-5H-cyclopenta[b]pyridin-7-yl]-1H-imidazol-5-yl}phenyl)carbamate | 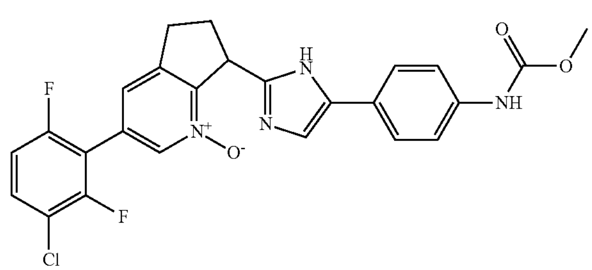 [SMILES: COC(=O)Nc1ccc(-c2cnc(C3CCc4cc(-c5c(F)ccc(Cl)c5F)c[n+]([O-])c43)[nH]2)cc1] | racemic | 497 |

| EX | IUPAC Name | Chiral Separation | LCMS [M + 1] |
|---|---|---|---|
| 79 | methyl (4-{2-[3-(3-chloro-2,6-difluorophenyl)-7-hydroxy-1-oxido-6,7-dihydro-5H-cyclopenta[b]pyridin-7-yl]-1H-imidazol-5-yl}phenyl)carbamate | IC column, fast eluting isomer | 513 |
| 80 | methyl (4-{2-[3-(3-chloro-2,6-difluorophenyl)-7-hydroxy-1-oxido-6,7-dihydro-5H-cyclopenta[b]pyridin-7-yl]-1H-imidazol-5-yl}phenyl)carbamate | IC column, slow eluting isomer | 513 |
| 81 | (S)-methyl (4-{2-[3-(5-chloro-2-cyanophenyl)-7-hydroxy-1-oxido-6,7-dihydro-5H-cyclopenta[b]pyridin-7-yl]-1H-imidazol-5-yl}phenyl)carbamate | From chiral intermediate | 502 |
| 82 | (R)-methyl (4-{2-[3-(5-chloro-2-cyanophenyl)-7-hydroxy-1-oxido-6,7-dihydro-5H-cyclopenta[b]pyridin-7-yl]-1H-imidazol-5-yl}phenyl)carbamate | From chiral intermediate | 502 |
| 83 | 2-{7-[5-(6-amino-2-chloropyridin-3-yl)-1H-imidazol-2-yl]-7-hydroxy-1-oxido-6,7-dihydro-5H-cyclopenta[b]pyridin-3-yl}-4-chloro-3-fluorobenzonitrile | IC column, fast eluting isomer | 497 |
| 84 | 2-{7-[5-(6-amino-2-chloropyridin-3-yl)-1H-imidazol-2-yl]-7-hydroxy-1-oxido-6,7-dihydro-5H-cyclopenta[b]pyridin-3-yl}-4-chloro-3-fluorobenzonitrile | IC column, slow eluting isomer | 497 |

-continued

| EX | IUPAC Name | Structure | Chiral Separation | LCMS [M + 1] |
|---|---|---|---|---|
| 85 | methyl (4-{2-[3-(5-chloro-2-cyanophenyl)-7-hydroxy-4-methoxy-1-oxido-6,7-dihydro-5H-cyclopenta[b]pyridin-7-yl]-1H-imidazol-4-yl}phenyl)carbamate | 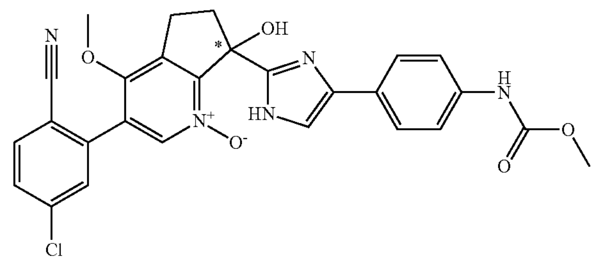 [SMILES: COC(=O)Nc1ccc(-c2c[nH]c(C3(O)CCc4c(OC)c(-c5cc(Cl)ccc5C#N)c[n+]([O-])c43)n2)cc1] | AD column, fast eluting isomer | 532 |
| 86 | methyl (4-{2-[3-(5-chloro-2-cyanophenyl)-7-hydroxy-4-methoxy-1-oxido-6,7-dihydro-5H-cyclopenta[b]pyridin-7-yl]-1H-imidazol-4-yl}phenyl)carbamate | 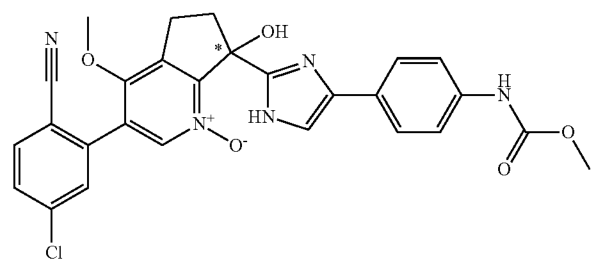 [SMILES: COC(=O)Nc1ccc(-c2c[nH]c(C3(O)CCc4c(OC)c(-c5cc(Cl)ccc5C#N)c[n+]([O-])c43)n2)cc1] | AD column, slow eluting isomer | 532 |
| 87 | 2-{7-[4-(6-amino-2-chloropyridin-3-yl)-1H-imidazol-2-yl]-7-hydroxy-4-methoxy-1-oxido-6,7-dihydro-5H-cyclopenta[b]pyridin-3-yl}-4-chlorobenzonitrile | 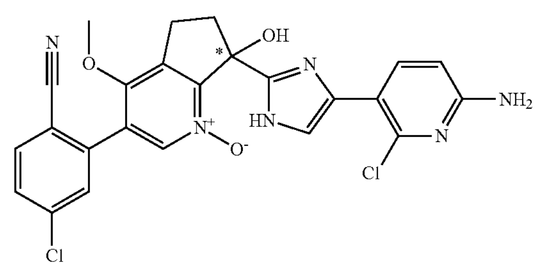 [SMILES: COc1c(-c2cc(Cl)ccc2C#N)c[n+]([O-])c2c1CCC2(O)c1nc(-c2ccc(N)nc2Cl)c[nH]1] | AD column, fast eluting isomer | 509 |
| 88 | 2-{7-[4-(6-amino-2-chloropyridin-3-yl)-1H-imidazol-2-yl]-7-hydroxy-4-methoxy-1-oxido-6,7-dihydro-5H-cyclopenta[b]pyridin-3-yl}-4-chlorobenzonitrile | 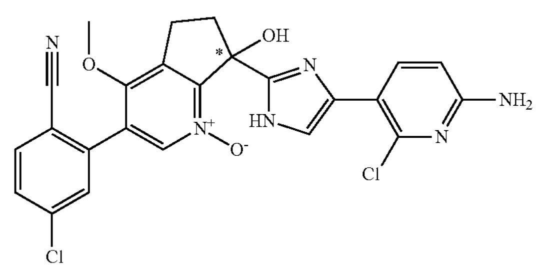 [SMILES: COc1c(-c2cc(Cl)ccc2C#N)c[n+]([O-])c2c1CCC2(O)c1nc(-c2ccc(N)nc2Cl)c[nH]1] | AD column, slow eluting isomer | 509 |
| 89 | methyl (4-{2-[3-(6-acetyl-3-chloro-2-fluorophenyl)-7-hydroxy-1-oxido-6,7-dihydro-5H-cyclopenta[b]pyridin-7-yl]-1H-imidazol-5-yl}phenyl)carbamate | 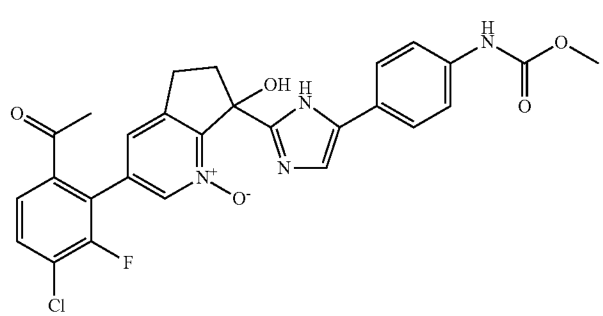 [SMILES: COC(=O)Nc1ccc(-c2cnc(C3(O)CCc4cc(-c5c(C(C)=O)ccc(Cl)c5F)c[n+]([O-])c43)[nH]2)cc1] | racemic | 537 |

-continued

| EX | IUPAC Name | Structure | Chiral Separation | LCMS [M + 1] |
|---|---|---|---|---|
| 90 | 3-(2-amino-5-chlorophenyl)-7-[5-(3-fluorophenyl)-1H-imidazol-2-yl]-6,7-dihydro-5H-cyclopenta[b]pyridin-7-ol 1-oxide | 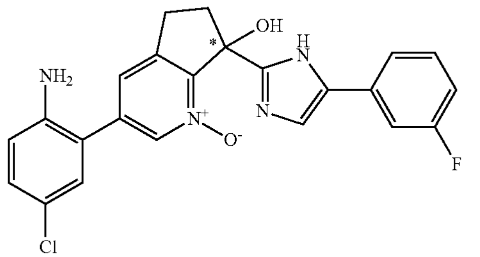 [SMILES: Nc1ccc(Cl)cc1-c1cc2c([n+]([O-])c1)C(O)(c1ncc(-c3cccc(F)c3)[nH]1)CC2] | racemic | 437 |
| 91 | 4-(2-{3-[5-chloro-2-(1,3-oxazol-5-yl)phenyl]-7-hydroxy-1-oxido-6,7-dihydro-5H-cyclopenta[b]pyridin-7-yl}-1H-imidazol-5-yl)-3-fluorothiophene-2-carboxylic acid | 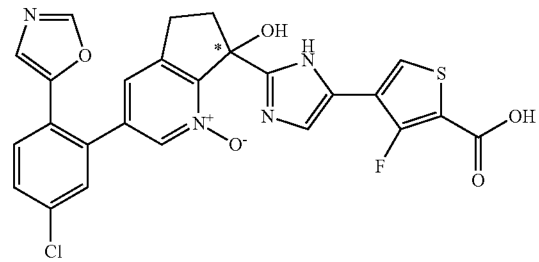 [SMILES: O=C(O)c1scc(-c2cnc(C3(O)CCc4cc(-c5cc(Cl)ccc5-c5cnco5)c[n+]([O-])c43)[nH]2)c1F] | OJ column, fast eluting isomer | 539 |
| 92 | 4-(2-{3-[5-chloro-2-(1,3-oxazol-5-yl)phenyl]-7-hydroxy-1-oxido-6,7-dihydro-5H-cyclopenta[b]pyridin-7-yl}-1H-imidazol-5-yl)-3-fluorothiophene-2-carboxylic acid | 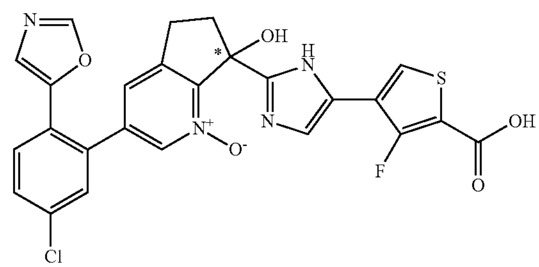 [SMILES: O=C(O)c1scc(-c2cnc(C3(O)CCc4cc(-c5cc(Cl)ccc5-c5cnco5)c[n+]([O-])c43)[nH]2)c1F] | OJ column, slow eluting isomer | 539 |
| 93 | 4-(4-chloro-2-{3-[5-chloro-2-(1,3-oxazol-5-yl)phenyl]-7-hydroxy-1-oxido-6,7-dihydro-5H-cyclopenta[b]pyridin-7-yl}-1H-imidazol-5-yl)-3-fluorothiophene-2-carboxylic acid | 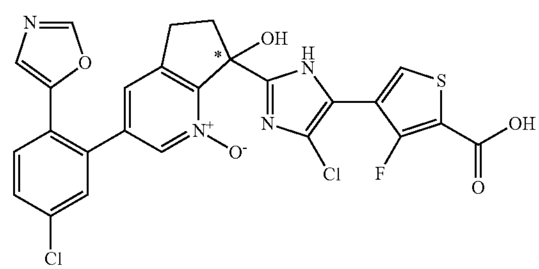 [SMILES: O=C(O)c1scc(-c2[nH]c(C3(O)CCc4cc(-c5cc(Cl)ccc5-c5cnco5)c[n+]([O-])c43)nc2Cl)c1F] | AD column, fast eluting isomer | 573 |
| 94 | 4-(4-chloro-2-{3-[5-chloro-2-(1,3-oxazol-5-yl)phenyl]-7-hydroxy-1-oxido-6,7-dihydro-5H-cyclopenta[b]pyridin-7-yl}-1H-imidazol-5-yl)-3-fluorothiophene-2-carboxylic acid | 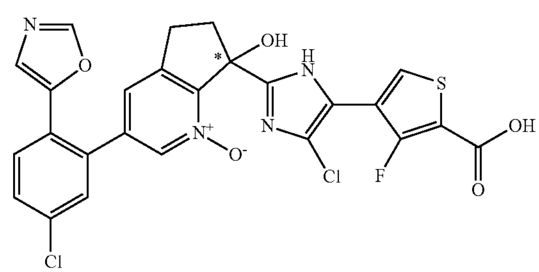 [SMILES: O=C(O)c1scc(-c2[nH]c(C3(O)CCc4cc(-c5cc(Cl)ccc5-c5cnco5)c[n+]([O-])c43)nc2Cl)c1F] | AD column, slow eluting isomer | 573 |

-continued

| EX | IUPAC Name | Structure | Chiral Separation | LCMS [M + 1] |
|---|---|---|---|---|
| 95 | (S)-7-[5-(6-amino-2-chloropyridin-3-yl)-1H-imidazol-2-yl]-3-[5-chloro-2-(1,3-oxazol-5-yl)phenyl]-6,7-dihydro-5H-cyclopenta[b]pyridin-7-ol 1-oxide | 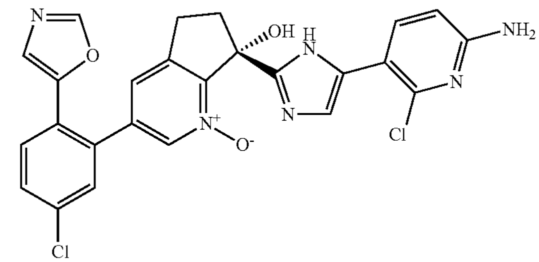 [SMILES: Nc1ccc(-c2cnc([C@]3(O)CCc4cc(-c5cc(Cl)ccc5-c5cnco5)c[n+]([O-])c43)[nH]2)c(Cl)n1] | from chiral intermediate | 521 |
| 96 | 7-[5-(6-amino-2-chloropyridin-3-yl)-4-chloro-1H-imidazol-2-yl]-3-[5-chloro-2-(1,3-oxazol-5-yl)phenyl]-6,7-dihydro-5H-cyclopenta[b]pyridin-7-ol 1-oxide | 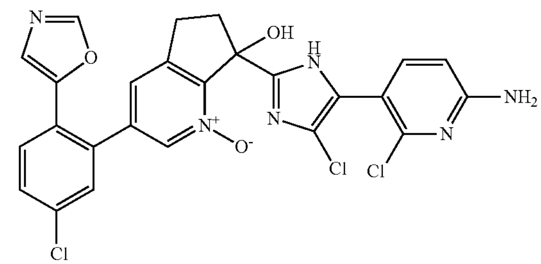 [SMILES: Nc1ccc(-c2[nH]c(C3(O)CCc4cc(-c5cc(Cl)ccc5-c5cnco5)c[n+]([O-])c43)nc2Cl)c(Cl)n1] | racemic | 555 |
| 97 | methyl [3-chloro-4-(2-{3-[5-chloro-2-(4-cyano-1H-1,2,3-triazol-1-yl)phenyl]-7-hydroxy-1-oxido-6,7-dihydro-5H-cyclopenta[b]pyridin-7-yl}-1H-imidazol-4-yl)phenyl]carbamate | 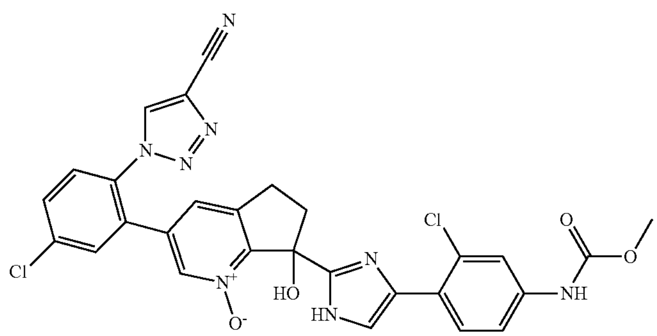 [SMILES: COC(=O)Nc1ccc(-c2c[nH]c(C3(O)CCc4cc(-c5cc(Cl)ccc5-n5cc(C#N)nn5)c[n+]([O-])c43)n2)c(Cl)c1] | racemic | 603 |
| 98 | methyl 4-(2-{3-[5-chloro-2-(1H-tetrazol-1-yl)phenyl]-7-hydroxy-1-oxido-6,7-dihydro-5H-cyclopenta[b]pyridin-7-yl}-1H-imidazol-5-yl)thiophene-2-carboxylate | 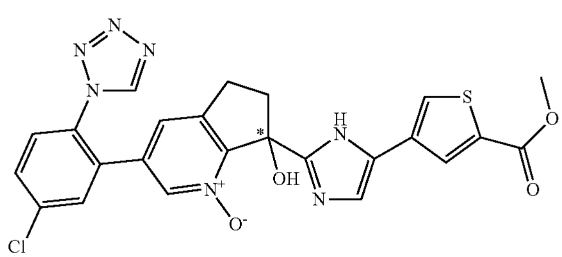 [SMILES: COC(=O)c1cc(-c2cnc(C3(O)CCc4cc(-c5cc(Cl)ccc5-n5cnnn5)c[n+]([O-])c43)[nH]2)cs1] | OD column, fast eluting isomer | 536 |
| 99 | methyl 4-(2-{3-[5-chloro-2-(1H-tetrazol-1-yl)phenyl]-7-hydroxy-1-oxido-6,7-dihydro-5H-cyclopenta[b]pyridin-7-yl}-1H-imidazol-5-yl)thiophene-2-carboxylate | 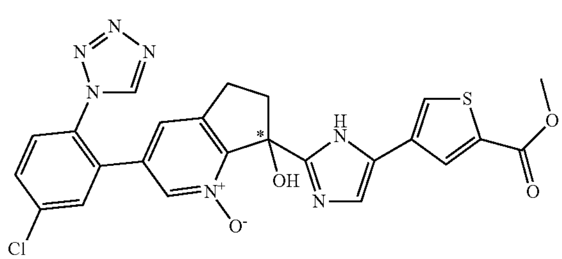 [SMILES: COC(=O)c1cc(-c2cnc(C3(O)CCc4cc(-c5cc(Cl)ccc5-n5cnnn5)c[n+]([O-])c43)[nH]2)cs1] | OD column, slow eluting isomer | 536 |

-continued

| EX | IUPAC Name | Structure | Chiral Separation | LCMS [M + 1] |
|---|---|---|---|---|
| 100 | 4-(2-{3-[5-chloro-2-(1H-tetrazol-1-yl)phenyl]-7-hydroxy-1-oxido-6,7-dihydro-5H-cyclopenta[b]pyridin-7-yl}-4-fluoro-1H-imidazol-5-yl)-3-fluorothiophene-2-carboxylic acid | 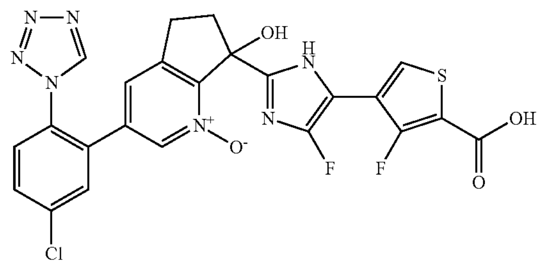 [SMILES: O=C(O)c1scc(-c2[nH]c(C3(O)CCc4cc(-c5cc(Cl)ccc5-n5cnnn5)c[n+]([O-])c43)nc2F)c1F] | racemic | 558 |
| 101 | 4-(4-chloro-2-{3-[5-chloro-2-(1H-tetrazol-1-yl)phenyl]-7-hydroxy-1-oxido-6,7-dihydro-5H-cyclopenta[b]pyridin-7-yl}-1H-imidazol-5-yl)-3-fluorothiophene-2-carboxylic acid | 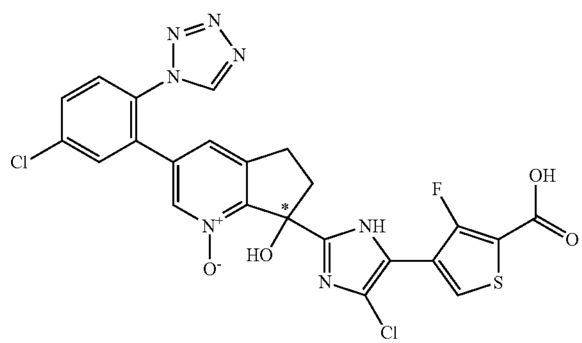 [SMILES: O=C(O)c1scc(-c2[nH]c(C3(O)CCc4cc(-c5cc(Cl)ccc5-n5cnnn5)c[n+]([O-])c43)nc2Cl)c1F] | AD column, fast eluting isomer | 574 |
| 102 | 4-(4-chloro-2-{3-[5-chloro-2-(1H-tetrazol-1-yl)phenyl]-7-hydroxy-1-oxido-6,7-dihydro-5H-cyclopenta[b]pyridin-7-yl}-1H-imidazol-5-yl)-3-fluorothiophene-2-carboxylic acid | 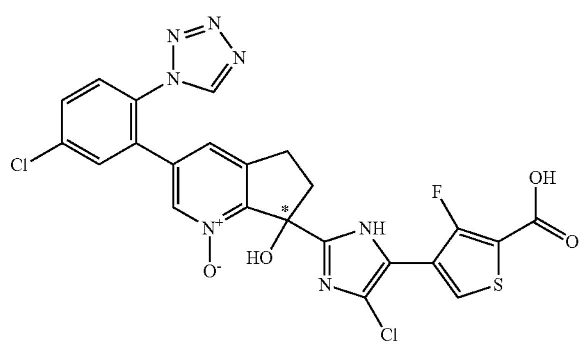 [SMILES: O=C(O)c1scc(-c2[nH]c(C3(O)CCc4cc(-c5cc(Cl)ccc5-n5cnnn5)c[n+]([O-])c43)nc2Cl)c1F] | AD column, fast eluting isomer | 574 |
| 103 | 5-(2-{3-[5-chloro-2-(1H-tetrazol-1-yl)phenyl]-7-hydroxy-1-oxido-6,7-dihydro-5H-cyclopenta[b]pyridin-7-yl}-4-methyl-1H-imidazol-5-yl)thiophene-2-carboxylic acid | 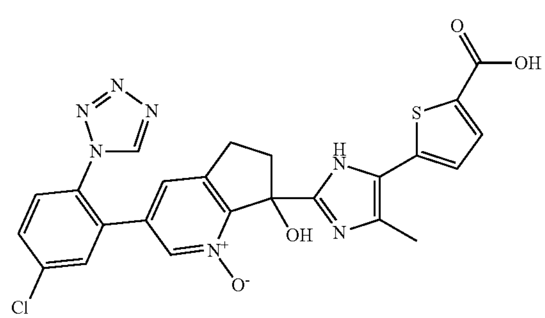 [SMILES: Cc1nc(C2(O)CCc3cc(-c4cc(Cl)ccc4-n4cnnn4)c[n+]([O-])c32)[nH]c1-c1ccc(C(=O)O)s1] | racemic | 536 |
| 104 | methyl [3-chloro-4-(2-{3-[3-chloro-6-(difluoromethyl)-2-fluorophenyl]-7-hydroxy-1-oxido-6,7-dihydro-5H-cyclopenta[b]pyridin-7-yl}-1H-imidazol-5-yl)phenyl]carbamate | 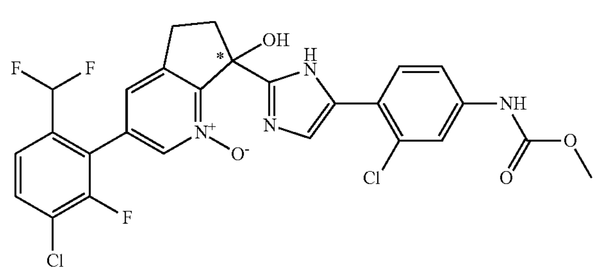 [SMILES: COC(=O)Nc1ccc(-c2cnc(C3(O)CCc4cc(-c5c(C(F)F)ccc(Cl)c5F)c[n+]([O-])c43)[nH]2)c(Cl)c1] | IC column, fast eluting isomer | 579 |

| EX | IUPAC Name | Structure | Chiral Separation | LCMS [M + 1] |
|---|---|---|---|---|
| 105 | methyl [3-chloro-4-(2-{3-[3-chloro-6-(difluoromethyl)-2-fluorophenyl]-7-hydroxy-1-oxido-6,7-dihydro-5H-cyclopenta[b]pyridin-7-yl}-1H-imidazol-5-yl)phenyl]carbamate | 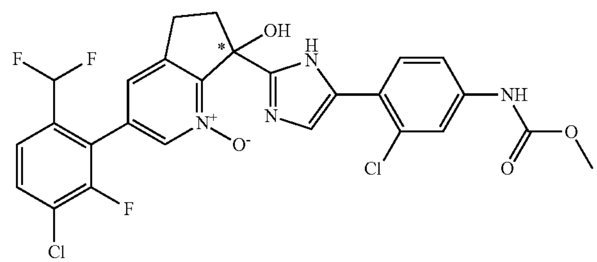 [SMILES: COC(=O)Nc1ccc(-c2cnc(C3(O)CCc4cc(-c5c(C(F)F)ccc(Cl)c5F)c[n+]([O-])c43)[nH]2)c(Cl)c1] | IC column, slow eluting isomer | 579 |
| 106 | methyl [3-chloro-4-(2-{3-[3-chloro-2-fluoro-6-(1H-tetrazol-1-yl)phenyl]-7-hydroxy-1-oxido-6,7-dihydro-5H-cyclopenta[b]pyridin-7-yl}-1H-imidazol-5-yl)phenyl]carbamate | 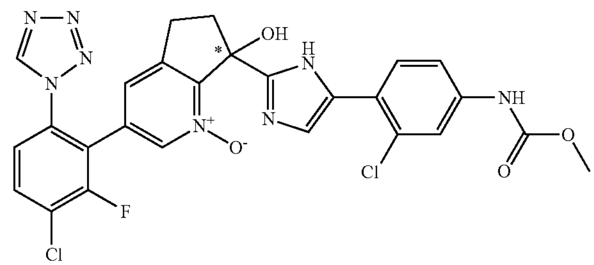 [SMILES: COC(=O)Nc1ccc(-c2cnc(C3(O)CCc4cc(-c5c(-n6cnnn6)ccc(Cl)c5F)c[n+]([O-])c43)[nH]2)c(Cl)c1] | IC column, fast eluting isomer | 597 |
| 107 | methyl [3-chloro-4-(2-{3-[3-chloro-2-fluoro-6-(1H-tetrazol-1-yl)phenyl]-7-hydroxy-1-oxido-6,7-dihydro-5H-cyclopenta[b]pyridin-7-yl}-1H-imidazol-5-yl)phenyl]carbamate | 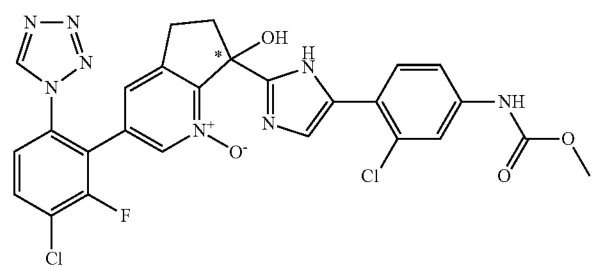 [SMILES: COC(=O)Nc1ccc(-c2cnc(C3(O)CCc4cc(-c5c(-n6cnnn6)ccc(Cl)c5F)c[n+]([O-])c43)[nH]2)c(Cl)c1] | IC column, slow eluting isomer | 597 |
| 108 | methyl [4-(2-{3-[5-chloro-2-(trifluoromethoxy)phenyl]-7-hydroxy-1-oxido-6,7-dihydro-5H-cyclopenta[b]pyridin-7-yl}-1H-imidazol-5-yl)phenyl]carbamate | 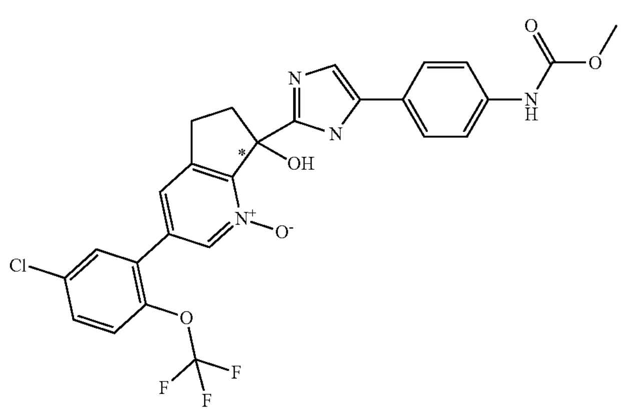 [SMILES: COC(=O)Nc1ccc(-c2cnc(C3(O)CCc4cc(-c5cc(Cl)ccc5OC(F)(F)F)c[n+]([O-])c43)[nH]2)cc1] | AD column, fast eluting isomer | 561 |

| EX | IUPAC Name | Structure | Chiral Separation | LCMS [M + 1] |
|---|---|---|---|---|
| 109 | methyl [4-(2-{3-[5-chloro-2-(trifluoromethoxy)phenyl]-7-hydroxy-1-oxido-6,7-dihydro-5H-cyclopenta[b]pyridin-7-yl}-1H-imidazol-5-yl)phenyl]carbamate | 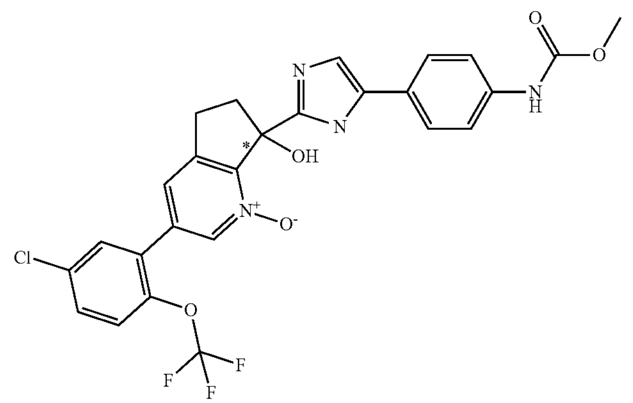 [SMILES: COC(=O)Nc1ccc(-c2cnc(C3(O)CCc4cc(-c5cc(Cl)ccc5OC(F)(F)F)c[n+]([O-])c43)[nH]2)cc1] | AD column, slow eluting isomer | 561 |
| 110 | methyl (4-{4-chloro-2-[(7S)-3-(5-chloro-2-cyanophenyl)-7-hydroxy-1-oxido-6,7-dihydro-5H-cyclopenta[b]pyridin-7-yl]-1H-imidazol-5-yl}phenyl)carbamate | 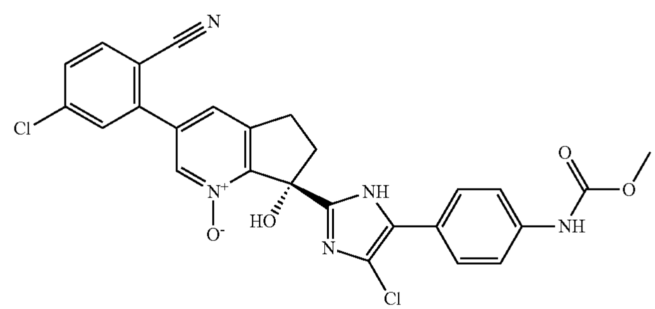 [SMILES: COC(=O)Nc1ccc(-c2[nH]c([C@]3(O)CCc4cc(-c5cc(Cl)ccc5C#N)c[n+]([O-])c43)nc2Cl)cc1] | From chiral intermediate | 536 |
| 111 | methyl {4-[2-(3-{5-chloro-2-[4-(difluoromethyl)-1H-1,2,3-triazol-1-yl]phenyl}-7-hydroxy-1-oxido-6,7-dihydro-5H-cyclopenta[b]pyridin-7-yl)-1H-imidazol-5-yl]phenyl}carbamate | 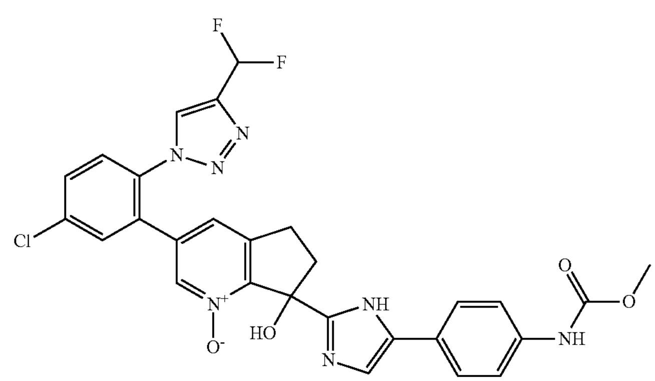 [SMILES: COC(=O)Nc1ccc(-c2cnc(C3(O)CCc4cc(-c5cc(Cl)ccc5-n5cc(C(F)F)nn5)c[n+]([O-])c43)[nH]2)cc1] | racemic | 594 |
| 112 | methyl [4-(2-{3-[5-chloro-2-(4-chloro-1H-1,2,3-triazol-1-yl)phenyl]-7-hydroxy-1-oxido-6,7-dihydro-5H-cyclopenta[b]pyridin-7-yl}-1H-imidazol-5-yl)phenyl]carbamate | 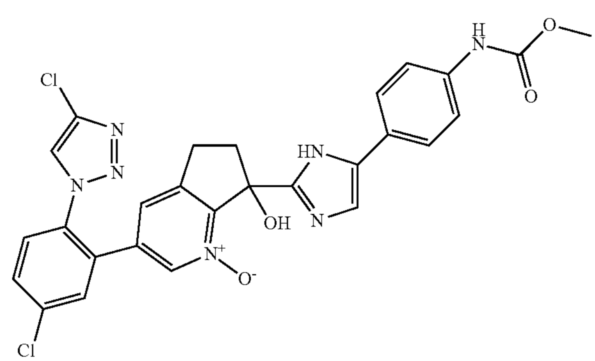 [SMILES: COC(=O)Nc1ccc(-c2cnc(C3(O)CCc4cc(-c5cc(Cl)ccc5-n5cc(Cl)nn5)c[n+]([O-])c43)[nH]2)cc1] | racemic | 578 |

| EX | IUPAC Name | Structure | Chiral Separation | LCMS [M + 1] |
|---|---|---|---|---|
| 113 | methyl (4-{2-[4-chloro-3-(5-chloro-2-cyanophenyl)-7-hydroxy-1-oxido-6,7-dihydro-5H-cyclopenta[b]pyridin-7-yl]-1H-imidazol-4-yl}phenyl)carbamate | 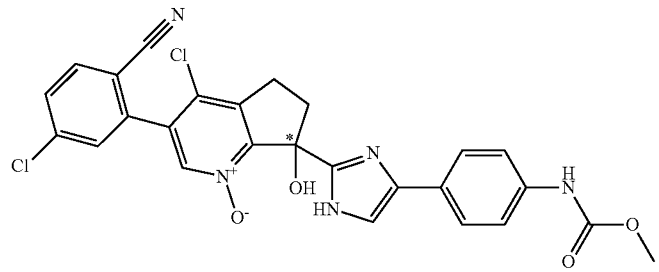 [SMILES: COC(=O)Nc1ccc(-c2c[nH]c(C3(O)CCc4c(Cl)c(-c5cc(Cl)ccc5C#N)c[n+]([O-])c43)n2)cc1] | OD column, slow eluting isomer | 536 |
| 114 | methyl (4-{2-[4-chloro-3-(5-chloro-2-cyanophenyl)-7-hydroxy-1-oxido-6,7-dihydro-5H-cyclopenta[b]pyridin-7-yl]-1H-imidazol-4-yl}phenyl)carbamate | 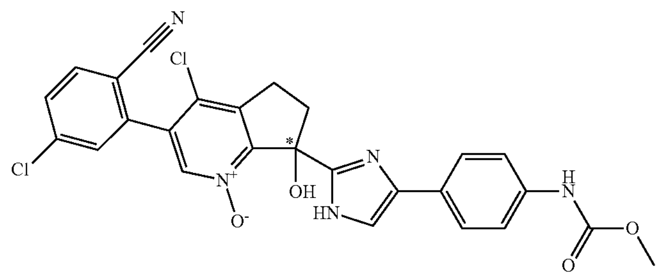 [SMILES: COC(=O)Nc1ccc(-c2c[nH]c(C3(O)CCc4c(Cl)c(-c5cc(Cl)ccc5C#N)c[n+]([O-])c43)n2)cc1] | OD column, fast eluting isomer | 536 |
| 115 | methyl [4-(2-{4-chloro-3-[5-chloro-2-(1H-tetrazol-1-yl)phenyl]-7-hydroxy-1-oxido-6,7-dihydro-5H-cyclopenta[b]pyridin-7-yl}-1H-imidazol-5-yl)phenyl]carbamate | 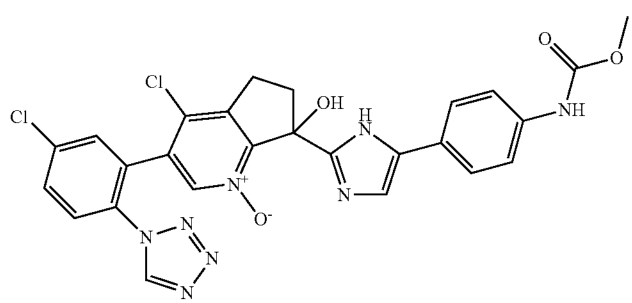 [SMILES: COC(=O)Nc1ccc(-c2cnc(C3(O)CCc4c(Cl)c(-c5cc(Cl)ccc5-n5cnnn5)c[n+]([O-])c43)[nH]2)cc1] | racemic | 579 |
| 116 | methyl (4-{5-chloro-2-[3-(5-chloro-2-cyanophenyl)-7-hydroxy-4-methoxy-1-oxido-6,7-dihydro-5H-cyclopenta[b]pyridin-7-yl]-1H-imidazol-4-yl}phenyl)carbamate | 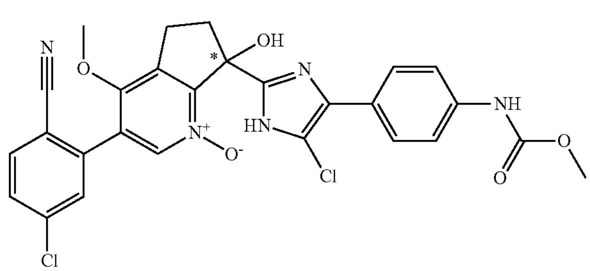 [SMILES: COC(=O)Nc1ccc(-c2nc(C3(O)CCc4c(OC)c(-c5cc(Cl)ccc5C#N)c[n+]([O-])c43)[nH]c2Cl)cc1] | AD column, fast eluting isomer | 566 |

-continued

| EX | IUPAC Name | Structure | Chiral Separation | LCMS [M + 1] |
|---|---|---|---|---|
| 117 | methyl (4-{5-chloro-2-[3-(5-chloro-2-cyanophenyl)-7-hydroxy-4-methoxy-1-oxido-6,7-dihydro-5H-cyclopenta[b]pyridin-7-yl]-1H-imidazol-4-yl}phenyl)carbamate | 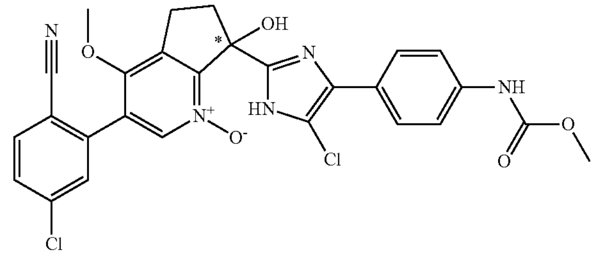 [SMILES: COC(=O)Nc1ccc(-c2nc(C3(O)CCc4c(OC)c(-c5cc(Cl)ccc5C#N)c[n+]([O-])c43)[nH]c2Cl)cc1] | AD column, slow eluting isomer | 566 |
| 118 | methyl [4-(2-{(7S)-3-[5-chloro-2-(1H-tetrazol-1-yl)phenyl]-7-hydroxy-1-oxido-6,7-dihydro-5H-cyclopenta[b]pyridin-7-yl}-1H-imidazol-5-yl)-3-fluorophenyl]carbamate | 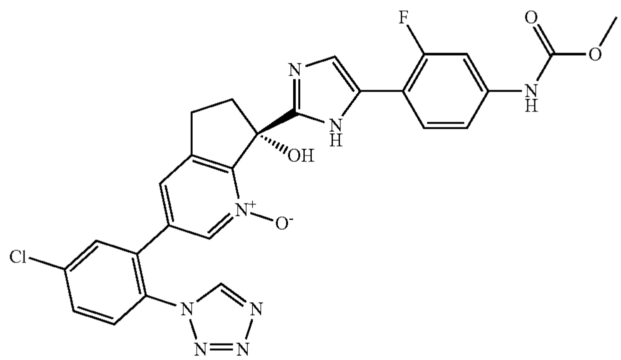 [SMILES: COC(=O)Nc1ccc(-c2cnc([C@]3(O)CCc4cc(-c5cc(Cl)ccc5-n5cnnn5)c[n+]([O-])c43)[nH]2)c(F)c1] | From chiral intermediate | 563 |
| 119 | methyl [4-(2-{3-[5-chloro-2-(1,2,3-thiadiazol-4-yl)phenyl]-7-hydroxy-1-oxido-6,7-dihydro-5H-cyclopenta[b]pyridin-7-yl}-1H-imidazol-4-yl)phenyl]carbamate | 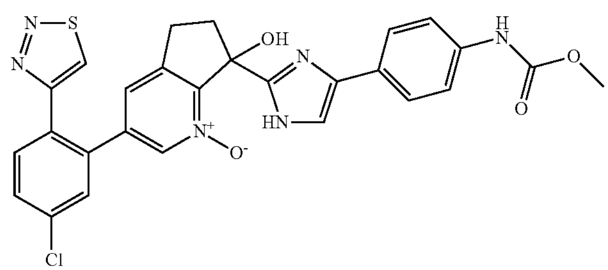 [SMILES: COC(=O)Nc1ccc(-c2c[nH]c(C3(O)CCc4cc(-c5cc(Cl)ccc5-c5csnn5)c[n+]([O-])c43)n2)cc1] | racemic | 561 |
| 120 | (7S)-7-[5-(4-aminophenyl)-4-chloro-1H-imidazol-2-yl]-3-[5-chloro-2-(1H-tetrazol-1-yl)phenyl]-6,7-dihydro-5H-cyclopenta[b]pyridin-7-ol 1-oxide | 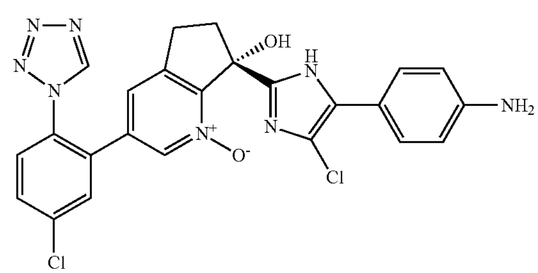 [SMILES: Nc1ccc(-c2[nH]c([C@]3(O)CCc4cc(-c5cc(Cl)ccc5-n5cnnn5)c[n+]([O-])c43)nc2Cl)cc1] | From chiral intermediate | 521 |

-continued

| EX | IUPAC Name | Structure | Chiral Separation | LCMS [M + 1] |
|---|---|---|---|---|
| 121 | methyl [4-(2-{(7S)-3-[5-chloro-2-(4-chloro-1H-1,2,3-triazol-1-yl)phenyl]-7-hydroxy-1-oxido-6,7-dihydro-5H-cyclopenta[b]pyridin-7-yl}-1H-imidazol-5-yl)phenyl]carbamate | 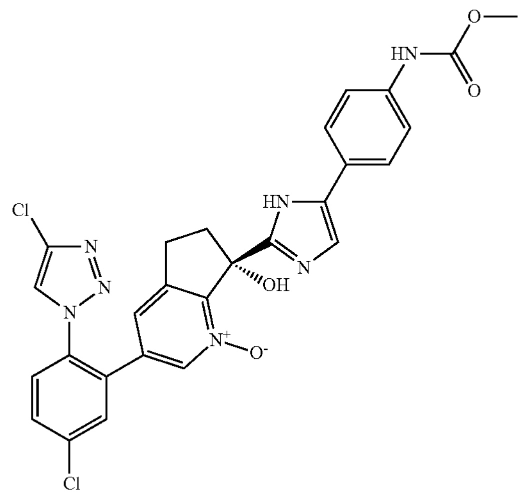 [SMILES: COC(=O)Nc1ccc(-c2cnc([C@]3(O)CCc4cc(-c5cc(Cl)ccc5-n5cc(Cl)nn5)c[n+]([O-])c43)[nH]2)cc1] | From chiral intermediate | 578 |
| 122 | methyl [4-(2-{3-[5-chloro-2-(1H-tetrazol-1-yl)phenyl]-7-(2-methoxyethyl)-1-oxido-6,7-dihydro-5H-cyclopenta[b]pyridin-7-yl}-1H-imidazol-4-yl)phenyl]carbamate | 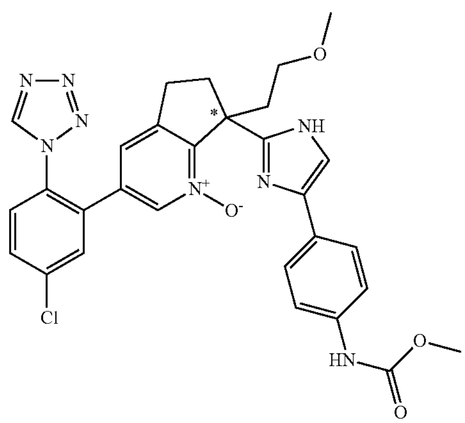 [SMILES: COCCC1(c2nc(-c3ccc(NC(=O)OC)cc3)c[nH]2)CCc2cc(-c3cc(Cl)ccc3-n3cnnn3)c[n+]([O-])c21] | OD column, fast eluting isomer | 587 |
| 123 | methyl [4-(2-{3-[5-chloro-2-(1H-tetrazol-1-yl)phenyl]-7-(2-methoxyethyl)-1-oxido-6,7-dihydro-5H-cyclopenta[b]pyridin-7-yl}-1H-imidazol-4-yl)phenyl]carbamate | 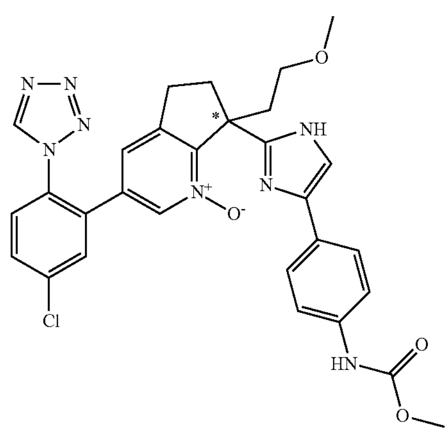 [SMILES: COCCC1(c2nc(-c3ccc(NC(=O)OC)cc3)c[nH]2)CCc2cc(-c3cc(Cl)ccc3-n3cnnn3)c[n+]([O-])c21] | OD column, slow eluting isomer | 587 |

EXAMPLE 124

1-{[(cyclohexyloxy)carbonyl]oxy}ethyl 4-(2-{-3-[5-chloro-2-(1H-tetrazol-1-yl)phenyl]-7-hydroxy-1-oxido-6,7-dihydro-5H-cyclopenta[b]pyridin-7-yl}-1H-imidazol-5-yl)-3-fluorothiophene-2-carboxylate

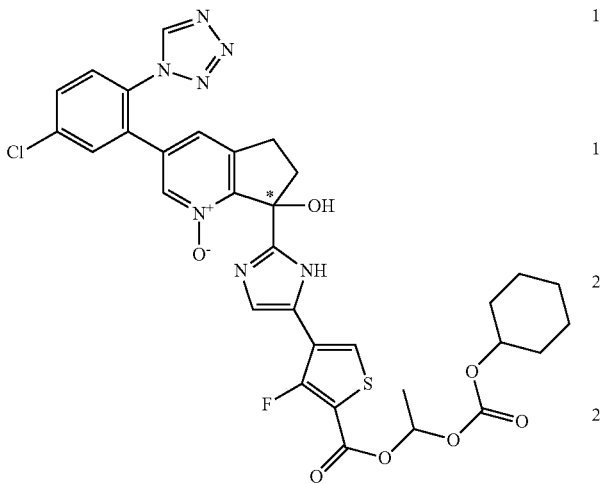

7-(4-(5-Carboxy-4-fluorothiophen-3-yl)-1H-imidazol-2-yl)-3-(5-chloro-2-(1H-tetrazol-1-yl)phenyl)-7-hydroxy-6,7-dihydro-5H-cyclopenta[b]pyridine 1-oxide (EX-50, 100 mg, 0.185 mmol) was mixed with 1-chloroethyl cyclohexyl carbonate (153 mg, 0.74 mmol), KI (123 mg, 0.74 mmol), and $K_2CO_3$ (102 mg, 0.741 mmol) in DMF (1 ml). The mixture was stirred at 60° C. overnight. The mixture was diluted with ethyl acetate (50 mL), and washed with brine. After being dried over anhydrous sodium sulfate, the solution was filtered and concentrated. The crude was purified by column chromatography on a silica gel column, eluting with 0~5% $CH_2Cl_2$/MeOH gradient to give the title product. MS (ESI) m/z: 710.1 (M+H).

EXAMPLE 125

4-(2-{3-[5-chloro-2-(1H-tetrazol-1-yl)phenyl]-7-hydroxy-1-oxido-6,7-dihydro-5H-cyclopenta[b]pyridin-7-yl}-1H-imidazol-5-yl)-3-fluoro-N-(methylsulfonyl)thiophene-2-carboxamide

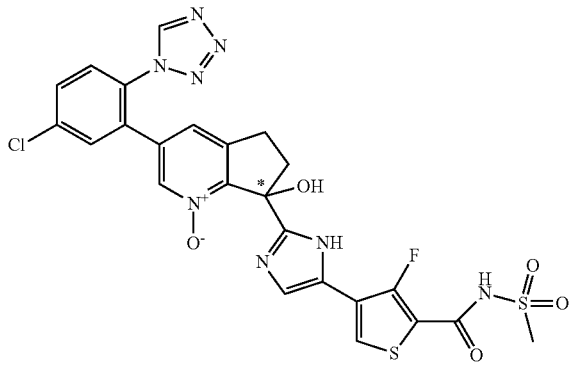 [SMILES: CS(=O)(=O)NC(=O)c1scc(-c2cnc(C3(O)CCc4cc(-c5cc(Cl)ccc5-n5cnnn5)c[n+]([O-])c43)[nH]2)c1F]

7-(4-(5-carboxy-4-fluorothiophen-3-yl)-1H-imidazol-2-yl)-3-(5-chloro-2-(1H-tetrazol-1-yl)phenyl)-7-hydroxy-6,7-dihydro-5H-cyclopenta[b]pyridine 1-oxide (EX-50, 60 mg, 0.11 mmol) was mixed with methanesulfonamide (10.6 mg, 0.11 mmol), N,N-dimethylpyridin-4-amine (27 mg, 0.22 mmol) and $N^1$-((ethylimino)methylene)-$N^3$,$N^3$-dimethylpropane-1,3-diamine hydrochloride (42 mg, 0.22 mmol) in acetonitrile (1 ml). The mixture was stirred at 50° C. for 2 hours. The mixture was diluted with 4 mL of DMF, and purified by preparative RP-HPLC (C-18), eluting with gradient of 0~80% acetonitrile/water+0.1% TFA, to give the title product. MS (ESI) m/z: 617.0 (M+H).

EXAMPLE 126 and 127

Methyl [4-(2-{3-[5-chloro-2-(1H-tetrazol-1-yl)phenyl]-1-oxido-5,6,7,8-tetrahydroquinolin-8-yl}-1H-imidazol-5-yl)phenyl]carbamate (enantiomer 1 and 2)

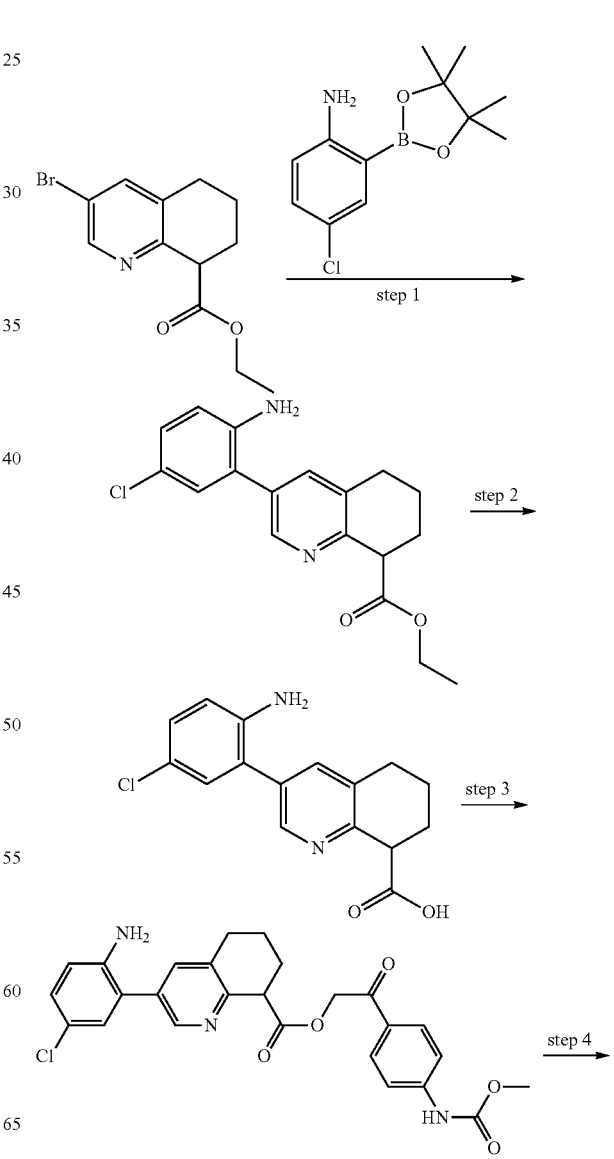

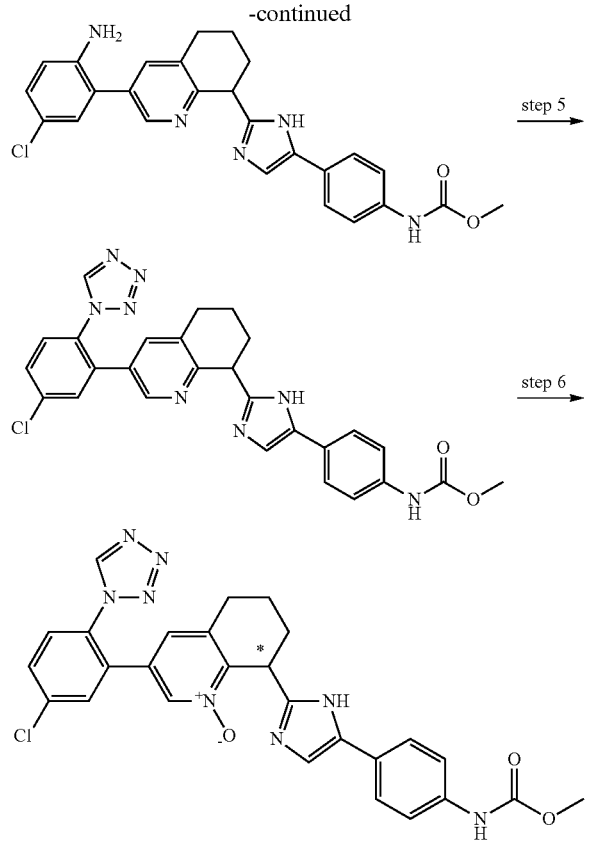

Example 126 (fast eluting enantiomer)
Example 127 (slow eluting enantiomer)

Step 1: ethyl 3-(2-amino-5-chlorophenyl)-5,6,7,8-tetrahydroquinoline-8-carboxylate A flask was charged with 4-chloro-2-(4,4,5,5-tetramethyl-1,3,2-dioxaborolan-2-yl)aniline (0.80 g, 3.17 mmol), ethyl 3-bromo-5,6,7,8-tetrahydroquinoline-8-carboxylate (0.6 g, 2.1 mmol), potassium carbonate (0.438 g, 3.17 mmol) and Tetrakis (0.366 g, 0.317 mmol), and then capped. Air was removed by vacuum and back-filled with nitrogen (×2). 1,4-Dioxane (10 ml) and water (2 ml) were added. The resulting mixture was heated at 95° C. for 2 hours in an oil bath. After it was cooled to rt, the mixture was diluted with water and extracted with EtOAc. The organic phase was dried over MgSO₄, filtered, concentrated and purified on silica gel, eluting with 0-60% EtOAc/hexane to give the title compound. MS (ESI) m/z: 331.0 (M+H).

Step 2: lithium 3-(2-amino-5-chlorophenyl)-5,6,7,8-tetrahydroquinoline-8-carboxylate A solution of ethyl 3-(2-amino-5-chlorophenyl)-5,6,7,8-tetrahydroquinoline-8-carboxylate (0.43 g, 1.3 mmol) in a mixed solvent of MeOH (5 ml), THF (4 mL) and water (4 ml) was mixed with LiOH.H₂O (60 mg, 1.43 mmol). The resulting mixture was stirred at 50° C. for 6 hours. The solvent was removed under reduced pressure and the product was further dried in vacuum oven at 50° C. overnight before being used in the next reaction.

Step 3: 2-(4-((methoxycarbonyl)amino)phenyl)-2-oxoethyl 3-(2-amino-5-chlorophenyl)-5,6,7,8-tetrahydroquinoline-8-carboxylate Lithium 3-(2-amino-5-chlorophenyl)-5,6,7,8-tetrahydroquinoline-8-carboxylate (0.40 g, 1.3 mmol) was dissolved in DMF (5 ml). Cesium carbonate (0.106 g, 0.33 mmol) and methyl (4-(2-bromoacetyl)phenyl)carbamate (0.89 g, 1.43 mmol) were added. The mixture was stirred at rt for 6 hours, then diluted with EtOAc and washed with water. The organic phase was separated and the aqueous layer was extracted with EtOAc. The combined organic phase was washed with brine and dried over MgSO₄. After filtering and concentrating under reduced pressure, the crude was purified on a silica gel column, eluting with gradient of 0-75% EtOAc/CH₂Cl₂ to give the title compound. MS (ESI) m/z: 494.0 (M+H).

Step 4: methyl (4-(2-(3-(2-amino-5-chlorophenyl)-5,6,7,8-tetrahydroquinolin-8-yl)-1H-imidazol-5-yl)phenyl)carbamate A microwave reaction vial was charged with 2-(4-((methoxycarbonyl)amino)phenyl)-2-oxoethyl 3-(2-amino-5-chlorophenyl)-5,6,7,8-tetrahydroquinoline-8-carboxylate (0.42 g, 0.85 mmol), ammonium acetate (0.66 g, 8.50 mmol), acetic acid (0.75 ml) and toluene (15 ml). The vial was then capped and the mixture was heated at 130° C. for 30 min. The mixture was concentrated under reduced pressure. The residue was purified by column chromatography on a silica gel column, eluting with 0-12% MeOH/DCM to give the title compound. MS (ESI) m/z: 474.0 (M+H).

Step 5: methyl (4-(2-(3-(5-chloro-2-(1H-tetrazol-1-yl)phenyl)-5,6,7,8-tetrahydroquinolin-8-yl)-1H-imidazol-5-yl)phenyl)carbamate A solution of methyl (4-(2-(3-(2-amino-5-chlorophenyl)-5,6,7,8-tetrahydroquinolin-8-yl)-1H-imidazol-5-yl)phenyl)carbamate (0.25 g, 0.53 mmol) in acetic acid (5 ml) and TFA (0.12 ml, 1.6 mmol) was mixed with sodium azide (0.21 g, 3.2 mmol) and trimethyl orthoformate (0.35 ml, 3.2 mmol) in a round-bottom flask. The flask was capped and the mixture was stirred at rt overnight. The mixture was concentrated under reduced pressure and the residue was purified by column chromatography on a silica gel column, eluting with 0-15% MeOH/DCM to give the title compound. MS (ESI) m/z: 527.0 (M+H).

Step 6: 3-(5-chloro-2-(1H-tetrazol-1-yl)phenyl)-8-(5-(4-((methoxycarbonyl)amino)phenyl)-1H-imidazol-2-yl)-5,6,7,8-tetrahydroquinoline 1-oxide (Example 126 and 127)

Peracetic acid (40%, 0.24 ml, 1.42 mmol) was added to a solution of methyl (4-(2-(3-(5-chloro-2-(1H-tetrazol-1-yl)phenyl)-5,6,7,8-tetrahydroquinolin-8-yl)-1H-imidazol-5-yl)phenyl)carbamate (0.15 g, 0.29 mmol) in acetic acid (3 ml). The mixture was stirred at rt overnight, then concentrated under reduced pressure. The residue was purified by preparative HPLC on C-18 column, eluting with 0~80% acetonitrile/water+0.1% TFA to give the racemic product, which was separated by SFC on IC column, eluting with 60% 2:1 MeOH:MeCN/CO₂, 100 bar, to give Example 126 (fast eluting enantiomer), MS (ESI) m/z: 543.0 (M+H), and Example 127 (slow eluting enantiomer), MS (ESI) m/z: 543.0 (M+H).

The following compounds were prepared following procedures similar to those described above using appropriate starting materials and characterized by LCMS.

| EX | IUPAC Name | Structure | Chiral separation | LCMS [M + 1] |
|---|---|---|---|---|
| 128 | methyl [4-(4-chloro-2-{3-[5-chloro-2-(1H-tetrazol-1-yl)phenyl]-1-oxido-5,6,7,8-tetrahydroquinolin-8-yl}-1H-imidazol-5-yl)phenyl]carbamate | 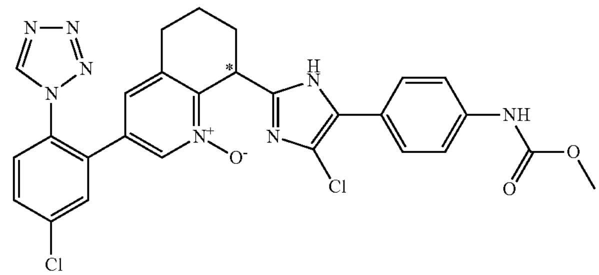 [SMILES: COC(=O)Nc1ccc(-c2[nH]c(C3CCCc4cc(-c5cc(Cl)ccc5-n5cnnn5)c[n+]([O-])c43)nc2Cl)cc1] | IA column, fast eluting isomer | 577 |
| 129 | methyl [4-(4-chloro-2-{3-[5-chloro-2-(1H-tetrazol-1-yl)phenyl]-1-oxido-5,6,7,8-tetrahydroquinolin-8-yl}-1H-imidazol-5-yl)phenyl]carbamate | 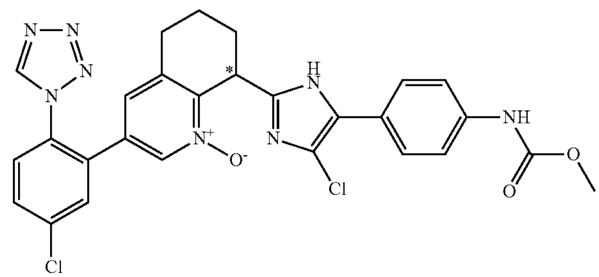 [SMILES: COC(=O)Nc1ccc(-c2[nH]c(C3CCCc4cc(-c5cc(Cl)ccc5-n5cnnn5)c[n+]([O-])c43)nc2Cl)cc1] | IA column, slow eluting isomer | 577 |
| 130 | methyl 4-(2-{3-[5-chloro-2-(1H-tetrazol-1-yl)phenyl]-1-oxido-5,6,7,8-tetrahydroquinolin-8-yl}-1H-imidazol-5-yl)-3-fluorothiophene-2-carboxylate | 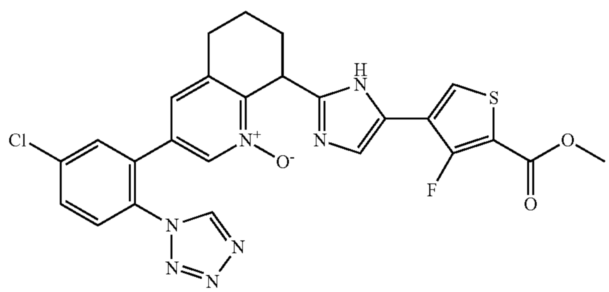 [SMILES: COC(=O)c1scc(-c2cnc(C3CCCc4cc(-c5cc(Cl)ccc5-n5cnnn5)c[n+]([O-])c43)[nH]2)c1F] | racemic | 552 |
| 131 | methyl [4-(2-{3-[5-chloro-2-(1H-tetrazol-1-yl)phenyl]-8-hydroxy-1-oxido-5,6,7,8-tetrahydroquinolin-8-yl}-1H-imidazol-4-yl)phenyl]carbamate | 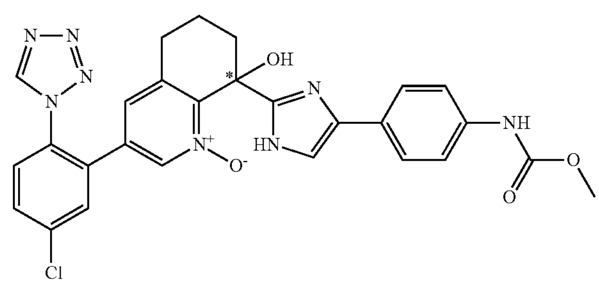 [SMILES: COC(=O)Nc1ccc(-c2c[nH]c(C3(O)CCCc4cc(-c5cc(Cl)ccc5-n5cnnn5)c[n+]([O-])c43)n2)cc1] | OJ column, fast eluting isomer | 559 |
| 132 | methyl [4-(2-{3-[5-chloro-2-(1H-tetrazol-1-yl)phenyl]-8-hydroxy-1-oxido-5,6,7,8-tetrahydroquinolin-8-yl}-1H-imidazol-4-yl)phenyl]carbamate | 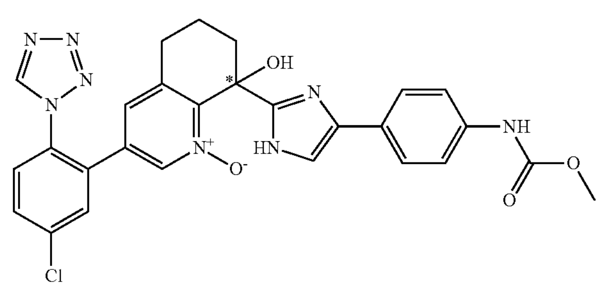 [SMILES: COC(=O)Nc1ccc(-c2c[nH]c(C3(O)CCCc4cc(-c5cc(Cl)ccc5-n5cnnn5)c[n+]([O-])c43)n2)cc1] | OJ column, slow eluting isomer | 559 |

| EX | IUPAC Name | Structure | Chiral separation | LCMS [M + 1] |
|---|---|---|---|---|
| 133 | methyl [4-(2-{3-[5-chloro-2-(1H-tetrazol-1-yl)phenyl]-1-oxido-5,6,7,8-tetrahydroquinolin-8-yl}-1H-imidazol-5-yl)-3-fluorophenyl]carbamate | 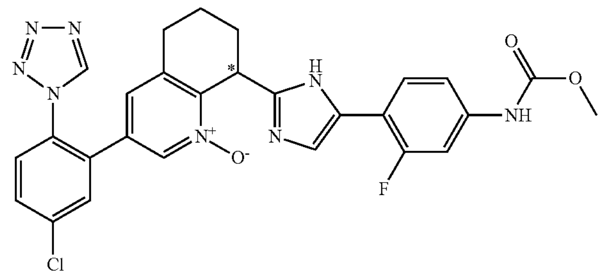 [SMILES: COC(=O)Nc1ccc(-c2cnc(C3CCCc4cc(-c5cc(Cl)ccc5-n5cnnn5)c[n+]([O-])c43)[nH]2)c(F)c1] | AD column, fast eluting isomer | 561 |
| 134 | methyl [4-(2-{3-[5-chloro-2-(1H-tetrazol-1-yl)phenyl]-1-oxido-5,6,7,8-tetrahydroquinolin-8-yl}-1H-imidazol-5-yl)-3-fluorophenyl]carbamate | 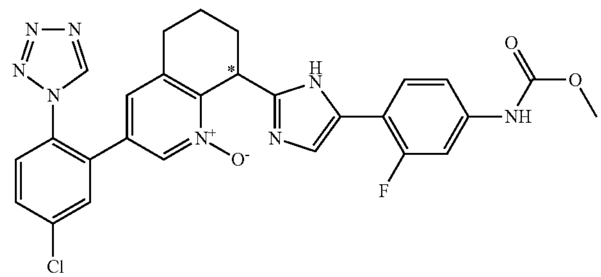 [SMILES: COC(=O)Nc1ccc(-c2cnc(C3CCCc4cc(-c5cc(Cl)ccc5-n5cnnn5)c[n+]([O-])c43)[nH]2)c(F)c1] | AD column, slow eluting isomer | 561 |

Factor XIa Assay

The effectiveness of a compound of the present invention as an inhibitor of Coagulation Factor XIa can be determined using a relevant purified serine protease, and an appropriate synthetic substrate. The rate of hydrolysis of the chromogenic or fluorogenic substrate by the relevant serine protease was measured both in the absence and presence of compounds of the present invention. Assays were conducted at room temperature or at 37° C. Hydrolysis of the substrate resulted in release of amino trifluoromethylcoumarin (AFC), which was monitored spectrofluorometrically by measuring the increase in emission at 510 nm with excitation at 405 nm. A decrease in the rate of fluorescence change in the presence of inhibitor is indicative of enzyme inhibition. Such methods are known to one skilled in the art. The results of this assay are expressed as the inhibitory constant, $K_i$.

Factor XIa determinations were made in 50 mM HEPES buffer at pH 7.4 containing 150 mM NaCl, 5 mM $CaCl_2$, and 0.1% PEG 8000 (polyethylene glycol; JT Baker or Fisher Scientific). Determinations were made using purified human Factor XIa at a final concentration of 40 pM (Sekisui Diagnostics) and the synthetic substrate, Z-Gly-Pro-Arg-AFC, TFA salt (Sigma #C0980) at a concentration of 10004.

Activity assays were performed by diluting a stock solution of substrate at least tenfold to a final concentration ≤0.1 $K_m$ into a solution containing enzyme or enzyme equilibrated with inhibitor. Times required to achieve equilibration between enzyme and inhibitor were determined in control experiments. Initial velocities of product formation in the absence ($V_o$) or presence of inhibitor ($V_i$) were measured. Assuming competitive inhibition, and that unity is negligible compared $K_m/[S]$, [I]/e, and [I]/e (where [S], [I], and e respectively represent the total concentrations, of substrate, inhibitor and enzyme), the equilibrium constant ($K_i$) for dissociation of the inhibitor from the enzyme can be obtained from the dependence of $V_o/V_i$ on [I] shown in the following equation.

$$V_o/V_i = 1 + [I]/K_i$$

The activities shown by this assay indicate that the compounds of the invention may be therapeutically useful for treating or preventing various cardiovascular and/or cerebrovascular thromboembolic conditions in patients suffering from unstable angina, acute coronary syndrome, refractory angina, myocardial infarction, transient ischemic attacks, atrial fibrillation, stroke such as thrombotic stroke or embolic stroke, venous thrombosis, coronary and cerebral arterial thrombosis, cerebral and pulmonary embolism, atherosclerosis, deep vein thrombosis, disseminated intravascular coagulation, and reocclusion or restenosis of recanalized vessels.

| Factor XIa inhibition | |
|---|---|
| EX | FXa $IC_{50}$/nM |
| 1 | 0.38 |
| 2 | 0.78 |
| 3 | 30.0 |
| 4 | 99.3 |
| 5 | 2661 |
| 6 | 215 |
| 7 | 0.69 |
| 9 | 0.32 |
| 10 | 25.2 |
| 11 | 1.80 |
| 12 | 5.94 |
| 13 | 6.26 |
| 14 | 1.81 |
| 15 | 1.61 |
| 16 | 0.52 |
| 17 | 0.96 |
| 18 | 0.52 |
| 19 | 62 |
| 20 | 1.00 |
| 21 | 0.52 |
| 22 | 94 |
| 23 | 57 |
| 24 | 1000 |
| 25 | 5.42 |
| 26 | 11.4 |
| 27 | 7.65 |

Factor XIa inhibition

| EX | FXa IC$_{50}$/nM |
|---|---|
| 28 | 598 |
| 29 | 0.56 |
| 30 | 94 |
| 31 | 1.47 |
| 32 | 0.56 |
| 33 | 52 |
| 34 | 36 |
| 35 | 1000 |
| 36 | 33 |
| 37 | 535 |
| 38 | 0.38 |
| 39 | 44.4 |
| 40 | 0.66 |
| 41 | 70.3 |
| 42 | 27 |
| 43 | 0.49 |
| 44 | 1.22 |
| 45 | 57.5 |
| 46 | 0.33 |
| 47 | 9.66 |
| 48 | 0.17 |
| 49 | 29.0 |
| 50 | 0.44 |
| 51 | 21.4 |
| 52 | 2.58 |
| 53 | 78 |
| 54 | 6.78 |
| 55 | 121 |
| 56 | 1000 |
| 57 | 9.12 |
| 58 | 76.9 |
| 59 | 1000 |
| 60 | 3.86 |
| 61 | 1.80 |
| 62 | 19 |
| 63 | 343 |
| 64 | 648 |
| 65 | 21.5 |
| 66 | 40 |
| 67 | 664 |
| 68 | 43 |
| 69 | 1000 |
| 70 | 13.1 |
| 71 | 90.9 |
| 72 | 41.9 |
| 73 | 1000 |
| 74 | 1000 |
| 75 | 214 |
| 76 | 86.7 |
| 77 | 72.5 |
| 78 | 272 |
| 79 | 111 |
| 80 | 1000 |
| 81 | 14.2 |
| 82 | 1000 |
| 83 | 11.6 |
| 84 | 1000 |
| 85 | 144 |
| 86 | 0.80 |
| 87 | 1.97 |
| 88 | 103 |
| 89 | 7.2 |
| 90 | 2290 |
| 91 | 43.4 |
| 92 | 147 |
| 93 | 210 |
| 94 | 410 |
| 95 | 90.1 |
| 96 | 1860 |
| 97 | 2.04 |
| 98 | 39 |
| 99 | 1000 |
| 100 | 0.34 |
| 101 | 1.33 |
| 102 | 66 |
| 103 | 16 |
| 104 | 32 |
| 105 | 1000 |
| 106 | 0.34 |
| 107 | 45.7 |
| 108 | 302 |
| 109 | 247 |
| 110 | 4.70 |
| 111 | 3.30 |
| 112 | 1.02 |
| 113 | 6.05 |
| 114 | 813 |
| 115 | 0.96 |
| 116 | 170 |
| 117 | 0.61 |
| 118 | 0.28 |
| 119 | 19.4 |
| 120 | 0.207 |
| 121 | 0.60 |
| 122 | 9.50 |
| 123 | 1000 |
| 124 | 250 |
| 125 | 1.41 |
| 126 | 1.66 |
| 127 | 121 |
| 128 | 198 |
| 129 | 0.64 |
| 130 | 323 |
| 131 | 1000 |
| 132 | 8.9 |
| 133 | 233 |
| 134 | 4.4 |

Kallikrein Assay

The effectiveness of a compound of the present invention as an inhibitor of Kallikrein can be determined using a relevant purified serine protease, and an appropriate synthetic substrate. The rate of hydrolysis of the chromogenic or fluorogenic substrate by the relevant serine protease was measured both in the absence and presence of compounds of the present invention. Assays were conducted at room temperature or at 37° C. Hydrolysis of the substrate resulted in release of amino trifluoromethylcoumarin (AFC), which was monitored spectrofluorometrically by measuring the increase in emission at 510 nm with excitation at 405 nm. A decrease in the rate of fluorescence change in the presence of inhibitor is indicative of enzyme inhibition. Such methods are known to one skilled in the art. The results of this assay are expressed as the inhibitory constant, $K_i$.

Kallikrein determinations were made in 50 mM HEPES buffer at pH 7.4 containing 150 mM NaCl, 5 mM CaCl$_2$, and 0.1% PEG 8000 (polyethylene glycol; Fisher Scientific). Determinations were made using purified Human plasma kallikrein at a final concentration of 0.5 nM (Enzyme Research Laboratories) and the synthetic substrate, Acetyl-K-P-R-AFC (Sigma # C6608) at a concentration of 100 mM.

Activity assays were performed by diluting a stock solution of substrate at least tenfold to a final concentration ≤0.2 $K_m$ into a solution containing enzyme or enzyme equilibrated with inhibitor. Times required to achieve equilibration between enzyme and inhibitor were determined in control experiments. The reactions were performed under linear progress curve conditions and fluorescence increase measured at 405 Ex/510 Em nm. Values were converted to percent inhibition of the control reaction (after subtracting 100% Inhibition value). IC$_{50}$ was determined by inflection point from a four parameter logistic curve fit. Ki was calculated using the Cheng Prusoff equation, Ki=IC$_{50}$/(1+ ([S]/Km)).

The activities shown by this assay indicate that the compounds of the invention may be therapeutically useful for treating or preventing various cardiovascular and/or cerebrovascular thromboembolic conditions in patients suffering from unstable angina, acute coronary syndrome, refractory angina, myocardial infarction, transient ischemic attacks, atrial fibrillation, stroke such as thrombotic stroke or embolic stroke, venous thrombosis, coronary and cerebral arterial thrombosis, cerebral and pulmonary embolism, atherosclerosis, deep vein thrombosis, disseminated intravascular coagulation, and reocclusion or restenosis of recanalized vessels.

What is claimed is:
1. A compound of the formula:

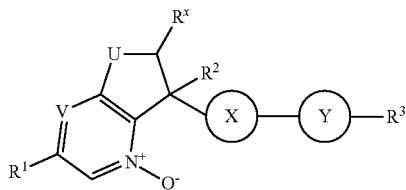

wherein $\widehat{X}$ is heteroaryl, aryl, heterocyclyl or C$_{3-6}$ cycloalkyl, wherein said heteroaryl, aryl, heterocyclyl and cycloalkyl groups are optionally substituted with one or two groups independently selected from the group consisting of halo, cyano, oxo, C$_{1-6}$ alkyl, C$_{2-6}$ alkenyl, C$_{2-6}$ alkynyl, OR$^4$, NR$^4$R$^5$, NH(C=O)R$^4$ and NH(C=O)OR$^4$;

$\widehat{Y}$ is absent, aryl or heteroaryl, wherein said aryl and heteroaryl groups are optionally substituted with halo or C$_{1-6}$ alkyl;
U is S, O, CHR$^x$ or CHR$^x$CH$_2$;
V is N or CR$^y$;
R$^1$ is aryl, heteroaryl, heterocyclyl or C$_{3-6}$ cycloalkyl, wherein said aryl, heteroaryl, heterocyclyl and cycloalkyl groups are optionally substituted with one to three substituents independently selected from the group consisting of halo, nitro, cyano, oxo, R$^4$, OR$^4$, (C=O)R$^4$, (C=O)OR$^4$, NR$^4$R$^5$, NH(C=O)R$^4$, NH(C=O)OR$^4$, C$_{3-6}$ cycloalkyl and heteroaryl (which is optionally substituted with cyano, halo, or R$^4$);
R$^2$ is hydrogen, hydroxy, C$_{1-6}$ alkyl, C$_{1-3}$ alkyl-OR$^4$, C$_{3-6}$ cycloalkyl, OR$^4$, OC$_{1-3}$ alkyl-C$_{3-6}$ cycloalkyl, O(C$_{3-6}$ cycloalkyl) or halo;
R$^3$ is halo, hydroxy, nitro, cyano, oxo, R$^4$, OR$^4$, C$_{1-6}$ alkyl, C$_{2-6}$ alkenyl, C$_{2-6}$ alkynyl, SO$_m$R$^4$, NHSO$_m$R$^4$, (C=O)NHSO$_m$R$^4$, (C=O)R$^4$, (C=O)OR$^4$, O(C=O)R$^4$, O(C=O)OR$^4$, NR$^4$R$^5$, NH(C=O)R$^4$, NH(C=O)OR$^4$, (C=O)OCHR$^4$—O(C=O)OC$_{3-6}$ cycloalkyl, heteroaryl, aryl, heterocyclyl or C$_{3-6}$ cycloalkyl, wherein said heteroaryl, aryl, heterocyclyl and cycloalkyl groups are optionally substituted with one or two groups independently selected from the group consisting of halo, cyano, oxo, R$^4$ and OR$^4$;

R$^4$ is hydrogen or C$_{1-6}$ alkyl, which is optionally substituted with one to three groups independently selected from the group consisting of halo, hydroxy and methoxy;
R$^5$ is hydrogen or C$_{1-6}$ alkyl, which is optionally substituted with one to three groups independently selected from the group consisting of halo and hydroxy;
R$^x$ is hydrogen, hydroxy, halo, R$^4$, OR$^4$, phenyl or benzyl;
R$^y$ is hydrogen, halo, OR$^4$, (C=O)R$^4$, (C=O)OR$^4$, (C=O)NR$^4$R$^5$, C$_{3-6}$ cycloalkyl or O(C$_{3-6}$ cycloalkyl);
m is an integer between 0 and 2;
or a pharmaceutically acceptable salt thereof.
2. The compound of claim 1 of the formula:

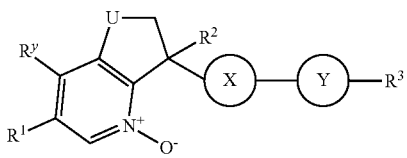

wherein $\widehat{X}$ is heteroaryl, which is optionally substituted with halo or C$_{1-6}$ alkyl;

$\widehat{Y}$ is aryl or heteroaryl, wherein said aryl and heteroaryl groups are optionally substituted with halo or methyl;
U is CHR$^x$,
R$^1$ is aryl, which is optionally substituted with one to three substituents independently selected from the group consisting of halo, nitro, cyano, R$^4$, OR$^4$, (C=O)R$^4$, (C=O)OR$^4$, NR$^4$R$^5$, NH(C=O)R$^4$, NH(C=O)OR$^4$, C$_{3-6}$ cycloalkyl and heteroaryl (which is optionally substituted with cyano, halo or R$^4$);
R$^2$ is hydrogen, hydroxy, methyl, methoxy, cyclopropyl or halo;
R$^3$ is halo, hydroxy, nitro, cyano, oxo, R$^4$, OR$^4$, (C=O)R$^4$, (C=O)OR$^4$, NR$^4$R$^5$, NH(C=O)R$^4$ or NH(C=O)OR$^4$;
R$^4$ is hydrogen or C$_{1-6}$ alkyl, which is optionally substituted with one to three groups independently selected from the group consisting of halo, hydroxy and methoxy;
R$^5$ is hydrogen or C$_{1-6}$ alkyl, which is optionally substituted with one to three groups independently selected from the group consisting of halo and hydroxy;
R$^x$ is hydrogen, hydroxy or halo;
R$^y$ is hydrogen, hydroxy, methoxy or halo;
or a pharmaceutically acceptable salt thereof.
3. The compound of claim 1 of the formula:

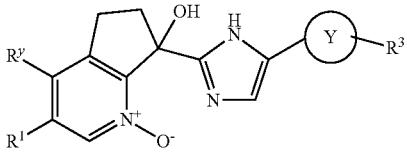

wherein $\widehat{Y}$ is aryl or heteroaryl, wherein said aryl and heteroaryl groups are optionally substituted with halo;
R$^1$ is phenyl, which is optionally substituted with one to three substituents independently selected from the group consisting of halo or heteroaryl (which is optionally substituted with cyano or $R^4$);

$R^3$ is halo, hydroxy, $R^4$, $OR^4$, $(C=O)R^4$, $(C=O)OR^4$, $NR^4R^5$, $NH(C=O)R^4$ or $NH(C=O)OR^4$;

$R^4$ is hydrogen or $C_{1-6}$ alkyl, which is optionally substituted with one to three groups independently selected from the group consisting of halo and hydroxy;

$R^5$ is hydrogen or $C_{1-6}$ alkyl, which is optionally substituted with one to three groups independently selected from the group consisting of halo and hydroxy;

$R^y$ is hydrogen, hydroxy, methoxy or halo;

or a pharmaceutically acceptable salt thereof.

4. The compound of claim 1 wherein $R^1$ is phenyl, which optionally is substituted with two or three substituents independently selected from the group consisting of halo and heteroaryl; or a pharmaceutically acceptable salt thereof.

5. The compound of claim 1 wherein $R^1$ is phenyl, which optionally is substituted with halo and tetrazolyl; or a pharmaceutically acceptable salt thereof.

6. The compound of claim 1 wherein $R^1$ is phenyl, which optionally is substituted with three halo; or a pharmaceutically acceptable salt thereof.

7. The compound of claim 1 wherein (X) is imidazolyl, oxazolyl, oxadiazolyl, benzimidaolyl or pyrazolyl, wherein said imidazolyl is optionally substituted with methyl or halo; or a pharmaceutically acceptable salt thereof.

8. The compound of claim 1 wherein (Y) is phenyl, which is optionally substituted with halo; or a pharmaceutically acceptable salt thereof.

9. The compound of claim 1 wherein (Y) is phenyl; or a pharmaceutically acceptable salt thereof.

10. The compound of claim 1 selected from:
methyl [4-(2-{3-[5-chloro-2-(1H-tetrazol-1-yl)phenyl]-1-oxido-6,7-dihydro-5H-cyclopenta[b]pyridin-7-yl}-1H-imidazol-4-yl)phenyl]carbamate;
methyl [4-(2-{3-[5-chloro-2-(1H-tetrazol-1-yl)phenyl]-1-oxido-6,7-dihydro-5H-cyclopenta[b]pyridin-7-yl}-4-methyl-1H-imidazol-5-yl)phenyl]carbamate;
3-[5-chloro-2-(1H-tetrazol-1-yl)phenyl]-7-[4-(3-fluorophenyl)-1H-imidazol-2-yl]-6,7-dihydro-5H-cyclopenta[b]pyridine 1-oxide;
methyl 4-(2-{3-[5-chloro-2-(1H-tetrazol-1-yl)phenyl]-1-oxido-6,7-dihydro-5H-cyclopenta[b]pyridin-7-yl}-1H-imidazol-4-yl)-3-fluorothiophene-2-carboxylate;
3-[5-chloro-2-(1H-tetrazol-1-yl)phenyl]-7-[4-(3-fluorophenyl)-1H-imidazol-2-yl]-7-methyl-6,7-dihydro-5H-cyclopenta[b]pyridine 1-oxide;
methyl [4-(2-{3-[5-chloro-2-(1H-tetrazol-1-yl)phenyl]-7-methyl-1-oxido-6,7-dihydro-5H-cyclopenta[b]pyridin-7-yl}-1H-imidazol-4-yl)phenyl]carbamate;
methyl [4-(5-chloro-2-{3-[5-chloro-2-(1H-tetrazol-1-yl)phenyl]-1-oxido-6,7-dihydro-5H-cyclopenta[b]pyridin-7-yl}-1H-imidazol-4-yl)phenyl]carbamate;
methyl [4-(5-chloro-2-{(7 S)-3-[5-chloro-2-(1H-tetrazol-1-yl)phenyl]-7-hydroxy-1-oxido-6,7-dihydro-5H-cyclopenta[b]pyridin-7-yl}-1H-imidazol-4-yl)phenyl]carbamate;
methyl [4-(5-chloro-2-{(7R)-3-[5-chloro-2-(1H-tetrazol-1-yl)phenyl]-7-hydroxy-1-oxido-6,7-dihydro-5H-cyclopenta[b]pyridin-7-yl}-1H-imidazol-4-yl)phenyl]carbamate;
4-(2-{3-[5-chloro-2-(1H-tetrazol-1-yl)phenyl]-1-oxido-6,7-dihydro-5H-cyclopenta[b]pyridin-7-yl}-1H-imidazol-4-yl)-3-fluorothiophene-2-carboxylic acid;
5-(2-{3-[5-chloro-2-(1H-tetrazol-1-yl)phenyl]-1-oxido-6,7-dihydro-5H-cyclopenta[b]pyridin-7-yl}-1H-imidazol-5-yl)thiophene-2-carboxylic acid;
5-(2-{3-[5-chloro-2-(1H-tetrazol-1-yl)phenyl]-1-oxido-6,7-dihydro-5H-cyclopenta[b]pyridin-7-yl}-1H-imidazol-4-yl)pyridin-2-amine;
7-[4-(6-aminopyridin-3-yl)-1H-imidazol-2-yl]-3-[5-chloro-2-(1H-tetrazol-1-yl)phenyl]-6,7-dihydro-5H-cyclopenta[b]pyridin-7-ol 1-oxide;
methyl [4-(2-{3-[5-chloro-2-(1H-tetrazol-1-yl)phenyl]-5-hydroxy-1-oxido-6,7-dihydro-5H-cyclopenta[b]pyridin-7-yl}-1H-imidazol-5-yl)phenyl]carbamate;
methyl [4-(2-{3-[5-chloro-2-(1H-tetrazol-1-yl)phenyl]-5,7-dihydroxy-1-oxido-6,7-dihydro-5H-cyclopenta[b]pyridin-7-yl}-1H-imidazol-5-yl)phenyl]carbamate;
methyl [4-(2-{3-[5-chloro-2-(1H-tetrazol-1-yl)phenyl]-5-fluoro-1-oxido-6,7-dihydro-5H-cyclopenta[b]pyridin-7-yl}-1H-imidazol-5-yl)phenyl]carbamate;
methyl [4-(2-{3-[5-chloro-2-(1H-tetrazol-1-yl)phenyl]-7-hydroxy-1-oxido-6,7-dihydro-5H-cyclopenta[b]pyridin-7-yl}-1H-imidazol-5-yl)phenyl]carbamate;
3-[5-chloro-2-(1H-tetrazol-1-yl)phenyl]-7-{5-[4-(trifluoromethyl)phenyl]-1H-imidazol-2-yl}-6,7-dihydro-5H-cyclopenta[b]pyridin-7-ol 1-oxide;
3-[5-chloro-2-(1H-tetrazol-1-yl)phenyl]-7-[5-(3-fluorophenyl)-1H-imidazol-2-yl]-6,7-dihydro-5H-cyclopenta[b]pyridin-7-ol 1-oxide;
3-[5-chloro-2-(1H-tetrazol-1-yl)phenyl]-7-[5-(4-fluorophenyl)-1H-imidazol-2-yl]-6,7-dihydro-5H-cyclopenta[b]pyridin-7-ol 1-oxide;
methyl [4-(2-{3-[5-chloro-2-(1H-tetrazol-1-yl)phenyl]-7-methoxy-1-oxido-6,7-dihydro-5H-cyclopenta[b]pyridin-7-yl}-1H-imidazol-5-yl)phenyl]carbamate;
methyl [3-chloro-4-(2-{3-[5-chloro-2-(1H-tetrazol-1-yl)phenyl]-7-hydroxy-1-oxido-6,7-dihydro-5H-cyclopenta[b]pyridin-7-yl}-1H-imidazol-5-yl)phenyl]carbamate;
methyl [4-(2-{3-[5-chloro-2-(1H-tetrazol-1-yl)phenyl]-7-hydroxy-1-oxido-6,7-dihydro-5H-cyclopenta[b]pyridin-7-yl}-1H-imidazol-5-yl)-3-fluorophenyl]carbamate;
methyl [4-(2-{3-[5-chloro-2-(1H-tetrazol-1-yl)phenyl]-7-hydroxy-1-oxido-6,7-dihydro-5H-cyclopenta[b]pyridin-7-yl}-1H-imidazol-5-yl)-3-methylphenyl]carbamate;
methyl 4-(2-{3-[5-chloro-2-(1H-tetrazol-1-yl)phenyl]-7-hydroxy-1-oxido-6,7-dihydro-5H-cyclopenta[b]pyridin-7-yl}-1H-imidazol-4-yl)-3-fluorothiophene-2-carboxylate;
7-(2-{3-[5-chloro-2-(1H-tetrazol-1-yl)phenyl]-7-hydroxy-1-oxido-6,7-dihydro-5H-cyclopenta[b]pyridin-7-yl}-1H-imidazol-5-yl)-3,4-dihydroquinolin-2(1H)-one;
2-methoxyethyl [4-(2-{3-[5-chloro-2-(1H-tetrazol-1-yl)phenyl]-7-hydroxy-1-oxido-6,7-dihydro-5H-cyclopenta[b]pyridin-7-yl}-1H-imidazol-5-yl)phenyl]carbamate;
7-[5-(6-amino-2-fluoropyridin-3-yl)-1H-imidazol-2-yl]-3-[5-chloro-2-(1H-tetrazol-1-yl)phenyl]-6,7-dihydro-5H-cyclopenta[b]pyridin-7-ol 1-oxide;
7-[5-(6-amino-2-chloropyridin-3-yl)-1H-imidazol-2-yl]-3-[5-chloro-2-(1H-tetrazol-1-yl)phenyl]-6,7-dihydro-5H-cyclopenta[b]pyridin-7-ol 1-oxide;

5-(2-{3-[5-chloro-2-(1H-tetrazol-1-yl)phenyl]-7-hydroxy-1-oxido-6,7-dihydro-5H-cyclopenta[b]pyridin-7-yl}-1H-imidazol-5-yl)thiophene-2-carboxylic acid;

5-(4-chloro-2-{3-[5-chloro-2-(1H-tetrazol-1-yl)phenyl]-7-hydroxy-1-oxido-6,7-dihydro-5H-cyclopenta[b]pyridin-7-yl}-1H-imidazol-5-yl)thiophene-2-carboxylic acid;

4-(4-chloro-2-{3-[5-chloro-2-(1H-tetrazol-1-yl)phenyl]-7-hydroxy-1-oxido-6,7-dihydro-5H-cyclopenta[b]pyridin-7-yl}-1H-imidazol-5-yl)thiophene-2-carboxylic acid;

4-(2-{3-[5-chloro-2-(1H-tetrazol-1-yl)phenyl]-7-hydroxy-1-oxido-6,7-dihydro-5H-cyclopenta[b]pyridin-7-yl}-1H-imidazol-4-yl)-3-fluorothiophene-2-carboxylic acid;

4-(2-{3-[5-chloro-2-(1H-tetrazol-1-yl)phenyl]-7-hydroxy-1-oxido-6,7-dihydro-5H-cyclopenta[b]pyridin-7-yl}-4-methyl-1H-imidazol-5-yl)thiophene-2-carboxylic acid;

4-(2-{3-[5-chloro-2-(1H-tetrazol-1-yl)phenyl]-7-hydroxy-1-oxido-6,7-dihydro-5H-cyclopenta[b]pyridin-7-yl}-4-methyl-1H-imidazol-5-yl)-3-fluorothiophene-2-carboxylic acid;

3-[5-chloro-2-(1H-tetrazol-1-yl)phenyl]-7-{5-[4-fluoro-5-(hydroxymethyl)thiophen-3-yl]-1H-imidazol-2-yl}-6,7-dihydro-5H-cyclopenta[b]pyridin-7-ol 1-oxide;

7-(2-{3-[5-chloro-2-(1H-tetrazol-1-yl)phenyl]-7-hydroxy-1-oxido-6,7-dihydro-5H-cyclopenta[b]pyridin-7-yl}-4-methyl-1H-imidazol-5-yl)-3,4-dihydroquinolin-2(1H)-one;

3-[5-chloro-2-(1H-tetrazol-1-yl)phenyl]-7-[5-(2-fluoro-6-hydroxypyridin-3-yl)-1H-imidazol-2-yl]-6,7-dihydro-5H-cyclopenta[b]pyridin-7-ol 1-oxide;

methyl [4-(5-{3-[5-chloro-2-(1H-tetrazol-1-yl)phenyl]-7-hydroxy-1-oxido-6,7-dihydro-5H-cyclopenta[b]pyridin-7-yl}-1H-imidazol-2-yl)phenyl]carbamate;

methyl [4-(5-{3-[5-chloro-2-(1H-tetrazol-1-yl)phenyl]-7-hydroxy-1-oxido-6,7-dihydro-5H-cyclopenta[b]pyridin-7-yl}-1,3,4-oxadiazol-2-yl)phenyl]carbamate;

7-[5-(4-chlorophenyl)-1,3,4-oxadiazol-2-yl]-3[5-chloro-2-(1H-tetrazol-1-yl)phenyl]-6,7-dihydro-5H-cyclopenta[b]pyridin-7-ol 1-oxide;

methyl [3-chloro-4-(4-{3-[5-chloro-2-(1H-tetrazol-1-yl)phenyl]-7-hydroxy-1-oxido-6,7-dihydro-5H-cyclopenta[b]pyridin-7-yl}-1H-pyrazol-1-yl)phenyl]carbamate;

methyl [4-(2-{3-[3-chloro-2-fluoro-6-(1H-tetrazol-1-yl)phenyl]-7-hydroxy-1-oxido-6,7-dihydro-5H-cyclopenta[b]pyridin-7-yl}-1,3-oxazol-5-yl)phenyl]carbamate;

3-[5-chloro-2-(1H-tetrazol-1-yl)phenyl]-7-(6-fluoro-1H-benzimidazol-2-yl)-6,7-dihydro-5H-cyclopenta[b]pyridin-7-ol 1-oxide;

2-{3-[5-chloro-2-(1H-tetrazol-1-yl)phenyl]-7-hydroxy-1-oxido-6,7-dihydro-5H-cyclopenta[b]pyridin-7-yl}-1H-benzimidazole-6-carboxylic acid;

3-[5-chloro-2-(1H-tetrazol-1-yl)phenyl]-7-[6-(trifluoromethyl)-1H-benzimidazol-2-yl]-6,7-dihydro-5H-cyclopenta[b]pyridin-7-ol 1-oxide;

7-[5-(6-amino-2-chloropyridin-3-yl)-1H-imidazol-2-yl]-3-[3-chloro-6-(difluoromethyl)-2-fluorophenyl]-6,7-dihydro-5H-cyclopenta[b]pyridin-7-ol 1-oxide;

methyl 4-{2-[3-(3-chloro-2,6-difluorophenyl)-7-hydroxy-1-oxido-6,7-dihydro-5H-cyclopenta[b]pyridin-7-yl]-1H-imidazol-5-yl}-3-fluorothiophene-2-carboxylate;

4-{2-[3-(3-chloro-2,6-difluorophenyl)-7-hydroxy-1-oxido-6,7-dihydro-5H-cyclopenta[b]pyridin-7-yl]-1H-imidazol-5-yl}-3-fluorothiophene-2-carboxylic acid;

methyl [3-chloro-4-(2-{3-[3-chloro-6-(difluoromethyl)-2-fluorophenyl]-7-hydroxy-1-oxido-6,7-dihydro-5H-cyclopenta[b]pyridin-7-yl}-1H-imidazol-5-yl)phenyl]carbamate;

7-[5-(6-amino-2-chloropyridin-3-yl)-1H-imidazol-2-yl]-3-[5-chloro-2-(difluoromethyl)phenyl]-6,7-dihydro-5H-cyclopenta[b]pyridin-7-ol 1-oxide;

methyl (4-{2-[3-(3-chloro-2,6-difluorophenyl)-1-oxido-6,7-dihydro-5H-cyclopenta[b]pyridin-7-yl]-1H-imidazol-5-yl}phenyl)carbamate;

methyl (4-{2-[3-(3-chloro-2,6-difluorophenyl)-7-hydroxy-1-oxido-6,7-dihydro-5H-cyclopenta[b]pyridin-7-yl]-1H-imidazol-5-yl}phenyl)carbamate;

methyl (4-{2-[3-(5-chloro-2-cyanophenyl)-7-hydroxy-1-oxido-6,7-dihydro-5H-cyclopenta[b]pyridin-7-yl]-1H-imidazol-5-yl}phenyl)carbamate;

2-{7-[5-(6-amino-2-chloropyridin-3-yl)-1H-imidazol-2-yl]-7-hydroxy-1-oxido-6,7-dihydro-5H-cyclopenta[b]pyridin-3-yl}-4-chloro-3-fluorobenzonitrile;

methyl (4-{2-[3-(5-chloro-2-cyanophenyl)-7-hydroxy-4-methoxy-1-oxido-6,7-dihydro-5H-cyclopenta[b]pyridin-7-yl]-1H-imidazol-4-yl}phenyl)carbamate;

2-{7-[4-(6-amino-2-chloropyridin-3-yl)-1H-imidazol-2-yl]-7-hydroxy-4-methoxy-1-oxido-6,7-dihydro-5H-cyclopenta[b]pyridin-3-yl}-4-chlorobenzonitrile;

methyl (4-{2-[3-(6-acetyl-3-chloro-2-fluorophenyl)-7-hydroxy-1-oxido-6,7-dihydro-5H-cyclopenta[b]pyridin-7-yl]-1H-imidazol-5-yl}phenyl)carbamate;

3-(2-amino-5-chlorophenyl)-7-[5-(3-fluorophenyl)-1H-imidazol-2-yl]-6,7-dihydro-5H-cyclopenta[b]pyridin-7-ol 1-oxide;

4-(2-{3-[5-chloro-2-(1,3-oxazol-5-yl)phenyl]-7-hydroxy-1-oxido-6,7-dihydro-5H-cyclopenta[b]pyridin-7-yl}-1H-imidazol-5-yl)-3-fluorothiophene-2-carboxylic acid;

4-(4-chloro-2-{3-[5-chloro-2-(1,3-oxazol-5-yl)phenyl]-7-hydroxy-1-oxido-6,7-dihydro-5H-cyclopenta[b]pyridin-7-yl}-1H-imidazol-5-yl)-3-fluorothiophene-2-carboxylic acid;

7-[5-(6-amino-2-chloropyridin-3-yl)-1H-imidazol-2-yl]-3-[5-chloro-2-(1,3-oxazol-5-yl)phenyl]-6,7-dihydro-5H-cyclopenta[b]pyridin-7-ol 1-oxide;

7-[5-(6-amino-2-chloropyridin-3-yl)-4-chloro-1H-imidazol-2-yl]-3-[5-chloro-2-(1,3-oxazol-5-yl)phenyl]-6,7-dihydro-5H-cyclopenta[b]pyridin-7-ol 1-oxide;

methyl [3-chloro-4-(2-{3-[5-chloro-2-(4-cyano-1H-1,2,3-triazol-1-yl)phenyl]-7-hydroxy-1-oxido-6,7-dihydro-5H-cyclopenta[b]pyridin-7-yl}-1H-imidazol-4-yl)phenyl]carbamate;

methyl 4-(2-{3-[5-chloro-2-(1H-tetrazol-1-yl)phenyl]-7-hydroxy-1-oxido-6,7-dihydro-5H-cyclopenta[b]pyridin-7-yl}-1H-imidazol-5-yl)thiophene-2-carboxylate;

4-(2-{3-[5-chloro-2-(1H-tetrazol-1-yl)phenyl]-7-hydroxy-1-oxido-6,7-dihydro-5H-cyclopenta[b]pyridin-7-yl}-4-fluoro-1H-imidazol-5-yl)-3-fluorothiophene-2-carboxylic acid;

4-(4-chloro-2-{3-[5-chloro-2-(1H-tetrazol-1-yl)phenyl]-7-hydroxy-1-oxido-6,7-dihydro-5H-cyclopenta[b]pyridin-7-yl}-1H-imidazol-5-yl)-3-fluorothiophene-2-carboxylic acid;

5-(2-{3-[5-chloro-2-(1H-tetrazol-1-yl)phenyl]-7-hydroxy-1-oxido-6,7-dihydro-5H-cyclopenta[b]pyridin-7-yl}-4-methyl-1H-imidazol-5-yl)thiophene-2-carboxylic acid;

methyl [3-chloro-4-(2-{3-[3-chloro-6-(difluoromethyl)-2-fluorophenyl]-7-hydroxy-1-oxido-6,7-dihydro-5H-cyclopenta[b]pyridin-7-yl}-1H-imidazol-5-yl)phenyl]carbamate;

methyl [3-chloro-4-(2-{3-[3-chloro-2-fluoro-6-(1H-tetrazol-1-yl)phenyl]-7-hydroxy-1-oxido-6,7-dihydro-5H-cyclopenta[b]pyridin-7-yl}-1H-imidazol-5-yl)phenyl]carbamate;

methyl [4-(2-{3-[5-chloro-2-(trifluoromethoxy)phenyl]-7-hydroxy-1-oxido-6,7-dihydro-5H-cyclopenta[b]pyridin-7-yl}-1H-imidazol-5-yl)phenyl]carbamate;

methyl (4-{4-chloro-2-[(7S)-3-(5-chloro-2-cyanophenyl)-7-hydroxy-1-oxido-6,7-dihydro-5H-cyclopenta[b]pyridin-7-yl]-1H-imidazol-5-yl}phenyl)carbamate;

methyl {4-[2-(3-{5-chloro-2-[4-(difluoromethyl)-1H-1,2,3-triazol-1-yl]phenyl}-7-hydroxy-1-oxido-6,7-dihydro-5H-cyclopenta[b]pyridin-7-yl)-1H-imidazol-5-yl]phenyl}carbamate;

methyl [4-(2-{3-[5-chloro-2-(4-chloro-1H-1,2,3-triazol-1-yl)phenyl]-7-hydroxy-1-oxido-6,7-dihydro-5H-cyclopenta[b]pyridin-7-yl}-1H-imidazol-5-yl)phenyl]carbamate;

methyl (4-{2-[4-chloro-3-(5-chloro-2-cyanophenyl)-7-hydroxy-1-oxido-6,7-dihydro-5H-cyclopenta[b]pyridin-7-yl]-1H-imidazol-4-yl}phenyl)carbamate;

methyl [4-(2-{4-chloro-3-[5-chloro-2-(1H-tetrazol-1-yl)phenyl]-7-hydroxy-1-oxido-6,7-dihydro-5H-cyclopenta[b]pyridin-7-yl}-1H-imidazol-5-yl)phenyl]carbamate;

methyl (4-{5-chloro-2-[3-(5-chloro-2-cyanophenyl)-7-hydroxy-4-methoxy-1-oxido-6,7-dihydro-5H-cyclopenta[b]pyridin-7-yl]-1H-imidazol-4-yl}phenyl)carbamate;

methyl [4-(2-{(7S)-3-[5-chloro-2-(1H-tetrazol-1-yl)phenyl]-7-hydroxy-1-oxido-6,7-dihydro-5H-cyclopenta[b]pyridin-7-yl}-1H-imidazol-5-yl)-3-fluorophenyl]carbamate;

methyl [4-(2-{3-[5-chloro-2-(1,2,3-thiadiazol-4-yl)phenyl]-7-hydroxy-1-oxido-6,7-dihydro-5H-cyclopenta[b]pyridin-7-yl}-1H-imidazol-4-yl)phenyl]carbamate;

(7S)-7-[5-(4-aminophenyl)-4-chloro-1H-imidazol-2-yl]-3-[5-chloro-2-(1H-tetrazol-1-yl)phenyl]-6,7-dihydro-5H-cyclopenta[b]pyridin-7-ol 1-oxide;

methyl [4-(2-{(7S)-3-[5-chloro-2-(4-chloro-1H-1,2,3-triazol-1-yl)phenyl]-7-hydroxy-1-oxido-6,7-dihydro-5H-cyclopenta[b]pyridin-7-yl}-1H-imidazol-5-yl)phenyl]carbamate;

methyl [4-(2-{3-[5-chloro-2-(1H-tetrazol-1-yl)phenyl]-7-(2-methoxyethyl)-1-oxido-6,7-dihydro-5H-cyclopenta[b]pyridin-7-yl}-1H-imidazol-4-yl)phenyl]carbamate;

1-{[(cyclohexyloxy)carbonyl]oxy}ethyl 4-(2-{-3-[5-chloro-2-(1H-tetrazol-1-yl)phenyl]-7-hydroxy-1-oxido-6,7-dihydro-5H-cyclopenta[b]pyridin-7-yl}-1H-imidazol-5-yl)-3-fluorothiophene-2-carboxylate;

4-(2-{3-[5-chloro-2-(1H-tetrazol-1-yl)phenyl]-7-hydroxy-1-oxido-6,7-dihydro-5H-cyclopenta[b]pyridin-7-yl}-1H-imidazol-5-yl)-3-fluoro-N-(methylsulfonyl)thiophene-2-carboxamide;

methyl [4-(2-{3-[5-chloro-2-(1H-tetrazol-1-yl)phenyl]-1-oxido-5,6,7,8-tetrahydroquinolin-8-yl}-1H-imidazol-5-yl)phenyl]carbamate;

methyl [3-chloro-4-(2-{3-[3-chloro-6-(difluoromethyl)-2-fluorophenyl]-7-hydroxy-1-oxido-6,7-dihydro-5H-cyclopenta[b]pyridin-7-yl}-1H-imidazol-5-yl)phenyl]carbamate;

methyl 4-(2-{3-[5-chloro-2-(1H-tetrazol-1-yl)phenyl]-1-oxido-5,6,7,8-tetrahydroquinolin-8-yl}-1H-imidazol-5-yl)-3-fluorothiophene-2-carboxylate;

methyl [4-(2-{3-[5-chloro-2-(1H-tetrazol-1-yl)phenyl]-8-hydroxy-1-oxido-5,6,7,8-tetrahydroquinolin-8-yl}-1H-imidazol-4-yl)phenyl]carbamate;

methyl [4-(2-{3-[5-chloro-2-(1H-tetrazol-1-yl)phenyl]-1-oxido-5,6,7,8-tetrahydroquinolin-8-yl}-1H-imidazol-5-yl)-3-fluorophenyl]carbamate;

or a pharmaceutically acceptable salt thereof.

11. A pharmaceutical composition comprising a compound of claim 1 or a pharmaceutically acceptable salt thereof and a pharmaceutically acceptable carrier.

* * * * *